(12) United States Patent
Nishimura et al.

(10) Patent No.: US 9,145,564 B2
(45) Date of Patent: Sep. 29, 2015

(54) **PERSISTENTLY INFECTIVE *SENDAI VIRUS* VECTOR**

(75) Inventors: Ken Nishimura, Tsukuba (JP); Hiroaki Segawa, Tsukuba (JP); Mahito Nakanishi, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 1168 days.

(21) Appl. No.: 12/595,497

(22) PCT Filed: Apr. 11, 2008

(86) PCT No.: PCT/JP2008/057212
§ 371 (c)(1),
(2), (4) Date: Dec. 1, 2009

(87) PCT Pub. No.: WO2008/129971
PCT Pub. Date: Oct. 30, 2008

(65) Prior Publication Data
US 2010/0196993 A1    Aug. 5, 2010

(30) Foreign Application Priority Data
Apr. 13, 2007    (JP) .................. 2007-105786

(51) Int. Cl.
C12N 15/00    (2006.01)
C07H 21/02    (2006.01)
C12N 7/01     (2006.01)
A61K 39/12    (2006.01)
(Continued)

(52) U.S. Cl.
CPC ............. *C12N 15/86* (2013.01); *A61K 38/162* (2013.01); *C12N 7/00* (2013.01); *A61K 35/12* (2013.01); *A61K 35/13* (2013.01); *C12N 2760/18821* (2013.01); *C12N 2760/18843* (2013.01)

(58) Field of Classification Search
None
See application file for complete search history.

(56) References Cited

U.S. PATENT DOCUMENTS 6,746,860 B1    6/2004    Tokusumi et al.
7,101,685 B2    9/2006    Nagai et al.
(Continued)

FOREIGN PATENT DOCUMENTS

JP    2006-180780    7/2006
JP    2006-325531    12/2006
(Continued)

OTHER PUBLICATIONS

Nishio et al. Recombinant *Sendai viruses* with L1618V mutation in their L polymerase protein establish persistent infection, but not temperature sensitivity. Virology 2004, vol. 329, pp. 289-301.*

(Continued)

*Primary Examiner* — Zachariah Lucas
*Assistant Examiner* — M. Franco Salvoza
(74) *Attorney, Agent, or Firm* — Locke Lord LLP

(57) ABSTRACT

A persistently infective virus vector is produced by using a gene so modified as to encode an amino acid sequence including a valine substituted for an amino acid residue at position-1618 in the amino acid sequence for an L protein of a persistently non-infective Sendai virus. A non-transmissible, persistently infective virus vector is also produced by defecting or deleting at least one of M gene, F gene, and HN gene. These virus vectors have no cytotoxicity, can achieve the sustained gene expression over a long period of time, is safe, and is therefore useful.

22 Claims, 30 Drawing Sheets

Figure 1:
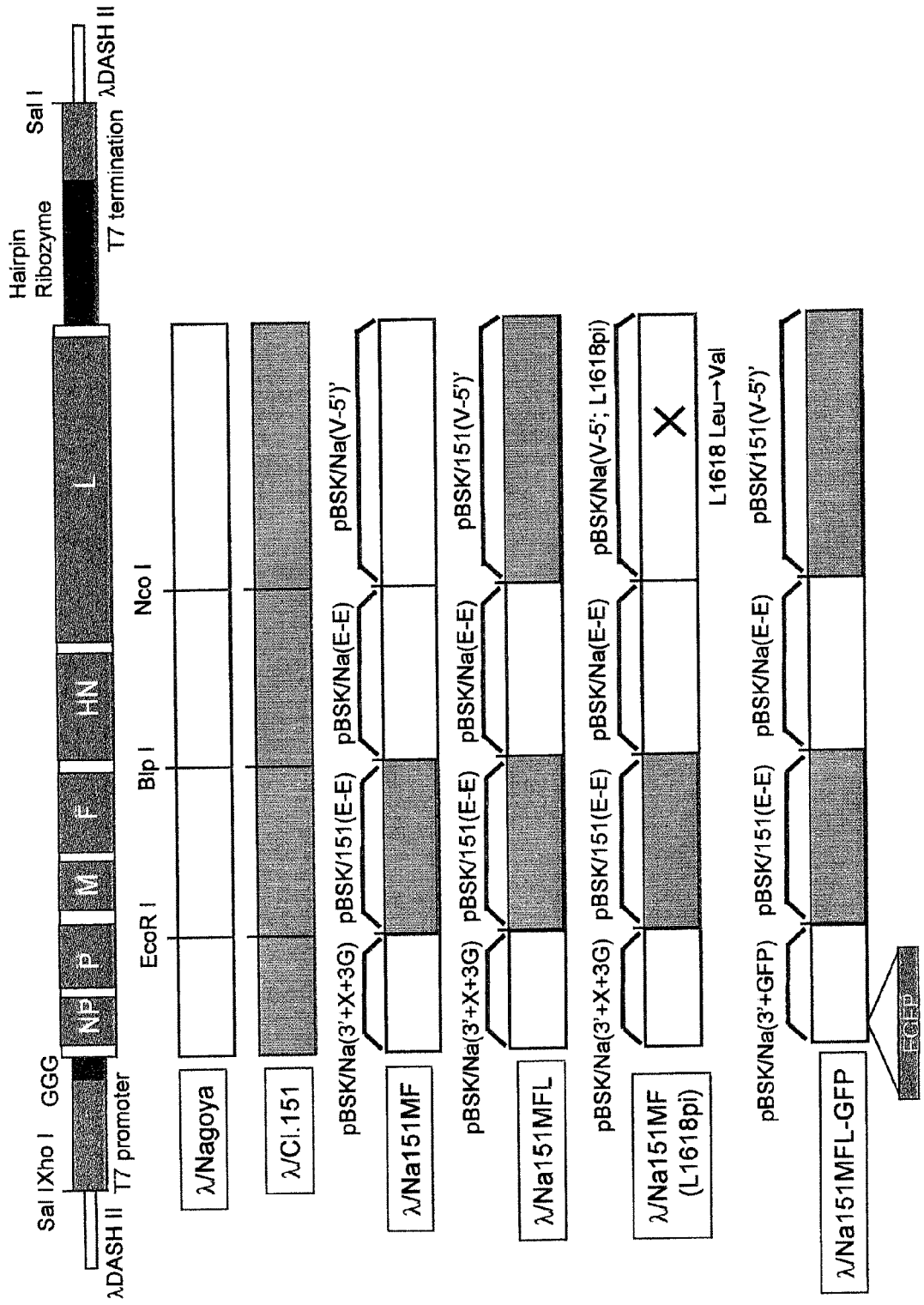

(51) Int. Cl.
  A61K 39/155    (2006.01)
  A01N 63/00     (2006.01)
  C12N 15/86     (2006.01)
  A61K 38/16     (2006.01)
  C12N 7/00      (2006.01)
  A61K 35/12     (2015.01)
  A61K 35/13     (2015.01)

(56) References Cited

U.S. PATENT DOCUMENTS

| | | |
|---|---|---|
| 7,144,579 B2 | 12/2006 | Nagai et al. |
| 7,442,544 B2 | 10/2008 | Nagai et al. |
| 2002/0098576 A1 | 7/2002 | Nagai et al. |
| 2002/0169306 A1 | 11/2002 | Kitazato et al. |
| 2003/0022376 A1 | 1/2003 | Kitazato et al. |
| 2003/0166252 A1 | 9/2003 | Kitazato et al. |
| 2003/0170266 A1 | 9/2003 | Kitazato et al. |
| 2004/0121308 A1 | 6/2004 | Nagai et al. |
| 2004/0137627 A1 | 7/2004 | Tokusumi et al. |
| 2005/0130123 A1 | 6/2005 | Inoue et al. |
| 2005/0266566 A1 | 12/2005 | Nagai et al. |
| 2007/0009949 A1 | 1/2007 | Kitazato et al. |
| 2010/0196993 A1 | 8/2010 | Nishimura et al. |

FOREIGN PATENT DOCUMENTS

| | | | |
|---|---|---|---|
| WO | WO 0132898 A2 | * | 5/2001 |
| WO | 2008-129971 A1 | | 10/2008 |

OTHER PUBLICATIONS

Kato et al. Initiation of *Sendai virus* multiplication from transfected cDNA or RNA with negative or positive sense. Genes to Cells 1996, vol. 1, p. 569-579.*

Fujii et al. Identification of Mutations Associated with Attenuation of Virulence of a Field *Sendai virus* Isolate by Egg Passage. Virus Genes 2002, vol. 25, No. 2, pp. 189-193.*

Inoue et al. Recombinant *Sendai virus* vectors deleted in both the matrix and the fusion genes: efficient gene transfer with preferable properties. The Journal of Gene Medicine 2004, vol. 6, pp. 1069-1081.*

Yoshizaki et al., "Naked *Sendai virus* vector lacking all of the envelope-related genes: reduced cytopathogenicity and immunogenicity," The Journal of Gene Medicine, 8: 1151-1159 (2006).*

Komatsu, et al., "C and V proteins of *Sendai virus* target signaling pathways leading to IRF-3 activation for the negative regulation of interferon-β production," Virology, 325:137-148 (2004).

Gotoh, et al., "Paramyxovirus Accessory Proteins as Interferon Antagonists," Microbiology and Immunology, 45(12):787-800 (2001).

Yoshida, et al., "Studies on the Role of M Protein in Virus Assembly Using a ts Mutant of HVJ (*Sendai virus*)," Virology, 92:139-154 (1979).

Jin, C. et al. "Recombinant *Sendai virus* provides a highly efficient gene transfer into human cord blood-derived hematopoietic stem cells", Gene Therapy 10, pp. 272-277 (2003).

Takahashi, K. et al. "Induction of Pluripotent Stem Cells from Mouse Embryonic and Adult Fibroblast Cultures by Defined Factors", Cell 126, pp. 663-676 (Aug. 25, 2006).

T. Wakayama, et al., "Differentiation of Embryonic Stem Cell Lines Generated from Adult Somatic Cells by Nuclear Transfer", Science, Apr. 27, 2001, pp. 740-743, vol. 292.

F. Ohbayashi et al., "Correction of Chromosomal Mutation and Random Integration in Embryonic Stem Cells with Helper-Dependent Adenoviral Vectors", Proceedings of the National Academy of Sciences, Sep. 20, 2005, pp. 13628-13633, vol. 102, No. 38.

E. Hurley, et al., "When Epstein-Barr Virus Persistently Infects B-Cell Lines, it Frequently Integrates", Journal of Virology, Mar. 1991, pp. 1245-1254.

S. Hacein-Bey-Abina, et al., "LMO2-Associated Clonal T cell Proliferation in Two Patients After Gene Therapy for SCID-X1", Science, Oct. 17, 2003 and Science, Erratum Post Date Oct. 24, 2003, vol. 302, pp. 415-419.

A. Harui, et al., "Frequency and Stability of Chromosomal Integration of Adenovirus Vectors", Journal of Virology, Jul. 1999, pp. 6141-6146.

* cited by examiner

FIG. 12

| SeV cDNA | cell | MVAGKT7 | HAU |
|---|---|---|---|
| Z [pSeV(+)] | BHK/T7 | - | >4096 |
| | BSR-T7-5 | - | 0 |
| | BSR-T7-5 | + | >4096 |

FIG. 14

|  | colony |
|---|---|
| r151-Bsr | 5 |
| r151(Mp+Bsr) | 50 |
| rNa151(Mp+Bsr) | 1200 |
| rNa151MFL(Mp+Bsr) | 3600 |

FIG. 18

| Vector carrier cell | | cDNA transfection | target cell | Bsr' colony |
|---|---|---|---|---|
| cell | SeV genome | | | |
| BHK/T7 | rNa151FL(ΔM+Bsr) | - | LLCMK₂ | 0 |
| | | pMKIT-151M | LLCMK₂ | >500 |

| Vector carrier cell | | cDNA transfection | target cell | Bsr' colony |
|---|---|---|---|---|
| cell | SeV genome | | | |
| LLCMK₂ | rNa151FL(ΔM+Bsr) | - | LLCMK₂ | 0 |

FIG. 23

| rSeV | target cell | positive(%) | | |
|---|---|---|---|---|
| | | 0d | 18d | 41d |
| rN FIG. 27
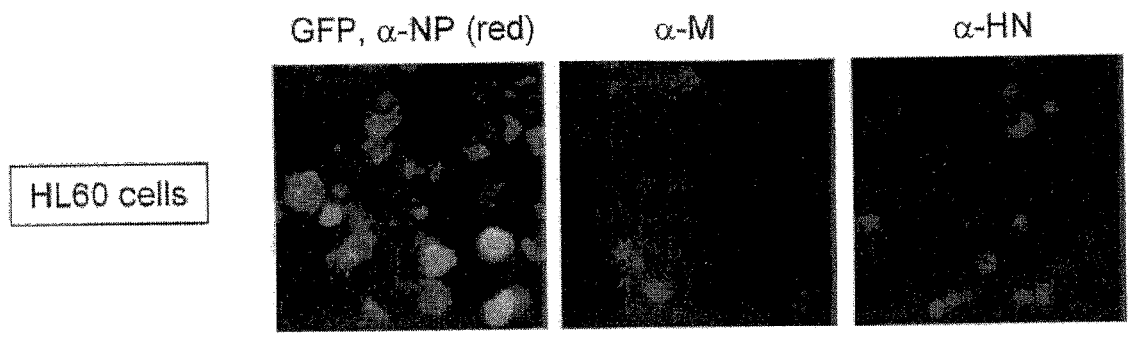
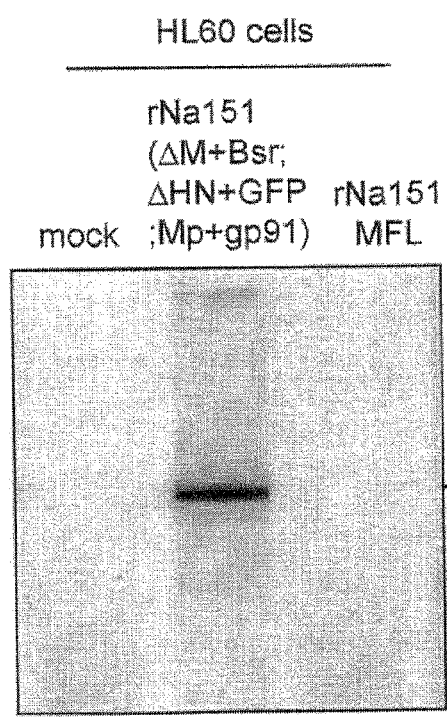

FIG. 30

| cell | vector carrier cell | | F protein vector | infection efficiency (%) | | | |
|---|---|---|---|---|---|---|---|
| | SeV genome | | | -trypsine | | +trypsine | |
| | | | | x 1 | | x 1 | x 20 concentrate |
| BHK/T7 | rNa151(ΔM+Bsr,ΔF+GFP) | | pMKIT-151F | n.d. | | 59.7 | 98.4 |
| | | | pSRD-ZFmut | 97.9 | | 100.0 | 100.0 |
| BHK/T7 | rNa151(ΔM+Bsr,ΔF+GFP,ΔHN+Cluc) | | pMKIT-151F | n.d. | | 1.9 | 4.4 |
| | | | pSRD-ZFmut | 63.8 | | 53.6 | 99.3 |

# PERSISTENTLY INFECTIVE *SENDAI VIRUS* VECTOR

CROSS-REFERENCE TO RELATED APPLICATIONS

This application is the national stage application pursuant to 35 U.S.C. §371 of PCT International Application No. PCT/JP2008/057212, filed Apr. 11, 2008, which claims priority to Japanese patent application no. 2007/105786, filed Apr. 13, 2007. The contents of these applications are incorporated herein by reference in their entirety.

SEQUENCE LISTING

The instant application contains a Sequence Listing which has been submitted via EFS-Web and is hereby incorporated by reference in its entirety. Said ASCII copy, created on Mar. 29, 2010, is named 84975709.txt and is 287,420 bytes in size.

TECHNICAL FIELD

The present invention relates to virus vectors which is useful for gene therapy among other purposes, stably expresses exogenous genes over a long period of time, or is furthermore non-transmissible and safe. The invention also relates to genetic material for assembling the vector.

BACKGROUND ART

In gene therapy for inherited metabolic disorder and other diseases, an introduced exogenous gene is expected to be continuously expressed over a long period of time. This objective has been achieved conventionally by incorporating genetic information into a chromosome of a host by means of a retrovirus vector. Safety is a concern, however, because there have been some clinical reports of cells turning cancerous under the influence of the integrated genes. A suggested approach to the problem is to develop a genetic information expression system which is able to exist stably and independently from chromosomes. The approach has been so far not successful.

Sendai virus is a negative-sense, single-stranded RNA virus of the paramyxovirus family. The virus is attracting attention for its characters as potential material for gene therapy vectors. The virus is not pathogenic for human beings. Transcription and replication of the virus take place inside the cytoplasm and does not affect genetic information of the host. Furthermore, the virus exhibits high gene expression activity and low species-specificity.

A process has been so far established which produces recombinant Sendai virus through transfection with an expression vector from which T7 RNA polymerase transcribes a complementary strand for the full length genome RNA of Sendai virus and an expression vector for each NP, P, and L gene related to the transcription and replication of Sendai virus in cultured cells in which T7 RNA polymerase is forcefully expressed using a vaccinia virus vector or a plasmid vector. This process is used to produce recombinant Sendai virus from a Sendai virus producing vector in which an exogenous gene is inserted. The process has been successfully applied to produce recombinant Sendai viruses from which one of the F, M, and HN Sendai virus genes is defected. Further applications are being studied to realize a protein production system by making these recombinant Sendai viruses express a desired protein.

Many research groups are exploring possible applications for gene therapy as a genetic information expression system that can exist independently from chromosomes by using recombinant Sendai viruses produced from these Sendai virus producing vectors. However, these Sendai virus vectors are based on the cytotoxic Z strain and have a gene defected from the viruses to reduce their cytotoxicity. The vector infected cells are killed in a single generation; safety is thus improved, but gene expression lasts no longer than a limited period.

In contrast, there are known strains of Sendai virus with various nature, one of which was reported in 1979 by Tetsuya YOSHIDA (currently, professor at the University of Hiroshima) and his colleagues. The strain (temperature-sensitive mutant strain C1.151) is sensitive to temperature, generating few virus particles at 38° C. At 32° C., replication cycle is activated, and the strain generates virus particles.

The inventors of the present invention have focused on the fact that Sendai virus temperature-sensitive mutant strain C1.151 generate few virus particles and causes persistent infection at 38° C. and cloned the full length genome cDNAs of strain C1.151 and its parent strain, or Nagoya strain, to assemble a Sendai virus vector from which a gene is expressed over a long period of time. The inventors have reconstituted a virus by combining various fragments cut out with restriction enzymes from full length gene (+) stranded cDNAs of the two strains, so as to investigate whether the combinations exhibit temperature sensitivity and persistent infectiveness. The investigation has discovered that persistent infectiveness requires more than one mutation among those mutations where, in the M gene and F gene of strain C1.151, amino acid residues at positions-69, -116, and -183 in an M protein form a glutamate (E), an alanine (A), and a serine (S) respectively and amino acid residues at positions-6, -115, and -137 in an F protein form an arginine (R), a leucine (L), and a threonine (T) respectively.

The inventors also inserted an exogenous gene expressing cassette into the full length genome cDNA to examine sustainability of resultant exogenous gene expression by recombinant Sendai virus. The expression in cultured cells was sustained for a short period due to the extinction of infected cells when the Sendai virus vector derived from the Z strain was used, whereas the expression was sustained for 4 months or even longer when the Sendai virus vector derived from strain C1.151 was used. Infecting a rat's colon, the Sendai virus vector derived from the Z strain sustained expression no longer than about 2 weeks. In contrast, the Sendai virus vector derived from strain C1.151 sustained expression at least 2 months in colon epithelial cells.

These findings have established the Sendai virus vector derived from strain C1.151 as a very useful vector capable of persistent expression of an introduced gene, including inside living bodies. Nevertheless, the mechanism of persistent infection is not well understood. In addition, it is hoped that the vector be modified, without losing its sustainability, so that it does not release infective particles and is non-transmissible, in order to improve safety of the vector.

Citation List
  Patent Literature 1
   WO97/16539
  Patent Literature 2
   WO00/70070
  Patent Literature 3
   Japanese Patent Application Publication, Tokukai, No. 2002-272465)

Patent Literature 4
Japanese Patent Application Publication, Tokukai, No. 2006-325531)
Patent Literature 5
Japanese Patent Application Publication, Tokukai, No. 2006-180780)
Non-Patent Literature 1
T. Yoshida et al. (1979) Virology 92, 139-154.

SUMMARY OF INVENTION

Technical Problem

Accordingly, the present invention has an objective of providing a novel virus vector which has no cytotoxicity, achieves sustained gene expression over a long period of time, is improved to be non-transmissible for better safety, and is extremely useful in gene therapy vector and other applications.

Solution to Problem

To achieve the objective, the inventors of the present invention, as a preparation for developing a new gene therapy vector, first explored a stably and persistently infective Sendai virus genome structure.

It has been known that mutations in the M and F proteins of strain Cl.151 are important for persistent infection. The inventors additionally confirmed, a few days after infection, cytotoxicity of a recombinant Sendai virus (rNa151MF) produced with a chimera cDNA which was composed of M and F proteins derived from strain Cl.151 and the rest derived from Nagoya strain. The observation indicated that it was also necessary to add other mutations derived from strain Cl.151. Accordingly, the inventors produced and analyzed new recombinant Sendai viruses from a chimera cDNA. The analysis showed that recombinant Sendai virus (rNa151MFL) produced from a cDNA which was composed of M, F, L proteins derived from Cl.151 and the rest derived from Nagoya strain exhibited stable persistent infection. It was thus found that mutations in the L protein was important to persistent infection as well as those on M and F proteins. The inventors also analyzed which of the two Cl.151-specific mutations in the L protein, from alanine to serine at position-1088 and from leucine to valine at position-1618, was related to persistent infection. The analysis established that persistent infection is achieved if the amino acid in the L protein at position-1618 is mutated in addition to the mutations in the M and F proteins.

To establish how the mutations in the L protein of strain Cl.151 are related to persistent infection, first, the inventors prepared a recombinant Sendai virus (rNa(L1618pi)) from a cDNA prepared from a Nagoya-strain full length cDNA by mutating only the amino acid in the L protein at position-1618 as derived from strain Cl.151, and investigated properties of the virus. The investigation established that the mutation of the amino acid in the L protein at position-1618 reduces the cytotoxicity of the Sendai virus and the expression induction of interferon. The investigation also indicated a possible cause of the reduction of interferon expression induction: a decrease in the copy number of an antigenome RNA. Specifically, it was suggested that a decrease in the copy number of an RNA transcripted starting from the 3' terminus of a genome RNA and read through to after the leader RNA was related. A recombinant Sendai virus (r(+E)Na) modified so as to decrease the expression of the virus-derived interferon inducing RNA indeed exhibited reduced interferon inducibility.

These results established that decreasing interferon expression induction is important to persistent infectiveness of the virus and that expression induction is decreased by mutating an amino acid of the L protein at position-1618.

Next, to efficiently produce recombinant Sendai viruses, the inventors attempted to establish a cell strain constitutively expressing T7 RNA polymerase. A cell strain was separated which constitutively expressed a T7 RNA polymerase (human-type T7 RNA polymerase) of which the base sequence was modified, without changing the amino acid sequence, to use humanized codons. The cell strain (BHK/T7 cells) expressed the T7 RNA polymerase in markedly greater quantities than the previous cell strain (BSR-T7-5 cells) expressed a conventional bacteria-type T7 RNA polymerase. In addition, the BHK/T7 cells could produce recombinant Sendai virus more efficiently than the BSR-T7-5 cells. Thus, the inventors established a method to efficiently produce a recombinant Sendai virus using BHK/T7 cells without using a cytotoxic T7-RNA-polymerase expressing vaccinia virus, and subsequently used BHK/T7 cells for the vector production.

Transfecting the BHK/T7 cells with a persistently infective Sendai virus producing vector containing an inserted blasticidin-resistant gene expressing cassette, as well as with NP, P, and L protein expression vectors, enabled selection of recombinant Sendai virus producing cells owing to blasticidin. Based on this finding, a new method for producing a recombinant Sendai virus was successfully established in which a persistently infective virus vector was isolated using a drug-resistant gene. By placing a drug-resistant gene on a vector as above, it becomes possible to obtain vector-introduced cells in sufficient quantity through selective growth of the cells in which the vector is introduced even when the vector titer is low. The inventors also established that a recombinant Sendai virus is produced most efficiently if rNa151MFL is used as a scaffold in the process.

Next, the inventors attempted to produce a recombinant virus which was rendered non-transmissible by defecting a virus gene in a full length cDNA using the recombinant Sendai virus production system. As a result, an M-defected recombinant Sendai virus was successfully produced from a persistently infective Sendai virus producing vector in which an M gene was defected using M protein expressing BHK/T7 cells. F gene-defected and HN gene-defected recombinant Sendai viruses were successfully produced by similar methods. The recombinant Sendai viruses showed persistent infection, which indicated that each of M, F, and HN proteins may be defected without losing persistent infectivity. The inventors also established that the cells produced under the influence of these gene-defected Sendai viruses do not release infective particles (non-transmissible) unless the defected gene is supplemented.

Recombinant Sendai viruses in which two or all three of the M, F, and HN genes were defected were also successfully produced by similar methods. Infected cells were investigated for omission from them of the genome of the numerous gene-defected recombinant Sendai viruses. The investigation established that the persistent infectiveness is basically preserved even if these genes were defected, except in a few structures. The inventors thus concluded that it is possible to produce non-transmissible, persistently infective Sendai virus vectors from a cDNA encoding only the NP, P, and L proteins which are presumably essential and sufficient to replicate the Sendai virus genome. In addition, quantifying virus particles released by the cells infected with the non-transmissible, persistently infective Sendai virus vectors revealed that the release of virus particles was almost completely suppressed by defecting the three genes, which confirmed that the vectors in which the three genes are defected are safer.

An α-galactosidase A gene expressing cassette was inserted into a non-transmissible, persistently infective Sendai virus vector. The α-galactosidase A gene is a cause of Fabry's disease which is a type of lysosomal disease and used, for example, in protein substitution therapy. Quantification of the α-galactosidase A protein generated by cells infected with the vector revealed that the protein was obtained more simply and conveniently and in equivalent or greater quantities by using the non-transmissible, persistently infective Sendai virus vector than by conventional methods. Furthermore, a non-transmissible, persistently infective Sendai virus vector was produced in which a gp91phox expressing cassette was inserted. gp91phox is a gene used in the treatment of chronic granulomatous disease (CGD). By using that vector, gp91phox was successfully expressed persistently. Furthermore, hematopoietic stem cells separated from mice or humans were infected with a non-transmissible, persistently infective Sendai virus vector and cultured in vitro. It was confirmed that the vector sustained persistent infection at least 2 weeks in mice and as long as 7 weeks or even longer in humans. The inventors have found, from these results, that the vector is applicable in the medical and other fields as a highly safe, stable, high exogenous gene expression vector, which has led to the completion of the invention.

The present invention may be described as follows:
(1) A genetic material characterized in that it encodes at least part of L protein of a Sendai virus for use in attenuation of cytotoxicity of a persistently non-infective Sendai virus or an analogous virus thereof, the material encoding at least a protein with an amino acid sequence including a valine substituted for an amino acid residue at position-1618 in the L protein.
(2) The genetic material as set forth in (1), wherein the cytotoxicity is attenuated by restraining interferon expression induction by the persistently non-infective Sendai virus or the analogous virus thereof.
(3) The genetic material as set forth in (1), wherein the cytotoxicity is attenuated by reducing a copy number of an RNA transcripted starting from a 3' terminus of a genome RNA of the persistently non-infective Sendai virus or the analogous virus thereof.
(4) A genetic material for use in restraining interferon expression induction, characterized by a transcription termination sequence being added to a 3' terminus of a leader RNA sequence of a Sendai virus or an analogous virus thereof.
(5) A genetic material for use in imparting persistent infectiveness to a persistently non-infective Sendai virus or an analogous virus thereof, the material being characterized in that it includes:
the genetic material as set forth in (1); and
a gene encoding a protein with at least amino acid mutations 1) to 6):
1) 69E, 2) 116A, 3) 183S, 4) 6R, 5) 115L, 6) 137T,
where numerals in 1) to 3) are position numbers in an amino acid sequence of M protein of the Sendai virus, numerals in 4) to 6) are position numbers in an amino acid sequence of F protein of the Sendai virus, and alphabetic letters in 1) to 6) indicate amino acid residues mutated at those positions.
(6) The genetic material as set forth in (5) characterized by the material further including a genetic material containing a transcription termination sequence added to a 3' terminus of a leader RNA sequence of the Sendai virus or the analogous virus thereof.
(7) The genetic material as set forth in any one of (1) to (6), characterized by being composed of a positive-sense stranded cDNA.
(8) A persistently non-infective Sendai virus gene, characterized by being modified to encode a protein including a valine substituted for an amino acid residue at position-1618 in L protein.
(9) The Sendai virus gene as set forth in (8), characterized by being further modified to encode a protein with at least amino acid mutations below:
1) 69E, 2) 116A, 3) 183S, 4) 6R, 5) 115L, 6) 137T,
where numerals in 1) to 3) are position numbers in an amino acid sequence of M protein of the Sendai virus, numerals in 4) to 6) are position numbers in an amino acid sequence of F protein of the Sendai virus, and alphabetic letters in 1) to 6) indicate amino acid residues mutated at those positions.
(10) The Sendai virus gene as set forth in either one of (8) and (9), characterized in that a transcription termination sequence is added to a 3' terminus of a leader RNA sequence of a Sendai virus or an analogous virus thereof.
(11) The Sendai virus gene as set forth in either one of (8) and (9), characterized in that at least any one of M, F, and HN genes is defected.
(12) The Sendai virus gene as set forth in (11), wherein at least any one of M, F, and HN genes is defected by inserting a marker gene to the gene(s).
(13) A Sendai virus gene, characterized by including:
a mutated L gene modified to encode a protein including a valine substituted for an amino acid residue at position-1618 in L protein of a persistently non-infective Sendai virus;
an NP gene; and
a P gene.
(14) The Sendai virus gene as set forth in any one of (11) to (13), characterized in that a transcription termination sequence is added to a 3' terminus of a leader RNA sequence of a Sendai virus or an analogous virus thereof.
(15) The Sendai virus gene as set forth in any one of (8) to (14), characterized by being composed of a positive-sense stranded cDNA.
(16) A persistently infective, recombinant virus producing genetic material, characterized by including the Sendai virus gene cDNA as set forth in any one of (8) to (10).
(17) A non-transmissible, persistently infective virus producing genetic material, characterized by including the Sendai virus gene cDNA as set forth in any one of (11) to (14).
(18) A persistently infective, recombinant virus producing vector, characterized by including introduced thereto the recombinant virus producing genetic material as set forth in (17).
(19) A non-transmissible, persistently infective, recombinant virus producing vector, characterized by including introduced thereto the recombinant virus producing genetic material as set forth in (18).
(20) The persistently infective, recombinant virus producing vector as set forth in (18), characterized by further including an exogenous gene DNA introduced thereto.
(21) The recombinant virus producing vector as set forth in (20), wherein the exogenous gene encodes a bioactive peptide or a protein.
(22) The non-transmissible, persistently infective, recombinant virus producing vector as set forth in (19), characterized by further including an exogenous gene DNA introduced thereto.

(23) The non-transmissible, persistently infective, recombinant virus producing vector as set forth in (22), characterized in that:
at least any one of M, F, and HN genes is defected; and
the exogenous gene is inserted in at least any one of the M, F, and HN genes.
(24) The recombinant virus producing vector as set forth in either one of (22) and (23), wherein the exogenous gene encodes a bioactive peptide or a protein.
(25) A cell, characterized by including introduced thereto the recombinant virus producing vector as set forth in either one of (20) and (21).
(26) A cell, characterized by including introduced thereto the recombinant virus producing vector as set forth in any one of (22) to (24).
(27) A cell, including introduced thereto a plurality of the recombinant virus producing vector as set forth in any one of (20) to (24), characterized in that:
each vector carries a different exogenous gene; and
the plural exogenous genes are simultaneously expressed.
(28) A cell, characterized by including introduced thereto the recombinant virus producing vector as set forth in any one of (20) to (24) and another recombinant vector containing a gene lacking to form a virus particle.
(29) The cell as set forth in (28), characterized in that:
the gene lacking to form a virus particle is F gene; and
the F gene is modified at positions-112 to 116 in F protein so as to form a base sequence encoding an amino acid sequence of arginine-arginine-X-lysine or arginine-arginine, where X in the amino acid sequence is any appropriate amino acid residue.
(30) The cell as set forth in any one of (25) to (29), characterized by further including introduced thereto a T7 RNA polymerase gene modified to constitute humanized codons.
(31) A Sendai virus RNP complex reconstituted in the cell as set forth in (26).
(32) A method of manufacturing an exogenous gene product, characterized by including the step of culturing the cell as set forth in any one of (25) to (29) in a medium.
(33) A method of manufacturing a Sendai virus particle containing an exogenous gene, characterized by including the step of culturing the cell as set forth in any one of (25) to (29) in a medium.
(34) A Sendai virus particle containing an exogenous gene, the particle being obtained by culturing the cell as set forth in any one of (25) to (29) in a medium.
(35) A virus particle, characterized by being modified in L gene of a full length gene of a persistently non-infective Sendai virus so as to encode a protein including a valine substituted for an amino acid residue at position-1618 in L protein.
(36) A virus particle, characterized by being modified in L gene of a full length gene of a persistently non-infective Sendai virus so as to encode a protein including a valine substituted for an amino acid residue at position-1618 in L protein and modified in M and F genes so as to encode an amino acid sequence with mutations 1) to 6):
1) 69E, 2) 116A, 3) 183S, 4) 6R, 5) 115L, 6) 137T,
where numerals in 1) to 3) are position numbers in an amino acid sequence of M protein of the Sendai virus, numerals in 4) to 6) are position numbers in an amino acid sequence of F protein of the Sendai virus, and alphabetic letters in 1) to 6) indicate amino acid residues mutated at those positions.
(37) A virus particle, characterized by including as a genome a full length gene of a persistently non-infective Sendai virus, the gene including L gene modified to encode a protein including a valine substituted for an amino acid residue at position-1618 in L protein and at least any one of M, F, and HN genes defected,
wherein
at least any one of M, F, and HN proteins lacking to form the particle is supplemented by a gene expression system other than the genome.
(38) A virus particle, characterized by including at least a mutated L gene, an NP gene, and a P gene as a genome, the mutated L gene being modified to encode a protein including a valine substituted for an amino acid residue at position-1618 in L protein of a persistently non-infective Sendai virus, the particle not containing one or more of M, F, and HN genes as a genome,
wherein
at least any one of M, F, and HN proteins lacking to form the particle is supplemented by a gene expression system other than the genome.
(39) The virus particle as set forth in either one of (37) and (38), characterized in that:
the protein(s) lacking to form the particle is/are at least F protein; and
an amino acid sequence at positions-112 to 116 in the F protein is modified to form a sequence of arginine-arginine-X-lysine or arginine-arginine, where X in the amino acid sequence is any appropriate amino acid residue.
(40) The virus particle as set forth in any one of (34) to (39), characterized in that a transcription termination sequence is added to a 3' terminus of a leader RNA sequence of a Sendai virus or an analogous virus thereof.
(41) A recombinant virus, characterized by including an exogenous gene being introduced to the particle as set forth in any one of (34) to (40).
(42) A gene therapy drug, characterized by including the recombinant virus as set forth in (41) as an active agent.

Advantageous Effects of Invention

The present invention provides a non-transmissible, recombinant Sendai virus vector persistently expressing an exogenous gene. That in turn achieves a high-safety genetic information expression system which can exist independently from chromosomes, which was impossible with conventional gene therapy vectors. The vector is useful in introducing gene therapy drugs. In addition, the techniques used to produce the recombinant virus vector of the present invention is applicable to various virus vectors by changing the gene sequence in a marker gene (e.g. a drug-resistant gene) or vector viral genes. Furthermore, the persistent infection-related mutation (the mutation of the amino acid at position-1618 in L protein) described in the present invention provides a potentially useful genetic material because presumably by introducing and substituting the recombinant Sendai virus vector for another recombinant vector or virus that is not persistently infective, the latter's cytotoxicity is attenuated and its expression becomes sustainable.

BRIEF DESCRIPTION OF DRAWINGS

FIG. 1

A drawing of the structure of a recombinant Sendai virus producing vector produced in accordance with the present invention (λ/Na151MF, λ/Na151MFL, λ/Na151MF (L1618pi), λ/Na151MFL-GFP).

FIG. 2

A drawing showing the shape of CV-1 cells and LLCMK$_2$ cells and images of those cells stained with an antibody against NP protein, all the cells being infected with a recombinant Sendai virus (M.O.I.=100).

FIG. 3

Fluorescent microscopy photographs showing changes in EGFP gene and NP protein expression over time for LLCMK$_2$ cells infected with an EGFP gene expressing recombinant Sendai virus.

FIG. 4

A drawing showing the shape of LLCMK$_2$ cells and images of those cells stained with an antibody against NP protein, the cells being infected with a recombinant Sendai virus (M.O.I.=50).

FIG. 5

A drawing of the structure of a recombinant Sendai virus producing vector produced in accordance with the present invention (λ/Na151L, λ/Na(L1618pi)).

FIG. 6

A drawing of cytotoxicity of LLCMK$_2$ cells infected with an L-protein-mutated recombinant Sendai virus (M.O.I.=5, except for C1.151 for which M.O.I.=100).

FIG. 7

A drawing showing a comparison of induction efficiency luciferase activity which corresponds to interferon expression induction for a cloned interferon induction activity measurement cell strain (LLCMK$_2$/pIV3) infected with a Sendai virus (Z strain).

FIG. 8

A drawing showing changes over time in interferon induction activity of LLCMK$_2$/pIV3#16 cells infected with an L-protein-mutated recombinant Sendai virus.

FIG. 9

A drawing showing changes over time in the copy numbers of NP mRNA, antigenome RNA, and genome RNA for an L-protein-mutated recombinant Sendai virus as quantified with S1 nuclease assays. The structure of each RNA is shown at the top.

FIG. 10

A drawing showing results of quantification of virus-derived RNA and the interferon induction activity for infection with a recombinant Sendai virus in which a transcription termination sequence is inserted at the 3' terminus of the leader RNA.

FIG. 11

A drawing showing the quantity of the expressed T7 RNA polymerase for a cell strain constitutively expressing T7 RNA polymerase. Relative band densities are shown below a photograph.

FIG. 12

A drawing showing virus titer obtained for a recombinant Sendai virus produced using T7 RNA polymerase expressing cells.

FIG. 13

A drawing of the structure of a recombinant Sendai virus producing vector produced in accordance with the present invention (λ/151-Bsr, λ/151(Mp+Bsr), λ/Na151(Mp+Bsr), λ/Na151MFL(Mp+Bsr)).

FIG. 14

A drawing showing the number of colonies of blastcidin-resistant recombinant Sendai virus producing cells for recombinant Sendai viruses produced using BHK/T7 cells.

FIG. 15

A drawing the structure of a recombinant Sendai virus producing vector produced in accordance with the present invention (λ/Na151FL(ΔM+Bsr), λ/Na151(ΔF+Bsr), λ/Na151(ΔHN+Bsr)).

FIG. 16

A drawing illustrating a method of producing a defective recombinant Sendai virus by using a blastcidin-resistant gene developed in accordance with the present invention.

FIG. 17

A drawing showing fluorescent microscopy photographs of cells stained with an antibody against Sendai virus protein to verify gene defection in each M, F, and HN gene-defected recombinant Sendai virus and persistence of infection.

FIG. 18

A drawing showing the titer of an infective recombinant Sendai virus released in a culture supernatant of defective recombinant Sendai virus producing cells in terms of the number of colonies of blastcidin-resistant recombinant Sendai virus introduced cells, for an M gene-defected recombinant Sendai virus with or without supplementing the defected gene.

FIG. 19

A drawing of fluorescent microscopy photographs verifying M gene defection and EGFP gene expression for an M gene-defected EGFP gene expression non-transmissible Sendai virus vector.

FIG. 20

A drawing of the structure of a recombinant Sendai virus producing vector produced in accordance with the present invention (λ/Na151(ΔM+Bsr;ΔF+GFP), λ/Na151(ΔF+GFP;ΔHN+Bsr), λ/Na151(ΔM+Bsr;ΔHN+GFP)).

FIG. 21

A drawing of the structure of a recombinant Sendai virus producing vector produced in accordance with the present invention (λ/Na151FL(ΔM+Bsr;Mp+GFP), λ/Na151FL(ΔM+Bsr;Mp+GFP;Mp+gp91), λ/Na151(ΔM+Bsr;ΔF+GFP;ΔHN+Cluc)).

FIG. 22

A drawing showing fluorescent microscopy photographs of cells stained with an antibody against proteins to verify gene defection in a recombinant Sendai virus in which two or more of the M, F, and HN genes are defected.

FIG. 23

A drawing showing infection sustainability of LLCMK$_2$ cells, CV-1 cells, and HL60 cells infected with a gene-defected recombinant Sendai virus produced in accordance with the present invention, cultured in a medium to which no blastcidin is added.

FIG. 24

A drawing showing results of quantification of virus-like particles released from vector producing cells cultured at 32° C., for a non-transmissible, persistently infective Sendai virus vector produced in accordance with the present invention.

FIG. 25

A drawing of the structure of a recombinant Sendai virus producing vector produced in accordance with the present invention (λ/151(NPp+α-gal;ΔM+Bsr;ΔFp+GFP), λ/Na151(ΔM+Bsr;ΔF+GFP;ΔHN+gp91), λ/Na151(ΔM+Zeo;ΔF+hKO;ΔHN+Cluc)).

FIG. 26

A drawing showing results of quantification of the α-galactosidase A protein produced by BHK cells infected with a α-galactosidase A expressing, non-transmissible, persistently infective Sendai virus vector.

FIG. 27

A drawing showing fluorescent microscopy photographs verifying M and HN gene defection and EGFP gene expression and results of Northern hybridization verifying gp91phox mRNA expression for a gp91phox expressing, non-transmissible, persistently infective Sendai virus vector.

FIG. 28

A drawing showing fluorescent microscopy photographs verifying colony formation and EGFP gene expression by murine and human hematopoietic stem cells infected with a non-transmissible, persistently infective Sendai virus vector.

FIG. 29

A drawing showing fluorescent microscopy photographs verifying EGFP gene and hKO gene expression and also showing Cluc protein and gp91phox protein expression, for simultaneous infection with two types of non-transmissible, persistently infective Sendai virus vectors.

FIG. 30

A drawing showing the titer of an infective recombinant Sendai virus released in a culture supernatant of recombinant Sendai virus producing cells in terms of an infect rate of target cells for an M and F gene- or M, F, and HN gene-defected recombinant Sendai virus.

DESCRIPTION OF EMBODIMENTS

The present invention relates to: genetic materials for modifying persistently non-infective Sendai viruses or analogous viruses thereof so that they have no cytotoxicity or persistent infectiveness; genetic materials which, obtained using the genes, are used for production of persistently infective or furthermore non-transmissible recombinant viruses; recombinant virus producing vectors obtained by introducing an exogenous gene to the genetic material; virus particles containing an exogenous gene; and gene therapy drugs containing the virus particles as an active agent, to name several examples. Throughout the specification, the "gene" and "genetic material" include negative-sense stranded RNAs and cDNAs and complementary positive-sense stranded RNA and cDNAs. In other words, The present invention encompasses anything from or based on which any one of these genes or genetic materials can be synthesized by transcription or reverse-transcription. Examples of the persistently non-infective Sendai viruses include Nagoya strains, Z strains, and Hamamatsu strains of Sendai virus. Examples of the analogous viruses thereof include measles viruses.

Sendai virus, composed of NP, P/C/V, M, F, HN, and L genes, is an RNA virus with a full length, negative-sense, single-stranded genome RNA of about 15 kb. The genes encode NP, P/C/V, M, F, HN, and L proteins respectively.

Different strains of Sendai virus with various properties are known. The temperature-sensitive types of strains, especially, Sendai virus strain C1.151, generate few virus particles at 38° C. and generate virus particles at 32° C. due to the activation of duplication cycle. Therefore, the strains exhibit almost no cytotoxicity at body temperature of mammals including the human.

The base sequences of the genome RNA of strain C1.151 and the corresponding full length gene (+) stranded cDNA, and the amino acid sequences of the NP to L proteins encoded by the cDNA are shown in SEQ ID NOs 1 and 2. The base sequences of the genome RNA of Nagoya strain (their parent strain) and the corresponding full length gene (+) stranded cDNA, and the amino acid sequences of the NP to L proteins encoded by the cDNA are shown in SEQ ID NOs 3 to 10. SEQ ID NOs 5 to 11 are presented so that the amino acid sequences of the proteins of Nagoya strain starts from 1.

Fragments were cut out with restriction enzymes from the full length gene (+) stranded cDNAs of strain C1.151 and its parent strain (i.e. Nagoya strain). The fragments were then combined in various combinations to reconstitute viruses. The viruses were examined for persistent infectiveness to identify the gene in which the persistent-infection-causing mutation of strain C1.151 occurred. Results are presented in FIG. 2, which show that the recombinant viruses containing M, F, and L proteins derived from strain C1.151 exhibited persistent infection with the least cytotoxicity.

Figure 4:
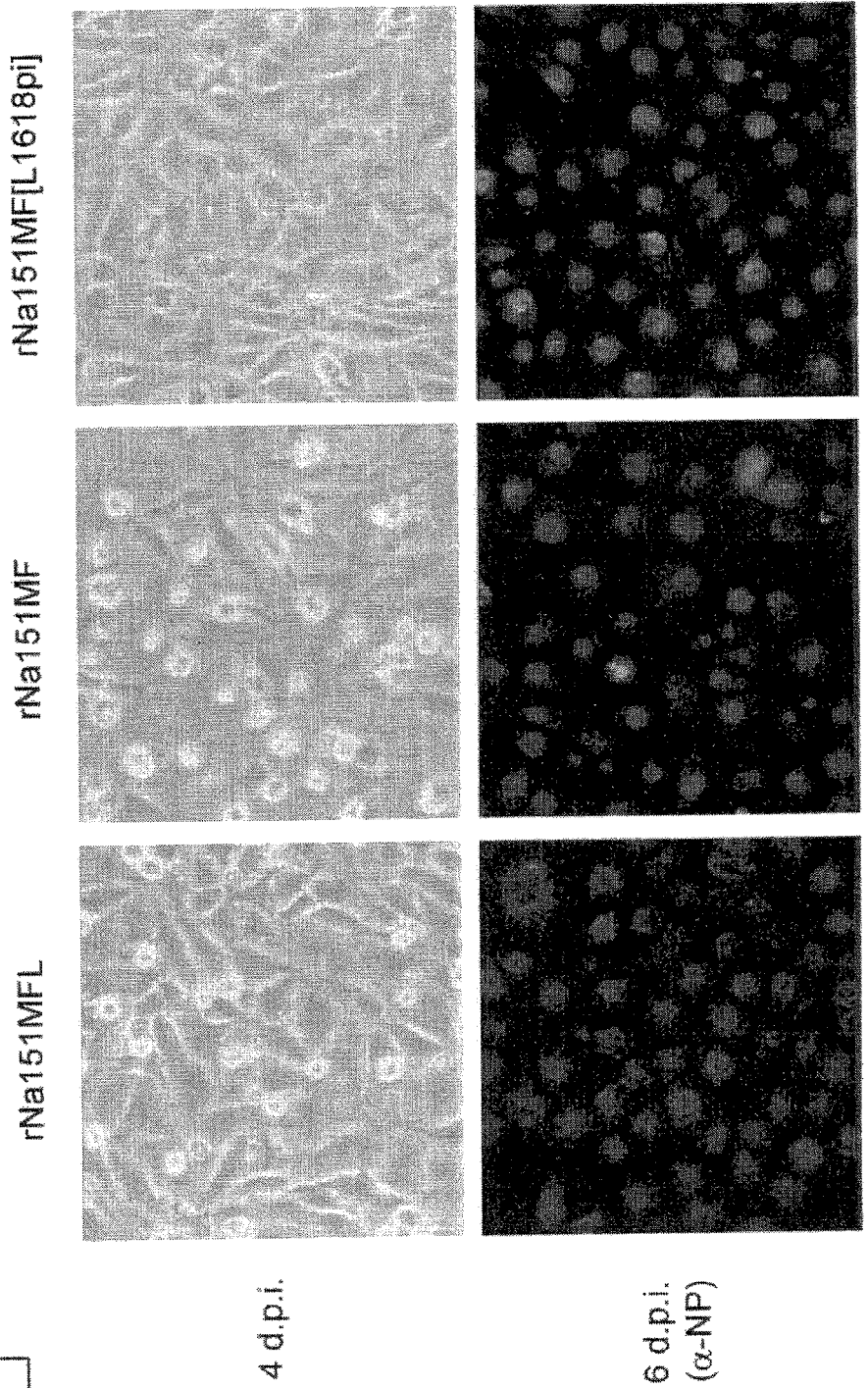
Figure 9:
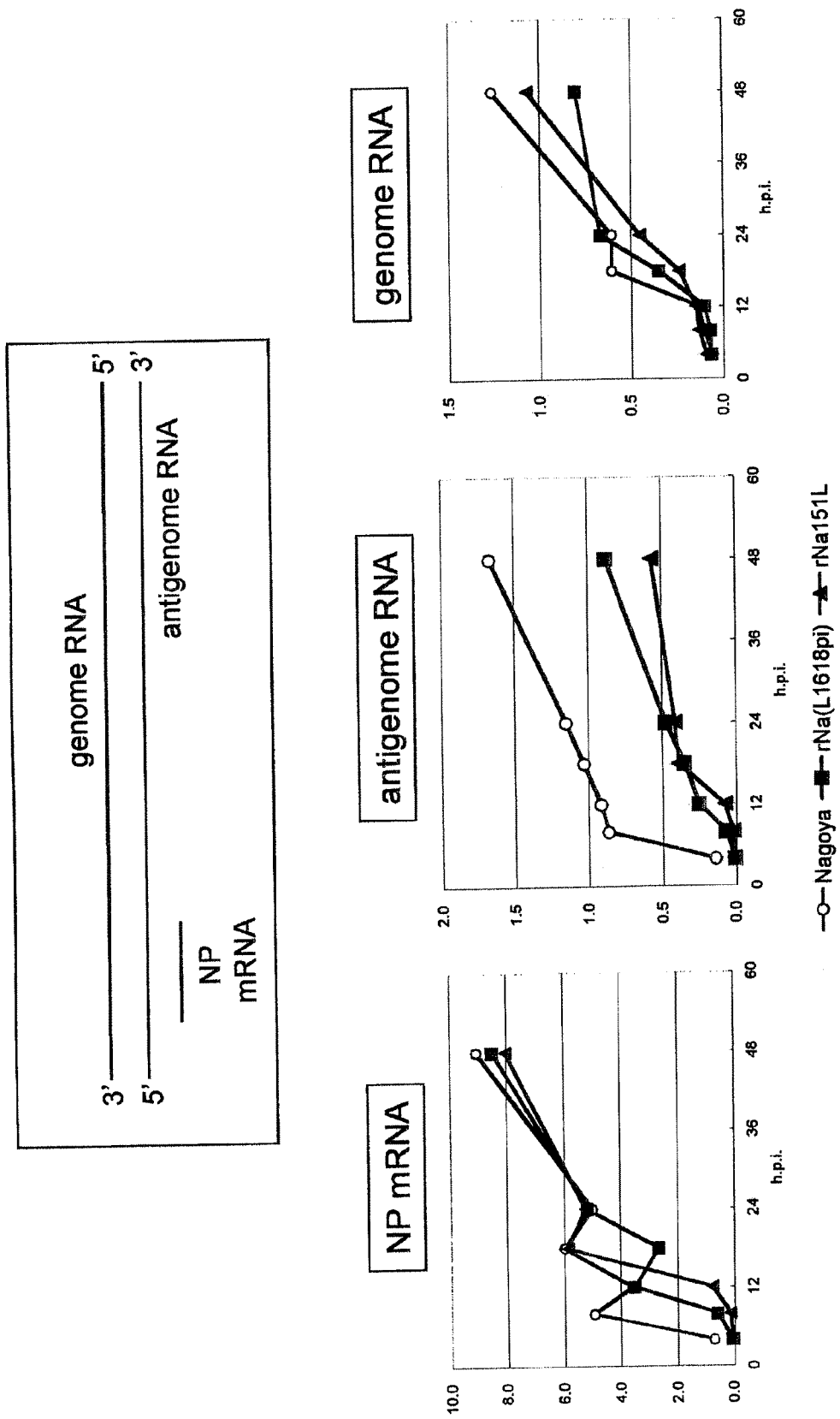
Figure 10:
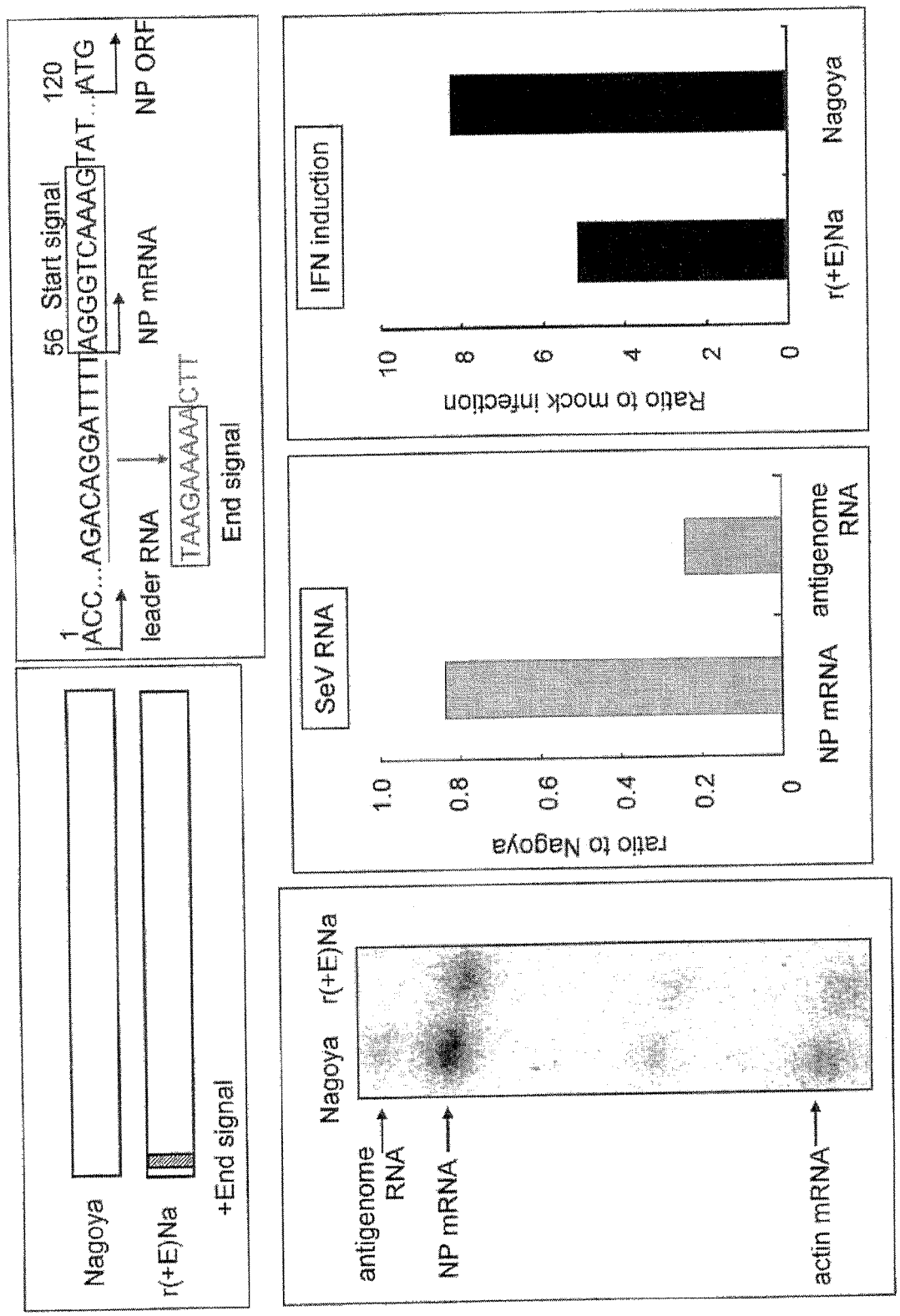

Of the strain C1.151-derived mutations in the L protein, the leucine-to-valine mutation at position-1618 seemed to be important to persistent infection (FIG. 4). The recombinant Sendai virus having that mutation had cytotoxicity (FIG. 6) and interferon inducibility (FIG. 8) greatly attenuated. A probable cause was reduction in the copy number of the antigenome RNA of the virus (FIG. 9). The observation indicated that to produce a recombinant Sendai virus vector capable of stable persistent infection, it was important to introduce the mutations in the L protein to a vector cDNA, introduce a mutation causing attenuation of interferon inducibility, or introduce a mutation causing attenuation of the copy number the RNA generated by virus infection. A recombinant Sendai virus into which a transcription termination sequence of Sendai virus was artificially inserted at the 3' terminus of the leader RNA was actually produced to restrain the transcription of the virus antigenome RNA. In the recombinant Sendai virus, the transcription of the antigenome RNA decreased, and the interferon inducibility decreased (FIG. 10).

A first genetic material according to the present invention contains a gene including a valine substituted for the amino acid residue at position-1618 in L protein (hereinafter, may be called a "mutated L gene"). The gene, when substituted for the corresponding part of the full length gene of a persistently non-infective Sendai virus or an analogous virus thereof, attenuates the cytotoxicity of the persistently non-infective Sendai virus or the analogous virus. The mutant gene provides a useful genetic material for production of non-cytotoxic, persistently infective Sendai viruses.

Examples of the mutated L gene include base sequences composed of an L protein encoding region containing the mutation and those containing the encoding region. The gene however does not necessarily contain the entire sequence corresponding to the encoding region; the gene only needs to include at least a valine-substituted region.

In addition, the inventors of the present invention, in Japanese Patent Application Publication, Tokukai, No. 2006-180780, made earlier clarification about the gene obtained by mutating the M and F genes of Sendai virus (hereinafter, may be called "mutated M and F genes") to impart persistent infectiveness. The genetic material in combination with the mutated L gene, when substituted for the corresponding part of the full length gene of a persistently non-infective Sendai virus or an analogous virus thereof, modifies the persistently non-infective Sendai virus or the analogous virus for enhanced persistent infectiveness.

The mutated M and F genes encodes an amino acid sequence with at least mutation sites 1) to 6) below for the M and F proteins of Sendai virus:

1) 69E, 2) 116A, 3) 183S, 4) 6R, 5) 115L, 6) 137T, where numerals in 1) to 3) are position numbers in the amino acid sequence of M protein of Sendai virus, numerals in 4) to 6) are position numbers in the amino acid sequence of F protein of Sendai virus, and alphabetic letters in 1) to 6) indicate amino acid residues mutated at those positions.

Examples of the mutant genes include RNAs and cDNAs having a base sequence from position-3874 to position-5274 in the full length gene of the (+) strand of Sendai virus strain C1.151 and complementary RNAs and DNAs. Other examples of the mutant gene may include M and F genes of persistently non-infective Sendai virus in which substitution has been made to encode proteins with mutations 1) to 6). The mutant gene also does not necessarily contain the entire encoding region from M protein to F protein; the gene only needs to encode a region containing at least mutation sites 1) to 6). Logically, the mutated M and F genes may be composed of an encoding region for M protein through F protein with mutations 1) to 6) or may have a base sequence containing these encoding regions.

A second genetic material according to the present invention is a material containing a mutated L gene substituted for the L gene of the full length gene of a persistently non-infective Sendai virus and at least any one of M, F, and HN genes of the persistently non-infective Sendai virus defected. The genetic material enables imparting non-transmissibility, as well as persistent infectiveness, to the virus.

The defect in the M, F, and HN genes can be made, for example, by inserting a marker gene (e.g. drug-resistant gene) to these genes. By so doing, the target cells to which a Sendai virus containing these defected genes has been introduced as a vector can be readily screened in a selection medium containing corresponding drugs, for example.

The defect in the genes is not necessarily made by inserting a marker gene. Alternatively, another gene or simply a DNA fragment may be inserted to achieve the same result. An exogenous gene may be inserted which is to be expressed inside a living body or cells. The gene defection technique by way of exogenous gene insertion provides an extremely efficient means of defecting a target gene. A further alternative is, for example, to defect one of M, F, and HN genes by means of marker gene insertion and to defect the others by means of exogenous gene insertion.

If M gene or F gene is not selected as a defected gene for the defect-containing Sendai virus genetic material, the remaining M or F gene is preferably the mutated M or F gene. Furthermore, non-transmissibility may be imparted according to the present invention, not only by way of the marker gene insertion and consequent M, F, or HN gene defection, but also by deleting these genes so that the material is composed only of NP gene, P gene, and a mutated L gene of Sendai virus.

The Sendai virus gene whose M, F, or HN gene is defected or deleted in its full length cannot by itself form infective, complete virus particles in a cell at virus particle producing temperature for strain C1.151, i.e. 32° C. The gene can only form an RNP complex (nucleocapsid) at that temperature. The virus is thus completely non-transmissible and highly safe. Also, the virus contains a mutated L gene and is non-cytotoxic and persistently infective.

The first and second genetic materials of the present invention are inserted to a phage DNA or like cloning vector to provide a recombinant Sendai virus producing vector. An exogenous gene is introduced to the recombinant Sendai virus producing vector. The obtained recombinant Sendai virus producing vector is used to transform cells. The transformed cells form Sendai virus particles at 32° C. if the recombinant Sendai virus producing vector used contains the first genetic material. If the recombinant Sendai virus producing vector contains the second genetic material, however, the transformed cells do not form infective virus particles (non-transmissible) at 32° C. in the cells as mentioned above. Therefore, the protein derived from the introduced exogenous gene can be more safely manufactured in vitro by culturing the transformed cells in a medium.

Figure 17:
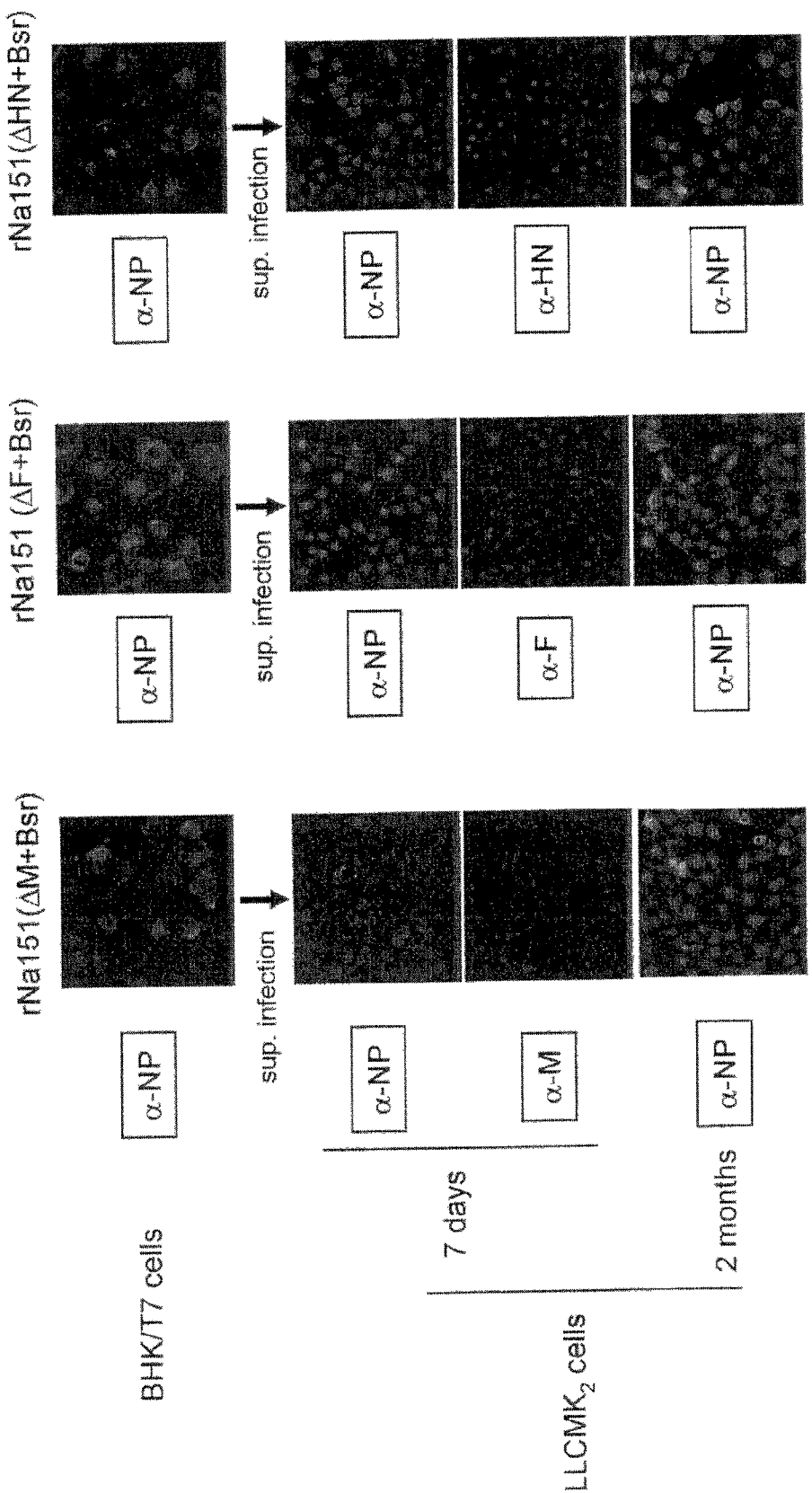

The transformed cells are cultured in a medium to form virus particles. When a recombinant Sendai virus producing vector containing the second genetic material is used, however, the gene in Sendai virus is an incomplete genome; duplication is possible, but the expressed protein is insufficient to form complete virus particles. That renders the gene non-infective and difficult to introduce into a living body. Therefore, an expression system for the defected genes is separately needed. Another recombinant vector containing the defected or deleted genes (M, F, and HN genes) is introduced in advance to the transformed cells so that the transformed cells for which the second genetic material is used can form virus particles when cultured in a medium (FIG. 17).

As described above, the prepared virus particles of the present invention contain either the first or second genetic material and an exogenous gene, and can be introduced to a living body for use, for example, as a gene therapy drug. Inside living tissues, the virus particles are non-cytotoxic and permanently infective, and persistently generate exogenous-gene-derived pharmacological protein to achieve pharmacological benefit over an extended period of time. The virus particles containing the first genetic material are safe at ordinary body temperature because they do not reproduce themselves. The virus particles containing the second genetic material provides a higher level of safety because they cannot reproduce themselves at all in living tissues or cells at any temperature ranges and are therefore non-transmissible.

The following will more specifically describe the present invention sequentially by the production steps for the persistently infective, recombinant Sendai virus vector using the mutated L gene.

The mutated L gene of the present invention contains such a substitution as to encode a valine in place of the amino acid residue at position-1618 in L protein of a persistently non-infective Sendai virus. The mutated M gene contains such substitutions as to encode a glutamate (E), an alanine (A), and a serine (S) in place of the amino acid residues at positions-69, -116, and -183 respectively in M protein of a persistently non-infective Sendai virus. The mutated F gene contains such substitutions as to encode an arginine (R), a leucine (L), and a threonine (T) in place of the amino acid residues at positions-6, -115, and -137 respectively in F protein of a persistently non-infective Sendai virus. These substitutions may be done by an ordinary method, for example, by mutation PCR with a persistently non-infective Sendai virus cDNA as a template. Alternatively, a DNA containing these mutation regions may be synthesized to substitute the DNA for the corresponding sites of a persistently non-infective Sendai virus.

Meanwhile, the second genetic material of the present invention needs to contain mutation so that any one of M, F, and HN gene cDNAs of Sendai virus or a plurality of the genes do not express. This is achieved, for example, by the substitution of another gene (in FIG. 16, blasticidin-resistant gene substitutes for M gene). The virus gene expression can be stopped not only by the substitution of another gene, but also by introducing a stop codon or through complete deletion.

The first and second genetic materials of the present invention obtained in this manner may further include an exogenous gene. The exogenous gene can be inserted to a site where no gene cDNA of Sendai virus is encoded. As mentioned earlier, in the case of the second genetic material, the exogenous gene may be inserted to the gene to be defected.

The gene expression of Sendai virus has a polar effect where the gene closer to the 3' terminus of a genome RNA expresses more strongly. An exogenous gene expresses most strongly when inserted to the upstream end of NP gene and most weakly when inserted downstream of L gene.

The downstream end of the exogenous gene, when inserted, is provided with a termination sequence which stops the transcription of the exogenous gene and a start sequence which starts the transcription of a subsequent Sendai virus gene. The exogenous gene is not limited in any specific manner. Any exogenous gene for use in gene therapy may be used. Examples of such an exogenous gene include an enzyme, a hormone, or like bioactive peptide or a protein that is only generated in a small quantity or that is not generated at all in the patient. The exogenous gene may be inserted in advance in the first and second genetic materials as above. Alternatively, those first and second genetic materials detailed in the following may be introduced into the integrated recombinant Sendai virus producing vector.

In addition, an exogenous gene, such as a drug-resistant gene, may be inserted to the first and second genetic materials of the present invention to enable easy selection of recombinant vector producing cells. When the second genetic material is to be used, the M, F, and HN genes can be defected by inserting the second genetic material to the M, F, and HN genes as mentioned earlier. That is efficient.

To obtain the recombinant Sendai virus producing vector of the present invention modified for persistent infectiveness and optionally also for non-transmissibility, the first or second genetic material cDNA is integrated to a cloning vector, such as λDASHII, so that a (+) stranded genome RNA can be biosynthesized in cells. Also, a T7 promoter sequence and three guanidine residues are arranged in this order upstream of the full length cDNA (3' terminus end of the genome RNA), whilst a hairpin ribozyme sequence of a tobacco ring spot virus and a T7 RNA polymerase termination sequence are arranged in this order downstream of the full length cDNA (the 5' terminus end of the genome RNA).

The T7 promoter sequence is added so that a (+) stranded genome RNA can be biosynthesized from the 3' terminus end of the genome RNA by T7 RNA polymerase. Three guanidine residues are added so as to increase efficiency of RNA transcription by the T7 RNA polymerase (S. Leyrer et al. (1998) J. Virol. Methods 75; 47-58), The hairpin ribozyme sequence of a tobacco ring spot virus is added so that the transcripted (+) stranded genome RNA can be accurately cleaved at the terminus. The T7 RNA polymerase termination sequence is added so that the RNA transcription by the T7 RNA polymerase can be accurately terminated.

The recombinant Sendai virus producing vector with an exogenous gene modified for persistent infectiveness and optionally also for non-transmissibility, produced as above, is introduced to virus generation cells. In so doing, however, an expression vector containing an NP gene, a P gene, an L gene, and a defected gene is preferably also introduced to the cells to aid virus protein formation and efficient virus particle generation.

The T7 RNA polymerase also needs to be supplied. The supply source may be, for example, cells infected with a T7-RNA-polymerase expressing vaccinia virus or a cell strain cloned to constitutively express T7 RNA polymerase.

A cell strain (BHK/T7 cells) constitutively expressing a human-type T7 RNA polymerase expresses T7 RNA polymerase in markedly greater quantities than does a cell strain (BSR-T7-5 cell) expressing a conventional bacteria-type T7 RNA polymerase. Using these cells, recombinant virus can be generated and collected efficiently (FIG. 12). Using a cell strain which is reinforced for expression of greater quantities of T7 RNA polymerase is effective to efficiently generate recombinant virus.

In this example, the T7 promoter and the subsequent part of the vector DNA are transcripted to the RNA by the T7 RNA polymerase in the virus producing cells to which the recombinant Sendai virus producing vector has been introduced. In the transcription, the generated RNA molecule is cleaved by the hairpin ribozyme sequence with its subsequent sequence removed, thus forming an RNP complex containing NP, P, and L gene products bound to an antigenome RNA molecule of the recombinant Sendai virus to which the RNA corresponding to the exogenous gene DNA is inserted.

Next, cells containing the RNP complex containing the antigenome RNA molecule of the recombinant Sendai virus to which the RNA transformed as above and corresponding to the exogenous gene DNA is inserted are cultured at virus particle producing temperature, i.e. 32° C. In the cells, transcription to a (−) strand is carried out by the virus RNA polymerase with the RNP complex acting as a template, to reconstitute a recombinant Sendai virus vector. Since the vector has persistent infectiveness, the vector producing cells can be selected by inserting a drug-resistant gene as above. Alternatively, the calls can be selectively obtained by using an EGFP gene or like marker gene as an indicator.

Figure 15:
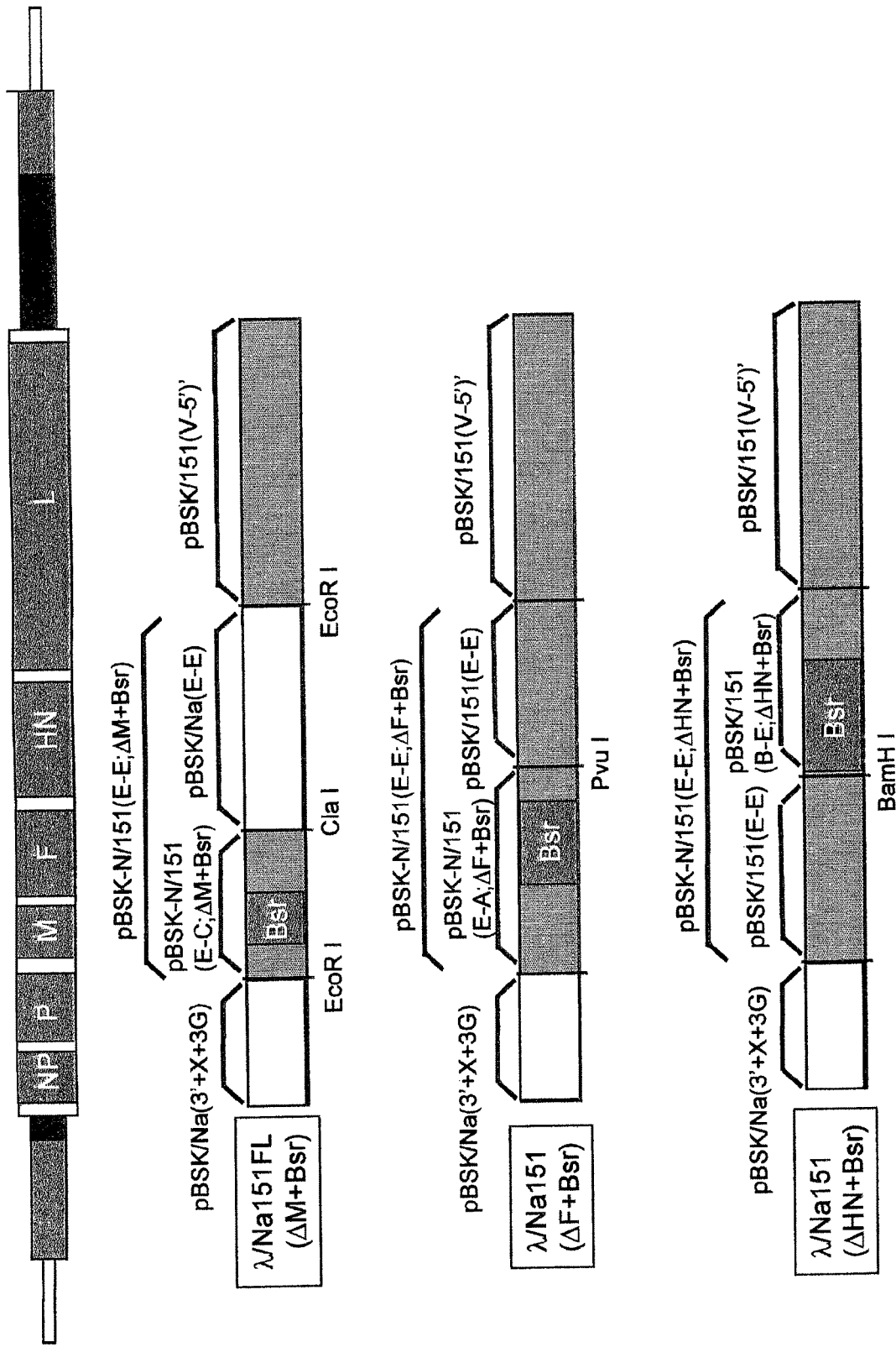

In the vector producing cells obtained as above, the cells to which the recombinant Sendai virus producing vector using the first genetic material is introduced can generate virus particles. The cells to which the recombinant Sendai virus producing vector having at least one of M, F, and HN genes defected or deleted for non-transmissibility is introduced do not by themselves form virus particles and do not infect living tissues. Accordingly, in the present invention, an expression system for the virus protein (M protein in FIG. 15) derived from the defected or deleted gene is separately introduced to the cells. Examples of the expression system include vectors to which the M, F, or HN gene is introduced and vectors to which two or more missing genes are introduced. These vectors, when introduced to the vector producing cells, enable virus particles to be collected from a culture supernatant of the vector producing cells.

The virus particle obtained as above contains, as a genome, an L gene modified in the full length gene of a persistently non-infective Sendai virus, so as to encode a protein with a valine substituted for an amino acid residue at position-1618 in L protein. Furthermore, the particle: has at least any one of M, F, and HN genes defected; contains, as a genome, an NP, P, and mutated L gene and none of M, F, and HN genes; or lacks any one or two of M, F, and HN genes, but has any of the M, F, and HN proteins that is lacking to form a virus particle supplemented by a gene expression system other than the genome.

Meanwhile, all the recombinant Sendai virus vectors of the present invention are capable of being introduced to target cells and tissues after being subjected to a trypsin treatment to acquire infectivity. The vectors persistently express an exogenous gene even in the tissues.

In supplementing F protein as a defected gene, if an expression system for F protein having a mutation introduced to a periphery of a split site (H. Taira et al. (1995) Arch. Virol. 140; 187-194) (splitting F protein) is further introduced to the recombinant Sendai virus vector producing cells to achieve easy splitting and activation through a processing pathway inside the cells without a trypsin treatment, a Sendai virus vector with higher infection efficiency can be obtained (FIG. 30).

Examples of the splitting F protein include mutant proteins modified to contain an amino acid sequence at positions-112 to 116 in F protein in place of the arginine-arginine-X-lysine or arginine-arginine sequence (SEQ ID NO 67; X is any appropriate amino acid residue). A concrete example of the mutation region is an arginine-arginine-glutamine-lysine-arginine sequence (SEQ ID NO 68). To express the mutant protein in the recombinant Sendai virus vector producing cells, a gene encoding the mutant protein is introduced to an expression vector, and the obtained recombinant vector is introduced to the recombinant Sendai virus vector producing cells. The F gene introducing the mutation may be the F gene of either a persistently infective Sendai virus or a persistently non-infective Sendai virus.

Infectivity becomes manipulable by this introduction of a gene having, for example, a mutation to the Sendai virus vector producing cells in supplementing the defected gene.

Figure 23:
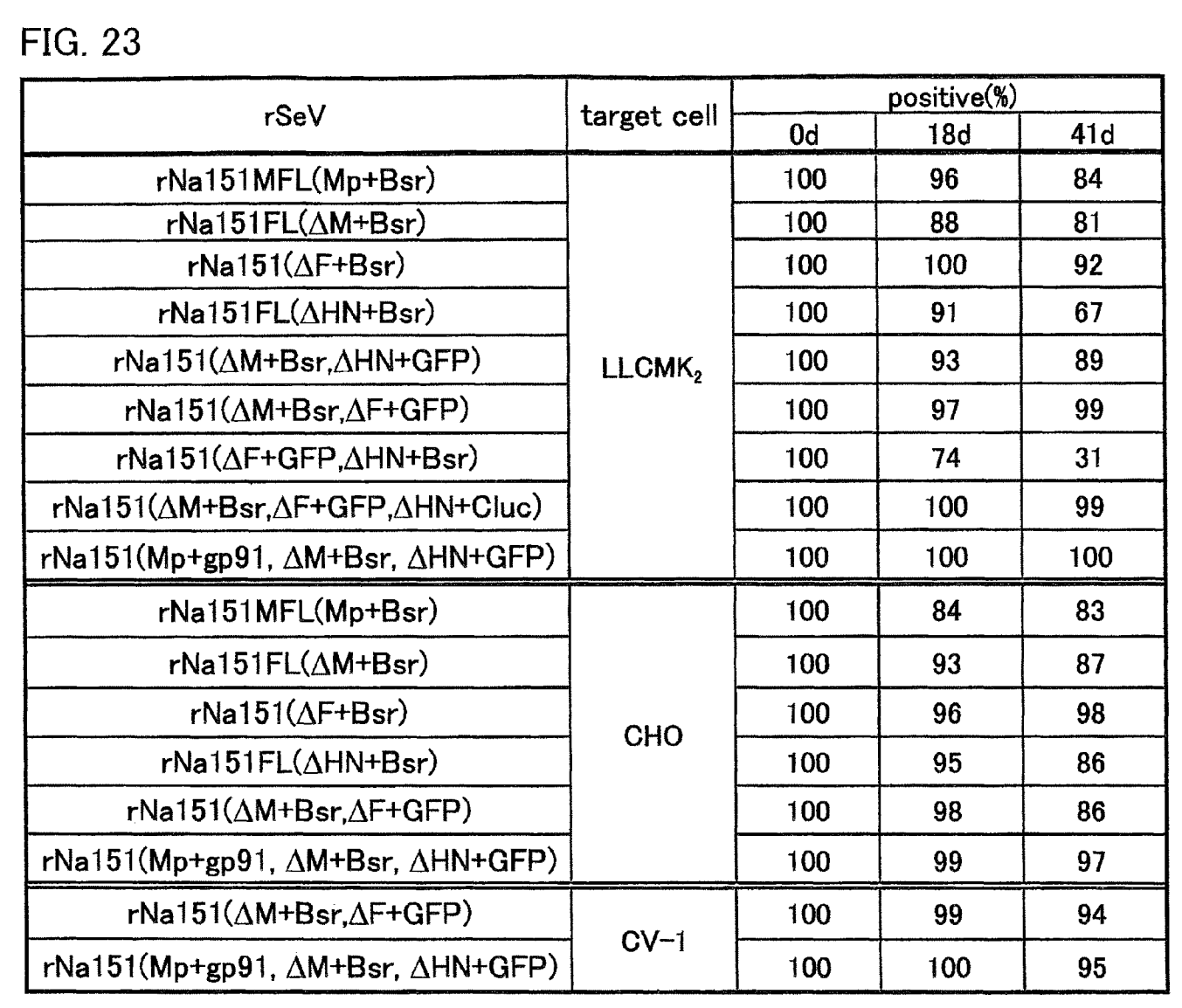

As the combination of defected genes of the M, F, and HN genes, a defective recombinant Sendai virus of any combination can be produced in producing the second genetic material of the present invention. A majority of these combinations preserved the persistent infectiveness of the defective recombinant Sendai virus even when no drug selection was carried out (FIG. 23).

Meanwhile, in the Sendai virus containing defected F and HN genes, difference was observed in the ease of omission of another recombinant Sendai virus and a genome. Nevertheless, by designing a vector based on a structure in which a genome can be easily omitted in this manner, a persistently infective Sendai virus vector can be produced whose expression sustainability is adjusted so that genome is omitted and exogenous gene expression disappears after a period of persistent expression. A gene, once introduced, cannot be removed in persistent expression achieved by integration of, for example, a retrovirus to a chromosome. Therefore, this artificial omission of the vector used for persistent expression will likely be an important technique.

Figure 29:
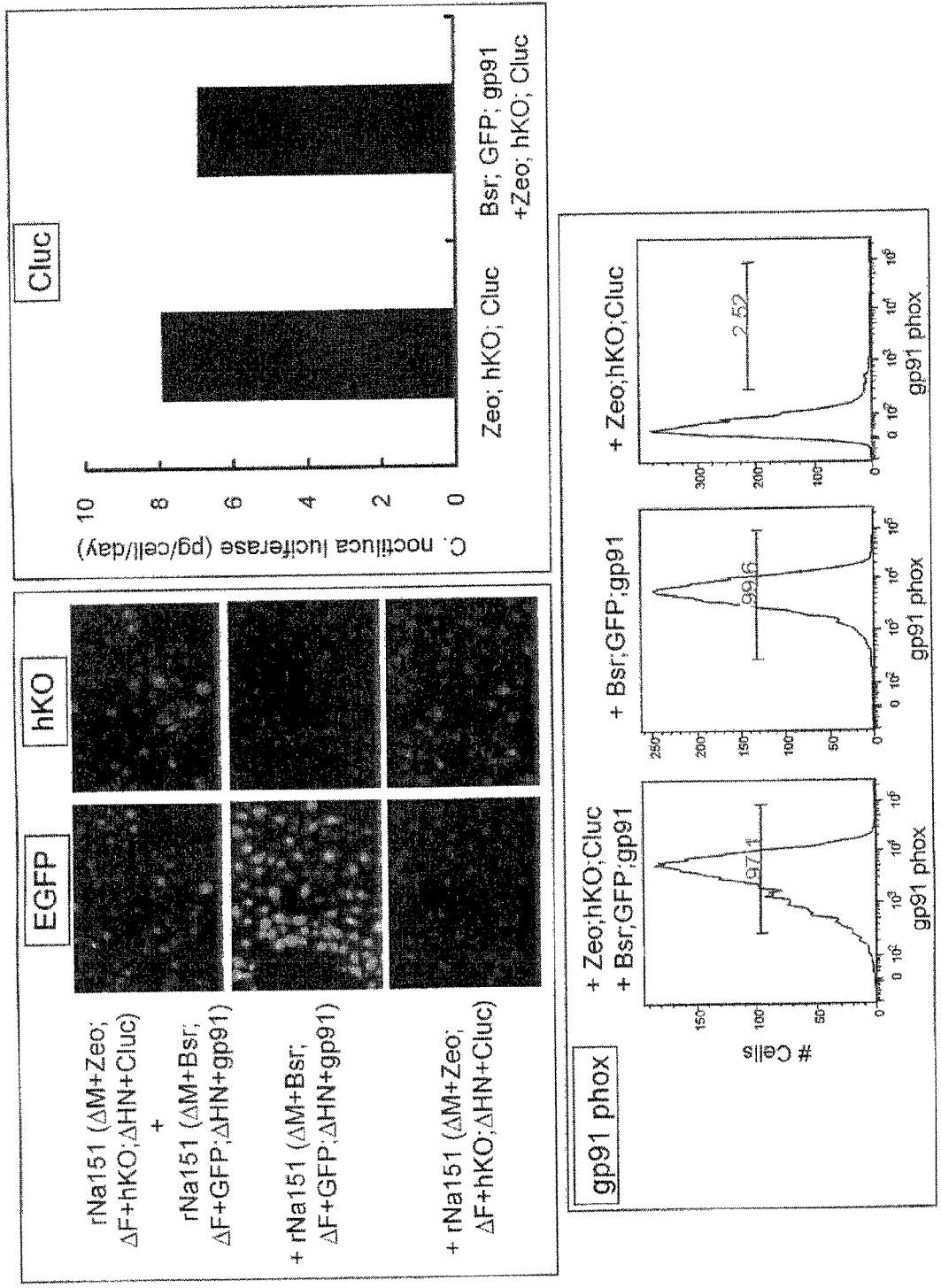

Cells persistently containing two vectors carrying different drug-resistant genes could be separated by preparing the vectors, simultaneously infecting the cells with the vectors, and afterward selecting with both drugs (FIG. 29). It is expected that a single cell can be infected with plural vectors by this method, to simultaneously introduce many genes.

The present invention is not limited to these examples. Various genetic engineering materials and methodologies may be used.

The following is examples of the present invention which are by no means limiting the present invention.

EXAMPLES

Example 1

Producing Recombinant Sendai Virus (rNa151MFL and rNa151MF)

(1) Producing Recombinant Sendai Virus Producing Vector

A cDNA obtained by cloning the full length cDNA of Sendai virus strain C1.151 or Nagoya strain was separated into three fragments. A T7 promoter sequence and a guanidine residue including three bases were inserted in this order immediately upstream of the sequence containing a Sendai virus cDNA in the sequence of a fragment containing SeV: 1-2875 (pBSK/Na(3'-E) [derived from Nagoya strain], pBSK/151(3'-E) [derived from strain C1.151]) (pBSK/Na (3'+X+3G), pBSK/151(3'+X+3G)). A SeV: 15351-15384 part was cut out from a fragment containing SeV: 10479-15384 (pBSK/Na(E-5'), pBSK/151(E-5')). That part, immediately downstream of which the hairpin ribozyme sequence of a tobacco ring spot virus and a T7 RNA polymerase termination sequence were inserted in this order, was recloned into pET30a(+) (Novagen) (pET/Na(5'+HrD), pET/151(5'+HrD)). Furthermore, this fragment of SeV: 15351-15384 to the T7 RNA polymerase termination sequence was inserted to pBSK/Na(E-5')', pBSK/N151(E-5')', (pBSK/Na(E-5')', pBSK/151(E-5')'). A fragment containing SeV: 9015-10479 from a fragment containing SeV: 2870-10484 (pBSK/Na(E-E), pBSK/151(E-E)) was inserted immediately upstream of SeV: 10479-15384 of pBSK/Na(E-5')', pBSK/151(E-5')' (pBSK/Na(V-5')', pBSK/151(V-5')').

Of the plasmids obtained as above, the T7 promoter sequence to SeV: 1-2875 was cut out from pBSK/Na(3'+X+3G) or pBSK/151(3'+X+3G), SeV: 2870-6303 (EcoR I-Blp I) was cut out from pBSK/151(E-E), SeV: 6300-9598 (Blp I-Nco I) was cut out from pBSK/Na(E-E), and SeV: 9593-15384 to a T7 RNA polymerase termination sequence was cut out from pBSK/Na(V-5')' or pBSK/151(V-5')'. The fragments thus cut out were recloned in this order into λDASHII (STRATAGENE). In the recloning, λ/Na151MF was produced using a DNA fragment from pBSK/Na(V-5')' on 9593-15384 to the T7 RNA polymerase termination sequence, and λ/Na151MFL was produced using a DNA fragment from pBSK/151(V-5')' on that sequence (FIG. 1).

(2) Reconstituting Sendai Virus from Recombinant Virus Producing Vector

LLCMK$_2$ cells were plated on a 6-well plate at 1×10$^6$ cells/well and cultured for 24 hours. After the culturing, the cells were infected with a weakly toxic vaccinia virus (MVAGKT7) which expresses T7 RNA polymerase at 7° C. for 1 hour (M.O.I.=1.0). After washing the cells, 5 μg of the recombinant virus producing vector (full length cDNA of Sendai virus) cloned into λDASHII, 2 μg of pGEM/NP, 1 μg of pGEM/P, and 2 μg of pGEM/L were each suspended in 300 μl of OptiMEM (GIBCO), mixed with 300 μl of OptiMEM containing 10 μl of Lipofectamine 2000 (Invitrogen), let sit at room temperature for 20 minutes, added to the cells, and cultured for 4 hours. Thereafter, a medium containing 20% serum and 80 μg/μl cytosine arabinoside C (AraC) was added to each plate, and the cells were cultured further at 32° C. for 48 hours.

These cells were collected. Pellets were suspended in 500 μl of PBS and subjected to 4 cycles of freezing and melting. 100 μl of each of these was inoculated into a hen egg incubated for 10 days. The eggs were incubated further at 32° C. for 5 days. After that, a chorioallantoic liquid was collected. The collected chorioallantoic liquids were diluted 10$^{-4}$ to 10$^{-8}$ folds to render them free from vaccinia, and reinoculated into hen eggs. Chorioallantoic liquids were similarly collected, distributed, and stored at −80° C. Reconstituted virus titer was confirmed by examining hemagglutination activity of the chorioallantoic liquids containing a recombinant Sendai virus. The chorioallantoic liquids of about 20 ml each, containing a recombinant Sendai virus, was centrifuged at 15,000 rpm for 30 minutes. Precipitates were washed in BSS, suspended in 1 ml of BSS to form virus suspensions. The recombinant virus produced from λ/Na151MF was named rNa151MF, and the recombinant virus produced from λ/Na151MFL was named rNa151MFL.

Example 2

Confirming Persistent Infectiveness of Recombinant Sendai Virus in Cells

CV-1 cells or LLCMK$_2$ cells were plated on a 12-well plate and cultured for 24 hours. After the culturing, the virus suspensions were diluted with a medium to M.O.I.=100 and distributed in the wells to cause infection at 37° C. The cells were washed 24 hours later. Then, a medium containing no virus was added. The infected cells were observed to see whether they were dead or alive while culturing them at 37°

C. In addition, infection of the cells was confirmed by a fluorescent antibody test using an antibody against Sendai virus.

Figure 2:
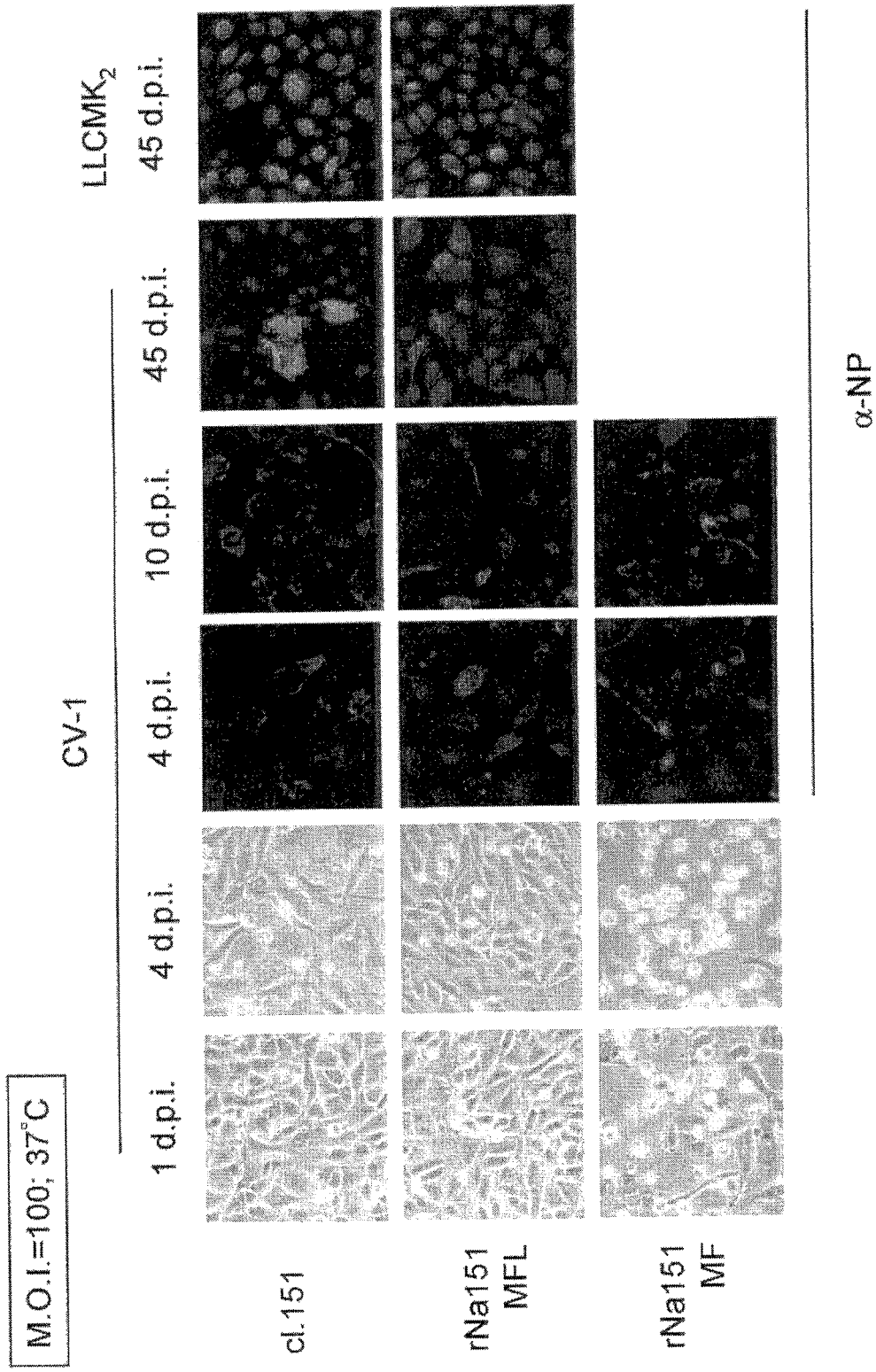

As shown in FIG. 2, cytotoxicity was observed in the CV-1 cells infected with rNa151MF about as late as 4 days after the infection. No cytotoxicity could be observed in CV-1 cells infected with rNa151MFL, similarly to CV-1 cells infected with strain C1.151. Later, 10 days after the infection, marked omission of the virus from the infected cells was confirmed in the CV-1 cells infected with rNa151MF. Furthermore, similar omission of infection was confirmed with the CV-1 cells infected with strain C1.151 45 days after the infection. These observations established that infection sustainability decreases in the order of rNa151MFL>C1.151>rNa151MF. Omission of infection with strain C1.151 was hardly confirmed with the LLCMK$_2$ cells. Omission was therefore thought to be cell-specific.

These results established that persistent infection requires a mutation in M, F, and L protein derived from strain C1.151 and that rNa151MFL strain is persistently infective more stably than strain C1.151.

Example 3

Producing Exogenous-Gene-Inserted rNa151MFL Strain (1); Integrating Exogenous Gene Insertion Site A Not I recognition sequence was inserted to pBSK/Na(3'+X+3G) after SeV: 119 by Quikchange Site-directed Mutagenesis II (STRATAGENE) by using 5'-GCCAAAGT-TCACGCGGCCGCAGATCTTCACGATGGCCGGGTT GT-3' (SEQ ID NO 11 (sense strand) in the Sequence Listing) and 5'-ACAACCCGGCCATCGTGAAGATCTGCG-GCCGCGTGAACTTTG GC-3' (SEQ ID NO 12 (antisense strand) in the Sequence Listing) as an exogenous-gene-insertion-site producing primer (pBSK/Na(3'+Not)).

(2) Introducing Exogenous Gene (EGFP Gene)

An EGFP gene was amplified from pEGFP-C1 (Clontech) by using two primers, 5'-ACTTGCGGCCGCTCGCCAC-CATGGTGAGCAAGGGCGAGGA-3' (SEQ ID NO 13 (N terminus end) in the Sequence Listing) and 5'-ACTTGCG-GCCGCGATGAACTTTCACCCTAAGTTTTTCTTAGAC GGCCGCTTTACTTGTACAGCTCGTCCA-3' (SEQ ID NO 14 (C terminus end) in the Sequence Listing) as EGFP gene insertion primers. The termini of the obtained double-stranded DNA were cleaved with Not I and inserted to the Not I sites of pBSK/Na(3'+Not) to obtain pBSK/Na(3'+GFP).

(3) Producing rNa151MFL-GFP

λ/Na151MFL-GFP (FIG. 1) was produced by the same method as in Example 1, except that pBSK/Na(3'+GFP) was used in place of pBSK/Na(3'+X+3G). Using the resultant recombinant virus producing vector, a recombinant Sendai virus (rNa151MFL-GFP) was produced by the same method as in Example 2.

Figure 3:
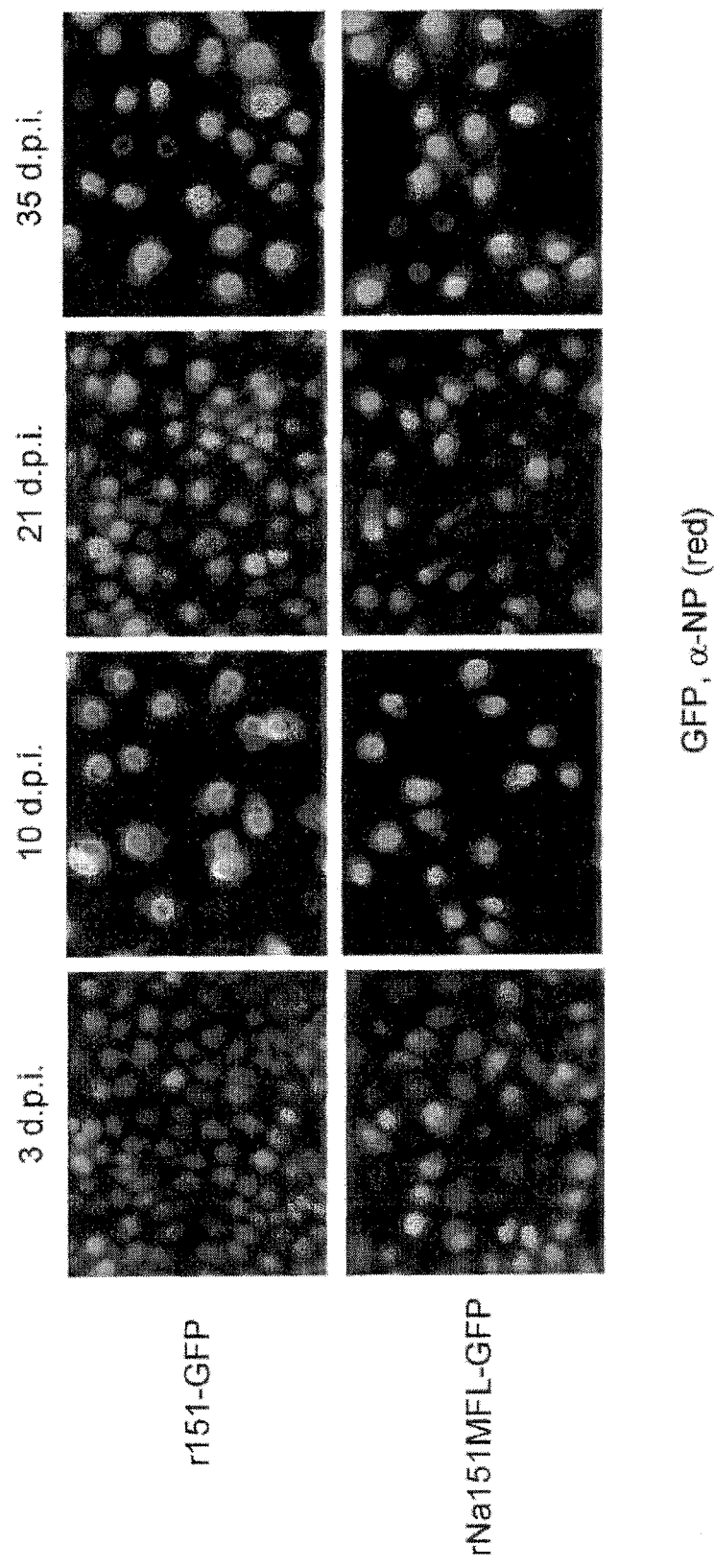

As shown in FIG. 3, the rNa151MFL-GFP persistently expressed a GFP gene in cultured cells similarly to a GFP express Sendai virus (r151-GFP) derived from strain C1.151.

Example 4

Producing L Protein Point Mutation Recombinant Sendai Virus (rNa151MF(L1618pi)), Confirming Persistent Infectiveness Thereof A mutation was introduced to pBSK/Na(V-5')' by using point mutation introducing primers, 5'-GCATACCTATG-CAGCGTGGCAGAGATATCT-3' (SEQ ID NO (sense strand) in the Sequence Listing) and 5'-AGATATCTCTGC-CACGCTGCATAGGTATGC-3' (SEQ ID NO 16 (antisense strand) in the Sequence Listing), designed to cause a mutation from a leucine at position-1618 in L protein to a valine, to obtain pBSK/Na(V-5';L1618pi).

λ/Na151MF(L1618pi) was produced by the same method as in Example 1, except that pBSK/Na(V-5';L1618pi) was used in place of pBSK/Na(V-5')'. Using the resultant cDNA, a recombinant Sendai virus (rNa151MF(L1618pi)) was produced by the same method as in Example 2.

As shown in FIG. 4, no cytotoxicity was confirmed with cells infected with rNa151MF(L1618pi) even 4 days after infection, similarly to those infected with rNa151MFL. The result established that the persistent infection-related mutation in the L protein is a mutation from a leucine at position-1618 to a valine and that this mutation, combined with mutations in the M and F proteins, causes persistent infection.

Example 5

Producing L-Protein-Mutated Recombinant Sendai Virus (rNa151L and rNa(L1618pi))

Figure 5:
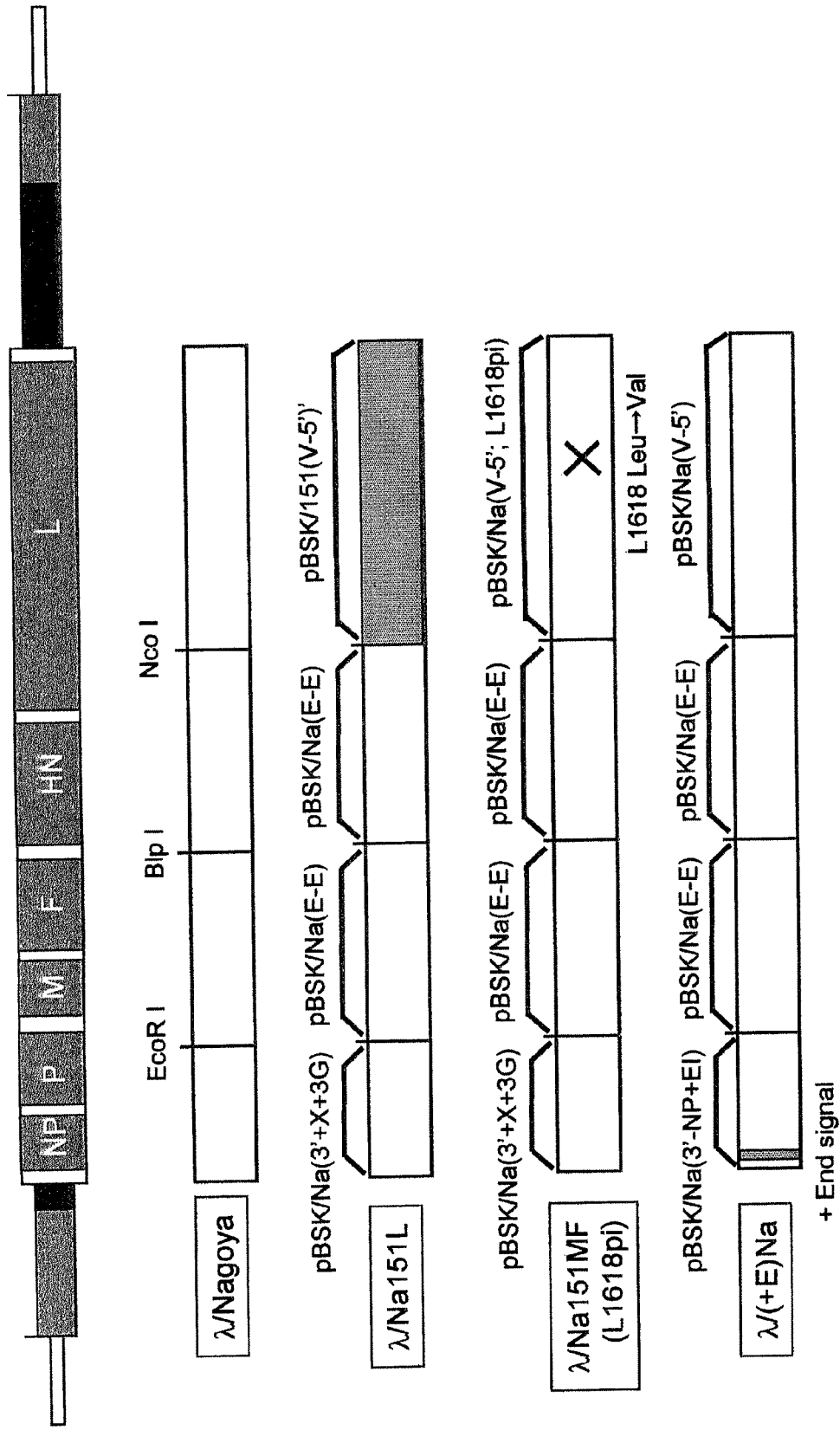

The T7 promoter sequence to SeV: 1-2875 was cut out from pBSK/Na(3'+X+3G). SeV: 2870-10484 (EcoR I-EcoR I) was cut out from pBSK/Na(E-E). A fragment of SeV: 10479-15384 to a T7 RNA polymerase termination sequence was cut out from pBSK/151(V-5')' or pBSK/Na(V-5';L1618pi). The fragments thus cut out were recloned in this order into λDASHII (STRATAGENE). In the recloning, λ/Na151L was produced using a DNA fragment from pBSK/151(V-5')' on 10479-15384 to a T7 RNA polymerase termination sequence, and λ/Na(L1618pi) was produced using a DNA fragment from pBSK/Na(V-5';L1618pi) on that sequence (FIG. 5). Recombinant Sendai viruses (rNa151L and rNa(L1618pi)) were then produced by the same method as in Example 2 using the recombinant virus producing vector.

Example 6

Comparing Cytotoxicity of L-protein-mutated Recombinant Sendai Viruses

LLCMK$_2$ cells were plated on a 96-well plate and cultured for 24 hours. After the culturing, virus suspensions of strain C1.151, rNa151L, rNa(L1618pi), and Nagoya strain were diluted with a medium to M.O.I.=5, except for strain C1.151 for which M.O.I.=100, and distributed in the wells to cause infection at 37° C. The cells were washed 24 hours later. Then, a medium containing no phenol red was added. The cells were further cultured at 37° C. for 24 hours. Thereafter, the viruses were compared in cytotoxicity with a Cell Death Detection Kit (LDH) (Roche), using released lactate dehydrogenase (LDH) as an indicator.

Figure 6:
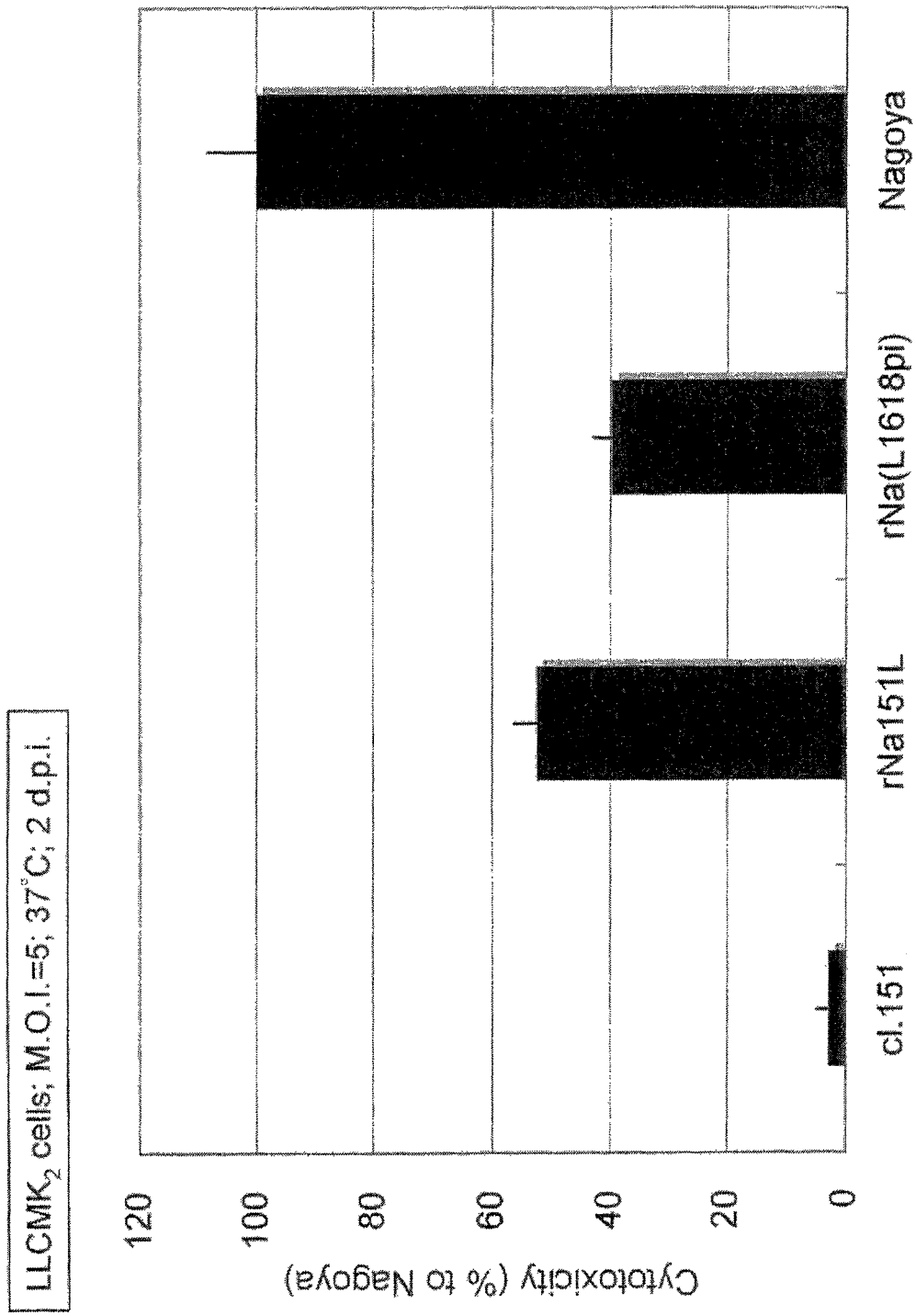

As depicted in FIG. 6, marked decrease in cytotoxicity was confirmed with rNa151L and rNa(L1618pi) in comparison to Nagoya strain. The result established that the L protein mutation attenuates the cytotoxicity of the Sendai viruses. Noting that rNa151L and rNa(L1618pi) still has relatively high cytotoxicity when compared to strain C1.151, it was also established that the L protein mutation alone cannot achieve persistent infection.

Example 7

Measuring Interferon Induction Activity of Recombinant Sendai Virus (1) Producing Interferon Induction Activity Measuring Reporter Plasmid (pIV3)

A sequence containing a promoter for a human interferon β (IFN β) of pGL3-IFN β-promoter-luc (courtesy of Prof. SHIMOTONO, Kyoto Univ.) was inserted between Kpn I and Hind III in pGL4.12 (Promega), to obtain an interferon induction activity measuring reporter plasmid (pIV3).

(2) Establishing Interferon Induction Activity Measuring Cell Strain (LLCMK$_2$/pIV3)

Figure 7:
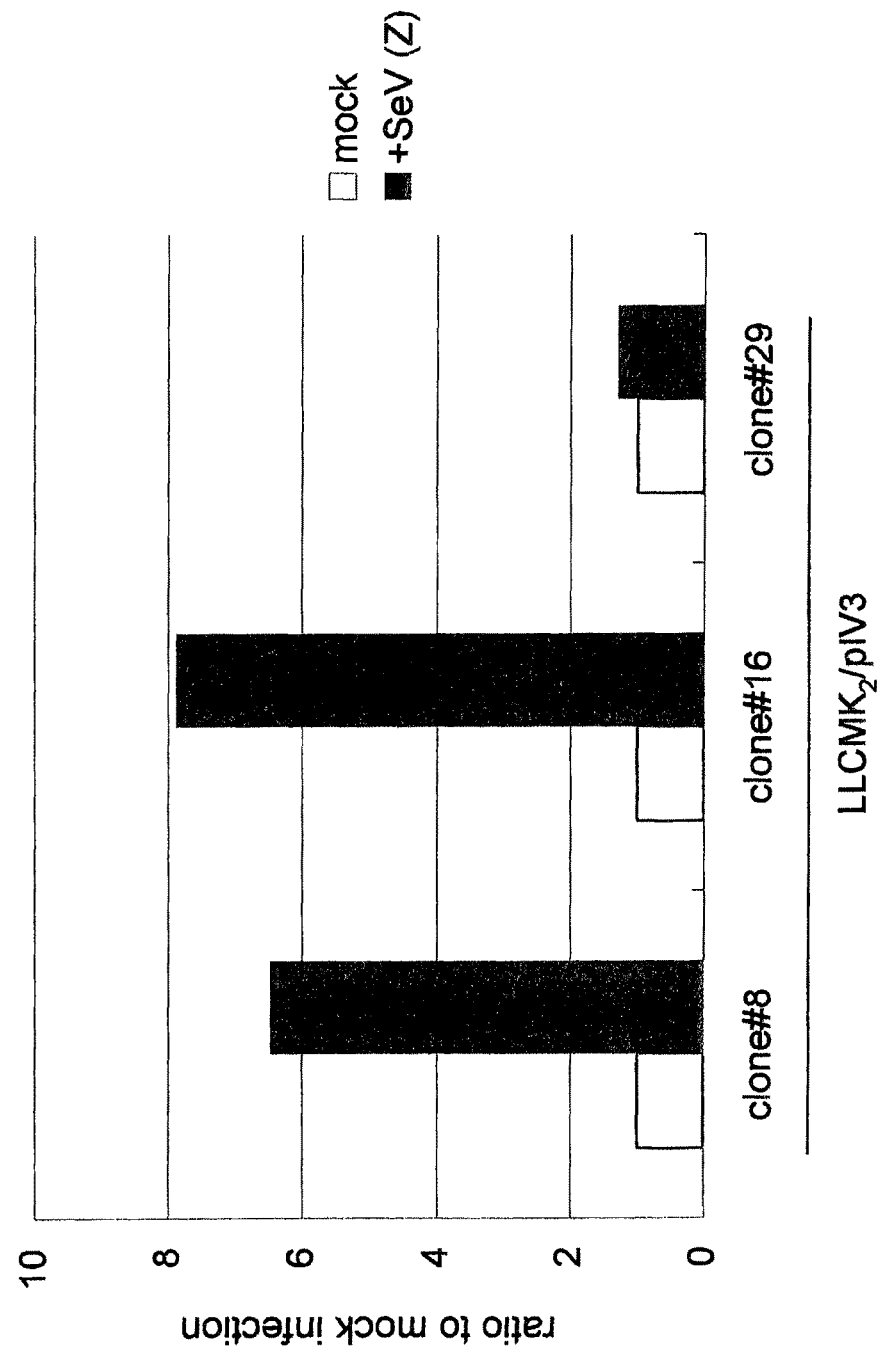

LLCMK$_2$ cells were transfected with pIV3 and a hygromycin resistant gene expression vector (pRSVHyg (Roche)) by using DOTAP transfection regent (Roche). The cells were moved 2 days later to a medium containing 40 μg/ml of hygromycin, to separate hygromycin-resistant cells. Expression of luciferase in accordance with interferon induction was confirmed by infecting the isolated cells with Sendai virus Z strain. The result showed that the highest induction efficiency for LLCMK$_2$/pIV3#16 cells (FIG. 7). So, the cells were used in the subsequent interferon induction activity measurement.

(3) Measuring Interferon Induction Activity

The LLCMK$_2$/pIV3#16 cells were plated on a 12-well plate and cultured for 24 hours. After the culturing, virus suspensions of strain C1.151, rNa151L, rNa(L1618pi), and Nagoya strain were diluted with a medium to M.O.I.=5, except for strain C1.151 for which M.O.I.=100, and distributed in the wells to cause infection at 37° C. The cells were collected 4, 8, 12, 18, 24, and 48 hours after the infection, and their luciferase activity was measured using a Luciferase assay kit (Promega). Interferon induction activity was given in ratios to the luciferase activity of non-infected cells.

Figure 8:
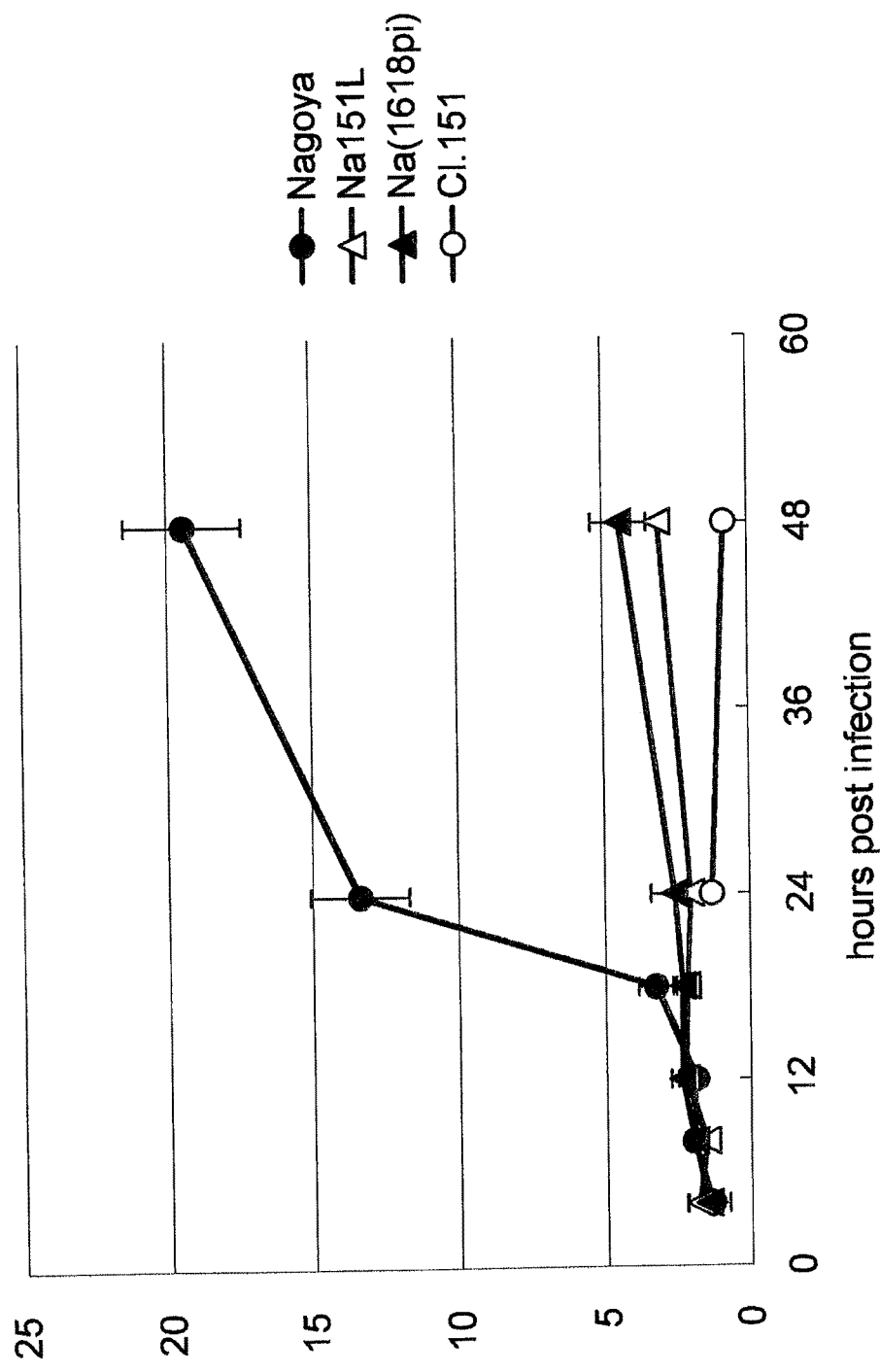

As depicted in FIG. 8, interferon expression is strongly induced in Nagoya strain infected cells, whilst expression was hardly induced in rNa151 L infected cells and rNa (L1618pi) infected cells similarly to strain C1.151 infected cells. The result established that the mutation of the L protein restrains interferon expression induction.

Example 8

Quantifying Copy Number of RNA Molecule Related to Recombinant Sendai Virus in Infected Cells Virus-derived RNAs are, for example, a genome RNA, a mRNA for each gene, a leader RNA, and an antigenome RNA (RNA transcripted from the 3' terminus of a genome RNA and transcripted by reading through the leader RNA and its subsequent part) as depicted in FIG. 9. To quantify them, probes were produced as follows.

(1) Cloning of S1 Nuclease Assay Probe

SeV: 1-526 was amplified from pBSK/Na(3'+X+3G) by using two primers, 5'-CGCGGATCCTAATACGACTCAC-TATAGGG-3' (SEQ ID NO 17 (3' terminus end) in the Sequence Listing) and 5'-CCAAACAGCCATTCTGTGGT-3' (SEQ ID NO 18 (5' terminus end) in the Sequence Listing). The termini of the obtained double-stranded DNA were cleaved with BamH I, Xba I and cloned into pBlue script II SK(+) (STRATAGENE) (pBSK/Na(3'-NP)). The Xho I-Nco I fragment (SeV: 1-359) cut out from pBSK/Na(3'-NP) was used as an NP mRNA, antigenome RNA probe.

SeV: 12385-12795 was amplified from pBSK/151(V-5')' by using two primers, 5'-CGCTCTAGAAGCTGCTGACTC-CTGTTTCA-3' (SEQ ID NO 19 (3' terminus end) in the Sequence Listing) and 5'-CGCGGATCCATAGCTCAAG-GTCCACATCC-3' (SEQ ID NO 20 (5' terminus end) in the Sequence Listing). The termini of the obtained double-stranded DNA were cleaved with BamH I, Xba I and cloned into pBlue script II SK(+) (pBSK/151(L)). The Xho I-Spe I fragment (SeV: 12471-12795) cut out from pBSK/151(L) was used as a genome RNA probe.

A single-stranded cDNA was produced from the entire RNA extracted from the LLCMK$_2$ cells through reverse-transcription using a SuperScript III First-strand Synthesis System for RT-PCR (Invitrogen). Meanwhile, 127-319 of a β-actin mRNA were amplified by using two primers, 5'-CGCGGATCCATCGTGGGGCGCCCCAG-GCACCAGGGCGTGAT-3' (SEQ ID NO 21 (5' terminus end) in the Sequence Listing) and 5'-CGCTCTAGAAG-GAGCCACACGCAGCTCATTGTAGAAGGTGT-3' (SEQ ID NO 22 (3' terminus end) in the Sequence Listing). The termini of the obtained double-stranded DNA were cleaved with BamH I, Xba I and cloned into pBlue script II SK(+) (pBSK/act). The Xho I-Bgl II fragment (β-actin mRNA: 127-277) cut out from pBSK/act was used as a β-actin RNA probe.

(2) S1 Nuclease Assay

LLCMK$_2$ cells were infected with rNa151L, rNa (L1618pi), and Nagoya strain. The cells were collected 4, 8, 12, 18, 24, and 48 hours after the infection, and their entire RNAs were extracted using ISOGEN (Nippon Gene).

The 5' termini of the S1 nuclease assay probe cut out from pBSK/Na(3'-NP) and pBSK/act were labelled with [γ-$^{32}$P] ATP. 2 fmol of an NP mRNA labeling probe, 2 fmol of a β-actin mRNA labeling probe, and 5 μg of the entire RNA of the infected cells were hybridized in 10 μl of a hybridization buffer (3-M sodium trichloroacetate, 50-mM PIPES-NaOH, 5-mM EDTA, pH 7) at 45° C. S1 nuclease was added 16 hours later, and the mixture was processed at 37° C. for 2 hours. This product, obtained by cleaving S1 nuclease, was separated by a gel containing 5% acrylamide and 8% urea. Signal strengths for NP mRNA, antigenome RNA, and β-actin mRNA were quantified on a STORM 830 (Molecular Dynamics). The ratios of the signal strength of β-actin mRNA to those of NP mRNA and antigenome RNA were calculated and compared in view of their conditions. Similarly, the ratio of the signal strength of genome RNA to that of β-actin mRNA was calculated using a genome RNA labeling probe and a β-actin mRNA labeling probe.

As depicted in FIG. 9, changes in copy numbers do not vary much for the NP mRNA and genome RNA among the three strains of rNa151L, rNa(L1618pi), and Nagoya strain. It was established that for the antigenome RNA, however, the copy number does not increase much in the cells infected with rNa151L and rNa(L1618pi) when compare to Nagoya strain. This result suggested that the copy number of the antigenome RNA not increasing due to the mutation of L protein was related to decrease in the interferon induction.

Example 9

Producing and Characterizing Virus Antigenome RNA

Transcription Restraining Recombinant Sendai Virus (1) Inserting Transcription Termination Sequence to Leader RNA 3' Termini SeV: 1-1135 in which a transcription termination sequence was inserted to the leader RNA 3' termini was amplified from pBSK/Na(3'+X+3G) by using two primers, 5'-CACGCTC-GAGTAATACGACTCACTATAGGGACCAAACAAGAG AAGAAACATGTATGGAATATATAAT-GAAGTTTAAGAAAAACTTAGG GTCAAAGTATCC-3' (SEQ ID NO 69 (3' terminus end) in the Sequence Listing) and 5'-ACTCCCATGGCGTAACTCCATAGTG-3' (SEQ ID NO 70 (5' terminus end) in the Sequence Listing) as transcription termination sequence insertion primers on pBSK/Na(3'+

X+3G). The termini of the obtained double-stranded DNA were cleaved with Xho I and Sph I, and cloned into equivalent sites in pBSK/Na(3'-Mp+NN) (detailed later), to obtain pBSK/Na(3'-NP+EI).
(2) Producing Transcription Termination Sequence Insertion Recombinant Sendai Virus (r(+E)Na)
The T7 promoter sequence to SeV: 1-2875 was cut out from pBSK/Na(3'-NP+EI). SeV: 2870-10484 (EcoR I-EcoR I) was cut out from pBSK/Na(E-E). SeV: 10479-15384 to a T7 RNA polymerase termination sequence was cut out from pBSK/Na (V-5'). The fragments thus cut out were recloned in this order into λDASHII to obtain λ/(+E) Na. See FIG. 5. A recombinant Sendai virus (r(+E)Na) was then produced by the same method as in Example 2 using the recombinant virus producing vector.
(3) Quantifying Virus RNA by S1 Nuclease Assay
The NP mRNA and antigenome RNA in $LLCMK_2$ cells infected with Nagoya strain or r(+E)Na were quantified by the same method as in Example 8. Results established that the insertion of a transcription termination sequence before the transcription start sequence in the NP mRNA selectively restrains transcription of the antigenome RNA (FIG. 10).
(4) Measuring Interferon Induction Activity
$LLCMK_2$/pIV3#16 cells were infected with Nagoya strain or r(+E)Na, and their interferon induction activity was measured, by the same method as in Example 7. Results established that r(+E)Na reduces interferon induction activity with decreasing quantity of the antigenome RNA (FIG. 10).

Example 10

Figure 11:
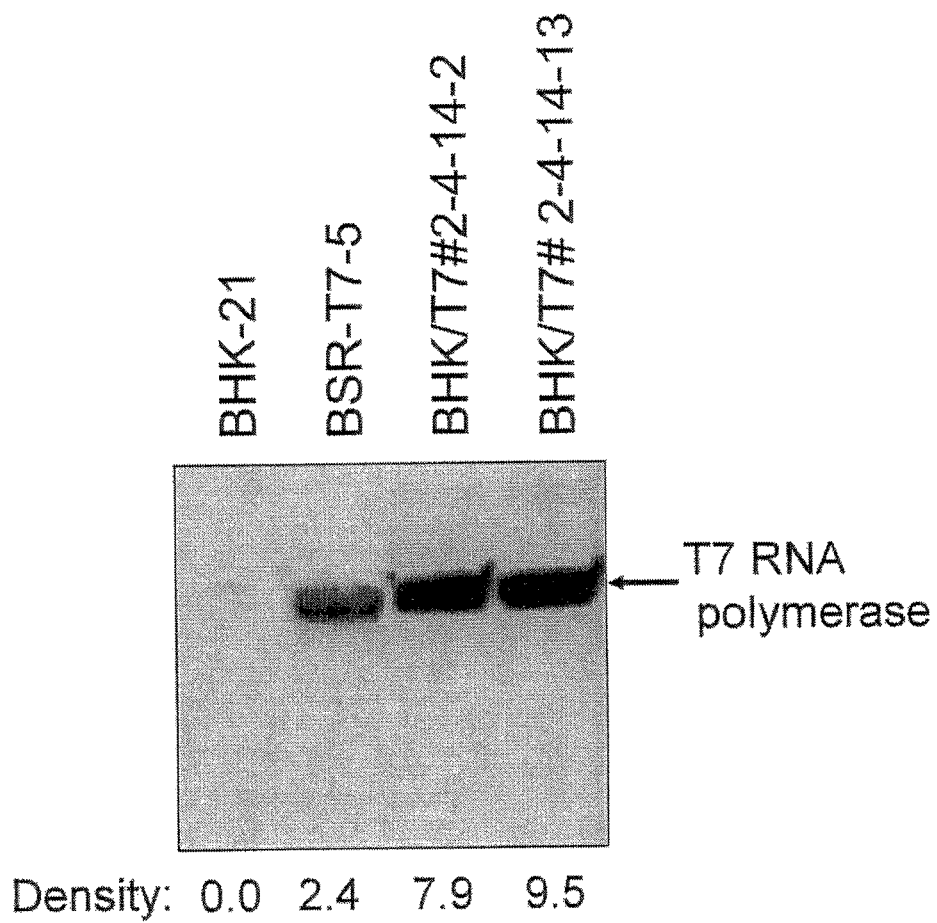

Producing Recombinant Sendai Virus Producing Human-Type T7 RNA Polymerase Expressing Cell Strain (1) Producing Human-type T7 RNA Polymerase Expressing Plasmid (pIP2)
The inventors had GenSconcript Corporation (120 Centennial Ave. Piscataway, N.J. 08854, USA) modify the sequence of the cDNA of a procaryotic T7 RNA polymerase gene without changing the amino acid sequence so as to use humanized codons. The human-type T7 RNA polymerase cDNA was recloned downstream of a CAG promoter, to obtain a human-type T7 RNA polymerase expressing plasmid (pIP2).
(2) Producing BHK/T7 Cells
BHK-21 cells were transfected with pIP2 and a puromycin resistant gene expression vector (pRSVpuro) by using Lipofectamine 2000. The cells were moved 2 days later to a medium containing 30 µg/ml of puromycin, to separate puromycin-resistant cells. Expression of T7 RNA polymerase by the isolated cells was confirmed by a fluorescent antibody test using anti-T7 RNA polymerase antibody. BHK/T7#2-4-14-13 cells (FIG. 11), a large number of which expressed and which exhibited high expression quantity, were used subsequently as recombinant Sendai virus vector producing cells.
(3) Producing Recombinant Sendai Virus Using BHK/T7 Cells
BHK/T7 cells were plated on a 6-well plate at $5 \times 10^5$ cells/well and cultured for 24 hours. After that, the cells were washed. 5 µg of a recombinant virus producing vector, 2 µg of pGEM/NP, 1 µg of pGEM/P, and 2 µg of pGEM/L were each suspended in 300 µl of OptiMEM, mixed with 300 µl of OptiMEM containing 10 µl of Lipofectamine 2000, let sit at room temperature for 20 minutes, added to the cells, and cultured for 4 hours. The cells were then washed. Thereafter, a DMEM medium containing 10% serum was added, and the mixture was further cultured at 32° C. for 48 hours.
These cells were collected. Pellets were suspended in 500 µl of PBS and subjected to 4 cycles of freezing and melting. 100 µl of each of these was inoculated into a hen egg incubated for 10 days. The eggs were further incubated at 32° C. for 5 days. After that, a chorioallantoic liquid was collected. The collected chorioallantoic liquids were distributed and stored at −80° C. Reconstituted virus titer was confirmed by examining hemagglutination activity of the chorioallantoic liquids containing a recombinant Sendai virus. A Sendai virus was reconstituted from a Z strain cDNA (pSeV(+)) using conventional, procaryotic T7 RNA polymerase expressing cells BSR-T7-5 and BHK/T7 cells as depicted in FIG. 12. No reconstituted viruses are collected from the BSR-T7-5 cells unless T7 RNA polymerase is also expressed through infection with a vaccinia virus (MVAGKT7), whereas a reconstituted virus was collected from the BHK/T7 cells without infection with a vaccinia virus. The result established that the BHK/T7 cells are recombinant Sendai virus producing cells which have better reconstitution efficiency than the conventional T7 RNA polymerase expressing cells.

Example 11

Producing Blastcidin-Resistant Gene Expressing Recombinant Sendai Virus cDNA (1) Producing pBSK/151(Nhe-Not)
A Not I site was introduced to pBSK/151(3'+X+3G) by the same method as in Example 3. The fifth, third, and second bases (T, C, A) immediately preceding the Not I site on the obtained pBSK/151(3'+Not) were replaced respectively by C, A, and G through PCR using the primers below, to introduce a Nhe I recognition sequence.
First, PCR was performed using pBSK/151(3'+Not) as a template, with two types of primer sets: M13 reverse-primer 5'-GGAAACAGCTATGACCATG-3' (SEQ ID NO 23 (N terminus end) in the Sequence Listing) and Nhe I recognition sequence introducing primer 1 5'-CTGCGGC-CGCGCTAGCTTTGGCAGCAAAGAA-3' (SEQ ID NO 24 (C terminus end) in the Sequence Listing); and Nhe I recognition sequence introducing primer 2 5'-AAGCTAGCGCG-GCCGCAGATCTTC-3' (SEQ ID NO 25 (N terminus end) in the Sequence Listing) NP C terminus end primer and 5'-CCG-GAATTCGTATGATCCTAGATTCCTCCT-3' (SEQ ID NO 26 (C terminus end) in the Sequence Listing). The produced PCR products were mixed for further PCR with the M13 reverse-primer and the NP C terminus end primer, to obtain a 3' DNA fragment of strain C1.151 into which a Nhe I recognition sequence had been introduced. The PCR product was cleaved with restriction enzyme Sac I and integrated to the pBSK/151(3'+Not) cleaved with the same enzyme to obtain pBSK/151(Nhe-Not).
(2) Producing pBSK-N/151(E-C+NN)
A mutation was introduced to pBSK-N/151(E-C), a vector to which strain C1.151 was cloned up to SeV: 2870-5335, by using mutation introducing primers, 5'-GAAA-GAAATTTCACCGCTAGCGCGGCCGCAT-GCTAACACGGC GCAATG-3' (SEQ ID NO 27 (sense strand) in the Sequence Listing) and 5'-CATTGCGCCGTGT-TAGCATGCGGCCGCGCTAGCGGTGAAATT TCTTTC-3' (SEQ ID NO 28 (antisense strand) in the Sequence Listing), designed to insert Nhe I and Not I sequences before the M gene start codon (pBSK-N/151(E-C+NN)).

(3) Inserting Blastcidin-Resistant Gene Expressing Cassette to Sendai Virus cDNA A blastcidin-resistant gene was amplified from pCX-Bsr (Clontech) by using two primers, 5'-ACTAGCTAGCA-GAATATATGAAAACATTTAACATTTCTCA-3' (SEQ ID NO 29 (N terminus end) in the Sequence Listing) and 5'-ACT-TGCGGCCGCGATGAACTTTCAC-CCTAAGTTTTTCTTAGGT AAAACTTTTAATTTCGGG-TATATTTGA-3' (SEQ ID NO 30 (C terminus end) in the Sequence Listing) as blastcidin-resistant gene insertion primers. The termini of the obtained double-stranded DNA were cleaved with Nhe I and Not I and inserted between Nhe I and Not I in pBSK/151(Nhe-Not) and pBSK-N/151(E-C+NN), obtain pBSK/151(3'+Bsr) and pBSK-N/151(E-C:Mp+Bsr).

Figure 13:
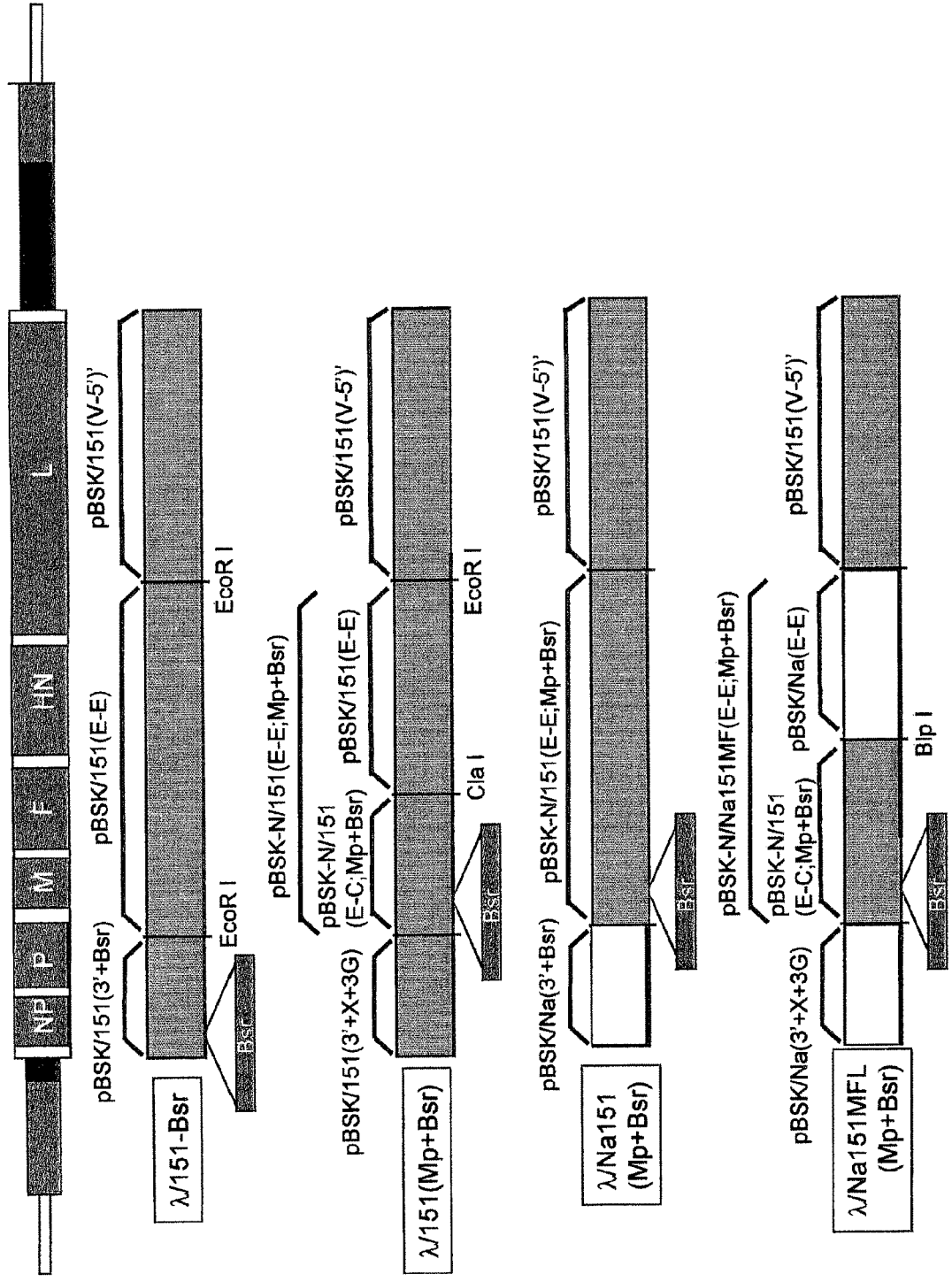

(4) Producing Blastcidin-Resistant Gene Expressing Recombinant Sendai Virus Producing Vector A SeV: 5336-10484 sequence derived from strain C1.151 was inserted after SeV: 5335 of pBSK-N/151(E-C:Mp+Bsr) to produce pBSK-N/151(E-E:Mp+Bsr). Furthermore, the SeV: 6300-10484 sequence in pBSK-N/151(E-E:Mp+Bsr) was changed to a sequence derived from Nagoya strain to obtain pBSK-N/Na151MF (E-E:Mp+Bsr). Recombinant Sendai virus producing vectors (λ/151-Bsr, λ/151(Mp+Bsr), λ/Na151(Mp+Bsr), λ/Na151MFL(Mp+Bsr)) were cloned by the same method as in Example 1 using a recombinant Sendai virus cDNA into which the cloned blastcidin-resistant gene expressing cassette was inserted (FIG. 13).

Example 12

Assembling Recombinant Sendai Virus Producing Cells Selecting System Using Blastcidin The BHK/T7 cells obtained in Example 10 were plated on a 6-well plate at $5 \times 10^5$ cells/well cultured for 24 hours. After that, the cells were washed. Then, 5 µg of a recombinant Sendai virus producing vector, 2 µg of pGEM/NP, 1 µg of pGEM/P, 2 µg of pGEM/L were each suspended in 300 µl of OptiMEM, mixed with 300 µl of OptiMEM containing 10 µl of Lipofectamine 2000, let sit at room temperature for 20 minutes, added to the cells, and cultured for 4 hours. The cells were then washed. Thereafter, a DMEM medium containing 10% serum was added, and the mixture was further cultured at 32° C. for 3 days. Thereafter, the cells were moved to a medium containing 10 µg/ml of blastcidin and further cultured. Blastcidin-resistant cells were separated as recombinant Sendai virus producing cells. Virus reconstitution in the recombinant Sendai virus producing cells was confirmed through staining by a fluorescent antibody test using an antibody against the Sendai virus. Virus reconstitution efficiency was compared by measuring the number of colonies of the blastcidin-resistant cells.

Reconstitution efficiency increased in the order λ/151-Bsr<λ/151(Mp+Bsr)<λ/Na151(Mp+Bsr)<λ/Na151MFL(Mp+Bsr) as depicted in FIG. 14. This result established that reconstitution efficiency is the highest if the Sendai virus vector is produced based on a cDNA containing rNa151MFL as a scaffold.

Example 13

Assembling M, F, or HN Gene Defected Sendai Virus cDNA (1) Producing M Gene Defected cDNA A Nhe I recognition sequence was inserted after SeV: 3655 in pBSK/151(E-C), and a Mlu I recognition sequence was inserted after SeV: 4722 (pBSK/151(E-C+NM)), by using a set of Nhe I recognition sequence introducing primers, 5'-AAAGAAATTTCAGCTAGCACGGCGCAATGG-3' (SEQ ID NO (sense strand) in the Sequence Listing) and 5'-CCATTGCGCCGTGCTAGCTGAAATTTCTTT-3' (SEQ ID NO 32 (antisense strand) in the Sequence Listing), and a set of Mlu I recognition sequence introducing primers, 5'-CT-GTAAATGTGCACGCGTCAGAGACCTGCA-3' (SEQ ID NO (sense strand) in the Sequence Listing) and 5'-TGCAG-GTCTCTGACGCGTGCACATTTACAG-3' (SEQ ID NO 34 (antisense strand) in the Sequence Listing).

A blastcidin-resistant gene was amplified from pCX-Bsr by using two primers, 5'-ACTAGCTAGCAGAATATAT-GAAAACATTTAACATTTCTCA-3' (SEQ ID NO 29 (N terminus end) in the Sequence Listing) and 5'-GGTC-CACGCGTTTTAATTTCGGGTATATTTGA-3' (SEQ ID NO 35 (C terminus end) in the Sequence Listing). The termini of the obtained double-stranded DNA were cleaved with Nhe I and Mlu I and inserted between Nhe I and Mlu I in pBSK-N/151(E-C+NN) to obtain pBSK/151(E-C; ΔM+Bsr). Furthermore, after SeV: 5335 in pBSK/151(E-C;ΔM+Bsr), a sequence derived from strain C1.151 was inserted to SeV: 5336-6299, and a sequence derived from Nagoya strain was inserted to SeV: 6300-10484, to obtain pBSK/Na151F (E-E; ΔM+Bsr).

(2) Producing HN Gene Defected cDNA

A Nhe I recognition sequence was inserted after SeV: 3655 in pBSK/151(B-E) (containing SeV: 5913-10484 derived from strain C1.151), and a Mlu I recognition sequence was inserted after SeV: 4722 in pBSK/151(B-E) (pBSK/151(B-E+NM)), by using a set of Nhe I recognition sequence introducing primers, 5'-GCGGTATTTTAGCTAGCATCTCAAA-CAAGC-3' (SEQ ID NO 36 (sense strand) in the Sequence Listing) and 5'-GCTTGTTTGAGATGCTAGCTAAAATAC-CGC-3' (SEQ ID NO 37 (antisense strand) in the Sequence Listing), and a set of Mlu I recognition sequence introducing primers, 5'-TAACTGACTAGCACGCGTGTCG-GCTTTGCT-3' (SEQ ID NO 38 (sense strand) in the Sequence Listing) and 5'-AGCAAAGCCGACACGCGT-GCTAGTCAGTTA-3' (SEQ ID NO 39 (antisense strand) in the Sequence Listing). Similarly to M gene defection, after a blastcidin-resistant gene was inserted between Nhe I and Mlu I, a SeV: 2871-6303 sequence derived from strain C1.151 was added before SeV: 6303 to obtain pBSK/151(E-E; ΔHN+Bsr).

(3) Producing F Gene Defected cDNA

A Bgl II recognition sequence was insert after SeV: 3655 in pBSK/151(E-A) (containing SeV: 2871-7000 derived from strain C1.151) (pBSK/151(E-A+Bgl)) by using a set of Bgl II recognition sequence introducing primers, 5'-GG-GATAAAGTCCCTTAGATCTGCTTGGTTGCAAAA-3' (SEQ ID NO 40 (sense strand) in the Sequence Listing) and 5'-TTTTGCAACCAAGCAGATCTAAGG-GACTTTATCCC-3' (SEQ ID NO 41 (antisense strand) in the Sequence Listing).

A blastcidin-resistant gene was amplified from pCX-Bsr by using two primers, 5'-CGCGGATCCGAAGAATATAT-GAAAACATT-3' (SEQ ID NO 42 (N terminus end) in the Sequence Listing) and 5'-CGCGGATCCTTAATTTCGGG-TATATTTGA-3' (SEQ ID NO 43 (C terminus end) in the Sequence Listing). The termini of the obtained double-stranded DNA were cleaved with BamH I and inserted between Bgl II and Bgl II (SeV: 3655-6612) in pBSK/151(E-A+Bgl) to obtain pBSK/151(E-A; ΔF+Bsr).

Furthermore, a SeV: 6304-10484 sequence derived from strain C1.151 was added after SeV: 6303 to obtain pBSK/151 (E-E; ΔF+Bsr).

(4) Assembling Recombinant Sendai Virus Producing Vector

Recombinant Sendai virus producing vectors (λ/Na151FL (ΔM+Bsr), λ/Na151(ΔF+Bsr), and λ/Na151(ΔHN+Bsr)) were cloned by the same method as in Example 1 using the M gene defected, the F gene defected, and the HN gene defected cDNA (FIG. 14).

Example 14

Assembling M, F, and HN Gene Expressing Plasmids

An M gene was amplified from pBSK/Na(E-E) or pBSK/151(E-E) by using two primers, 5'-CCGGAATTCGGCG-CAATGGCAGATATCTA-3' (SEQ ID NO 44 (N terminus end) in the Sequence Listing) and 5'-ACTTGCGGCCGCG-GTGCACATTTACAGCTTTC-3' (SEQ ID NO 45 (C terminus end) in the Sequence Listing). The termini of the obtained double-stranded DNA were cleaved with EcoR I and Not I and inserted between EcoR I and Not I in pMKIT-neo to obtain an M protein expressing plasmid (pMKIT-NaM, pMKIT-151 M).

Likewise, an F gene was amplified by using two primers, 5'-CCGGAATTCGAAACATGACAGCATATATC-3' (SEQ ID NO 46 (N terminus end) in the Sequence Listing) and 5'-ACTTGCGGCCGCGTCGTGATCATCTTTTCT-3' (SEQ ID NO 47 (C terminus end) in the Sequence Listing) to obtain an F protein expressing plasmid (pMKIT-NaF, pMKIT-151F).

Furthermore, an HN gene was amplified by using two primers, 5'-CCGGAATTCTCATGGATGGTGAT-AGGGGC-3' (SEQ ID NO 48 (N terminus end) in the Sequence Listing) and 5'-ACTTGCGGCCGCTTAA-GACTCGGCCTTGCA-3' (SEQ ID NO 49 (C terminus end) in the Sequence Listing) to obtain an HN protein expressing plasmid (pMKIT-NaHN, pMKIT-151HN).

In addition, a PCR product at the N terminus end of an FZ gene in which the 112-th to 116-th amino acids (APQSR) were replaced by RRQKR was obtained by using a plasmid pUC-F in which the F protein gene of Z strain was integrated as a template and also using two primers, 5'-GGGCTTGG-GAAACATGACAGC-3' (SEQ ID NO 50 (N terminus end) in the Sequence Listing) and 5'-GAAGAATCTCTTCTGGC-GACGACCGGC-3' (SEQ ID NO 51 (C terminus end) in the Sequence Listing). A splitting F protein gene was amplified by using this PCR product as an N terminus end primer and pUC-F as a template, together with a C terminus end primer, 5'-GACATCCTGATAATGGTCGTGATC-3' (SEQ ID NO 52 (C terminus end) in the Sequence Listing). The EcoRI site was integrated into a blunting expressing plasmid pSRD to obtain a splitting F protein expressing plasmid (pSRD-FZmut).

Example 15

Figure 16:
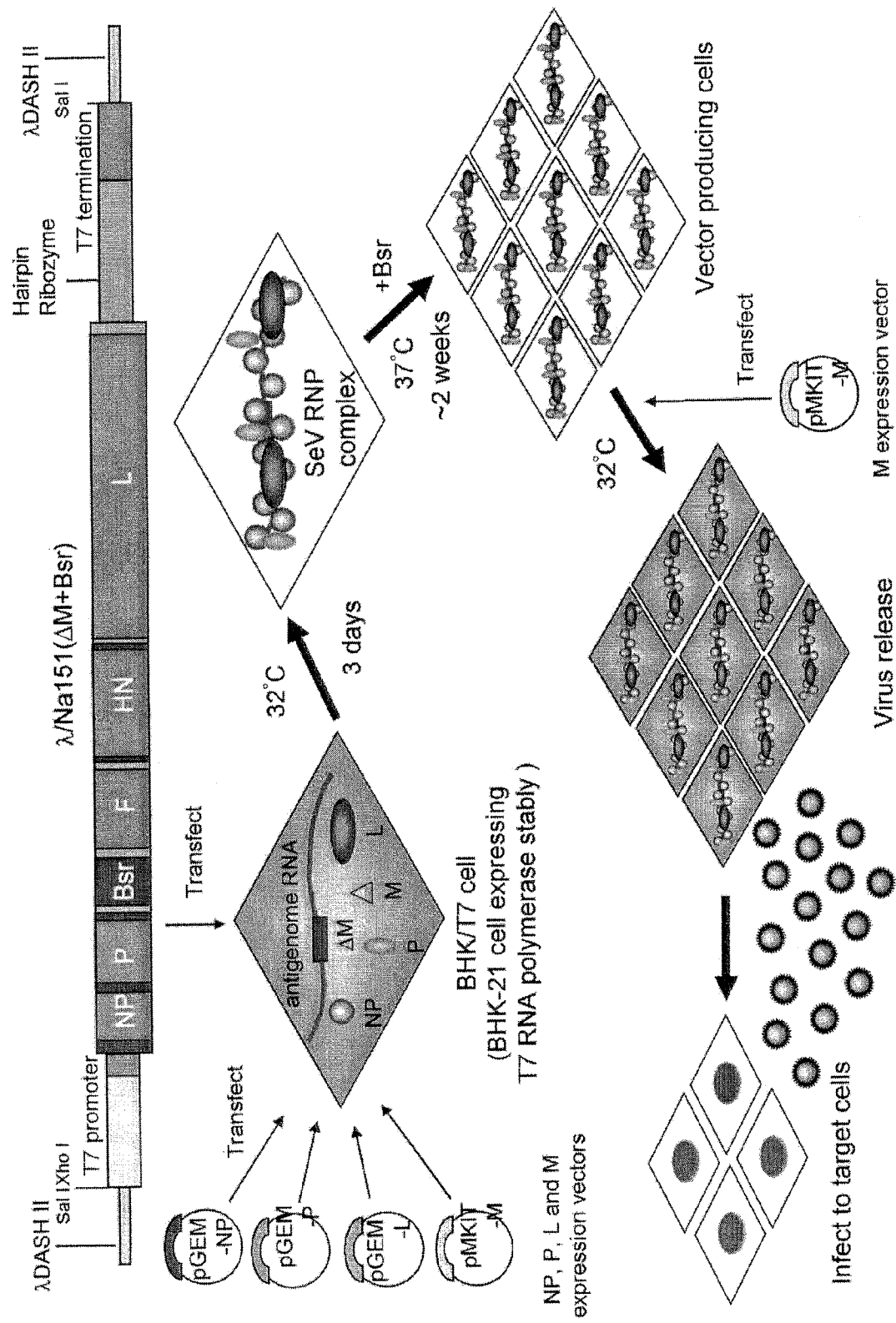

Separating Defective Recombinant Sendai Virus Producing Cells Using Blasticidin A defective recombinant Sendai virus was produced from the recombinant Sendai virus producing vector obtained in Example 13 by the same method as in Example 12. In the production, the defected gene expressing plasmid produced in Example 14 was simultaneously transfected (FIG. 16).

As shown in FIG. 17, M gene defected, F gene defected, and HN gene defected recombinant Sendai virus producing cells were successfully separated. The fact that the virus producing cells were grown in a medium containing blastcidin for 2 months established that these defective recombinant Sendai viruses preserve persistent infectiveness.

Example 16

Collecting and Infecting with Defective Recombinant Sendai Virus

The defective recombinant Sendai virus producing cells obtained in Example 15 were transfected with the defected gene expressing plasmid produced in Example 14 by using Lipofectamine 2000. The cells were washed 24 hours later. After that, a DMEM medium containing 10% serum was added, and the mixture was further cultured at 32° C. for 3 days. Thereafter, the culture supernatant was collected and filtered with a 0.45-μm filter. After the filtering, 7.5 μg/ml of trypsin was added, and the mixture was added to a medium for new target cells and cultured at 32° C. for 2 days. Thereafter, the cells were moved to a medium containing 10 μg/ml of blastcidin for further culturing. Blastcidin-resistant cells were separated as recombinant Sendai virus introduced cells (FIG. 16). The titers of the defective recombinant Sendai viruses in the culture supernatant were compared by measuring the number of colonies of the blastcidin-resistant cells.

As depicted in FIG. 18, it was established that the defective recombinant Sendai virus is collectable from the supernatant obtained by culturing producing cells and able to infect other cells and tissues. In addition, the fact that no virus was generated from the expressing plasmid unless a defected gene was supplemented established that the defective recombinant Sendai virus is non-transmissible.

Example 17

Producing Exogenous Gene Inserted, M Gene Defected Sendai Virus Vector (1) Integrating Exogenous Gene Insertion Site A Not I recognition sequence was inserted immediately before the Nhe I recognition sequence inserted to SeV: 3655 in pBSK/151(E-C;ΔM+Bsr), by using 5'-AGGGTGAAA-GAAATGCGGCCGCTTGCTAGCAGAATATA-3' (SEQ ID NO 53 (sense strand) in the Sequence Listing) and 5'-TATAT-TCTGCTAGCAAGCGGCCGCATTTCTTTCACCCT-3' (SEQ ID NO 54 (antisense strand) in the Sequence Listing), obtain pBSK/151(E-C;ΔM+Bsr;Mp+Not). Furthermore, after SeV: 5335 in pBSK/151(E-C;ΔM+Bsr;Mp+Not), a sequence derived from strain C1.151 was inserted to SeV: 5336-6299, and a sequence derived from Nagoya strain was inserted to SeV: 6300-10484, to obtain pBSK/Na151F (E-E; ΔM+Bsr;Mp+Not).

(2) Inserting EGFP Gene

SeV: 1-2871 (Xho I to EcoR I) in pBSK/Na(3'+X+3G) and SeV: 2871-3655 (EcoR I to Not I) in pBSK-N/151(E-C+NN) were stringed to obtain pBSK/Na(3'-Mp+NN). An EGFP gene was amplified from pEGFP-C1 by using two primers, 5'-ACTAGCTAGCCACCATGGTGAGCAAGGGCG-3' (SEQ ID NO (N terminus end) in the Sequence Listing) and 5'-ACTTGCGGCCGCGATGAACTTTCAC-CCTAAGTTTTTCTTAGAC GGCCGCTTTACTTGTA-CAGCTCGTCCA-3' (SEQ ID NO 14 (C terminus end) in the Sequence Listing) as EGFP gene insertion primers. The termini of the obtained double-stranded DNA were cleaved with Nhe I and Not I and inserted between Nhe I and Not I in pBSK/Na(3'-Mp+NN) to obtain pBSK/Na(3'-Mp+GFP).

(3) Assembling Recombinant Sendai Virus Producing Vector

Figure 21:
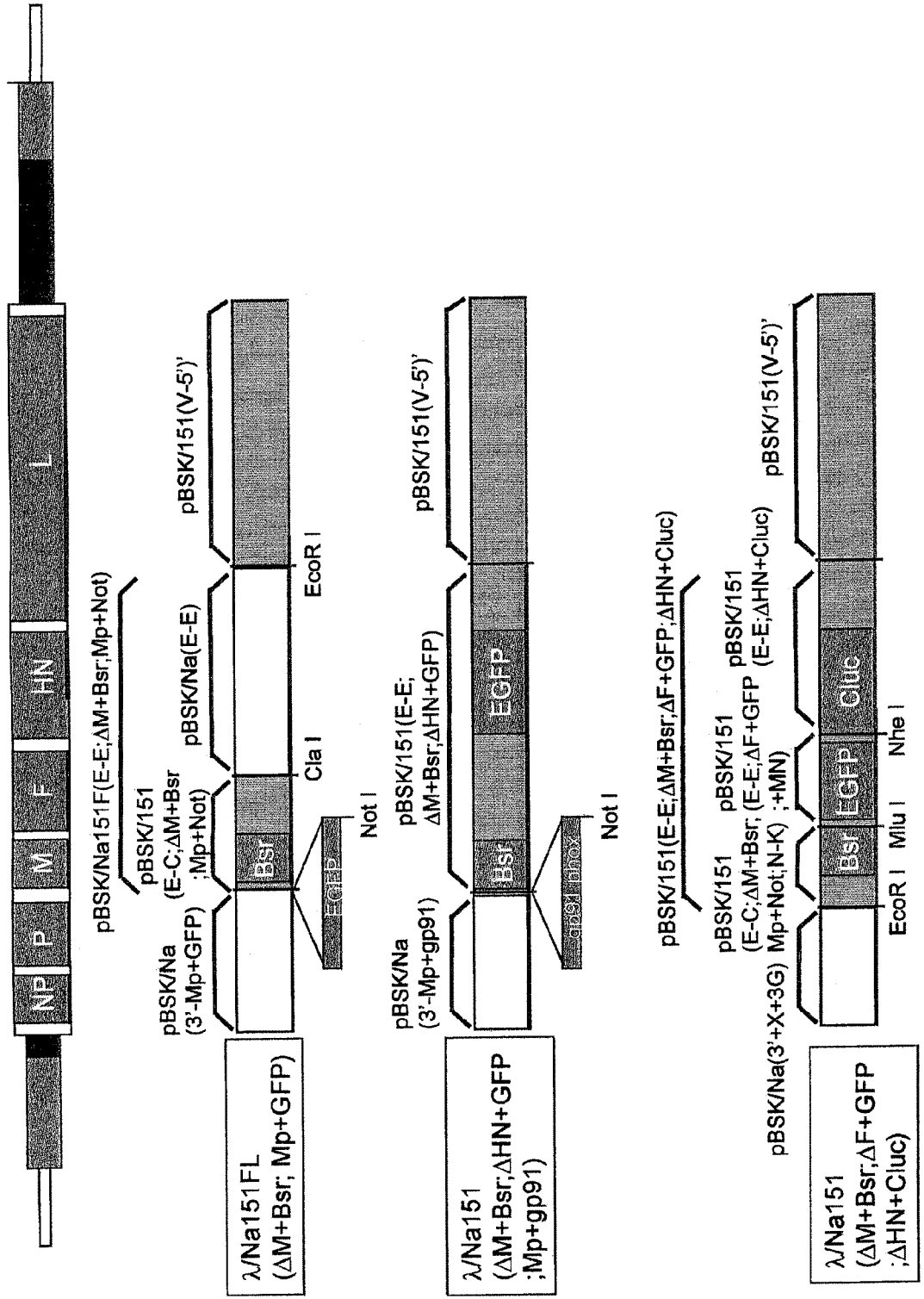

Among the plasmids obtained so far, the T7 promoter sequence to SeV: 1-3655+GFP (Xho I to Not I) was cut out from pBSK/Na(3'-Mp+GFP). SeV: 3655-10484 (Not I-EcoRI) was cut out from pBSK/Na151F (E-E;ΔM+Bsr; Mp+Not). SeV: 10480-15384 to a T7 RNA polymerase termination sequence was cut out from pBSK/151(V-5')'. The fragments thus cut out were cloned in this order into λDASHII to obtain λ/Na151FL(ΔM+Bsr;Mp+GFP) (FIG. 21).

(4) Reconstituting Virus Vector from Recombinant Sendai Virus Producing Vector

A defective recombinant Sendai virus (rNa151FL(ΔM+Bsr;Mp+GFP)) was produced from λ/Na151FL(ΔM+Bsr;Mp+GFP) by the same method as in Example 15. Furthermore, a vector was collected from the obtained vector producing cells for infection by the method as in Example 16.

Figure 19:
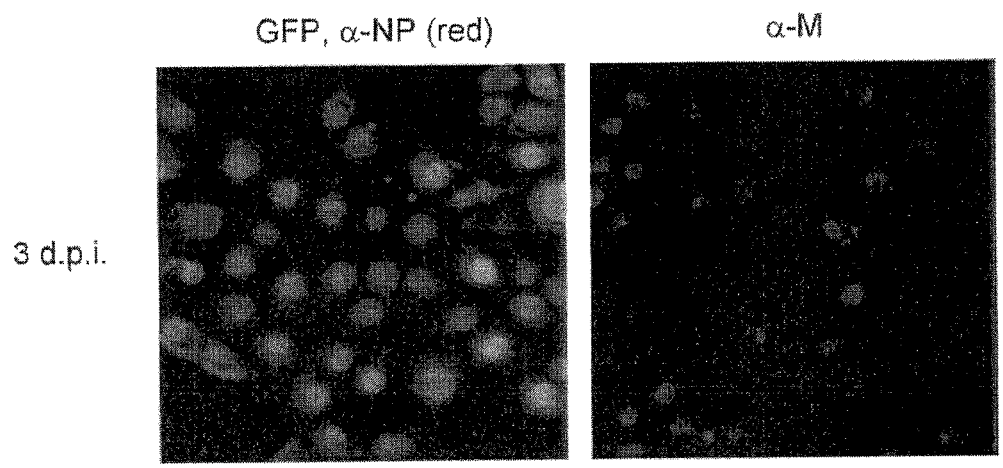

As shown in FIG. 19, it was established that an M gene defected, EGFP expressing, non-transmissible Sendai virus vector can be produced and upon infecting other cells, persistently express EGFP genes.

Example 18

Producing Plural-Gene-Defected Recombinant Sendai Virus (1) Producing M and F Gene Defected cDNA Amplification was carried out from pEGFP-C1 by using two primers, 5'-ACGAAGATCTCCGGTCGCCACCATGGTGAG-3' (SEQ ID NO 56 (N terminus end) in the Sequence Listing) and 5'-ACGAAGATCTTTACTTGTACAGCTCGTCCA-3' (SEQ ID NO 57 (C terminus end) in the Sequence Listing). An EGFP gene cleaved with Bgl II was inserted in place of a blastcidin-resistant gene in pBSK/151 (E-E;ΔF+Bsr), to obtain pBSK/151(E-E;ΔF+GFP).

A Mlu I recognition sequence was inserted after SeV: 4722 in pBSK/151(E-E;ΔF+GFP) by using a set of Mlu I recognition sequence introducing primers, 5'-CTGTAAATGTGCACGCGTCAGAGACCTGCA-3' (SEQ ID NO 33 (sense strand) in the Sequence Listing) and 5'-TGCAGGTCTCTGACGCGTGCACATTTACAG-3' (SEQ ID NO 34 (antisense strand) in the Sequence Listing), to obtain pBSK/151 (E-E;ΔF+GFP;+Mlu). SeV: 2871-4722 (EcoR I to Mlu I) in pBSK/151(E-C;ΔM+Bsr) and SeV: 4722-10480 (Mlu I to EcoR I) in pBSK/151(E-E;ΔF+GFP;+Mlu) were stringed to obtain pBSK/151(E-E;ΔM+Bsr; ΔF+GFP).

(2) Producing F and HN Gene Defected cDNA

A Nhe I recognition sequence was inserted after SeV: 6667 in pBSK/151(E-E; ΔF+GFP) by using a set of Nhe I recognition sequence introducing primers, 5'-GCGGTATTTTAGCTAGCATCTCAAACAAGC-3' (SEQ ID NO 36 (sense strand) in the Sequence Listing) and 5'-GCTTGTTTGAGATGCTAGCTAAAATACCGC-3' (SEQ ID NO 37 (antisense strand) in the Sequence Listing), to obtain pBSK/151(E-E; ΔF+GFP;+Nhe). SeV: 2871-6667 (EcoR I to Nhe I) in pBSK/151(E-E;ΔF+GFP;+Nhe) and SeV: 6667-10480 (Nhe I to EcoR I) in pBSK/151(E-E;ΔHN+Bsr) were stringed to obtain pBSK/151(E-E;ΔF+GFP;ΔHN+Bsr).

(3) Producing M and HN Gene Defected cDNA

An EGFP gene was amplified from pEGFP-C1 by using two primers, 5'-ACTAGCTAGCCACCATGGTGAGCAAGGGCG-3' (SEQ ID NO 55 (N terminus end) in the Sequence Listing) and 5'-GGTCCACGCGTTTTACTTGTACAGCTCGTCCA-3' (SEQ ID NO 58 (C terminus end) in the Sequence Listing). The termini of the obtained double-stranded DNA were cleaved with Nhe I and Mlu I and inserted between Nhe I and Mlu I in pBSK/151(E-E;ΔHN+Bsr) to obtain pBSK/151(E-E;ΔHN+GFP). SeV: 2871-5335 (EcoR I to Cla I) in pBSK/151(E-C;ΔM+Bsr;Mp+Not) and SeV: 5335-10480 (Cla I to EcoR I) in pBSK/151(E-E;ΔHN+GFP) were stringed to obtain pBSK/151(E-E;ΔM+Bsr;ΔHN+GFP).

(4) Producing M, F, and HN Genes Defected cDNA

A Nhe I recognition sequence in pBSK/151(E-C;ΔM+Bsr;Mp+Not) was modified to a Kas I recognition sequence by using 5'-AAATGCGGCCGCTTGGCGCCAGAATATATGAAAA-3' (SEQ ID NO 59 (sense strand) in the Sequence Listing) and 5'-TTTTCATATATTCTGGCGCCAAGCGGCCGCATTT-3' (SEQ ID NO 60 (antisense strand) in the Sequence Listing), obtain pBSK/151(E-C;ΔM+Bsr;Mp+Not;N-K).

A Mlu I recognition sequence in pBSK/151(E-E;ΔHN+Bsr) was modified to a Sph I recognition sequence by using 5'-TACCCGAAATTAAAGCATGCGTCGGCTTTGCTGA-3' (SEQ ID NO 61 (sense strand) in the Sequence Listing) and 5'-TCAGCAAAGCCGACGCATGCTTTAATTTCGGGTA-3' (SEQ ID NO 62 (antisense strand) in the Sequence Listing), to obtain pBSK/151(E-E; ΔHN+Bsr;M-S).

A secretion luciferase gene was amplified from pCLm (ATTO) by using two primers, 5'-ACTAGCTAGCCCTTATGAAGACCTTAATTCTTGC-3' (SEQ ID NO 63 (N terminus end) in the Sequence Listing) and 5'-GGTCCGCATGCTCTATTTGCATTCATCTGGTACT-3' (SEQ ID NO 64 (C terminus end) in the Sequence Listing). The termini of the obtained double-stranded DNA were cleaved with Nhe I and Sph I and inserted between Nhe I and Sph I in pBSK/151(E-E;ΔHN+Bsr;M-S) to obtain pBSK/151(E-E;ΔHN+Cluc).

A Mlu I recognition sequence was inserted after SeV: 4722 in pBSK/151(E-E;ΔF+GFP;+Nhe) by using 5'-CTGTAAATGTGCACGCGTCAGAGACCTGCA-3' (SEQ ID NO 33 (sense strand) in the Sequence Listing) and 5'-TGCAGGTCTCTGACGCGTGCACATTTACAG-3' (SEQ ID NO 34 (antisense strand) in the Sequence Listing), to obtain pBSK/151(E-E;ΔF+GFP;+MN).

Among these plasmids, SeV: 2871-4722 (EcoR I to Mlu I) in pBSK/151(E-C;ΔM+Bsr;Mp+Not;N-K), SeV: 4722-6667 (Mlu I to Nhe I) in pBSK/151(E-E;ΔF+GFP;+MN), and SeV: 6667-10484 (Nhe I to EcoR I) in pBSK/151(E-E;ΔHN+Cluc) stringed to obtain pBSK/151(E-E;ΔM+Bsr;ΔF+GFP;ΔHN+Cluc).

(5) Assembling Recombinant Sendai Virus Producing Vector

Figure 20:
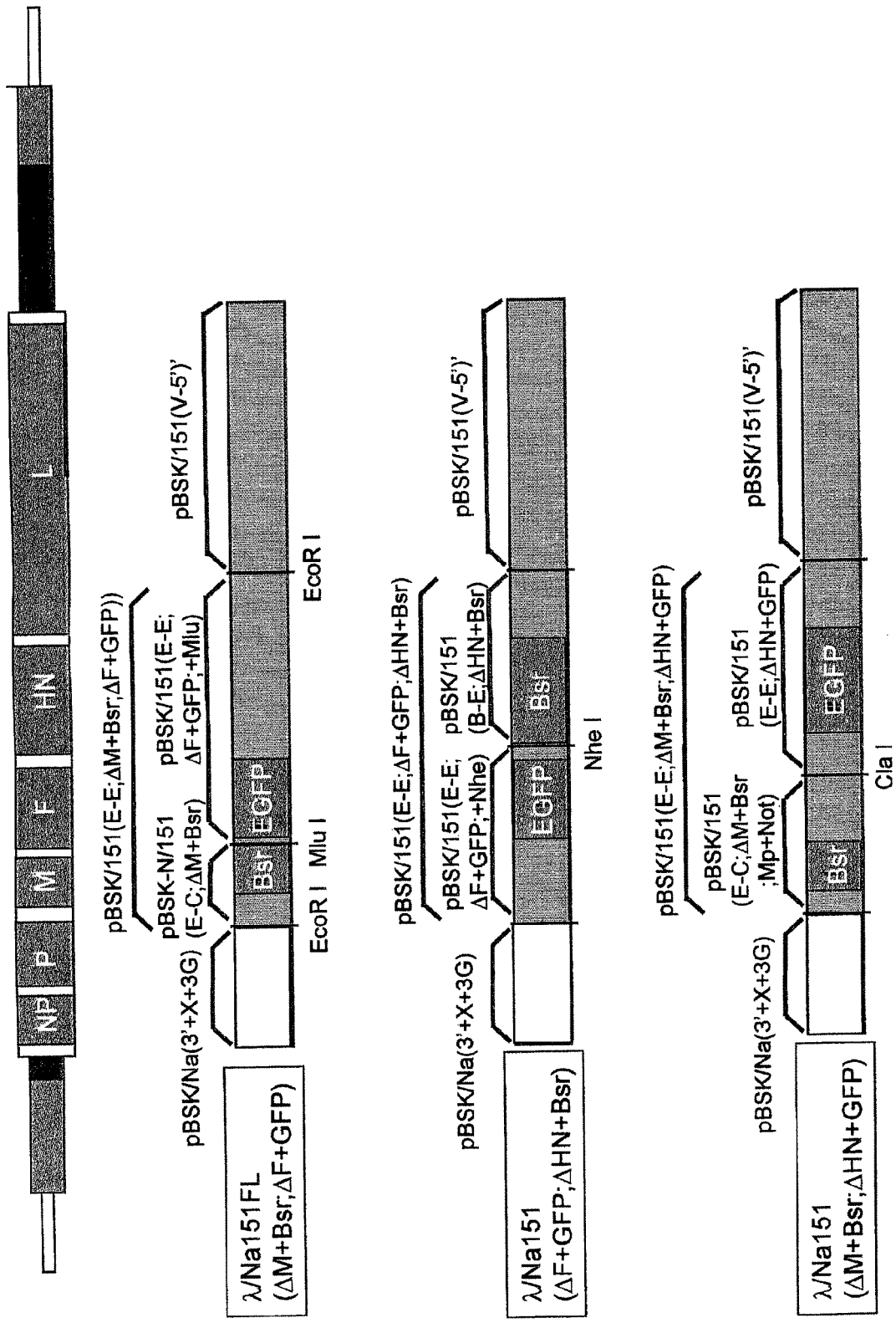

The full length cDNA of Sendai virus (λ/Na151(ΔM+Bsr; ΔF+GFP), λ/Na151(ΔF+GFP;ΔHN+Bsr), λ/Na151(ΔM+Bsr;ΔHN+GFP), λ/Na151(E-E;ΔM+Bsr;ΔF+GFP;ΔHN+Cluc)) was cloned by the same method as in Example 1 using the M gene defected, F gene defected, and HN gene defected cDNAs (FIG. 20).

(6) Reconstituting Recombinant Sendai Virus from Recombinant Sendai Virus Producing Vector A defective recombinant Sendai virus (rNa151(ΔM+Bsr; ΔF+GFP), rNa151(ΔF+GFP;ΔHN+Bsr), rNa151(ΔM+Bsr; ΔHN+GFP), rNa151(E-E;ΔM+Bsr;ΔF+GFP;ΔHN+Cluc)) was produced from the recombinant Sendai virus producing vector by the same method as in Example 15. A vector was collected by the method as in Example 16 from the further obtained vector producing cells. The collected vector was used for infection.

Figure 22:
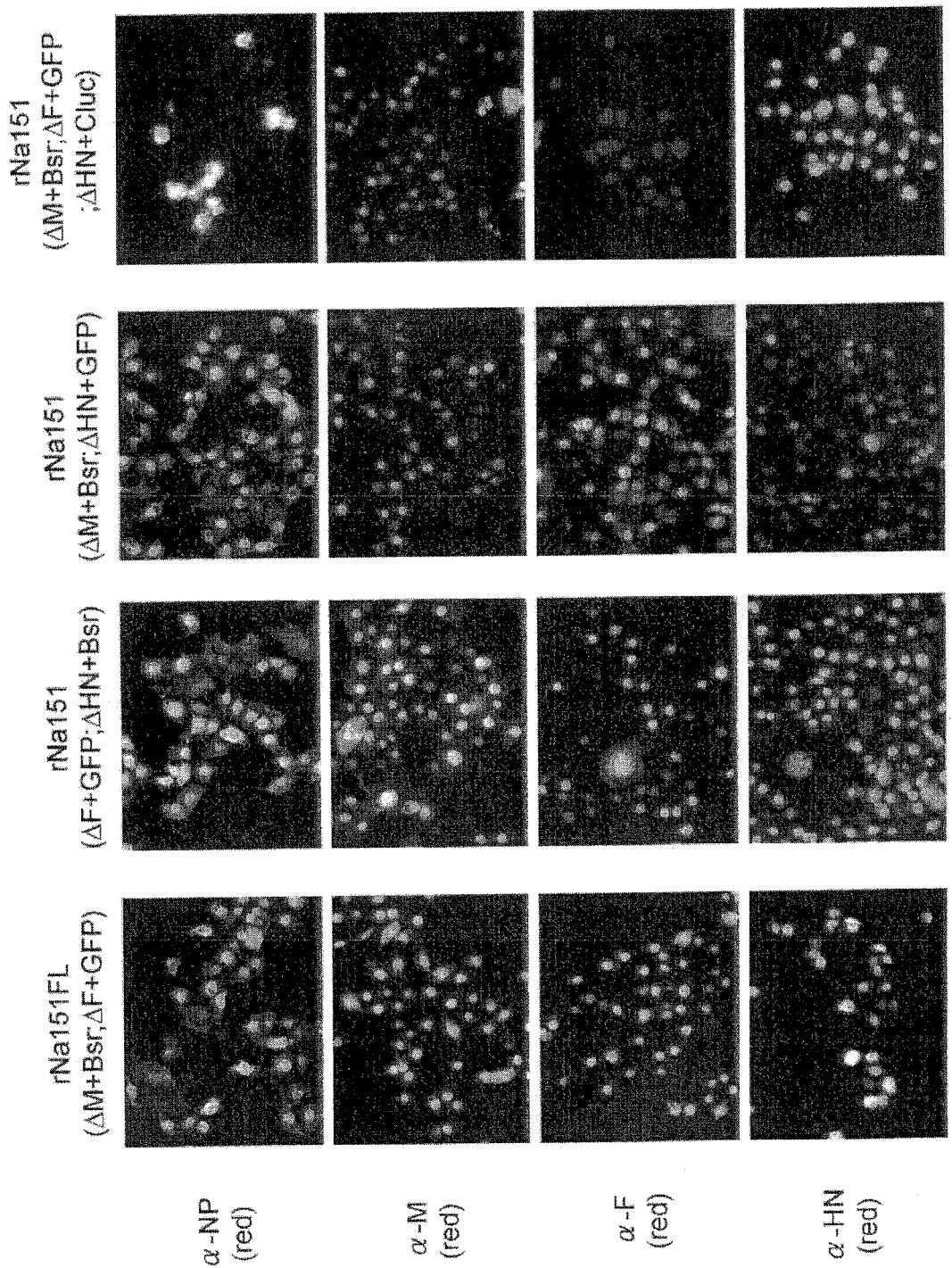

As shown in FIG. 22, it was established that any plural-gene-defected recombinant Sendai virus can be produced and that other cells can be infected by supplementing defected genes to virus producing cells.

Example 19

Confirming Infection Sustainability of Plural-Gene-Defected Recombinant Sendai Virus LLCMK$_2$ cells, CV-1 cells, and HL60 cells, were infected with the plural-gene-defected recombinant Sendai virus obtained in Example 18 and cultured for about 2 weeks under a condition that blastcidin was added. Subsequently, blastcidin-resistant plural-gene-defected recombinant Sendai virus introduced cells were cultured under different conditions, where blastcidin is added and no blastcidin is added. The cells were separated the numbers of days shown in FIG. 23 after the start of the culturing in no blastcidin. Infection with Sendai virus was confirmed by a fluorescent antibody test using an antibody against Sendai virus, and the ratio of recombinant Sendai virus infected cells to all cells in the microscope field of view was calculated.

As a result, as depicted in FIG. 23, most of the gene-defected recombinant Sendai viruses did not show much change in the persistent infectiveness when compared to the non-defected type under the condition where no blastcidin was added. It was noted however that recombinant Sendai viruses (rNa151(ΔHN+Bsr) and rNa151(ΔF+GFP;ΔHN+Bsr) having a blastcidin-resistant gene inserted into an HN gene showed a tendency for reduced persistent infectiveness.

These results established that persistent infectiveness is basically preserved even if genes are defected. Conversely, it was expected that designing a vector based on a structure from which a genome could easily be lost would enable production of a persistently infective Sendai virus vector with adjusted expression sustainability which sustained persistent expression for some period before the genome was lost when exogenous gene expression disappeared.

Under the condition where blastcidin was added, any gene-defected recombinant Sendai virus persistently infected cells.

Example 20

Quantifying Released Virus-Like Particles from Plural-Gene-Defected Recombinant Sendai Virus Infected Cells The defective recombinant Sendai virus producing cells obtained in Examples 15 and 18 were cultured at 32° C. for 3 days, and their culture supernatant was collected. The collected supernatant was processed with 0.1% Triton X-100, subsequently diluted with 5% skim milk/PBS, and added to a 96-well plate coated with a rabbit anti-Sendai virus antibody. The plate was let sit at room temperature for 1 hour and washed 4 times in PBS before adding an HRP-coupled, mouse anti-Sendai virus NP protein antibody. The plate was then let sit at room temperature for another hour, washed 4 times in PBS, and treated with TMB to develop color. A standard curve was produced using Sendai virus particles of known quantity. The number of virus particles in the culture supernatant was calculated based on the standard curve.

Figure 24:
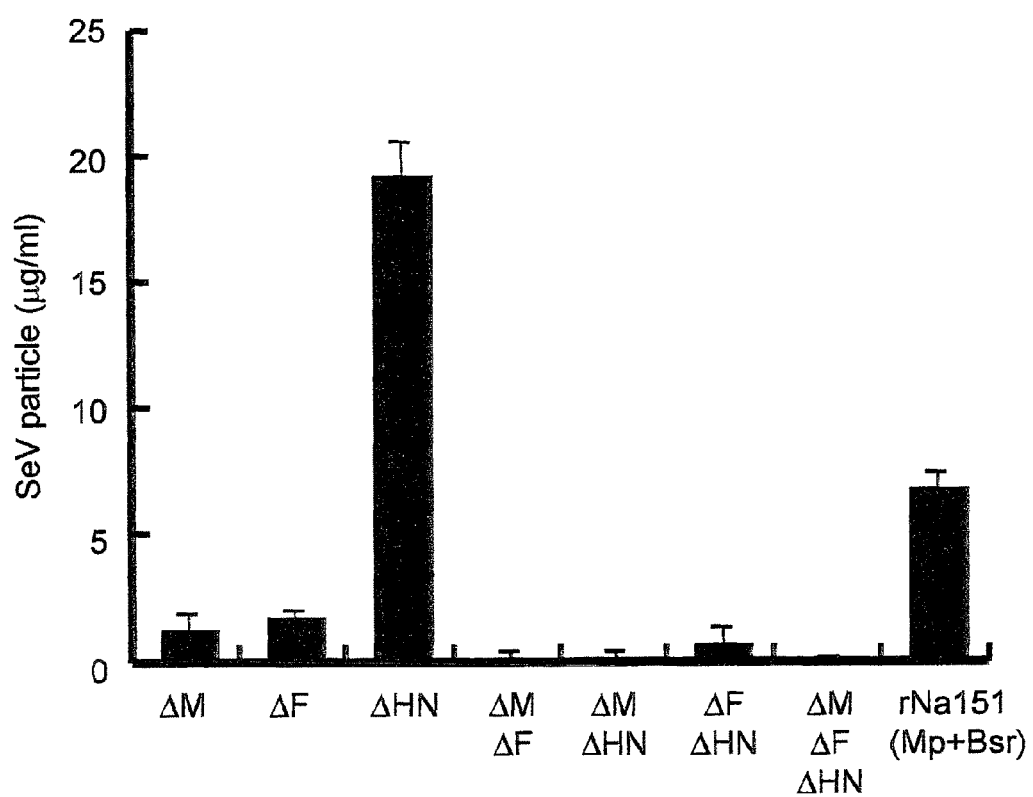

As depicted in FIG. 24, the result established that virus particles are released by recombinant Sendai viruses in which one of the M, F, and HN genes is singly defected. These particles, since exhibiting no infectivity as shown in Example 16, were thought to be virus-like particles (VLPs). It was also established that defecting plural genes restrains VLP release and that defecting three genes almost completely prohibits generation of the particles.

Example 21

Generating Protein Using Non-Transmissible, Persistently Infective Sendai Virus Vector (1) Assembling Exogenous Gene Inserting M, F Gene Defected Vector To insert a transcription termination signal and a transcription start signal for Nhe I, EcoR I, and Not I recognition sequences and Sendai virus, oligo DNA 5'-CTAGCGAATTCGCGGCCGCCGTACGGTAAAGATTTAAGAAAAACTTAGGGTGAAAGTTCAT (SEQ ID NO 71 in the Sequence Listing) and 5'-GGCCATGAACTTTCACCCTAAGTTTTTCTTAAATCTTTACCGTA CGGCGGCCGCGAATTCG (SEQ ID NO 72 in the Sequence Listing) was inserted to the Nhe I-Not I site in pBSK/151(Nhe-Not) by annealing, to obtain pBSK/151(Nhe I-EcoR I-Not I). pBSK/151(Nhe I-EcoR I-Not I) was cleaved with restriction enzymes Xho I and Kas I to separate SeV; 1 to 1899 (Xho I to Kas I) from the T7 promoter sequence. The SeV; 1 to 1899 (Xho I to Kas I) was integrated to the pBSK-N/151(E-C+NN) cleaved by the enzymes (pBSK/151(Nhe I-EcoR I-Not I)Le-M). SeV; 1 to 3558 fragment (Xho I to Xma I) was cut out from the T7 promoter sequence prepared by cleaving pBSK/151(Nhe-Eco-Not)Le-M with Xho I and Xma I. SeV; 3559 to 10484 fragment (Xma I-EcoR I) was cut out from pBSK/151(E-E;ΔM+Bsr; ΔF+GFP). SeV: 10479-15384 to a T7 RNA polymerase termination sequence was cut out from pBSK/151(V-5')'. The fragments thus cut out were recloned in this order into λDASHII (STRATAGENE) to obtain an exogenous gene inserting MF defected vector λ/151(NPp+Nhe I-EcoR I-Not I;ΔM+Bsr;ΔFp+GFP).

(2) Assembling α-Galactosidase a Gene Expressing Recombinant Sendai Virus Producing Vector A α-galactosidase A gene was amplified from a HeLa cDNA library (Stratagene) by using two primers, 5'-CGGAATTCGTGACAATGCAGCTGAGGAACCCAG (SEQ ID NO (N terminus end) in the Sequence Listing) and 5'-GTGCGGCCGCTTAAAGTAAGTCTTTTAATGACATCTGC-3' (SEQ ID NO 74 (C terminus end) in the Sequence Listing). The termini of the obtained double-stranded DNA were cleaved with EcoR I and Not I and inserted between EcoR I and Not I in pBlue script II to obtain pBSK-α-gal A. The α-galactosidase A gene cut out from pBSK-α-gal A with EcoR I and Not I was inserted between EcoR I-Not I in λ/151(NPp+Nhe I-EcoR I-Not I;ΔM+Bsr;ΔFp+GFP) to obtain λ/151(NPp+α-gal;ΔM+Bsr;ΔFp+GFP).

(3) Reconstituting Virus Vector from Recombinant Sendai Virus Producing Vector

A defective recombinant Sendai virus (r151(NPp+α-gal;ΔM+Bsr;ΔFp+GFP)) was produced from λ/151(NPp+α-gal;ΔM+Bsr;ΔFp+GFP) by the same method as in Example 14.

(4) Quantifying Generated α-galactosidase A

Figure 26:
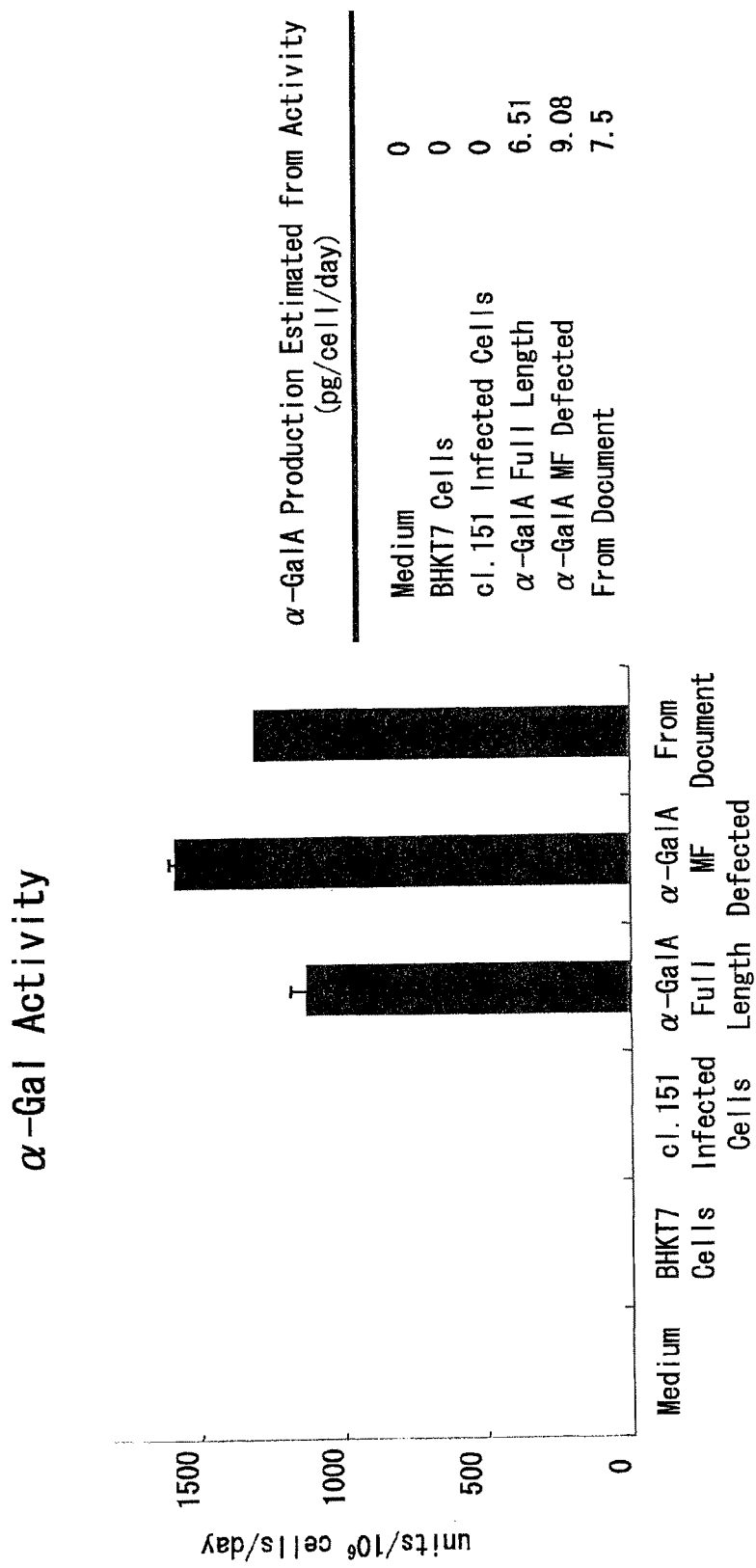

As depicted in FIG. 26, α-galactosidase A activity obtained from a culture solution for α-galactosidase A gene expressing recombinant Sendai virus vector producing cells was about 1,500 units/cell/day for an M, F gene defected vector and about 1,100 units/cell/day for a vector, derived from a C1.151 full length cDNA, in which no genes are defected. The quantity of expression, converted with respect to protein generation of about 1,300 units/10$^6$ cells/day (7.5 pg/cell/day) achieved by amplifying the gene copy number using a DHFR gene in CHO cells (Ioannou et. al. (1992) J. Cell Biol. 119, 1137-1150), was about 9.1 pg/cell/day. The non-transmissible, persistently infective Sendai virus vector achieved such a high rate of expression in a single infection. It was thus established that the virus achieves a high rate of expression in a simple and convenient manner and is useful in generation of protein using cultured cells.

Example 22

Producing Gp91Phox Expressing, Non-Transmissible, Persistently Infective Sendai Virus Vector (1) Inserting gp91phox Gene A gp91phox gene was amplified from gp91phox-pCI-neo using two primers, 5'-ACTAGCTAGCTGCCACCATGGG-GAACTGGGCTGTGAATGA-3' (SEQ ID NO 65 (N terminus end) in the Sequence Listing) and 5'-ACTTGCGGC-CGCGATGAACTTTCACCCTAAGTTTTTCTTAAAG AGACAAGTTAGAAGTTT-3' (SEQ ID NO 66 (C terminus end) in the Sequence Listing) as gp91phox gene insertion primers. The termini of the obtained double-stranded DNA were cleaved with Nhe I and Not I and inserted between Nhe I and Not I in pBSK/Na(3'-Mp+NN) to obtain pBSK/Na(3'-Mp+gp91).

(2) Assembling Recombinant Sendai Virus Producing Vector

A T7 promoter sequence to SeV: 1-3655+GFP (Xho I to Not I) was cut out from pBSK/Na(3'-Mp+gp91). SeV: 3655-10484 (Not I-EcoRI) was cut out from pBSK/151(E-E;ΔM+Bsr;ΔHN+GFP). SeV: 10480-15384 to a T7 RNA polymerase termination sequence (EcoR I to Sal I) was cut out from pBSK/151(V-5')'. The fragments thus cut out were cloned in this order into λDASHII to obtain λ/Na151FL(ΔM+Bsr; ΔHN+GFP; Mp+gp91) (FIG. 21).

(3) Reconstituting Virus Vector from Recombinant Sendai Virus Producing Vector

A defective recombinant Sendai virus (rNa151FL(ΔM+Bsr; ΔHN+GFP;Mp+gp91)) was produced from λ/Na151FL (ΔM+Bsr; ΔHN+GFP;Mp+gp91) by the same method as in Example 15. A vector was collected by the method as in Example 16 from the further obtained vector producing cells. The collected vector was used for infection.

As shown in FIG. 27, it was established that a gp91phox expressing, non-transmissible, persistently infective Sendai virus vector can be produced and that a gp91phox gene, along with an EGFP gene, is persistently expressed even if other cells are infected.

Example 23

Introducing Gene Persistently to Hematopoietic Stem Cells Using Non-Transmissible, Persistently Infective Sendai Virus Vector (1) Separating Hematopoietic Stem Cells A thigh bone and a cervical bone were separated from a 10- to 14-week-old mouse, and myelogenous cells were separated from the bones. The separated myelogenous cells were refined using Lymphoprep, and subjected to negative selection using anti-B-220, CD4, CD8a, Gr1, CD11b, TER119, and CD2 antibodies and then to positive selection using an anti-c-kit antibody, to separate c-kit (+), linage (−) cells (KL cells). For human hematopoietic stem cells, AC133 (+), linage (−) cells was separated by a similar method from umbilical blood.

(2) Introducing Gene to Hematopoietic Stem Cells

A non-transmissible, persistently infective Sendai virus vector for use in gene introduction was suspended in Stem-Pro-34 SFM medium (GIBCO) and added to the mouse KL cells. The cells were let sit at 37° C. for 4 hours and plated on a MethoCult medium at $5 \times 10^2$ cells per plate. The cells were cultured at 37° C. for about 2 weeks. Formed colonies were observed to see if a gene introduced by the vector was expressed and to examine differentiation tendency as an example.

For human hematopoietic stem cells, AC133 (+), linage (−) cells were infected with the non-transmissible, persistently infective Sendai virus vector by a similar method. Subsequently, OP9 cells were exposed to radiation and cultured for about 5 weeks as feeder cells. Subsequently, the cells were moved to a MethoCult medium to form colonies. The colonies were observed to examine expression sustainability at about 7 weeks.

Figure 28:
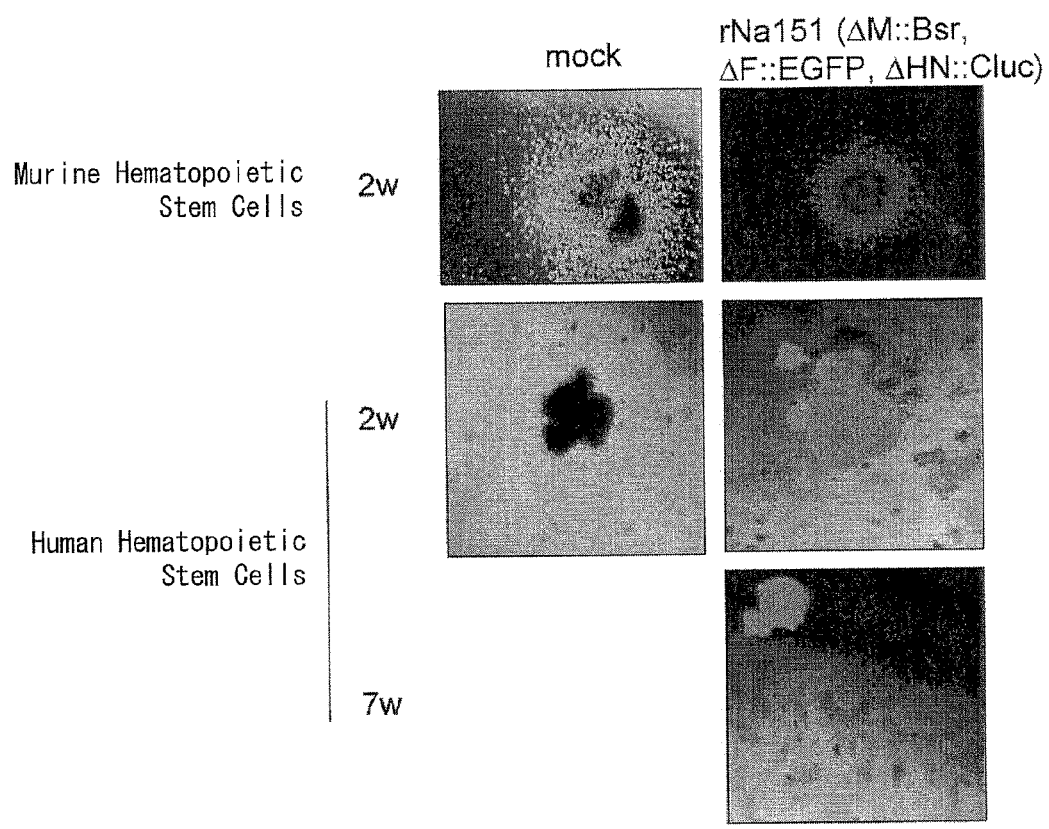

The result, as shown in FIG. 28, confirmed persistent expression of a vector-derived exogenous gene in colonies which were presumed to be derived from the hematopoietic stem cells for both mouse and human cases. The observation established that the non-transmissible, persistently infective Sendai virus vector is capable of persistently introducing a gene to hematopoietic stem cells.

Example 24

Multiple Infection with Non-Transmissible, Persistently Infective Sendai Virus Vector (1) Producing Exogenous Gene Inserting, Three Gene Defected cDNA An Sph I recognition sequence was modified to an Age I recognition sequence by using 5'-TGAATGCAAATA-GAACCGGTGTCGGCTTTGCTGA-3' (SEQ ID NO 75 (sense strand) in the Sequence Listing) and 5'-TCAG-CAAAGCCGACACCGGTTCTATTTGCATTCA-3' (SEQ ID NO 76 (antisense strand) in the Sequence Listing) on pBSK/151(E-E;ΔM+Bsr;ΔF+GFP;ΔHN+Cluc), to obtain pBSK/151(E-E;ΔM+Bsr;ΔF+GFP;ΔHN+ClucAge).

A gp91 phox gene was amplified from gp91phox-pCI-neo by using two primers, 5'-ACTAGCTAGCTGCCAC-CATGGGGAACTGGGCTGTGAATGA-3' (SEQ ID NO 65 (N terminus end) in the Sequence Listing) and 5'-GGTC-CACCGGTGTTAGAAGTTTTCCTTGTTGA-3' (SEQ ID NO 77 (C terminus end) in the Sequence Listing). The termini of the obtained double-stranded DNA were cleaved with Nhe I and Age I and inserted between Nhe I and Age I in pBSK/151(E-E;ΔM+Bsr;ΔF+GFP;ΔHN+ClucAge) to obtain pBSK/151(E-E;ΔM+Bsr;ΔF+GFP;ΔHN+gp91).

A Zeosin-resistant gene was amplified from pUT58 by using two primers, 5'-AATTGGCGCCAGCCACCATGGC-CAAGTTGACCAGTGCCGT-3' (SEQ ID NO 78 (N terminus end) in the Sequence Listing) and 5'-GGTC-CACGCGTTTCAGTCCTGCTCCTCGGCCACGAAGTG-3' (SEQ ID NO 79 (C terminus end) in the Sequence Listing). The termini of the obtained double-stranded DNA were cleaved with Kas I and Mlu I and inserted in place of a Bsr gene in pBSK/151(E-C;ΔM+Bsr;Mp+Not;N-K), to obtain pBSK/151(E-C;ΔM+Zeo).

Amplification was carried out from phKO1-MN1 (MBL) by using two primers, 5'-ACGAAGATCTAGCCTAGGGG-GACCATGGTGAGCGTGATCA-3' (SEQ ID NO 80 (N terminus end) in the Sequence Listing) and 5'-ACGAAGATCT-GACGTCTTCAGCAGTGGGCCACGGCGT-3' (SEQ ID NO 81 (C terminus end) in the Sequence Listing). The hKO gene cleaved with Bgl II was inserted in place of a GFP gene in pBSK/151(E-E;ΔF+GFP;+MN)) to obtain pBSK/151(E-E;ΔF+hKO;+MN). SeV: 2871-4722 (EcoR I to Mlu I) in pBSK/151(E-C;ΔM+Zeo), SeV: 4722-6667 (Mlu I to Nhe I) in pBSK/151(E-E;ΔF+hKO;+MN), and SeV: 6667-10484

(Nhe I to EcoR I) in pBSK/151(E-E;ΔHN+Cluc) were stringed to obtain pBSK/151(E-E;ΔM+Zeo;ΔF+hKO;ΔHN+Cluc).

(2) Assembling Recombinant Sendai Virus Producing Vector

Figure 25:
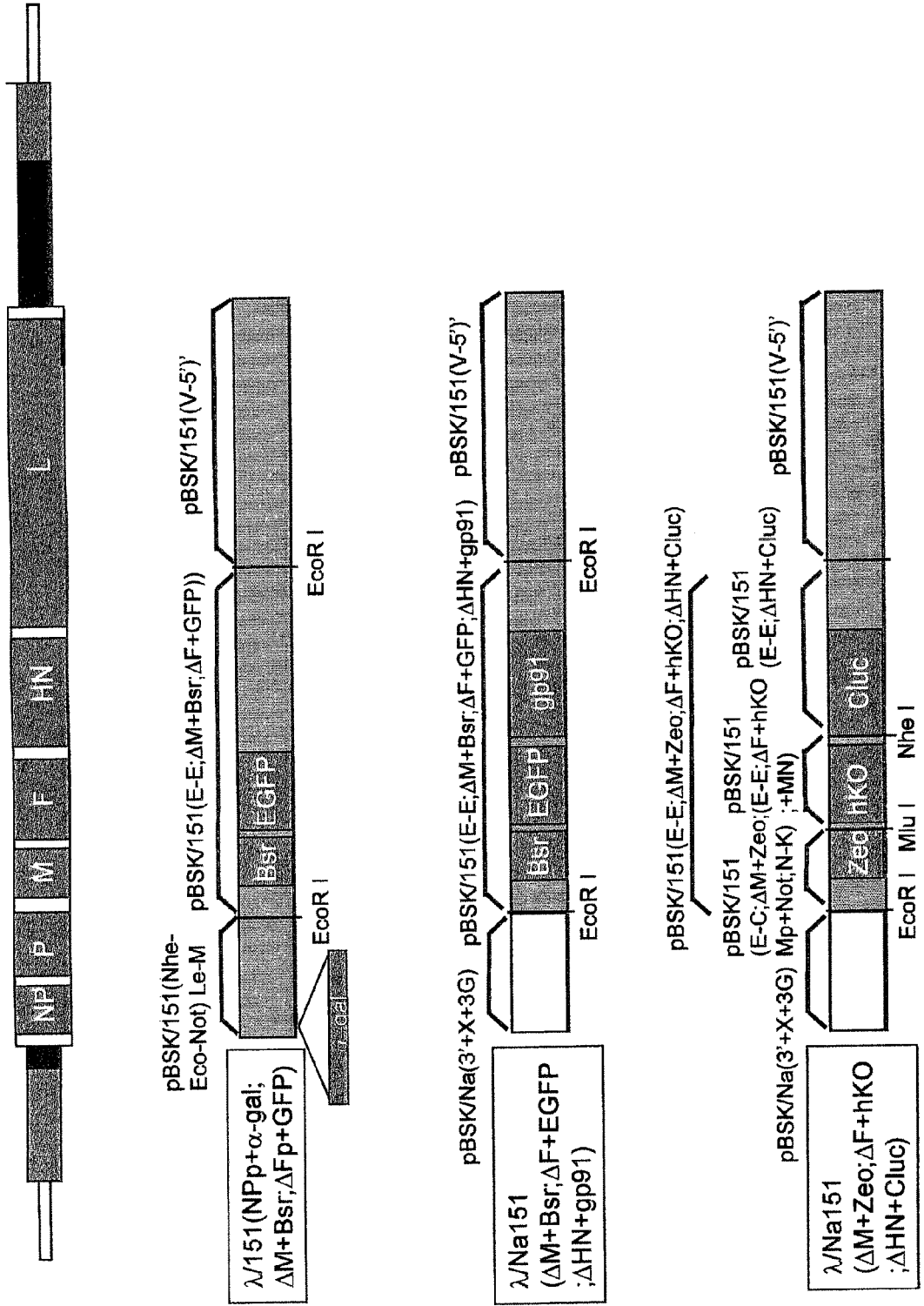

A full length cDNA of Sendai virus (λ/Na151(E-E;ΔM+Bsr;ΔF+GFP;ΔHN+gp91), λ/Na151(E-E;ΔM+Zeo;ΔF+hKO;ΔHN+Cluc)) was cloned by the same method as in Example 1 using the gene defected cDNAs (FIG. 25).

(3) Reconstituting Recombinant Sendai Virus from Recombinant Sendai Virus Producing Vector A defective recombinant Sendai virus (rNa151(E-E;ΔM+Bsr;ΔF+GFP;ΔHN+gp91), rNa151(E-E;ΔM+Zeo;ΔF+hKO;ΔHN+Cluc)) was produced from the recombinant Sendai virus producing vector by the same method as in Example 15. A vector was collected by the method as in Example 16 from the further obtained vector producing cells.

(4) Double Infection of Vector

LLCMK2 cells infected with rNa151(E-E;ΔM+Bsr;ΔF+GFP;ΔHN+gp91) were infected with rNa151(E-E;ΔM+Zeo;ΔF+hKO;ΔHN+Cluc)) by the same method as in Example 16 and subjected to selection using both drugs, blastcidin and Zeosin. Expression of EGFP, gp91, hKO, and Cluc was confirmed in the cells resistant to both drugs (FIG. 29).

The result established that multiple infection of vector is possible. It was further established that plural genes can be simultaneously introduced to single cells through applicable of this.

Example 25

Collecting and Infecting with Defective Recombinant Sendai Virus Using Splitting F Protein M, F gene defected or M, F, and HN genes defected recombinant Sendai virus producing cells obtained in Example 18 were transfected with a defected gene expressing plasmid produced in Example 14 using Lipofectamine 2000 and washed 24 hours later. A DMEM medium containing 10% serum was added to the cells. The cells were further cultured at 32° C. for 3 days. Thereafter, a culture supernatant was collected and filtered with a 0.45-μm filter. After the filtering, the supernatant was divided into two parts, one of which was processed with 7.5 μg/ml of trypsin and the other was not processed with trypsin. Both parts were added to a medium for new target cells and cultured at 32° C. for 2 days. Thereafter, Infection with recombinant Sendai virus was confirmed by a fluorescent antibody test using an antibody against Sendai virus, and the ratio of recombinant Sendai virus infected cells to all cells in the microscopic field of view was calculated.

As depicted in FIG. 30, it was established that for any defective recombinant Sendai virus, the target cells are infected with recombinant Sendai virus more efficiently and needs no trypsin treatment when no splitting F protein expression vector is used.

Sequence Listing Free Text

200900239Sequence listing.

The invention claimed is:

1. A recombinant Sendai virus genome, comprising: a mutated L gene which encodes a mutated L protein of a persistently non-infective Sendai virus, in which mutated L protein an amino acid residue at position-1088 is serine, an amino acid residue at position-1169 is threonine, an amino acid residue at position-1207 is cysteine, an amino acid residue at position-1618 is valine, and an amino acid residue at position-1664 is isoleucine; an NP gene of the persistently non-infective Sendai virus; a P gene of the persistently non-infective Sendai virus; and the recombinant Sendai virus genome lacking (A) an HN gene and (B) at least one of an M gene and an F gene, wherein a transcription termination sequence is added to the 3' terminus of a leader RNA sequence of a Sendai virus.

2. The Sendai virus genome as set forth in claim 1, further modified to encode a protein with at least amino acid mutations below: 1) 69E, 2) 116A, 3) 183S, 4) 6R, 5) 115L, 6) 137T, where numerals in 1) to 3) are position numbers in an amino acid sequence of M protein of the Sendai virus, numerals in 4) to 6) are position numbers in an amino acid sequence of F protein of the Sendai virus, and alphabetic letters in 1) to 6) indicate amino acid residues mutated at those positions.

3. The Sendai virus genome as set forth in claim 1, wherein at least any one of M, F, and HN genes is substituted with a marker gene.

4. A recombinant Sendai virus genome, consisting of: a mutated L gene which encodes a mutated L protein of a persistently non-infective Sendai virus, in which mutated L protein an amino acid residue at position-1088 is serine, an amino acid residue at position-1169 is threonine, an amino acid residue at position-1207 is cysteine, an amino acid residue at position-1618 is valine, and an amino acid residue at position-1664 is isoleucine; an NP gene of the persistently non-infective Sendai virus; a P gene of the persistently non-infective Sendai virus; three or more exogenous genes inserted between two parts of a restriction site, and a transcription termination sequence added to the 3' terminus of a leader RNA sequence.

5. The recombinant Sendai virus genome as set forth in claim 1, composed of a positive-sense stranded cDNA.

6. A persistently infective, recombinant virus producing genetic material, comprising the recombinant Sendai virus genome cDNA as set forth in claim 1.

7. A non-transmissible, persistently infective virus producing genetic material, comprising the Sendai virus genome cDNA as set forth in claim 1.

8. A persistently infective, recombinant virus producing vector, comprising introduced thereto the recombinant virus producing genetic material as set forth in claim 7.

9. A non-transmissible, persistently infective, recombinant virus producing vector, comprising introduced thereto the recombinant virus producing genetic material as set forth in claim 8.

10. The persistently infective, recombinant virus producing vector as set forth in claim 8, further comprising an exogenous gene DNA introduced thereto.

11. The recombinant virus producing vector as set forth in claim 10, wherein the exogenous gene encodes a bioactive peptide or a protein.

12. The non-transmissible, persistently infective, recombinant virus producing vector as set forth in claim 9, further comprising an exogenous gene DNA introduced thereto.

13. The non-transmissible, persistently infective, recombinant virus producing vector as set forth in claim 12, wherein: at least any one of M, F, and HN genes is deleted; and the exogenous gene is inserted in place of at least one of the M, F, and HN genes.

14. The recombinant virus producing vector as set forth in claim 12, wherein the exogenous gene encodes a bioactive peptide or a protein.

15. An isolated cell, comprising introduced thereto the recombinant virus producing vector as set forth in claim 10.

16. An isolated cell, comprising introduced thereto the recombinant virus producing vector as set forth in claim 12.

17. An isolated cell, comprising introduced thereto a plurality of the recombinant virus producing vector as set forth in claim 10, wherein: each vector carries a different exogenous gene; and the plural exogenous genes are simultaneously expressed.

18. An isolated cell having introduced thereto the virus producing vector of claim 10, and another recombinant vector expressing the HN and F and/or M genes lacking in the virus producing vector.

19. The cell of claim 18, wherein: the virus producing vector lacks the Sendai virus F gene, and the recombinant vector comprises a Sendai virus F gene modified at positions 112 to 116 so as to include an amino acid sequence of arginine-arginine-X-lysine or arginine-arginine, wherein X is any amino acid residue.

20. A method of manufacturing an exogenous gene product, comprising the step of culturing the cell as set forth in claim 15 in a medium.

21. A method of manufacturing a Sendai virus particle containing an exogenous gene, comprising the step of culturing the cell as set forth in claim 15 in a medium.

22. A Sendai virus particle containing an exogenous gene, said particle being obtained by culturing the cell as set forth in claim 15 in a medium.

* * * * *

```
SEQUENCE LISTING

<160> NUMBER OF SEQ ID NOS: 87

<210> SEQ ID NO 1
<211> LENGTH: 15384
<212> TYPE: RNA
<213> ORGANISM: Sendai virus
<220> FEATURE:
<223> OTHER INFORMATION: Sendai virus cl.151 genome RNA

<400> SEQUENCE: 1
accagacaag aguuuaagag auauguauuc uuuuaaauuu ucuugucuuc uuguaaguuu      60
uucuuacuau ugucauaugg aucaguccaa gacuuccagg uaccgcggag cuucgaucgu     120
ucugcacgau agggacuaau uauuacgagc ugucauaugg cucgauauca cccagugauc     180
caucaucaau cacggucgug uauucauuuu gccuggcccc gaacaucuug acugccccua     240
aaacuuucau caaaaucuuu auuucuuugg ugaggaaucu guacguuaua cuauguauaa     300
uauccucaaa ccggucuaau aaaguuuuug ugauaacccu cagguuccug auuucacggg     360
augauaauga aacuauuccc aauugaaguc uugcuucaaa cuucggguca gggaaugacc     420
caguuaccaa ucuuguggac auagauaaag auaccaagaa uagcacaagu cuucuagaaa     480
cugucuucaa uuugccugaa ucucucacag gauacagguc auacuuacca guuaguuuaa     540
gccuuuuauc ugacucaguu auucuagccc auucgaagau uguauccuuc aaaacccugu     600
ugaaagcuau caugcaguug uguguaucag cuauguucau ggugacaag aaaucucugc     660 ucaauuuaua caaguuuggu ucaaagccaa acgcucgcag ugcuugaugg uaaggucaaa     720
gcaucccuga ugaagagcuu ccuucucuca auucccgagu aacccauucg ugagccuuug     780
ccuucucuau uaagauccac uuuucuaucu ugaugcuauc uucuuuugac aaagggagga     840
gacuagcuaa caccgucuug cuguccucua uaaugucaga uuugggaugc cucgauagga     900
```

```
gauacaucuc uguggaagca ggguuagaug uuuuaagcac uauuagguua accucguccc      960
aguaucucag auauaggcug agcugccugg uccaauccgu gcccagccua ggagcaaucu     1020
ugcuuauaag cacaacgucu cgauccccca ccagauacgc gauccggauu acacuguaau     1080
gcucaugcag acaacuuga ucauccuuau gaucucccc cuccaugu ca caguggacua      1140 ggccaucga gcuauucugc aauucauucc aaaucaaagc cucacacuca ucauuccaa       1200 uccaugucga gccaggauuc ccguugaaua cacuuuaac ucuuugaccc agacuaguaa      1260
cauuguuuaa uuucuuuccc accagugcca ccucagcagg auauauauuu aacucucucu     1320
gcccauugac aucacaagag uauaccccug aguauaaua guugaugcau gggccaagag      1380
uagcgucaua acaggaaagc auggcccag c uccuucccc uaaauauagc cuaucuuuau     1440 ccuugcaac uaaggggcuc aauagguagg uaaguucaag ugcuuucaag cagcuaguac      1500
uguugaugcc aaagagccuc agcuggugag auagauaucu ccaucgaau gguaacguca      1560 gaccaacgcc ugaucugccu aucucacccu ugugaucuc cuuguacccc cggagacgca     1620
guaccuguga cuuggauacu cucaaccccc aaaaaggggc ucuagucuga uguccccaaag    1680 gaauauucug uuguauuucu gccgcgauac caucuaacag ugcauuaucu gccucgggau     1740
cccaaucuuc uaagacuuca gggacuccua uaccucuugu ccuuaacacu uuuauagaug     1800
acuuccggau auaggucaaa guagauggga auacuuugau gacuaggcca gucaacugac    1860
uguaccucag uaccggguca ucaagaaaug ugaguuccag guaacucuuu agugacucga    1920
gccucucuag agaguucauu gauucuaauc uuggcccauc ccagauauc ucugccacgc     1980 ugcauaggua ugcaagaugu cuugccaaga aagaggaccu cccaugucg ccacaucug     2040 ggucauuguc acagauaaag aucucaagcg guacaccccc uugccaaucg ugcaugaaua    2100
gauccacaga auauucacag acagagaggg ccaagaguau cuuguccuga uuugagaggu    2160
uaggcccaua cacagguucc acgacaccug cauuccagaa ucguuugaag auuuugggau    2220
gagauagagc auuagauaag acuuuuagaa cugcgugga gguaucuuua agaauccgga     2280
cuacaugucc ccauauuucu ucccuuccuc ugauguuuaa gccguagagu gaguaugcaa    2340
acugauugac uagaauaccc ccgaacguug agcaaaauaa aggaacauca auccaccauaa   2400 acucaguaau caggcuguug acaucaucgu cauuuacuag cgcgaucauc ucuuuaggu      2460 ugucucuauc uaauugagac auuguaucag cuaucgucau ugcaguacag auacugguug    2520
cucugauaac uucaucaucu gaccaauaag ucaugcaac uguauguaca acaucucuga     2580
ccuugcuaaa uagcucaagg uccacauccu ugaguggauc aggaucauag aucaauuuau    2640
uguucucuug uguaaucucu aaaucuaaug uggaccuugg ggga uauuc gccuccugug    2700 gggacuccau uauacagcac ccguuauuaa gauguaagug caaaucagu ggcuucccua     2760 aggaaccuuu cuuauaucuc auauugaacu cgaacaagcu uagcccaguu agcauaaucu    2820
gcugauacac gagauuagua uccuucgacu ccccugcuuc uuugagugcc auguaucau     2880 uugauauugu uaugaaccga cuugcacgga cuagguugc acuagagaac ucaucuggg      2940 uugccguauc uuucaaccua ugagauagau uaguggaggu ugaaacagga gucagcagcu    3000
uuagauucuc uaagcucaga uuagcucuug uuugggcuau aagagcggcu uccauccacg    3060
auaucucauc aguccguag gcccacguau acaccauagc uauccggaug gcagccuuug     3120
cggguuugcu uagauuucuu acauacccga guuggcuuc cgaccuuuca ucagugcug     3180 auccaaaaua ggggauucuu uagccggac auccguuugu aagcgugucc aggucuauau     3240
ugucagggag auagaaccau guauagaugg ggucugcucc cucagaccug caaagcuuge    3300
```

```
acaccucuga accuucgaua aauguucccc ucaagagcuc uaaagggucu gguguuucua   3360
gcccauguau gggucucccg uaaguuaggu ggauccacau uuucugccuu agaccgacag   3420
cuagcucaac ugaacacaua uacucauauu cgauguuguc uuucaccggu uccugagag    3480
uucuagucag ugucucguac ugcaauagau cauaauugaa aagccuccuc aauaucccau   3540
augauaaucc uccuuucuua acgcuggauc ucacuagaga cuuggucgua ucaagcaucc   3600
cugcaaucgc cucccuaacu ccaguuaagg aauuacccag gaucucauga gccacucucg   3660
gcaggaugac uuuccggucc auaaggaacg aggccagguu gagauccucu ucuccacuag   3720
ucucggugaa gagaccagac aguagaggau acggggauuc cugcagcaca gaucuagcag   3780
ugauauucuu uauaaucgua guuauacucu gagaaugcgg gagguuacau gaauaagggu   3840
cugaagccca aucuagaaag cuagagucac cgggucuug auucaugacc cuguauagua    3900
ccugcuuguc uaacagaucc gcucugauga aucuuugag aucagcuagg cugcuacug     3960
cggggucucc aauauuucua acaaagcauc uagauguaga cauguaguug aauccuccaa   4020
cauuugcugg aaucaacacu gcacaucuca gccaauucuu acccuuaaag uauugaucuc   4080
uuacggucgg gcugauaguu ggauuuauag ucaucccuag ugauaugcac accugcugac   4140
aggucuuaua caacgcaaug caguagccua guauaggaga auacccauuu cgauagcuu    4200
uugcuaugga uguugagaug uucgaacaag cagaucuguu ucaucuacc agugucucgg    4260
accagaauac acaccugguc aaggcuuuca ggcacugugg uaaaaucuuc ccaucauagu   4320
auauucuuuu acuauagaca aacaucuugc uacuaaugau ggucucguuc aauuuuagcu   4380
cgugcccuac aucaaacaug acgugucuua gagcaccaaa auauuggug aucuccuuau    4440
agacaugauu uuucuucgc uuguaagucu gagcuacagg uacuuugau gucacggcua     4500
uagcuugauu gucacccuga accauugcag agacccugac acccacucuc acagcugcua   4560
gguggauugc acugauugag auuaaggucc acagcuucug gcaguaaccu ucuaugcccc   4620
cccuaggauu auguaugaaa augccagagu cugcaugauc cuggaguugu cgaugcaucc   4680
ggucggcgac uggacaguaa ggaucccaa cauauauugu acaccuuuca aggacuggau    4740
gcauccaguu aaagaagguc uugaagccaa auaucguu gcaucucuga ccaaacaaug     4800
caguacuuuc aaaucuccag uuuaagcagu auuucuugag gucuguugug aggaagcaac   4860
uuaacguuuc uagccgucu guugaugaau cuguugccuu gaauucaugu cuggaccucu    4920
ucuuuucguc ccaguacccc ccagaguucu ucuuuucau gccuucguuu cucuucucug    4980
augauuuaga guuauuguac acugaaucag uccuggggac uccugagaca gaaagaguag   5040
ucaaucuuuu aaguaggucu aucucuccuu uaaccauccc auuucgcug aacagcucuc    5100
cuauuccuuu agcaguagu gucucugcca gcaccuguac ggcucgcauc uuauaaguca    5160
uuuuugcgaa uagacgaccc ucugcuuga ucucuuucuc uuugagacug uacgagaugu    5220
ugaacuucuc gucuuucaac caaucuccug acuccacaua auugauaauu cuucugggu    5280
ugaaauucuc aucauuuaug aacacuucaa uaagccgccg ggucucuuca gauucugggg   5340
cuuuauagua cagauuacua uccggguaua cagagcccca ugccuccuuc cuggggaua    5400
gugcuuugc uuucauauau auugagau cuucaucuag uuggguucu auaaacuucc       5460
gaaacuugaa gccaugaaa cuuguauagu ugucuacagc acauucauaa gagauugccg    5520
uauuggaccc uugagcguuc cuaguucua gacacacgug aucagggaag ucacaggggg    5580
gccacugucc gccaugccuc ucucuauacc cauuuaugau gauagugcaa aaaacugcau   5640
```

-continued

```
gacacucgua uagggucuua agcuuuauug ccuuugugc auacauaugg gcccuuaccu      5700
ugucggcggc agugacagcc ucuaagcugg gguggccaaa uguccuaaag aaggaaaaga     5760
ucucugcuuu cucaucaaua gagguuccau ggaaaauggc gaguaacgac uccacaauag     5820
ugucugcuuc agcaucugug uacacgucc uacuuguuaa aacagccugu agcucuguca      5880
acacaugccu cauaaaugcc ccacguagag guauaacugg aucauuuagu uguaugagag     5940
caagugauag gggcuccaau agugcgauga cauuguauau uccucucca agacuugaga      6000
agagggaauc cacuaguucc cauaauuccu caccuuugcu guuaucca auggacuucu       6060
uaucuagaug cccugcagca gacauauucc accuucccuc uacaacauca caauacauca    6120
agaccagcuc aggggu uagg auauacccug ucaaugucaa cuuguucagu ucaugauaa     6180
gaucuccgua uguuacuaga guguaugauu ugcauucuag gagguuaugu gaauuagagg     6240
uaucgagggg ucccccggu cuggucuucu gcauccaccg caugucauau ugaugcuga      6300
accaaguuag gaauggccua uaccaucuau uccugcugua uuuaucaguu aucuccggga    6360
uggugccgau auccugcaac ggaucguacc ccucucuucc uucuauauug ccaguugcu     6420
ugaagauauu caaccaaaga uccuggaacc cacuagauaa ucccuggguc agccgauccg    6480
agaccgcgaa gacggaucgg auuuugucac auaucucugg uauaucaagc cuaaguaauu    6540
ccugagagua gguugggu ac gguucaaagg uguaucgguc uaaauccuuu auugugcguu   6600
gaagagccuu acccagagac cugaucuaaa uuugacgagg ggacaauccu ccguccuaa      6660
uuuugugcuu uguaauauuu auuaugcugu cguccuuuag ucguagggc ugguucacau     6720
cuaacaagac gugcaacugu gcuaucuccc cccugacuau gggagaguuc agguggcauu    6780
cuggauagag uaugucagaa gggu uuuggg aggacuccug cccauccaug accauggca    6840
agcuucccau ucacccuggg uuuuucuaaa uacugugaga gacguaagag acugagagau    6900
auuguggaug uucggagaug acucuagugu cagcaaagcc gacaagccug cuagucaguu    6960
aaauuuaaga cucggccuug cauaauuuag ggaugcuagu cuuaaagagc aucggcugua    7020
agguauucag gcucuucuga uugaucucga ugaugugaaa gcaguagccc cuaccaaaau    7080
gcgugauaca cgaugucgug guauaugcag ccucuaaucg aacauccuuu auccuuaaca    7140
uauuuauaau guuaguagug uuagaauaca ugauguuggg uugacacgu gauguauugg      7200
cauauagcgu gacggucgcg acguuagcug caucagggga caauggauaa gcaucgugu     7260
auacgccuga uaugcauucc uucggacacg uauuguacca auugcacucu uuauuccug      7320
gucuagacaa ggccucauga ggugccagu ugauagucaa aggguggcug auaucaagua      7380
cuccuaucug caguugagag ugccagccug augaucuugu auagauguau acccgaucac    7440
ccaauuuuaa uaaucuaccu uccgccccga gauaguuuug agugauugga augguuguga    7500
cucuuaucuu uggccucucu gagagauagu cauugaccug gaugaucacg uugaccaccu    7560
guuucccucc uagccaugua auuuucagag cccauuugca ugucuugc gacaccuguu       7620
ggcauccuuu aguccuacau uuuguaucac ccugcagagg aguggu uagu ccaccauacc    7680
caagaaauau caauguqccu ucuguugcaa ugccguugcc uacacugggg uauagugcag    7740
agaacgggug aucaagaucu acccgcgugu ugcgauaccg gugagacuua guuccccuu     7800
ugagauccag gacaucaagg accagauccu cgauaccauc acuagaguag ucgguucuuu    7860
cgucuacagu cggcauggag caaagcugau aaccccuagu cccgguugcc accacagagc     7920
augauuuccg auugucguug augucauaag ugugggacac uacugggu ua agaucaggga     7980
acauaucuga auugagugau auauacccua gcugcaggac cugauaugau uucccuauau    8040
```

```
cagcacaacc uuguguaaug agauuugaug aauaggcaua gauugccucg ccaauugaga    8100
gugaagggag ccuaacacau ccagagaucg uguagaacc agauaacaag cucggaccag     8160
gcagcaauga gauuucagga ucugagcuaa gauacgguuc uccgacaggg caucuccaga    8220
aacuaugugg cucaagugggu guaauucccu cggcauggug gacugcgauc guacucucac   8280
agagcugagu gagcucuugu cugcugcacg acuuaucaau caucuggaug acaucccugc    8340
uguuuugucu caacaagacu gggauuccgg uuugcacaga gcucugaaug uugacagccc    8400
uugcuauaac cucuugccuu auuagacugg uaagugacuc uuucaccucc cguugcuca    8460 uguucaaugc cucuacaguc auugaguacu cuuucauacu uacccuugu cuagcagaaa    8520 uuaugauaca gaugaucacu guggcaauug acaaagccca cugggugaau gagagaauca    8580
gcaaccaugu gucaacuuua cuugaccucu cccaacuuga ugcuaauuuu guagugcuac    8640
cacuaggaga gguagaccag uacgagucac guuugccccu aucaccaucc augaucugug    8700
cuuguuugag augaaagcua aaauaccgcg caaccucacu uucacccuaa guuuuucuua    8760
uuauauacag aucucaacgg auaccaugcc ugcuuuacaa gacaucugau aauagucgug    8820
aucaucuuuu cucagccauu gcaucaaacc caccguuugu guacauaugu cugaucuucg    8880
gcucuaaugu guaugugucc cucgguauac ggucaucugg auuacccauu aacauugacc    8940 uucgagucu auaaagcaug augacgauca cuauaaugac caccaauauu acgaccauaa    9000
cuacuaugau cguaaucaca gucucucuug aguguacca ucuaccuacc ucagagagga    9060
uuuuccgugc uuucucaagc ucagccuuag agcuugcaa gaaauucgua gcaucagcaa    9120
gguugagaga aauaucaacg ggucugauag caauugcagg accgacuguc aaguucugga    9180
ccucucaagu ggcaucgugc ccucuccgau uagcauacaa uucuaccca uugacaccua    9240 uaagaccaca guugucaugg guuaggaaua cuacaccuuu agagcgaucc ugacugauug    9300
gucuucggcc uguccgcag guacauguggu augcuaugca guuagcaaca acgccccau    9360 ucacaaaagc aaacuugggg auaaggcugu ccacaacuuu ugugacagga cacuuuguug    9420 uguccccag gauacacuuu ugcuggcugu cagguaucag uugugcggga ucccuggggc    9480
auauauaggu caaucuggac ucaacacaau cgguuaugc ugcaccccu aagaaagaag    9540 cacgacugag uauauggcug gggacaguca cauaccauuc cucccgucu auguuguaag    9600 aaauagacga ugccuugugu augagcacac cuggacuuc agaaagaaua gggaucuuca    9660
cagacagggu aaccauguau cucuccagau cuacaucuau caccguuccu uugaucuguu    9720
cuguauaaau gacaucauag auguuagacu gcccugucc gauuguaguc auaaucaag    9780 uaauguuagc agaguaaagu gaagacagcg ccugcagcgu gaggcucuuc ucccgaugg    9840 uuccgaaauu cgagccgaac gcaguuaaca gcucggagua augcugguc aauuuuauac    9900 ccagucuuaa ggcagcaguc ucacagccua auucgcuuau ugcggguuug aucucaucau    9960
ucacgaaauc cuggagugc uuuagagcaa gaauuugu ccccacagcg uuuugcagca   10020
guucuauaga cuugugugu uuugucaucg auccuugau gagcgcuaug ucucuuugg     10080 ccucccucgc uucggcuagu gcaucccug uggauggcug ugcuggaugc gccacuccaa    10140
gugcgauagu accaaucaca gcaccgaaga aucucaacug uggaacaccg gcauuuugug   10200
ucguaucauu ggugacaguu aucagagccu ccugaagauc uaaggcaucc ucaauggga    10260 uuaacagccu guucaguagg cucuugacu ggauaaccug agcuguuccg cauccauucu    10320
caaggucuac ccccggaacu agacucagua cuauguaccu cgauucgugg gacccagcua   10380
```

| | | | | | |
|---|---|---|---|---|---|
| ucuucaguga | uuucccuuca | ucgacuauga | ccccuauguu | agagagcaua | ucccugggaa | 10440 |
| ucugacacga | gaccaaugug | gugagaacaa | ccaguaguga | uguugagaug | cacugugacc | 10500 |
| uccggauaua | ugcugucaug | uuucccaagg | ggagaguuuu | gcaaccaagc | acucacaagg | 10560 |
| gacuuuaucc | cuaaguuuuu | cuuauuuaag | acaaggagug | acccggugge | uccgacugcc | 10620 |
| aggugguguc | ugcuugagac | auuguugcag | gucucugaug | ggugcacauu | uacagcuuuc | 10680 |
| ugauccuucc | gauguucuua | gccacaacau | uagggauagua | gcggaaauca | cgagggaugg | 10740 |
| ccgguuggaa | caccgcaucg | acgccuguga | uuucuacaga | ugccgcccaa | aucaccaugu | 10800 |
| ucauauggggg | auucacaucc | aucaauggga | agcagacugc | ccucuuccau | gcgagcugac | 10860 |
| ucaugaaugu | cuuagauagu | gucccaguaa | ccugaacaug | gaagcuuaua | ccgccgauua | 10920 |
| acccaaguga | gaaaaucagc | cgcauucucu | caaucuugcu | cuugcaguac | ucaacagagu | 10980 |
| auaucuuccc | gaccuuucuc | cugaucaacc | cgaggugcac | cauaaaauug | agcuuuuucu | 11040 |
| cccccuugauc | aucaaguacu | ggaaguaccc | ccuuuuguuc | ugggagauc | ccggucuuga | 11100 |
| gugucaccag | uagauuaacg | gauauagagu | ugggcaaugc | aaggucugca | agggucuuug | 11160 |
| ggaucuugga | uauggugauu | gccccuagag | augucccauu | gacaaacacc | acucugaauc | 11220 |
| uuaugucccuu | guccacaggg | aggcauuggg | gagcuagugc | gaccuuguuu | gcauuaaaua | 11280 |
| ucauccccug | ucucagccua | ccugaccaug | uaggagugg | agcaccaaauc | gaauccacca | 11340 |
| uguauacgau | cauuucuccu | gcucgaacag | ccccuccucac | cgugauucug | agaucggugc | 11400 |
| aggccuuuaa | gaguuccuga | ucaguccccgu | aguauuuggc | cacaccuaug | gguaacgacc | 11460 |
| cggagccgca | uauugaguag | cuggucggcu | cugucaaguc | agauacgcuc | ucugauugg | 11520 |
| uuguuuguuu | cggugucuca | aagaaaccca | agagcaauaa | aucuagguau | cucacuccau | 11580 |
| guuuaggagg | gucuccuacc | uugacaauccc | ugaugugggg | gauggcuuuc | uuauccggac | 11640 |
| caguucucag | aggcaggggc | uccacaguac | cguuauccuc | auaugagaac | uuagggaauc | 11700 |
| uauagauauc | ugccauugcg | ccguguuagg | ugaaauuucu | uucacccuaa | guuuuucuua | 11760 |
| aucuuuacug | gcugaugcug | augguagauu | gggucucucu | gugacugagg | augguggggau | 11820 |
| gcccucacccg | ggaucuaguu | ggucagugac | ucuaugccu | cuucuacgag | uuccaugacu | 11880 |
| gccuuaaccu | cuuggucugu | cuugcacuug | gauaaugauu | ucacauaugc | ugcuuucuca | 11940 |
| gcucugcuua | ggggacugcu | cucuaugacg | agccugagag | agugcauugu | gggcuuucucu | 12000 |
| uuggagggga | agagacguga | ugcguuugag | gcccugggguu | cuguguccccu | cucuggguac | 12060 |
| accgggguugc | ggaucucauc | ucuaaauuca | uccucucgga | uuaggucccgg | uuuguacuuc | 12120 |
| auaucuucua | aggucuccau | agaugggguca | aaccugguag | ccuuagucuu | guucucuuuu | 12180 |
| gauuuugcaa | aaacggaggg | ggaccuugua | agggagucug | uguugucagu | cuugccaccu | 12240 |
| cuaucuguga | ugauaugaag | uguagauagg | uuggacauca | gcaaugaguu | cuguucuuuc | 12300 |
| ugauacucag | agaaucucuu | guaaauaucc | cggaaugauu | ccacgcucuc | uuggaucugu | 12360 |
| uugagcaguu | guuuguucuc | aucuaccuua | cgagcggaag | auuucucggc | agaaaggauc | 12420 |
| aggccgcaua | cauugaaugu | caucucugca | uaguugcag | acuuuagggc | acgucuugca | 12480 |
| aacacauaac | ucgcgucucg | ggaugacucg | aauucuugag | cagacuggau | uacaccaaga | 12540 |
| cucgucaaca | auguagccau | cucuuucaua | gaugaugugu | ucucuccuau | gcccuuuuuu | 12600 |
| guugagucgg | ucucuauacc | cggauggauu | gggcggccgu | uggcuggaca | aucgagaca | 12660 |
| gagcgagucc | cuauuggugg | uuccggucu | ugacccuga | cggcggggu | gucccagag | 12720 |
| uugaugugcu | cauccugugu | agaugggggu | uuccgggug | gugacccugu | gcuguuguaa | 12780 |

```
cgauucagcg gugggggaccg ggugccaggc acgguugcug gaguaagagg uuuggaccca  12840
cuguugguag gucuucuuuu guuccuccgu agcacagccu cuucaaguuc ggggcuagga  12900
aucaccagga ccccaguuac ucuugcacua ugugagcugc caggcuccau gcuucuucca  12960
uuauuacuug cuccaccuuc uccuucauca gguaggaug uaccuccucg uaccucuucu   13020
ggaaguccuu cagcuugguc uucuccccuc uuaucagggu gcgcagccau cucucuguuu  13080
ucaucuucaa uaccgaucu cggauauccu cucucauuug gaggauuuuc aaggauuccg   13140
gagucuccuc caucgcccag auccugagau acagauuuug uaccaguucu uccccuaaag  13200
gcccagugua uauuuuguuu ucaagguu cuagcaugug cuucugccuc uggcuugcuu    13260
guucucccag agacucuacu cuccucaccu gaucgauuau cuugggucga cgguguugag  13320
acuucuccuu cgcccucacu uuuggcucua ugagcagagc cugguccuug gaaguguug   13380 augguguugu ggagccagcu ucgucccccu ccgaugucag uuggucacu cgacaggaca   13440 gcaucgagga auccgauaac auccgagagc gacucucguc uccuggcgc cuccucuca   13500 acuucagaau cuucuuuaag aaugaaggca ucuugaucca ugcgguaagu guagccgaag  13560
ccgggucugu cucgacugcu ggguguggguc ggugggguug ggugugggccu ugccugagcc 13620 gaucgaugga ugaacuuca cccuaaguuu uucuuacugc ggaucaagua ccuugaggcc   13680
ucguaugauc cuagauuccu ccuaucccag cugcugcugc ggcaucguca ucuucuucgu  13740
gaucaacacc guuauugcgg ccuucaucuc caugggguugc agaauccucu ugccgucucu 13800
cugcgagucu cauggcuauu cuucucucua ugucugauac auccucauca uugguuuccu  13860
ccucuaaccg uucagcccca guaguguga caaaguggcc accaucacc ugacgugccc    13920 aucuuucacc acuaucucca ccccaaccc uagcgccug guccgcauga gcuucuguuu    13980
ccaggucgau aucggcauug ucuagagcua ccucaauugc accaccgccu guggguuugu   14040
gguaagcacc aucccccaccg gacaaguuug ccagaugaug ucgagccuc uccuuggcug   14100 uauccgucac uccuaacuca ucuuccaagg cacugcugau cuucgauuca gcauccuuug  14160
ccacggcuug uccuaguaag aacauuuccca uaucaaggua uguccucccu gugacguacu  14220
gcugcauugc cuuguucugu acgacggcga cucccauggc guaacccau agugcaggau    14280 aauugccugg agcaaauuca ccaugaacag ggucuugag gauacagaua aagggagcuc   14340
uggggccuuu ugacagguag gugucuauga ggcuucaaag cuuauuaaua ucgggccuca  14400
gguuugacaa cguuagagcu gccaucuuug ucuccacccc auauuaaua guguucauga   14460 aggaagccag cccugcaucu cggauguagu ucccaacgau cuggauguuc uucucuaaug  14520 ugguugagauc agaucuugca guauucauag ucacaagggu cucaaccaug agagauacaa 14580
ggcuuugcug agaucucaua accgagccua uccccucaac uguccccca gugaaaacua   14640 agacaccuuu cacggugccg ucuugucuga acgccucuaa ccguugaag aacccuuucc   14700 uuaagccggc gcugcuugug auggccuuca ccagcacaau ccagacuugg acaauuaug    14760 cuccuaggca ugcaggauac ccauagauuu gaaggagugu gucagggucu gcagcauccc  14820
guugacccug gaagagugg cucuuguuga cccuaggucc aaacagccau ucuggguccc   14880
ucucauauuc cauaucucuc gucuucacaa ugaauccguc ugucuucguc cucuuaggu   14940 cuuucucuau guuguagauc acauauuuga caucggcguu uacuccguuu guugucaagu  15000
acaauucugg acuacuguaa gccaugggcaa gcagagagac gaggaacccu ccucucgag   15060 agucugcuu aucuguguccc aaugagugag cuaggaaggu uguugcaaug aauaacuugu   15120
```

-continued

```
cugcaucauc agucacacuu gggccuagua ugaacacuga gacugugcuc cucuggccgg    15180
ggauaacagc accuccuccc gacuuauuaa uacuuucgcu ccuccuagag cuaaauguau    15240
cgaaggugcu caacaacccg gccaucguga acuuuggcag caaagaaaag gaucuggaac    15300
cugcuccuca ggguggauac uuugacccua aaauccuauc uaacuucauu guauauucca    15360
uacauguuuc uucucuuguu uggu                                          15384
```

<210> SEQ ID NO 2
<211> LENGTH: 15384
<212> TYPE: DNA
<213> ORGANISM: Artificial Sequence
<220> FEATURE:
<223> OTHER INFORMATION: Description of Artificial Sequence: Synthetic
      complete length gene cDNA of Sendai virus Cl.151
<220> FEATURE:
<221> NAME/KEY: CDS
<222> LOCATION: (120)..(1691)
<223> OTHER INFORMATION: NP protein
<220> FEATURE:
<221> NAME/KEY: CDS
<222> LOCATION: (1844)..(3547)
<223> OTHER INFORMATION: P protein
<220> FEATURE:
<221> NAME/KEY: CDS
<222> LOCATION: (3669)..(4712)
<223> OTHER INFORMATION: M protein
<220> FEATURE:
<221> NAME/KEY: CDS
<222> LOCATION: (4866)..(6560)
<223> OTHER INFORMATION: F protein
<220> FEATURE:
<221> NAME/KEY: CDS
<222> LOCATION: (6693)..(8417)
<223> OTHER INFORMATION: HN protein
<220> FEATURE:
<221> NAME/KEY: CDS
<222> LOCATION: (8556)..(15239)
<223> OTHER INFORMATION: L protein

<400> SEQUENCE: 2

```
accaaacaag agaagaaaca tgtatggaat atacaatgaa gttagatagg attttagggt     60
caaagtatcc accctgagga gcaggttcca gatcctttc tttgctgcca aagttcacg      119 atg gcc ggg ttg ttg agc acc ttc gat aca ttt agc tct agg agg agc     167
Met Ala Gly Leu Leu Ser Thr Phe Asp Thr Phe Ser Ser Arg Arg Ser
1               5                   10                  15 gaa agt att aat aag tcg gga gga ggt gct gtt atc ccc ggc cag agg     215
Glu Ser Ile Asn Lys Ser Gly Gly Gly Ala Val Ile Pro Gly Gln Arg
            20                  25                  30 agc aca gtc tca gtg ttc ata cta ggc cca agt gtg act gat gat gca     263
Ser Thr Val Ser Val Phe Ile Leu Gly Pro Ser Val Thr Asp Asp Ala
        35                  40                  45 gac aag tta ttc att gca aca acc ttc cta gct cac tca ttg gac aca     311
Asp Lys Leu Phe Ile Ala Thr Thr Phe Leu Ala His Ser Leu Asp Thr
    50                  55                  60 gat aag cag cac tct cag aga gga ggg ttc ctc gtc tct ctg ctt gcc     359
Asp Lys Gln His Ser Gln Arg Gly Gly Phe Leu Val Ser Leu Leu Ala
65                  70                  75                  80 atg gct tac agt agt cca gaa ttg tac ttg aca aca aac gga gta aac     407
Met Ala Tyr Ser Ser Pro Glu Leu Tyr Leu Thr Thr Asn Gly Val Asn
                85                  90                  95 gcc gat gtc aaa tat gtg atc tac aac ata gag aaa gac cct aag agg     455
Ala Asp Val Lys Tyr Val Ile Tyr Asn Ile Glu Lys Asp Pro Lys Arg
            100                 105                 110 acg aag aca gac gga ttc att gtg aag acg aga gat atg gaa tat gag     503
Thr Lys Thr Asp Gly Phe Ile Val Lys Thr Arg Asp Met Glu Tyr Glu
```

-continued

```
            115                 120                 125
agg acc aca gaa tgg ctg ttt gga cct agg gtc aac aag agc cca ctc    551
Arg Thr Thr Glu Trp Leu Phe Gly Pro Arg Val Asn Lys Ser Pro Leu
    130                 135                 140 ttc cag ggt caa cgg gat gct gca gac cct gac aca ctc ctt caa atc    599
Phe Gln Gly Gln Arg Asp Ala Ala Asp Pro Asp Thr Leu Leu Gln Ile
145                 150                 155                 160 tat ggg tat cct gca tgc cta gga gca ata att gtc caa gtc tgg att    647
Tyr Gly Tyr Pro Ala Cys Leu Gly Ala Ile Ile Val Gln Val Trp Ile
                165                 170                 175 gtg ctg gtg aag gcc atc aca agc agc gcc ggc tta agg aaa ggg ttc    695
Val Leu Val Lys Ala Ile Thr Ser Ser Ala Gly Leu Arg Lys Gly Phe
            180                 185                 190 ttc aac agg tta gag gcg ttc aga caa gac ggc acc gtg aaa ggt gtc    743
Phe Asn Arg Leu Glu Ala Phe Arg Gln Asp Gly Thr Val Lys Gly Val
        195                 200                 205 tta gtt ttc act ggg gag aca gtt gag ggg ata ggc tcg gtt atg aga    791
Leu Val Phe Thr Gly Glu Thr Val Glu Gly Ile Gly Ser Val Met Arg
    210                 215                 220 tct cag caa agc ctt gta tct ctc atg gtt gag acc ctt gtg act atg    839
Ser Gln Gln Ser Leu Val Ser Leu Met Val Glu Thr Leu Val Thr Met
225                 230                 235                 240 aat act gca aga tct gat ctc acc aca tta gag aag aac atc cag atc    887
Asn Thr Ala Arg Ser Asp Leu Thr Thr Leu Glu Lys Asn Ile Gln Ile
                245                 250                 255 gtt ggg aac tac atc cga gat gca ggg ctg gct tcc ttc atg aac act    935
Val Gly Asn Tyr Ile Arg Asp Ala Gly Leu Ala Ser Phe Met Asn Thr
            260                 265                 270 att aaa tat ggg gtg gag aca aag atg gca gct cta acg ttg tca aac    983
Ile Lys Tyr Gly Val Glu Thr Lys Met Ala Ala Leu Thr Leu Ser Asn
        275                 280                 285 ctg agg ccc gat att aat aag ctt aga agc ctc ata gac acc tac ctg   1031
Leu Arg Pro Asp Ile Asn Lys Leu Arg Ser Leu Ile Asp Thr Tyr Leu
    290                 295                 300 tca aaa ggc ccc aga gct ccc ttt atc tgt atc ctc aag gac cct gtt   1079
Ser Lys Gly Pro Arg Ala Pro Phe Ile Cys Ile Leu Lys Asp Pro Val
305                 310                 315                 320 cat ggt gaa ttt gct cca ggc aat tat cct gca cta tgg agt tac gcc   1127
His Gly Glu Phe Ala Pro Gly Asn Tyr Pro Ala Leu Trp Ser Tyr Ala
                325                 330                 335 atg gga gtc gcc gtc gta cag aac aag gca atg cag cag tac gtc aca   1175
Met Gly Val Ala Val Val Gln Asn Lys Ala Met Gln Gln Tyr Val Thr
            340                 345                 350 ggg agg aca tac ctt gat atg gaa atg ttc tta cta gga caa gcc gtg   1223
Gly Arg Thr Tyr Leu Asp Met Glu Met Phe Leu Leu Gly Gln Ala Val
        355                 360                 365 gca aag gat gct gaa tcg aag atc agc agt gcc ttg gaa gat gag tta   1271
Ala Lys Asp Ala Glu Ser Lys Ile Ser Ser Ala Leu Glu Asp Glu Leu
370                 375                 380 gga gtg acg gat aca gcc aag gag agg ctc aga cat cat ctg gca aac   1319
Gly Val Thr Asp Thr Ala Lys Glu Arg Leu Arg His His Leu Ala Asn
385                 390                 395                 400 ttg tcc ggt ggg gat ggt gct tac cac aaa cca aca ggc ggt gca       1367
Leu Ser Gly Gly Asp Gly Ala Tyr His Lys Pro Thr Gly Gly Ala
                405                 410                 415 att gag gta gct cta gac aat gcc gat atc gac ctg gaa aca gaa gct   1415
Ile Glu Val Ala Leu Asp Asn Ala Asp Ile Asp Leu Glu Thr Glu Ala
            420                 425                 430 cat gcg gac cag gac gct agg ggt tgg ggt gga gat agt ggt gaa aga   1463
```

```
                His Ala Asp Gln Asp Ala Arg Gly Trp Gly Asp Ser Gly Glu Arg
                            435                 440                 445 tgg gca cgt cag gtg agt ggt ggc cac ttt gtc aca cta cat ggg gct        1511
Trp Ala Arg Gln Val Ser Gly Gly His Phe Val Thr Leu His Gly Ala
        450                 455                 460 gaa cgg tta gag gag gaa acc aat gat gag gat gta tca gac ata gag        1559
Glu Arg Leu Glu Glu Glu Thr Asn Asp Glu Asp Val Ser Asp Ile Glu
465                 470                 475                 480 aga aga ata gcc atg aga ctc gca gag aga cgg caa gag gat tct gca        1607
Arg Arg Ile Ala Met Arg Leu Ala Glu Arg Arg Gln Glu Asp Ser Ala
                485                 490                 495 acc cat gga gat gaa ggc cgc aat aac ggt gtt gat cac gaa gaa gat        1655
Thr His Gly Asp Glu Gly Arg Asn Asn Gly Val Asp His Glu Glu Asp
            500                 505                 510 gac gat gcc gca gca gca gct ggg ata gga gga atc taggatcata             1701
Asp Asp Ala Ala Ala Ala Ala Gly Ile Gly Gly Ile
        515                 520 cgaggcctca aggtacttga tccgcagtaa gaaaaactta gggtgaaagt tcatccatcg      1761
atcggctcag gcaaggccac acccaacccc accgaccaca cccagcagtc gagacagcca      1821
cggcttcggc tacacttacc gc atg gat caa gat gcc ttc att ctt aaa gaa      1873
                         Met Asp Gln Asp Ala Phe Ile Leu Lys Glu
                         525                 530 gat tct gaa gtt gag agg aag gcg cca gga gga cga gag tcg ctc tcg        1921
Asp Ser Glu Val Glu Arg Lys Ala Pro Gly Gly Arg Glu Ser Leu Ser
535                 540                 545                 550 gat gtt atc gga ttc ctc gat gct gtc ctg tcg agt gaa cca act gac        1969
Asp Val Ile Gly Phe Leu Asp Ala Val Leu Ser Ser Glu Pro Thr Asp
                555                 560                 565 atc gga ggg gac aga agc tgg ctc cac aac acc atc aac act tcc caa        2017
Ile Gly Gly Asp Arg Ser Trp Leu His Asn Thr Ile Asn Thr Ser Gln
            570                 575                 580 gga cca ggc tct gct cat aga gcc aaa agt gag ggc gaa gga gaa gtc        2065
Gly Pro Gly Ser Ala His Arg Ala Lys Ser Glu Gly Glu Gly Glu Val
        585                 590                 595 tca aca ccg tcg acc caa gat aat cga tca ggt gag gag agt aga gtc        2113
Ser Thr Pro Ser Thr Gln Asp Asn Arg Ser Gly Glu Glu Ser Arg Val
600                 605                 610 tct ggg aga aca agc aag cca gag gca gaa gca cat gct aga aac ctt        2161
Ser Gly Arg Thr Ser Lys Pro Glu Ala Glu Ala His Ala Arg Asn Leu
615                 620                 625                 630 gat aaa caa aat ata cac tgg gcc ttt agg gga aga act ggt aca aaa        2209
Asp Lys Gln Asn Ile His Trp Ala Phe Arg Gly Arg Thr Gly Thr Lys
                635                 640                 645 tct gta tct cag gat ctg ggc gat gga gga gac tcc gga atc ctt gaa        2257
Ser Val Ser Gln Asp Leu Gly Asp Gly Gly Asp Ser Gly Ile Leu Glu
            650                 655                 660 aat cct cca aat gag aga gga tat ccg aga tca ggt att gaa gat gaa        2305
Asn Pro Pro Asn Glu Arg Gly Tyr Pro Arg Ser Gly Ile Glu Asp Glu
        665                 670                 675 aac aga gag atg gct gcg cac cct gat aag agg gga gaa gac caa gct        2353
Asn Arg Glu Met Ala Ala His Pro Asp Lys Arg Gly Glu Asp Gln Ala
680                 685                 690 gaa gga ctt cca gaa gag gta cga gga ggt aca tcc cta cct gat gaa        2401
Glu Gly Leu Pro Glu Glu Val Arg Gly Gly Thr Ser Leu Pro Asp Glu
695                 700                 705                 710 gga gaa ggt gga gca agt aat aat gga aga agc atg gag cct ggc agc        2449
Gly Glu Gly Gly Ala Ser Asn Asn Gly Arg Ser Met Glu Pro Gly Ser
                715                 720                 725
```

-continued

| | | |
|---|---|---|
| tca cat agt gca aga gta act ggg gtc ctg gtg att cct agc ccc gaa<br>Ser His Ser Ala Arg Val Thr Gly Val Leu Val Ile Pro Ser Pro Glu<br>730                         735                    740 | 2497 |
| ctt gaa gag gct gtg cta cgg agg aac aaa aga aga cct acc aac agt<br>Leu Glu Glu Ala Val Leu Arg Arg Asn Lys Arg Arg Pro Thr Asn Ser<br>         745                    750                    755 | 2545 |
| ggg tcc aaa cct ctt act cca gca acc gtg cct ggc acc cgg tcc cca<br>Gly Ser Lys Pro Leu Thr Pro Ala Thr Val Pro Gly Thr Arg Ser Pro<br>760                         765                    770 | 2593 |
| ccg ctg aat cgt tac aac agc aca ggg tca cca cca gga aaa ccc cca<br>Pro Leu Asn Arg Tyr Asn Ser Thr Gly Ser Pro Pro Gly Lys Pro Pro<br>775                   780                    785                  790 | 2641 |
| tct aca cag gat gag cac atc aac tct ggg gac acc ccc gcc gtc agg<br>Ser Thr Gln Asp Glu His Ile Asn Ser Gly Asp Thr Pro Ala Val Arg<br>             795                    800                    805 | 2689 |
| gtc aaa gac cgg aaa cca cca ata ggg act cgc tct gtc tca gat tgt<br>Val Lys Asp Arg Lys Pro Pro Ile Gly Thr Arg Ser Val Ser Asp Cys<br>810                         815                    820 | 2737 |
| cca gcc aac ggc cgc cca atc cat ccg ggt ata gag acc gac tca aca<br>Pro Ala Asn Gly Arg Pro Ile His Pro Gly Ile Glu Thr Asp Ser Thr<br>         825                    830                    835 | 2785 |
| aaa aag ggc ata gga gag aac aca tca tct atg aaa gag atg gct aca<br>Lys Lys Gly Ile Gly Glu Asn Thr Ser Ser Met Lys Glu Met Ala Thr<br>840                         845                    850 | 2833 |
| ttg ttg acg agt ctt ggt gta atc cag tct gct caa gaa ttc gag tca<br>Leu Leu Thr Ser Leu Gly Val Ile Gln Ser Ala Gln Glu Phe Glu Ser<br>855                   860                    865                  870 | 2881 |
| tcc cga gac gcg agt tat gtg ttt gca aga cgt gcc cta aag tct gca<br>Ser Arg Asp Ala Ser Tyr Val Phe Ala Arg Arg Ala Leu Lys Ser Ala<br>             875                    880                    885 | 2929 |
| aac tat gca gag atg aca ttc aat gta tgc ggc ctg atc ctt tct gcc<br>Asn Tyr Ala Glu Met Thr Phe Asn Val Cys Gly Leu Ile Leu Ser Ala<br>890                         895                    900 | 2977 |
| gag aaa tct tcc gct cgt aag gta gat gag aac aaa caa ctg ctc aaa<br>Glu Lys Ser Ser Ala Arg Lys Val Asp Glu Asn Lys Gln Leu Leu Lys<br>         905                    910                    915 | 3025 |
| cag atc caa gag agc gtg gaa tca ttc cgg gat att tac aag aga ttc<br>Gln Ile Gln Glu Ser Val Glu Ser Phe Arg Asp Ile Tyr Lys Arg Phe<br>920                       925                    930 | 3073 |
| tct gag tat cag aaa gaa cag aac tca ttg ctg atg tcc aac cta tct<br>Ser Glu Tyr Gln Lys Glu Gln Asn Ser Leu Leu Met Ser Asn Leu Ser<br>935                       940                    945                  950 | 3121 |
| aca ctt cat atc atc aca gat aga ggt ggc aag act gac aac aca gac<br>Thr Leu His Ile Ile Thr Asp Arg Gly Gly Lys Thr Asp Asn Thr Asp<br>             955                    960                    965 | 3169 |
| tcc ctt aca agg tcc ccc tcc gtt ttt gca aaa tca aaa gag aac aag<br>Ser Leu Thr Arg Ser Pro Ser Val Phe Ala Lys Ser Lys Glu Asn Lys<br>970                       975                    980 | 3217 |
| act aag gct acc agg ttt gac cca tct atg gag acc tta gaa gat atg<br>Thr Lys Ala Thr Arg Phe Asp Pro Ser Met Glu Thr Leu Glu Asp Met<br>985                       990                    995 | 3265 |
| aag tac aaa ccg gac cta atc cga gag gat gaa ttt aga gat gag<br>Lys Tyr Lys Pro Asp Leu Ile Arg Glu Asp Glu Phe Arg Asp Glu<br>1000                         1005                     1010 | 3310 |
| atc cgc aac ccg gtg tac caa gag agg gac aca gaa ccc agg gcc<br>Ile Arg Asn Pro Val Tyr Gln Glu Arg Asp Thr Glu Pro Arg Ala<br>1015                         1020                     1025 | 3355 |
| tca aac gca tca cgt ctc ttc ccc tcc aaa gag aag ccc aca atg<br>Ser Asn Ala Ser Arg Leu Phe Pro Ser Lys Glu Lys Pro Thr Met<br>1030                         1035                     1040 | 3400 |

```
cac tct ctc agg ctc gtc ata gag agc agt ccc cta agc aga gct       3445
His Ser Leu Arg Leu Val Ile Glu Ser Ser Pro Leu Ser Arg Ala
    1045                1050                1055 gag aaa gca gca tat gtg aaa tca tta tcc aag tgc aag aca gac       3490
Glu Lys Ala Ala Tyr Val Lys Ser Leu Ser Lys Cys Lys Thr Asp
    1060                1065                1070 caa gag gtt aag gca gtc atg gaa ctc gta gaa gag gac ata gag       3535
Gln Glu Val Lys Ala Val Met Glu Leu Val Glu Glu Asp Ile Glu
    1075                1080                1085 tca ctg acc aac tagatcccgg gtgaggcatc ccaccatcct cagtcacaga       3587
Ser Leu Thr Asn
    1090 gagacccaat ctaccatcag catcagccag taaagattaa gaaaaactta gggtgaaaga 3647 aatttcacct aacacggcgc a atg gca gat atc tat aga ttc cct aag ttc  3698
                        Met Ala Asp Ile Tyr Arg Phe Pro Lys Phe
                                1095                1100 tca tat gag gat aac ggt act gtg gag ccc ctg cct ctg aga act       3743
Ser Tyr Glu Asp Asn Gly Thr Val Glu Pro Leu Pro Leu Arg Thr
        1105                1110                1115 ggt ccg gat aag aaa gcc atc ccc cac atc agg att gtc aag gta       3788
Gly Pro Asp Lys Lys Ala Ile Pro His Ile Arg Ile Val Lys Val
        1120                1125                1130 gga gac cct cct aaa cat gga gtg aga tac cta gat tta ttg ctc       3833
Gly Asp Pro Pro Lys His Gly Val Arg Tyr Leu Asp Leu Leu Leu
        1135                1140                1145 ttg ggt ttc ttt gag aca ccg aaa caa aca acc aat cta gag agc       3878
Leu Gly Phe Phe Glu Thr Pro Lys Gln Thr Thr Asn Leu Glu Ser
        1150                1155                1160 gta tct gac ttg aca gag ccg acc agc tac tca ata tgc ggc tcc       3923
Val Ser Asp Leu Thr Glu Pro Thr Ser Tyr Ser Ile Cys Gly Ser
        1165                1170                1175 ggg tcg tta ccc ata ggt gtg gcc aaa tac tac ggg act gat cag       3968
Gly Ser Leu Pro Ile Gly Val Ala Lys Tyr Tyr Gly Thr Asp Gln
        1180                1185                1190 gaa ctc tta aag gcc tgc acc gat ctc aga atc acg gtg agg agg       4013
Glu Leu Leu Lys Ala Cys Thr Asp Leu Arg Ile Thr Val Arg Arg
        1195                1200                1205 gct gtt cga gca gga gaa atg atc gta tac atg gtg gat tcg att       4058
Ala Val Arg Ala Gly Glu Met Ile Val Tyr Met Val Asp Ser Ile
        1210                1215                1220 ggt gct cca ctc cta cca tgg tca ggt agg ctg aga cag gga atg       4103
Gly Ala Pro Leu Leu Pro Trp Ser Gly Arg Leu Arg Gln Gly Met
        1225                1230                1235 ata ttt aat gca aac aag gtc gca cta gct ccc caa tgc ctc cct       4148
Ile Phe Asn Ala Asn Lys Val Ala Leu Ala Pro Gln Cys Leu Pro
        1240                1245                1250 gtg gac aag gac ata aga ttc aga gtg gtg ttt gtc aat ggg aca       4193
Val Asp Lys Asp Ile Arg Phe Arg Val Val Phe Val Asn Gly Thr
        1255                1260                1265 tct cta ggg gca atc acc ata tcc aag atc cca aag acc ctt gca       4238
Ser Leu Gly Ala Ile Thr Ile Ser Lys Ile Pro Lys Thr Leu Ala
        1270                1275                1280 gac ctt gca ttg ccc aac tct ata tcc gtt aat cta ctg gtg aca       4283
Asp Leu Ala Leu Pro Asn Ser Ile Ser Val Asn Leu Leu Val Thr
        1285                1290                1295 ctc aag acc ggg atc tcc aca gaa caa aag ggg gta ctt cca gta       4328
Leu Lys Thr Gly Ile Ser Thr Glu Gln Lys Gly Val Leu Pro Val
        1300                1305                1310
```

```
ctt gat gat caa ggg gag aaa aag ctc aat ttt atg gtg cac ctc        4373
Leu Asp Asp Gln Gly Glu Lys Lys Leu Asn Phe Met Val His Leu
        1315            1320                1325 ggg ttg atc agg aga aag gtc ggg aag ata tac tct gtt gag tac        4418
Gly Leu Ile Arg Arg Lys Val Gly Lys Ile Tyr Ser Val Glu Tyr
    1330                1335                1340 tgc aag agc aag att gag aga atg cgg ctg att ttc tca ctt ggg        4463
Cys Lys Ser Lys Ile Glu Arg Met Arg Leu Ile Phe Ser Leu Gly
        1345            1350                1355 tta atc ggc ggt ata agc ttc cat gtt cag gtt act ggg aca cta        4508
Leu Ile Gly Gly Ile Ser Phe His Val Gln Val Thr Gly Thr Leu
    1360                1365                1370 tct aag aca ttc atg agt cag ctc gca tgg aag agg gca gtc tgc        4553
Ser Lys Thr Phe Met Ser Gln Leu Ala Trp Lys Arg Ala Val Cys
        1375            1380                1385 ttc cca ttg atg gat gtg aat ccc cat atg aac atg gtg att tgg        4598
Phe Pro Leu Met Asp Val Asn Pro His Met Asn Met Val Ile Trp
    1390                1395                1400 gcg gca tct gta gaa atc aca ggc gtc gat gcg gtg ttc caa ccg        4643
Ala Ala Ser Val Glu Ile Thr Gly Val Asp Ala Val Phe Gln Pro
        1405            1410                1415 gcc atc cct cgt gat ttc cgc tac tac cct aat gtt gtg gct aag        4688
Ala Ile Pro Arg Asp Phe Arg Tyr Tyr Pro Asn Val Val Ala Lys
    1420                1425                1430 aac atc gga agg atc aga aag ctg taaatgtgca cccatcagag              4732
Asn Ile Gly Arg Ile Arg Lys Leu
        1435            1440 acctgcaaca atgtctcaag cagacaccac ctggcagtcg agccaccgg gtcactcctt   4792 gtcttaaata agaaaaactt agggataaag tcccttgtga gtgcttggtt gcaaaactct  4852 cccccttggga aac atg aca gca tat atc cgg agg tca cag tgc atc tca   4901
            Met Thr Ala Tyr Ile Arg Arg Ser Gln Cys Ile Ser
                            1445                1450 aca tca cta ctg gtt gtt ctc acc aca ttg gtc tcg tgt cag att       4946
Thr Ser Leu Leu Val Val Leu Thr Thr Leu Val Ser Cys Gln Ile
        1455            1460                1465 ccc agg gat atg ctc tct aac ata ggg gtc ata gtc gat gaa ggg       4991
Pro Arg Asp Met Leu Ser Asn Ile Gly Val Ile Val Asp Glu Gly
    1470                1475                1480 aaa tca ctg aag ata gct ggg tcc cac gaa tcg agg tac ata gta       5036
Lys Ser Leu Lys Ile Ala Gly Ser His Glu Ser Arg Tyr Ile Val
        1485            1490                1495 ctg agt cta gtt ccg ggg gta gac ctt gag aat gga tgc gga aca       5081
Leu Ser Leu Val Pro Gly Val Asp Leu Glu Asn Gly Cys Gly Thr
    1500                1505                1510 gct cag gtt atc cag tac aag agc cta ctg aac agg ctg tta atc       5126
Ala Gln Val Ile Gln Tyr Lys Ser Leu Leu Asn Arg Leu Leu Ile
        1515            1520                1525 cca ttg agg gat gcc tta gat ctt cag gag gct ctg ata act gtc       5171
Pro Leu Arg Asp Ala Leu Asp Leu Gln Glu Ala Leu Ile Thr Val
    1530                1535                1540 acc aat gat acg aca caa aat gcc ggt gtt cca cag ttg aga ttc       5216
Thr Asn Asp Thr Thr Gln Asn Ala Gly Val Pro Gln Leu Arg Phe
        1545            1550                1555 ttc ggt gct gtg att ggt act atc gca ctt gga gtg gcg aca tca       5261
Phe Gly Ala Val Ile Gly Thr Ile Ala Leu Gly Val Ala Thr Ser
    1560                1565                1570 gca cag atc acc aca ggg att gca cta gcc gaa gcg agg gag gcc       5306
Ala Gln Ile Thr Thr Gly Ile Ala Leu Ala Glu Ala Arg Glu Ala
        1575            1580                1585
```

-continued

| | | |
|---|---|---|
| aaa aga gac ata gcg ctc atc aag gaa tcg atg aca aaa aca cac<br>Lys Arg Asp Ile Ala Leu Ile Lys Glu Ser Met Thr Lys Thr His<br>      1590                  1595               1600 | 5351 |
| aag tct ata gaa ctg ctg caa aac gct gtg ggg gaa caa att ctt<br>Lys Ser Ile Glu Leu Leu Gln Asn Ala Val Gly Glu Gln Ile Leu<br>1605                  1610                  1615 | 5396 |
| gct cta aag aca ctc cag gat ttc gtg aat gat gag atc aaa ccc<br>Ala Leu Lys Thr Leu Gln Asp Phe Val Asn Asp Glu Ile Lys Pro<br>      1620                  1625               1630 | 5441 |
| gca ata agc gaa tta ggc tgt gag act gct gcc tta aga ctg ggt<br>Ala Ile Ser Glu Leu Gly Cys Glu Thr Ala Ala Leu Arg Leu Gly<br>           1635                  1640              1645 | 5486 |
| ata aaa ttg aca cag cat tac tcc gag ctg tta act gcg ttc ggc<br>Ile Lys Leu Thr Gln His Tyr Ser Glu Leu Leu Thr Ala Phe Gly<br>1650                  1655                1660 | 5531 |
| tcg aat ttc gga acc atc gga gag aag agc ctc acg ctg cag gcg<br>Ser Asn Phe Gly Thr Ile Gly Glu Lys Ser Leu Thr Leu Gln Ala<br>      1665                  1670               1675 | 5576 |
| ctg tct tca ctt tac tct gct aac att act gag att atg act aca<br>Leu Ser Ser Leu Tyr Ser Ala Asn Ile Thr Glu Ile Met Thr Thr<br>           1680                  1685              1690 | 5621 |
| atc agg aca ggg cag tct aac atc tat gat gtc att tat aca gaa<br>Ile Arg Thr Gly Gln Ser Asn Ile Tyr Asp Val Ile Tyr Thr Glu<br>1695                    1700                  1705 | 5666 |
| cag atc aaa gga acg gtg ata gat gta gat ctg gag aga tac atg<br>Gln Ile Lys Gly Thr Val Ile Asp Val Asp Leu Glu Arg Tyr Met<br>      1710                  1715               1720 | 5711 |
| gtt acc ctg tct gtg aag atc cct att ctt tct gaa gtc cca ggt<br>Val Thr Leu Ser Val Lys Ile Pro Ile Leu Ser Glu Val Pro Gly<br>           1725                  1730              1735 | 5756 |
| gtg ctc ata cac aag gca tcg tct att tct tac aac ata gac ggg<br>Val Leu Ile His Lys Ala Ser Ser Ile Ser Tyr Asn Ile Asp Gly<br>1740                  1745                1750 | 5801 |
| gag gaa tgg tat gtg act gtc ccc agc cat ata ctc agt cgt gct<br>Glu Glu Trp Tyr Val Thr Val Pro Ser His Ile Leu Ser Arg Ala<br>      1755                  1760               1765 | 5846 |
| tct ttc tta ggg ggt gca gac ata acc gat tgt gtt gag tcc aga<br>Ser Phe Leu Gly Gly Ala Asp Ile Thr Asp Cys Val Glu Ser Arg<br>           1770                  1775              1780 | 5891 |
| ttg acc tat ata tgc ccc agg gat ccc gca caa ctg ata cct gac<br>Leu Thr Tyr Ile Cys Pro Arg Asp Pro Ala Gln Leu Ile Pro Asp<br>1785                  1790                  1795 | 5936 |
| agc cag caa aag tgt atc ctg ggg gac aca aca aag tgt cct gtc<br>Ser Gln Gln Lys Cys Ile Leu Gly Asp Thr Thr Lys Cys Pro Val<br>      1800                  1805               1810 | 5981 |
| aca aaa gtt gtg gac agc ctt atc ccc aag ttt gct ttt gtg aat<br>Thr Lys Val Val Asp Ser Leu Ile Pro Lys Phe Ala Phe Val Asn<br>           1815                  1820              1825 | 6026 |
| ggg ggc gtt gtt gct aac tgc ata gca tcc aca tgt acc tgc ggg<br>Gly Gly Val Val Ala Asn Cys Ile Ala Ser Thr Cys Thr Cys Gly<br>1830                  1835                1840 | 6071 |
| aca ggc cga aga cca atc agt cag gat cgc tct aaa ggt gta gta<br>Thr Gly Arg Arg Pro Ile Ser Gln Asp Arg Ser Lys Gly Val Val<br>      1845                  1850               1855 | 6116 |
| ttc cta acc cat gac aac tgt ggt ctt ata ggt gtc aat ggg gta<br>Phe Leu Thr His Asp Asn Cys Gly Leu Ile Gly Val Asn Gly Val<br>           1860                  1865              1870 | 6161 |
| gaa ttg tat gct aat cgg aga ggg cac gat gcc act tgg agg gtc<br>Glu Leu Tyr Ala Asn Arg Arg Gly His Asp Ala Thr Trp Arg Val | 6206 |

|  |  |  |  | 1875 |  |  |  |  | 1880 |  |  |  |  | 1885 |  |  |
|---|---|---|---|---|---|---|---|---|---|---|---|---|---|---|---|---|
| cag | aac | ttg | aca | gtc | ggt | cct | gca | att | gct | atc | aga | ccc | gtt | gat |  | 6251 |
| Gln | Asn | Leu | Thr | Val | Gly | Pro | Ala | Ile | Ala | Ile | Arg | Pro | Val | Asp |  |  |
|  |  |  |  | 1890 |  |  |  |  | 1895 |  |  |  |  | 1900 |  |  |
| att | tct | ctc | aac | ctt | gct | gat | gct | acg | aat | ttc | ttg | caa | gac | tct |  | 6296 |
| Ile | Ser | Leu | Asn | Leu | Ala | Asp | Ala | Thr | Asn | Phe | Leu | Gln | Asp | Ser |  |  |
|  |  |  |  | 1905 |  |  |  |  | 1910 |  |  |  |  | 1915 |  |  |
| aag | gct | gag | ctt | gag | aaa | gca | cgg | aaa | atc | ctc | tct | gag | gta | ggt |  | 6341 |
| Lys | Ala | Glu | Leu | Glu | Lys | Ala | Arg | Lys | Ile | Leu | Ser | Glu | Val | Gly |  |  |
|  |  |  |  | 1920 |  |  |  |  | 1925 |  |  |  |  | 1930 |  |  |
| aga | tgg | tac | aac | tca | aga | gag | act | gtg | att | acg | atc | ata | gta | gtt |  | 6386 |
| Arg | Trp | Tyr | Asn | Ser | Arg | Glu | Thr | Val | Ile | Thr | Ile | Ile | Val | Val |  |  |
|  |  |  |  | 1935 |  |  |  |  | 1940 |  |  |  |  | 1945 |  |  |
| atg | gtc | gta | ata | ttg | gtg | gtc | att | ata | gtg | atc | gtc | atc | atg | ctt |  | 6431 |
| Met | Val | Val | Ile | Leu | Val | Val | Ile | Ile | Val | Ile | Val | Ile | Met | Leu |  |  |
|  |  |  |  | 1950 |  |  |  |  | 1955 |  |  |  |  | 1960 |  |  |
| tat | aga | ctc | aga | agg | tca | atg | tta | atg | ggt | aat | cca | gat | gac | cgt |  | 6476 |
| Tyr | Arg | Leu | Arg | Arg | Ser | Met | Leu | Met | Gly | Asn | Pro | Asp | Asp | Arg |  |  |
|  |  |  |  | 1965 |  |  |  |  | 1970 |  |  |  |  | 1975 |  |  |
| ata | ccg | agg | gac | aca | tac | aca | tta | gag | ccg | aag | atc | aga | cat | atg |  | 6521 |
| Ile | Pro | Arg | Asp | Thr | Tyr | Thr | Leu | Glu | Pro | Lys | Ile | Arg | His | Met |  |  |
|  |  |  |  | 1980 |  |  |  |  | 1985 |  |  |  |  | 1990 |  |  |
| tac | aca | aac | ggt | ggg | ttt | gat | gca | atg | gct | gag | aaa | aga | tgatcacgac |  | 6570 |
| Tyr | Thr | Asn | Gly | Gly | Phe | Asp | Ala | Met | Ala | Glu | Lys | Arg |  |  |  |  |
|  |  |  |  | 1995 |  |  |  |  | 2000 |  |  |  |  | 2005 |  |  | tattatcaga tgtcttgtaa agcaggcatg gtatccgttg agatctgtat ataataagaa    6630 aaacttaggg tgaaagtgag gttgcgcggt attttagctt tcatctcaaa caagcacaga    6690

| tc | atg | gat | ggt | gat | agg | ggc | aaa | cgt | gac | tcg | tac | tgg | tct | acc | tct | 6737 |
|---|---|---|---|---|---|---|---|---|---|---|---|---|---|---|---|---|
|  | Met | Asp | Gly | Asp | Arg | Gly | Lys | Arg | Asp | Ser | Tyr | Trp | Ser | Thr | Ser |  |
|  |  |  |  | 2010 |  |  |  |  | 2015 |  |  |  |  | 2020 |  |  |
| cct | agt | ggt | agc | act | aca | aaa | tta | gca | tca | agt | tgg | gag | agg | tca |  | 6782 |
| Pro | Ser | Gly | Ser | Thr | Thr | Lys | Leu | Ala | Ser | Ser | Trp | Glu | Arg | Ser |  |  |
|  |  |  |  | 2025 |  |  |  |  | 2030 |  |  |  |  | 2035 |  |  |
| agt | aaa | gtt | gac | aca | tgg | ttg | ctg | att | ctc | tca | ttc | acc | cag | tgg |  | 6827 |
| Ser | Lys | Val | Asp | Thr | Trp | Leu | Leu | Ile | Leu | Ser | Phe | Thr | Gln | Trp |  |  |
|  |  |  |  | 2040 |  |  |  |  | 2045 |  |  |  |  | 2050 |  |  |
| gct | ttg | tca | att | gcc | aca | gtg | atc | atc | tgt | atc | ata | att | tct | gct |  | 6872 |
| Ala | Leu | Ser | Ile | Ala | Thr | Val | Ile | Ile | Cys | Ile | Ile | Ile | Ser | Ala |  |  |
|  |  |  |  | 2055 |  |  |  |  | 2060 |  |  |  |  | 2065 |  |  |
| aga | caa | ggg | tat | agt | atg | aaa | gag | tac | tca | atg | act | gta | gag | gca |  | 6917 |
| Arg | Gln | Gly | Tyr | Ser | Met | Lys | Glu | Tyr | Ser | Met | Thr | Val | Glu | Ala |  |  |
|  |  |  |  | 2070 |  |  |  |  | 2075 |  |  |  |  | 2080 |  |  |
| ttg | aac | atg | agc | aac | agg | gag | gtg | aaa | gag | tca | ctt | acc | agt | cta |  | 6962 |
| Leu | Asn | Met | Ser | Asn | Arg | Glu | Val | Lys | Glu | Ser | Leu | Thr | Ser | Leu |  |  |
|  |  |  |  | 2085 |  |  |  |  | 2090 |  |  |  |  | 2095 |  |  |
| ata | agg | caa | gag | gtt | ata | gca | agg | gct | gtc | aac | att | cag | agc | tct |  | 7007 |
| Ile | Arg | Gln | Glu | Val | Ile | Ala | Arg | Ala | Val | Asn | Ile | Gln | Ser | Ser |  |  |
|  |  |  |  | 2100 |  |  |  |  | 2105 |  |  |  |  | 2110 |  |  |
| gtg | caa | acc | gga | atc | cca | gtc | ttg | ttg | aac | aaa | aac | agc | agg | gat |  | 7052 |
| Val | Gln | Thr | Gly | Ile | Pro | Val | Leu | Leu | Asn | Lys | Asn | Ser | Arg | Asp |  |  |
|  |  |  |  | 2115 |  |  |  |  | 2120 |  |  |  |  | 2125 |  |  |
| gtc | atc | cag | atg | att | gat | aag | tcg | tgc | agc | aga | caa | gag | ctc | act |  | 7097 |
| Val | Ile | Gln | Met | Ile | Asp | Lys | Ser | Cys | Ser | Arg | Gln | Glu | Leu | Thr |  |  |
|  |  |  |  | 2130 |  |  |  |  | 2135 |  |  |  |  | 2140 |  |  |
| cag | ctc | tgt | gag | agt | acg | atc | gca | gtc | cac | cat | gcc | gag | gga | att |  | 7142 |
| Gln | Leu | Cys | Glu | Ser | Thr | Ile | Ala | Val | His | His | Ala | Glu | Gly | Ile |  |  |
|  |  |  |  | 2145 |  |  |  |  | 2150 |  |  |  |  | 2155 |  |  |
| acc | cca | ctt | gag | cca | cat | agt | ttc | tgg | aga | tgc | cct | gtc | gga | gaa |  | 7187 |

```
Thr Pro Leu Glu Pro  His Ser Phe Trp Arg  Cys Pro Val Gly Glu
                2160               2165                2170 ccg tat ctt agc tca  gat cct gaa atc tca  ttg ctg cct ggt ccg       7232
Pro Tyr Leu Ser Ser  Asp Pro Glu Ile Ser  Leu Leu Pro Gly Pro
                2175               2180                2185 agc ttg tta tct ggt  tct aca acg atc tct  gga tgt gtt agg ctc       7277
Ser Leu Leu Ser Gly  Ser Thr Thr Ile Ser  Gly Cys Val Arg Leu
                2190               2195                2200 cct tca ctc tca att  ggc gag gca atc tat  gcc tat tca tca aat       7322
Pro Ser Leu Ser Ile  Gly Glu Ala Ile Tyr  Ala Tyr Ser Ser Asn
                2205               2210                2215 ctc att aca caa ggt  tgt gct gat ata ggg  aaa tca tat cag gtc       7367
Leu Ile Thr Gln Gly  Cys Ala Asp Ile Gly  Lys Ser Tyr Gln Val
                2220               2225                2230 ctg cag cta ggg tat  ata tca ctc aat tca  gat atg ttc cct gat       7412
Leu Gln Leu Gly Tyr  Ile Ser Leu Asn Ser  Asp Met Phe Pro Asp
                2235               2240                2245 ctt aac cca gta gtg  tcc cac act tat gac  atc aac gac aat cgg       7457
Leu Asn Pro Val Val  Ser His Thr Tyr Asp  Ile Asn Asp Asn Arg
                2250               2255                2260 aaa tca tgc tct gtg  gtg gca acc ggg act  agg ggt tat cag ctt       7502
Lys Ser Cys Ser Val  Val Ala Thr Gly Thr  Arg Gly Tyr Gln Leu
                2265               2270                2275 tgc tcc atg ccg act  gta gac gaa aga acc  gac tac tct agt gat       7547
Cys Ser Met Pro Thr  Val Asp Glu Arg Thr  Asp Tyr Ser Ser Asp
                2280               2285                2290 ggt atc gag gat ctg  gtc ctt gat gtc ctg  gat ctc aaa ggg aga       7592
Gly Ile Glu Asp Leu  Val Leu Asp Val Leu  Asp Leu Lys Gly Arg
                2295               2300                2305 act aag tct cac cgg  tat cgc aac agc gag  gta gat ctt gat cac       7637
Thr Lys Ser His Arg  Tyr Arg Asn Ser Glu  Val Asp Leu Asp His
                2310               2315                2320 ccg ttc tct gca cta  tac ccc agt gta ggc  aac ggc att gca aca       7682
Pro Phe Ser Ala Leu  Tyr Pro Ser Val Gly  Asn Gly Ile Ala Thr
                2325               2330                2335 gaa ggc aca ttg ata  ttt ctt ggg tat ggt  gga cta acc act cct       7727
Glu Gly Thr Leu Ile  Phe Leu Gly Tyr Gly  Gly Leu Thr Thr Pro
                2340               2345                2350 ctg cag ggt gat aca  aaa tgt agg act aaa  gga tgc caa cag gtg       7772
Leu Gln Gly Asp Thr  Lys Cys Arg Thr Lys  Gly Cys Gln Gln Val
                2355               2360                2365 tcg caa gac aca tgc  aat gag gct ctg aaa  att aca tgg cta gga       7817
Ser Gln Asp Thr Cys  Asn Glu Ala Leu Lys  Ile Thr Trp Leu Gly
                2370               2375                2380 ggg aaa cag gtg gtc  aac gtg atc atc cag  gtc aat gac tat ctc       7862
Gly Lys Gln Val Val  Asn Val Ile Ile Gln  Val Asn Asp Tyr Leu
                2385               2390                2395 tca gag agg cca aag  ata aga gtc aca acc  att cca atc act caa       7907
Ser Glu Arg Pro Lys  Ile Arg Val Thr Thr  Ile Pro Ile Thr Gln
                2400               2405                2410 aac tat ctc ggg gcg  gaa ggt aga tta tta  aaa ttg ggt gat cgg       7952
Asn Tyr Leu Gly Ala  Glu Gly Arg Leu Leu  Lys Leu Gly Asp Arg
                2415               2420                2425 gta tac atc tat aca  aga tca tca ggc tgg  cac tct caa ctg cag       7997
Val Tyr Ile Tyr Thr  Arg Ser Ser Gly Trp  His Ser Gln Leu Gln
                2430               2435                2440 ata gga gta ctt gat  atc agc cac cct ttg  act atc aac tgg aca       8042
Ile Gly Val Leu Asp  Ile Ser His Pro Leu  Thr Ile Asn Trp Thr
                2445               2450                2455
```

| | | | | | | | | | | |
|---|---|---|---|---|---|---|---|---|---|---|
| cct | cat | gag | gcc | ttg | tct | aga | cca | gga | aat | |
| Pro | His | Glu | Ala | Leu | Ser | Arg | Pro | Gly | Asn | |
| | | | 2460 | | | | | 2465 | | | cct cat gag gcc ttg tct aga cca gga aat aaa gag tgc aat tgg      8087
Pro His Glu Ala Leu Ser Arg Pro Gly Asn Lys Glu Cys Asn Trp
            2460                    2465                2470 tac aat acg tgt ccg aag gaa tgc ata tca ggc gta tac act gat      8132
Tyr Asn Thr Cys Pro Lys Glu Cys Ile Ser Gly Val Tyr Thr Asp
            2475                    2480                2485 gct tat cca ttg tcc cct gat gca gct aac gtc gct acc gtc acg      8177
Ala Tyr Pro Leu Ser Pro Asp Ala Ala Asn Val Ala Thr Val Thr
            2490                    2495                2500 cta tat gcc aat aca tca cgt gtc aac cca aca atc atg tat tct      8222
Leu Tyr Ala Asn Thr Ser Arg Val Asn Pro Thr Ile Met Tyr Ser
            2505                    2510                2515 aac act act aac att ata aat atg tta agg ata aag gat gtt cga      8267
Asn Thr Thr Asn Ile Ile Asn Met Leu Arg Ile Lys Asp Val Arg
            2520                    2525                2530 tta gag gct gca tat acc acg aca tcg tgt atc acg cat ttt ggt      8312
Leu Glu Ala Ala Tyr Thr Thr Thr Ser Cys Ile Thr His Phe Gly
            2535                    2540                2545 agg ggc tac tgc ttt cac atc atc gag atc aat cag aag agc ctg      8357
Arg Gly Tyr Cys Phe His Ile Ile Glu Ile Asn Gln Lys Ser Leu
            2550                    2555                2560 aat acc tta cag ccg atg ctc ttt aag act agc atc cct aaa tta      8402
Asn Thr Leu Gln Pro Met Leu Phe Lys Thr Ser Ile Pro Lys Leu
            2565                    2570                2575 tgc aag gcc gag tct     taaatttaac tgactagcag gcttgtcggc tttgctgaca   8457
Cys Lys Ala Glu Ser
            2580 ctagagtcat ctccgaacat ccacaatatc tctcagtctc ttacgtctct cacagtatta    8517 agaaaaaccc agggtgaatg gaagcttgc cataggtc atg gat ggg cag gag         8570
                                         Met Asp Gly Gln Glu
                                                        2585 tcc tcc caa aac cct tct gac ata ctc tat cca gaa tgc cac ctg      8615
Ser Ser Gln Asn Pro Ser Asp Ile Leu Tyr Pro Glu Cys His Leu
            2590                    2595                2600 aac tct ccc ata gtc agg ggg aag ata gca cag ttg cac gtc ttg      8660
Asn Ser Pro Ile Val Arg Gly Lys Ile Ala Gln Leu His Val Leu
            2605                    2610                2615 tta gat gtg aac cag ccc tac aga cta aag gac gac agc ata ata      8705
Leu Asp Val Asn Gln Pro Tyr Arg Leu Lys Asp Asp Ser Ile Ile
            2620                    2625                2630 aat att aca aag cac aaa att agg aac gga gga ttg tcc cct cgt      8750
Asn Ile Thr Lys His Lys Ile Arg Asn Gly Gly Leu Ser Pro Arg
            2635                    2640                2645 caa att aag atc agg tct ctg ggt aag gct ctt caa cgc aca ata      8795
Gln Ile Lys Ile Arg Ser Leu Gly Lys Ala Leu Gln Arg Thr Ile
            2650                    2655                2660 aag gat tta gac cga tac acc ttt gaa ccg tac cca acc tac tct      8840
Lys Asp Leu Asp Arg Tyr Thr Phe Glu Pro Tyr Pro Thr Tyr Ser
            2665                    2670                2675 cag gaa tta ctt agg ctt gat ata cca gag ata tgt gac aaa atc      8885
Gln Glu Leu Leu Arg Leu Asp Ile Pro Glu Ile Cys Asp Lys Ile
            2680                    2685                2690 cga tcc gtc ttc gcg gtc tcg gat cgg ctg acc agg gag tta tct      8930
Arg Ser Val Phe Ala Val Ser Asp Arg Leu Thr Arg Glu Leu Ser
            2695                    2700                2705 agt ggg ttc cag gat ctt tgg ttg aat atc ttc aag caa cta ggc      8975
Ser Gly Phe Gln Asp Leu Trp Leu Asn Ile Phe Lys Gln Leu Gly
            2710                    2715                2720 aat ata gaa gga aga gag ggg tac gat ccg ttg cag gat atc ggc      9020

```
                Asn Ile Glu Gly Arg   Glu Gly Tyr Asp Pro   Leu Gln Asp Ile Gly
                                2725                  2730                  2735 acc atc ccg gag ata   act gat aaa tac agc   agg aat aga tgg tat               9065
Thr Ile Pro Glu Ile   Thr Asp Lys Tyr Ser   Arg Asn Arg Trp Tyr
                2740                  2745                  2750 agg cca ttc cta act   tgg ttc agc atc aaa   tat gac atg cgg tgg               9110
Arg Pro Phe Leu Thr   Trp Phe Ser Ile Lys   Tyr Asp Met Arg Trp
                2755                  2760                  2765 atg cag aag acc aga   ccg ggg gga ccc ctc   gat acc tct aat tca               9155
Met Gln Lys Thr Arg   Pro Gly Gly Pro Leu   Asp Thr Ser Asn Ser
                2770                  2775                  2780 cat aac ctc cta gaa   tgc aaa tca tac act   cta gta aca tac gga               9200
His Asn Leu Leu Glu   Cys Lys Ser Tyr Thr   Leu Val Thr Tyr Gly
                2785                  2790                  2795 gat ctt atc atg ata   ctg aac aag ttg aca   ttg aca ggg tat atc               9245
Asp Leu Ile Met Ile   Leu Asn Lys Leu Thr   Leu Thr Gly Tyr Ile
                2800                  2805                  2810 cta acc cct gag ctg   gtc ttg atg tat tgt   gat gtt gta gag gga               9290
Leu Thr Pro Glu Leu   Val Leu Met Tyr Cys   Asp Val Val Glu Gly
                2815                  2820                  2825 agg tgg aat atg tct   gct gca ggg cat cta   gat aag aag tcc att               9335
Arg Trp Asn Met Ser   Ala Ala Gly His Leu   Asp Lys Lys Ser Ile
                2830                  2835                  2840 ggg ata aca agc aaa   ggt gag gaa tta tgg   gaa cta gtg gat tcc               9380
Gly Ile Thr Ser Lys   Gly Glu Glu Leu Trp   Glu Leu Val Asp Ser
                2845                  2850                  2855 ctc ttc tca agt ctt   gga gag gaa ata tac   aat gtc atc gca cta               9425
Leu Phe Ser Ser Leu   Gly Glu Glu Ile Tyr   Asn Val Ile Ala Leu
                2860                  2865                  2870 ttg gag ccc cta tca   ctt gct ctc ata caa   cta aat gat cca gtt               9470
Leu Glu Pro Leu Ser   Leu Ala Leu Ile Gln   Leu Asn Asp Pro Val
                2875                  2880                  2885 ata cct cta cgt ggg   gca ttt atg agg cat   gtg ttg aca gag cta               9515
Ile Pro Leu Arg Gly   Ala Phe Met Arg His   Val Leu Thr Glu Leu
                2890                  2895                  2900 cag gct gtt tta aca   agt agg gac gtg tac   aca gat gct gaa gca               9560
Gln Ala Val Leu Thr   Ser Arg Asp Val Tyr   Thr Asp Ala Glu Ala
                2905                  2910                  2915 gac act att gtg gag   tcg tta ctc gcc att   ttc cat gga acc tct               9605
Asp Thr Ile Val Glu   Ser Leu Leu Ala Ile   Phe His Gly Thr Ser
                2920                  2925                  2930 att gat gag aaa gca   gag atc ttt tcc ttc   ttt agg aca ttt ggc               9650
Ile Asp Glu Lys Ala   Glu Ile Phe Ser Phe   Phe Arg Thr Phe Gly
                2935                  2940                  2945 cac ccc agc tta gag   gct gtc act gcc gcc   gac aag gta agg gcc               9695
His Pro Ser Leu Glu   Ala Val Thr Ala Ala   Asp Lys Val Arg Ala
                2950                  2955                  2960 cat atg tat gca caa   aag gca ata aag ctt   aag acc cta tac gag               9740
His Met Tyr Ala Gln   Lys Ala Ile Lys Leu   Lys Thr Leu Tyr Glu
                2965                  2970                  2975 tgt cat gca gtt ttt   tgc act atc atc ata   aat ggg tat aga gag               9785
Cys His Ala Val Phe   Cys Thr Ile Ile Ile   Asn Gly Tyr Arg Glu
                2980                  2985                  2990 agg cat ggc gga cag   tgg ccc ccc tgt gac   ttc cct gat cac gtg               9830
Arg His Gly Gly Gln   Trp Pro Pro Cys Asp   Phe Pro Asp His Val
                2995                  3000                  3005 tgt cta gaa cta agg   aac gct caa ggg tcc   aat acg gca atc tct               9875
Cys Leu Glu Leu Arg   Asn Ala Gln Gly Ser   Asn Thr Ala Ile Ser
                3010                  3015                  3020
```

```
                                    -continued tat gaa tgt gct gta gac aac tat aca agt ttc ata ggc ttc aag       9920
Tyr Glu Cys Ala Val Asp Asn Tyr Thr Ser Phe Ile Gly Phe Lys
                3025                3030                3035 ttt cgg aag ttt ata gaa cca caa cta gat gaa gat ctc aca ata       9965
Phe Arg Lys Phe Ile Glu Pro Gln Leu Asp Glu Asp Leu Thr Ile
                3040                3045                3050 tat atg aaa gac aaa gca cta tcc ccc agg aag gag gca tgg gac       10010
Tyr Met Lys Asp Lys Ala Leu Ser Pro Arg Lys Glu Ala Trp Asp
                3055                3060                3065 tct gta tac ccg gat agt aat ctg tac tat aaa gcc cca gaa tct       10055
Ser Val Tyr Pro Asp Ser Asn Leu Tyr Tyr Lys Ala Pro Glu Ser
                3070                3075                3080 gaa gag acc cgg cgg ctt att gaa gtg ttc ata aat gat gag aat       10100
Glu Glu Thr Arg Arg Leu Ile Glu Val Phe Ile Asn Asp Glu Asn
                3085                3090                3095 ttc aac cca gaa gaa att atc aat tat gtg gag tca gga gat tgg       10145
Phe Asn Pro Glu Glu Ile Ile Asn Tyr Val Glu Ser Gly Asp Trp
                3100                3105                3110 ttg aaa gac gag aag ttc aac atc tcg tac agt ctc aaa gag aaa       10190
Leu Lys Asp Glu Lys Phe Asn Ile Ser Tyr Ser Leu Lys Glu Lys
                3115                3120                3125 gag atc aag caa gag ggt cgt cta ttc gca aaa atg act tat aag       10235
Glu Ile Lys Gln Glu Gly Arg Leu Phe Ala Lys Met Thr Tyr Lys
                3130                3135                3140 atg cga gcc gta cag gtg ctg gca gag aca cta ctg gct aaa gga       10280
Met Arg Ala Val Gln Val Leu Ala Glu Thr Leu Leu Ala Lys Gly
                3145                3150                3155 ata gga gag ctg ttc agc gaa aat ggg atg gtt aaa gga gag ata       10325
Ile Gly Glu Leu Phe Ser Glu Asn Gly Met Val Lys Gly Glu Ile
                3160                3165                3170 gac cta ctt aaa aga ttg act act ctt tct gtc tca gga gtc ccc       10370
Asp Leu Leu Lys Arg Leu Thr Thr Leu Ser Val Ser Gly Val Pro
                3175                3180                3185 agg act gat tca gtg tac aat aac tct aaa tca tca gag aag aga       10415
Arg Thr Asp Ser Val Tyr Asn Asn Ser Lys Ser Ser Glu Lys Arg
                3190                3195                3200 aac gaa ggc atg aaa aag aag aac tct ggg ggg tac tgg gac gaa       10460
Asn Glu Gly Met Lys Lys Lys Asn Ser Gly Gly Tyr Trp Asp Glu
                3205                3210                3215 aag aag agg tcc aga cat gaa ttc aag gca aca gat tca tca aca       10505
Lys Lys Arg Ser Arg His Glu Phe Lys Ala Thr Asp Ser Ser Thr
                3220                3225                3230 gac ggc tat gaa acg tta agt tgc ttc ctc aca aca gac ctc aag       10550
Asp Gly Tyr Glu Thr Leu Ser Cys Phe Leu Thr Thr Asp Leu Lys
                3235                3240                3245 aaa tac tgc tta aac tgg aga ttt gaa agt act gca ttg ttt ggt       10595
Lys Tyr Cys Leu Asn Trp Arg Phe Glu Ser Thr Ala Leu Phe Gly
                3250                3255                3260 cag aga tgc aac gag ata ttt ggc ttc aag acc ttc ttt aac tgg       10640
Gln Arg Cys Asn Glu Ile Phe Gly Phe Lys Thr Phe Phe Asn Trp
                3265                3270                3275 atg cat cca gtc ctt gaa agg tgt aca ata tat gtt ggg gat cct       10685
Met His Pro Val Leu Glu Arg Cys Thr Ile Tyr Val Gly Asp Pro
                3280                3285                3290 tac tgt cca gtc gcc gac cgg atg cat cga caa ctc cag gat cat       10730
Tyr Cys Pro Val Ala Asp Arg Met His Arg Gln Leu Gln Asp His
                3295                3300                3305 gca gac tct ggc att ttc ata cat aat cct agg ggg ggc ata gaa       10775
Ala Asp Ser Gly Ile Phe Ile His Asn Pro Arg Gly Gly Ile Glu
                3310                3315                3320
```

| | | | | | | | | | | | | |
|---|---|---|---|---|---|---|---|---|---|---|---|---|
| ggt | tac | tgc | cag | aag | ctg | tgg | acc | tta | atc | tca | atc | agt | gca | atc | 10820 |
| Gly | Tyr | Cys | Gln | Lys | Leu | Trp | Thr | Leu | Ile | Ser | Ile | Ser | Ala | Ile | |
| | | | 3325 | | | | 3330 | | | | 3335 | | | | |

| cac | cta | gca | gct | gtg | aga | gtg | ggt | gtc | agg | gtc | tct | gca | atg | gtt | 10865 |
| His | Leu | Ala | Ala | Val | Arg | Val | Gly | Val | Arg | Val | Ser | Ala | Met | Val | |
| | | | 3340 | | | | 3345 | | | | 3350 | | | | |

| cag | ggt | gac | aat | caa | gct | ata | gcc | gtg | aca | tca | aga | gta | cct | gta | 10910 |
| Gln | Gly | Asp | Asn | Gln | Ala | Ile | Ala | Val | Thr | Ser | Arg | Val | Pro | Val | |
| | | | 3355 | | | | 3360 | | | | 3365 | | | | |

| gct | cag | act | tac | aag | cag | aag | aaa | aat | cat | gtc | tat | aag | gag | atc | 10955 |
| Ala | Gln | Thr | Tyr | Lys | Gln | Lys | Lys | Asn | His | Val | Tyr | Lys | Glu | Ile | |
| | | | 3370 | | | | 3375 | | | | 3380 | | | | |

| acc | aaa | tat | ttt | ggt | gct | cta | aga | cac | gtc | atg | ttt | gat | gta | ggg | 11000 |
| Thr | Lys | Tyr | Phe | Gly | Ala | Leu | Arg | His | Val | Met | Phe | Asp | Val | Gly | |
| | | | 3385 | | | | 3390 | | | | 3395 | | | | |

| cac | gag | cta | aaa | ttg | aac | gag | acc | atc | att | agt | agc | aag | atg | ttt | 11045 |
| His | Glu | Leu | Lys | Leu | Asn | Glu | Thr | Ile | Ile | Ser | Ser | Lys | Met | Phe | |
| | | | 3400 | | | | 3405 | | | | 3410 | | | | |

| gtc | tat | agt | aaa | aga | ata | tac | tat | gat | ggg | aag | att | tta | cca | cag | 11090 |
| Val | Tyr | Ser | Lys | Arg | Ile | Tyr | Tyr | Asp | Gly | Lys | Ile | Leu | Pro | Gln | |
| | | | 3415 | | | | 3420 | | | | 3425 | | | | |

| tgc | ctg | aaa | gcc | ttg | acc | agg | tgt | gta | ttc | tgg | tcc | gag | aca | ctg | 11135 |
| Cys | Leu | Lys | Ala | Leu | Thr | Arg | Cys | Val | Phe | Trp | Ser | Glu | Thr | Leu | |
| | | | 3430 | | | | 3435 | | | | 3440 | | | | |

| gta | gat | gaa | aac | aga | tct | gct | tgt | tcg | aac | atc | tca | aca | tcc | ata | 11180 |
| Val | Asp | Glu | Asn | Arg | Ser | Ala | Cys | Ser | Asn | Ile | Ser | Thr | Ser | Ile | |
| | | | 3445 | | | | 3450 | | | | 3455 | | | | |

| gca | aaa | gct | atc | gaa | aat | ggg | tat | tct | cct | ata | cta | ggc | tac | tgc | 11225 |
| Ala | Lys | Ala | Ile | Glu | Asn | Gly | Tyr | Ser | Pro | Ile | Leu | Gly | Tyr | Cys | |
| | | | 3460 | | | | 3465 | | | | 3470 | | | | |

| att | gcg | ttg | tat | aag | acc | tgt | cag | cag | gtg | tgc | ata | tca | cta | ggg | 11270 |
| Ile | Ala | Leu | Tyr | Lys | Thr | Cys | Gln | Gln | Val | Cys | Ile | Ser | Leu | Gly | |
| | | | 3475 | | | | 3480 | | | | 3485 | | | | |

| atg | act | ata | aat | cca | act | atc | agc | ccg | acc | gta | aga | gat | caa | tac | 11315 |
| Met | Thr | Ile | Asn | Pro | Thr | Ile | Ser | Pro | Thr | Val | Arg | Asp | Gln | Tyr | |
| | | | 3490 | | | | 3495 | | | | 3500 | | | | |

| ttt | aag | ggt | aag | aat | tgg | ctg | aga | tgt | gca | gtg | ttg | att | cca | gca | 11360 |
| Phe | Lys | Gly | Lys | Asn | Trp | Leu | Arg | Cys | Ala | Val | Leu | Ile | Pro | Ala | |
| | | | 3505 | | | | 3510 | | | | 3515 | | | | |

| aat | gtt | gga | gga | ttc | aac | tac | atg | tct | aca | tct | aga | tgc | ttt | gtt | 11405 |
| Asn | Val | Gly | Gly | Phe | Asn | Tyr | Met | Ser | Thr | Ser | Arg | Cys | Phe | Val | |
| | | | 3520 | | | | 3525 | | | | 3530 | | | | |

| aga | aat | att | gga | gac | ccc | gca | gta | gca | gcc | cta | gct | gat | ctc | aaa | 11450 |
| Arg | Asn | Ile | Gly | Asp | Pro | Ala | Val | Ala | Ala | Leu | Ala | Asp | Leu | Lys | |
| | | | 3535 | | | | 3540 | | | | 3545 | | | | |

| aga | ttc | atc | aga | gcg | gat | ctg | tta | gac | aag | cag | gta | cta | tac | agg | 11495 |
| Arg | Phe | Ile | Arg | Ala | Asp | Leu | Leu | Asp | Lys | Gln | Val | Leu | Tyr | Arg | |
| | | | 3550 | | | | 3555 | | | | 3560 | | | | |

| gtc | atg | aat | caa | gaa | ccc | ggt | gac | tct | agc | ttt | cta | gat | tgg | gct | 11540 |
| Val | Met | Asn | Gln | Glu | Pro | Gly | Asp | Ser | Ser | Phe | Leu | Asp | Trp | Ala | |
| | | | 3565 | | | | 3570 | | | | 3575 | | | | |

| tca | gac | cct | tat | tca | tgt | aac | ctc | ccg | cat | tct | cag | agt | ata | act | 11585 |
| Ser | Asp | Pro | Tyr | Ser | Cys | Asn | Leu | Pro | His | Ser | Gln | Ser | Ile | Thr | |
| | | | 3580 | | | | 3585 | | | | 3590 | | | | |

| acg | att | ata | aag | aat | atc | act | gct | aga | tct | gtg | ctg | cag | gaa | tcc | 11630 |
| Thr | Ile | Ile | Lys | Asn | Ile | Thr | Ala | Arg | Ser | Val | Leu | Gln | Glu | Ser | |
| | | | 3595 | | | | 3600 | | | | 3605 | | | | |

| ccg | aat | cct | cta | ctg | tct | ggt | ctc | ttc | acc | gag | act | agt | gga | gaa | 11675 |
| Pro | Asn | Pro | Leu | Leu | Ser | Gly | Leu | Phe | Thr | Glu | Thr | Ser | Gly | Glu | |

```
              3610                3615                3620 gag gat ctc aac ctg gcc tcg ttc ctt atg gac cgg aaa gtc atc      11720
Glu Asp Leu Asn Leu Ala Ser Phe Leu Met Asp Arg Lys Val Ile
            3625                3630                3635 ctg ccg aga gtg gct cat gag atc ctg ggt aat tcc tta act gga      11765
Leu Pro Arg Val Ala His Glu Ile Leu Gly Asn Ser Leu Thr Gly
            3640                3645                3650 gtt agg gag gcg att gca ggg atg ctt gat acg acc aag tct cta      11810
Val Arg Glu Ala Ile Ala Gly Met Leu Asp Thr Thr Lys Ser Leu
            3655                3660                3665 gtg aga tcc agc gtt aag aaa gga gga tta tca tat ggg ata ttg      11855
Val Arg Ser Ser Val Lys Lys Gly Gly Leu Ser Tyr Gly Ile Leu
            3670                3675                3680 agg agg ctt gtc aat tat gat cta ttg cag tac gag aca ctg act      11900
Arg Arg Leu Val Asn Tyr Asp Leu Leu Gln Tyr Glu Thr Leu Thr
            3685                3690                3695 aga act ctc agg aaa ccg gtg aaa gac aac atc gaa tat gag tat      11945
Arg Thr Leu Arg Lys Pro Val Lys Asp Asn Ile Glu Tyr Glu Tyr
            3700                3705                3710 atg tgt tca gtt gag cta gct gtc ggt cta agg cag aaa atg tgg      11990
Met Cys Ser Val Glu Leu Ala Val Gly Leu Arg Gln Lys Met Trp
            3715                3720                3725 atc cac cta act tac ggg aga ccc ata cat ggg cta gaa aca cca      12035
Ile His Leu Thr Tyr Gly Arg Pro Ile His Gly Leu Glu Thr Pro
            3730                3735                3740 gac cct tta gag ctc ttg agg gga aca ttt atc gaa ggt tca gag      12080
Asp Pro Leu Glu Leu Leu Arg Gly Thr Phe Ile Glu Gly Ser Glu
            3745                3750                3755 gtg tgc aag ctt tgc agg tct gag gga gca gac ccc atc tat aca      12125
Val Cys Lys Leu Cys Arg Ser Glu Gly Ala Asp Pro Ile Tyr Thr
            3760                3765                3770 tgg ttc tat ctc cct gac aat ata gac ctg gac acg ctt aca aac      12170
Trp Phe Tyr Leu Pro Asp Asn Ile Asp Leu Asp Thr Leu Thr Asn
            3775                3780                3785 gga tgt ccg gct ata aga atc ccc tat ttt gga tca gcc act gat      12215
Gly Cys Pro Ala Ile Arg Ile Pro Tyr Phe Gly Ser Ala Thr Asp
            3790                3795                3800 gaa agg tcg gaa gcc caa ctc ggg tat gta aga aat cta agc aaa      12260
Glu Arg Ser Glu Ala Gln Leu Gly Tyr Val Arg Asn Leu Ser Lys
            3805                3810                3815 ccc gca aag gct gcc atc cgg ata gct atg gtg tat acg tgg gcc      12305
Pro Ala Lys Ala Ala Ile Arg Ile Ala Met Val Tyr Thr Trp Ala
            3820                3825                3830 tac ggg act gat gag ata tcg tgg atg gaa gcc gct ctt ata gcc      12350
Tyr Gly Thr Asp Glu Ile Ser Trp Met Glu Ala Ala Leu Ile Ala
            3835                3840                3845 caa aca aga gct aat ctg agc tta gag aat cta aag ctg ctg act      12395
Gln Thr Arg Ala Asn Leu Ser Leu Glu Asn Leu Lys Leu Leu Thr
            3850                3855                3860 cct gtt tca acc tcc act aat cta tct cat agg ttg aaa gat acg      12440
Pro Val Ser Thr Ser Thr Asn Leu Ser His Arg Leu Lys Asp Thr
            3865                3870                3875 gca acc cag atg aag ttc tct agt gca aca cta gtc cgt gca agt      12485
Ala Thr Gln Met Lys Phe Ser Ser Ala Thr Leu Val Arg Ala Ser
            3880                3885                3890 cgg ttc ata aca ata tca aat gat aac atg gca ctc aaa gaa gca      12530
Arg Phe Ile Thr Ile Ser Asn Asp Asn Met Ala Leu Lys Glu Ala
            3895                3900                3905 ggg gag tcg aag gat act aat ctc gtg tat cag cag att atg cta      12575
```

-continued

| | | |
|---|---|---|
| Gly Glu Ser Lys Asp Thr Asn Leu Val Tyr Gln Gln Ile Met Leu<br>3910                                 3915                          3920 | | |
| act ggg cta agc ttg ttc gag ttc aat atg aga tat aag aaa ggt<br>Thr Gly Leu Ser Leu Phe Glu Phe Asn Met Arg Tyr Lys Lys Gly<br>3925                                 3930                          3935 | 12620 |
| tcc tta ggg aag cca ctg ata ttg cac tta cat ctt aat aac ggg<br>Ser Leu Gly Lys Pro Leu Ile Leu His Leu His Leu Asn Asn Gly<br>3940                                 3945                          3950 | 12665 |
| tgc tgt ata atg gag tcc cca cag gag gcg aat atc ccc cca agg<br>Cys Cys Ile Met Glu Ser Pro Gln Glu Ala Asn Ile Pro Pro Arg<br>3955                                 3960                          3965 | 12710 |
| tcc aca tta gat tta gag att aca caa gag aac aat aaa ttg atc<br>Ser Thr Leu Asp Leu Glu Ile Thr Gln Glu Asn Asn Lys Leu Ile<br>3970                                 3975                          3980 | 12755 |
| tat gat cct gat cca ctc aag gat gtg gac ctt gag cta ttt agc<br>Tyr Asp Pro Asp Pro Leu Lys Asp Val Asp Leu Glu Leu Phe Ser<br>3985                                 3990                          3995 | 12800 |
| aag gtc aga gat gtt gta cat aca gtt gac atg act tat tgg tca<br>Lys Val Arg Asp Val Val His Thr Val Asp Met Thr Tyr Trp Ser<br>4000                                 4005                          4010 | 12845 |
| gat gat gaa gtt atc aga gca acc agt atc tgt act gca atg acg<br>Asp Asp Glu Val Ile Arg Ala Thr Ser Ile Cys Thr Ala Met Thr<br>4015                                 4020                          4025 | 12890 |
| ata gct gat aca atg tct caa tta gat aga gac aac cta aaa gag<br>Ile Ala Asp Thr Met Ser Gln Leu Asp Arg Asp Asn Leu Lys Glu<br>4030                                 4035                          4040 | 12935 |
| atg atc gcg cta gta aat gac gat gat gtc aac agc ctg att act<br>Met Ile Ala Leu Val Asn Asp Asp Asp Val Asn Ser Leu Ile Thr<br>4045                                 4050                          4055 | 12980 |
| gag ttt atg gtg att gat gtt cct tta ttt tgc tca acg ttc ggg<br>Glu Phe Met Val Ile Asp Val Pro Leu Phe Cys Ser Thr Phe Gly<br>4060                                 4065                          4070 | 13025 |
| ggt att cta gtc aat cag ttt gca tac tca ctc tac ggc tta aac<br>Gly Ile Leu Val Asn Gln Phe Ala Tyr Ser Leu Tyr Gly Leu Asn<br>4075                                 4080                          4085 | 13070 |
| atc aga gga agg gaa gaa ata tgg gga cat gta gtc cgg att ctt<br>Ile Arg Gly Arg Glu Glu Ile Trp Gly His Val Val Arg Ile Leu<br>4090                                 4095                          4100 | 13115 |
| aaa gat acc tcc cac gca gtt cta aaa gtc tta tct aat gct cta<br>Lys Asp Thr Ser His Ala Val Leu Lys Val Leu Ser Asn Ala Leu<br>4105                                 4110                          4115 | 13160 |
| tct cat ccc aaa atc ttc aaa cga ttc tgg aat gca ggt gtc gtg<br>Ser His Pro Lys Ile Phe Lys Arg Phe Trp Asn Ala Gly Val Val<br>4120                                 4125                          4130 | 13205 |
| gaa cct gtg tat ggg cct aac ctc tca aat cag gac aag ata ctc<br>Glu Pro Val Tyr Gly Pro Asn Leu Ser Asn Gln Asp Lys Ile Leu<br>4135                                 4140                          4145 | 13250 |
| ttg gcc ctc tct gtc tgt gaa tat tct gtg gat cta ttc atg cac<br>Leu Ala Leu Ser Val Cys Glu Tyr Ser Val Asp Leu Phe Met His<br>4150                                 4155                          4160 | 13295 |
| gat tgg caa ggg ggt gta ccg ctt gag atc ttt atc tgt gac aat<br>Asp Trp Gln Gly Gly Val Pro Leu Glu Ile Phe Ile Cys Asp Asn<br>4165                                 4170                          4175 | 13340 |
| gac cca gat gtg gcc gac atg agg agg tcc tct ttc ttg gca aga<br>Asp Pro Asp Val Ala Asp Met Arg Arg Ser Ser Phe Leu Ala Arg<br>4180                                 4185                          4190 | 13385 |
| cat ctt gca tac cta tgc agc gtg gca gag ata tct agg gat ggg<br>His Leu Ala Tyr Leu Cys Ser Val Ala Glu Ile Ser Arg Asp Gly<br>4195                                 4200                          4205 | 13430 |

```
cca aga tta gaa tca  atg aac tct cta gag  agg ctc gag tca cta           13475
Pro Arg Leu Glu Ser  Met Asn Ser Leu Glu  Arg Leu Glu Ser Leu
            4210                   4215                   4220 aag agt tac ctg gaa  ctc aca ttt ctt gat  gac ccg gta ctg agg           13520
Lys Ser Tyr Leu Glu  Leu Thr Phe Leu Asp  Asp Pro Val Leu Arg
            4225                   4230                   4235 tac agt cag ttg act  ggc cta gtc atc aaa  gta ttc cca tct act           13565
Tyr Ser Gln Leu Thr  Gly Leu Val Ile Lys  Val Phe Pro Ser Thr
            4240                   4245                   4250 ttg acc tat atc cgg  aag tca tct ata aaa  gtg tta agg aca aga           13610
Leu Thr Tyr Ile Arg  Lys Ser Ser Ile Lys  Val Leu Arg Thr Arg
            4255                   4260                   4265 ggt ata gga gtc cct  gaa gtc tta gaa gat  tgg gat ccc gag gca           13655
Gly Ile Gly Val Pro  Glu Val Leu Glu Asp  Trp Asp Pro Glu Ala
            4270                   4275                   4280 gat aat gca ctg tta  gat ggt atc gcg gca  gaa ata caa cag aat           13700
Asp Asn Ala Leu Leu  Asp Gly Ile Ala Ala  Glu Ile Gln Gln Asn
            4285                   4290                   4295 att cct ttg gga cat  cag act aga gcc cct  ttt tgg ggg ttg aga           13745
Ile Pro Leu Gly His  Gln Thr Arg Ala Pro  Phe Trp Gly Leu Arg
            4300                   4305                   4310 gta tcc aag tca cag  gta ctg cgt ctc cgg  ggg tac aag gag atc           13790
Val Ser Lys Ser Gln  Val Leu Arg Leu Arg  Gly Tyr Lys Glu Ile
            4315                   4320                   4325 aca aga ggt gag ata  ggc aga tca ggc gtt  ggt ctg acg tta cca           13835
Thr Arg Gly Glu Ile  Gly Arg Ser Gly Val  Gly Leu Thr Leu Pro
            4330                   4335                   4340 ttc gat gga aga tat  cta tct cac cag ctg  agg ctc ttt ggc atc           13880
Phe Asp Gly Arg Tyr  Leu Ser His Gln Leu  Arg Leu Phe Gly Ile
            4345                   4350                   4355 aac agt act agc tgc  ttg aaa gca ctt gaa  ctt acc tac cta ttg           13925
Asn Ser Thr Ser Cys  Leu Lys Ala Leu Glu  Leu Thr Tyr Leu Leu
            4360                   4365                   4370 agc ccc tta gtt gac  aag gat aaa gat agg  cta tat tta ggg gaa           13970
Ser Pro Leu Val Asp  Lys Asp Lys Asp Arg  Leu Tyr Leu Gly Glu
            4375                   4380                   4385 gga gct ggg gcc atg  ctt tcc tgt tat gac  gct act ctt ggc cca           14015
Gly Ala Gly Ala Met  Leu Ser Cys Tyr Asp  Ala Thr Leu Gly Pro
            4390                   4395                   4400 tgc atc aac tat tat  aac tca ggg gta tac  tct tgt gat gtc aat           14060
Cys Ile Asn Tyr Tyr  Asn Ser Gly Val Tyr  Ser Cys Asp Val Asn
            4405                   4410                   4415 ggg cag aga gag tta  aat ata tat cct gct  gag gtg gca ctg gtg           14105
Gly Gln Arg Glu Leu  Asn Ile Tyr Pro Ala  Glu Val Ala Leu Val
            4420                   4425                   4430 gga aag aaa tta aac  aat gtt act agt ctg  ggt caa aga gtt aaa           14150
Gly Lys Lys Leu Asn  Asn Val Thr Ser Leu  Gly Gln Arg Val Lys
            4435                   4440                   4445 gtg tta ttc aac ggg  aat cct ggc tcg aca  tgg att gga aat gat           14195
Val Leu Phe Asn Gly  Asn Pro Gly Ser Thr  Trp Ile Gly Asn Asp
            4450                   4455                   4460 gag tgt gag gct ttg  att tgg aat gaa ttg  cag aat agc tcg ata           14240
Glu Cys Glu Ala Leu  Ile Trp Asn Glu Leu  Gln Asn Ser Ser Ile
            4465                   4470                   4475 ggc cta gtc cac tgt  gac atg gag gga gga  gat cat aag gat gat           14285
Gly Leu Val His Cys  Asp Met Glu Gly Gly  Asp His Lys Asp Asp
            4480                   4485                   4490 caa gtt gta ctg cat  gag cat tac agt gta  atc cgg atc gcg tat           14330
Gln Val Val Leu His  Glu His Tyr Ser Val  Ile Arg Ile Ala Tyr
            4495                   4500                   4505
```

```
ctg gtg ggg gat cga gac gtt gtg ctt ata agc aag att gct cct      14375
Leu Val Gly Asp Arg Asp Val Val Leu Ile Ser Lys Ile Ala Pro
            4510                4515                4520 agg ctg ggc acg gat tgg acc agg cag ctc agc cta tat ctg aga      14420
Arg Leu Gly Thr Asp Trp Thr Arg Gln Leu Ser Leu Tyr Leu Arg
            4525                4530                4535 tac tgg gac gag gtt aac cta ata gtg ctt aaa aca tct aac cct      14465
Tyr Trp Asp Glu Val Asn Leu Ile Val Leu Lys Thr Ser Asn Pro
            4540                4545                4550 gct tcc aca gag atg tat ctc cta tcg agg cat ccc aaa tct gac      14510
Ala Ser Thr Glu Met Tyr Leu Leu Ser Arg His Pro Lys Ser Asp
            4555                4560                4565 att ata gag gac agc aag acg gtt tta gct agt ctc ctc cct ttg      14555
Ile Ile Glu Asp Ser Lys Thr Val Leu Ala Ser Leu Leu Pro Leu
            4570                4575                4580 tca aaa gaa gat agc atc aag ata gaa aag tgg atc tta ata gag      14600
Ser Lys Glu Asp Ser Ile Lys Ile Glu Lys Trp Ile Leu Ile Glu
            4585                4590                4595 aag gca aag gct cac gaa tgg gtt act cgg gaa ttg aga gaa gga      14645
Lys Ala Lys Ala His Glu Trp Val Thr Arg Glu Leu Arg Glu Gly
            4600                4605                4610 agc tct tca tca ggg atg ctt aga cct tac cat caa gca ctg cag      14690
Ser Ser Ser Ser Gly Met Leu Arg Pro Tyr His Gln Ala Leu Gln
            4615                4620                4625 acg ttt ggc ttt gaa cca aac ttg tat aaa ttg agc aga gat ttc      14735
Thr Phe Gly Phe Glu Pro Asn Leu Tyr Lys Leu Ser Arg Asp Phe
            4630                4635                4640 ttg tcc acc atg aac ata gct gat aca cac aac tgc atg ata gct      14780
Leu Ser Thr Met Asn Ile Ala Asp Thr His Asn Cys Met Ile Ala
            4645                4650                4655 ttc aac agg gtt ttg aag gat aca atc ttc gaa tgg gct aga ata      14825
Phe Asn Arg Val Leu Lys Asp Thr Ile Phe Glu Trp Ala Arg Ile
            4660                4665                4670 act gag tca gat aaa agg ctt aaa cta act ggt aag tat gac ctg      14870
Thr Glu Ser Asp Lys Arg Leu Lys Leu Thr Gly Lys Tyr Asp Leu
            4675                4680                4685 tat cct gtg aga gat tca ggc aaa ttg aag aca gtt tct aga aga      14915
Tyr Pro Val Arg Asp Ser Gly Lys Leu Lys Thr Val Ser Arg Arg
            4690                4695                4700 ctt gtg cta tct tgg ata tct tta tct atg tcc aca aga ttg gta      14960
Leu Val Leu Ser Trp Ile Ser Leu Ser Met Ser Thr Arg Leu Val
            4705                4710                4715 act ggg tca ttc cct gac cag aag ttt gaa gca aga ctt caa ttg      15005
Thr Gly Ser Phe Pro Asp Gln Lys Phe Glu Ala Arg Leu Gln Leu
            4720                4725                4730 gga ata gtt tca tta tca tcc cgt gaa atc agg aac ctg agg gtt      15050
Gly Ile Val Ser Leu Ser Ser Arg Glu Ile Arg Asn Leu Arg Val
            4735                4740                4745 atc aca aaa act tta tta gac cgg ttt gag gat att ata cat agt      15095
Ile Thr Lys Thr Leu Leu Asp Arg Phe Glu Asp Ile Ile His Ser
            4750                4755                4760 ata acg tac aga ttc ctc acc aaa gaa ata aag att ttg atg aag      15140
Ile Thr Tyr Arg Phe Leu Thr Lys Glu Ile Lys Ile Leu Met Lys
            4765                4770                4775 att tta ggg gca gtc aag atg ttc ggg gcc agg caa aat gaa tac      15185
Ile Leu Gly Ala Val Lys Met Phe Gly Ala Arg Gln Asn Glu Tyr
            4780                4785                4790 acg acc gtg att gat gat gga tca ctg ggt gat atc gag cca tat      15230
Thr Thr Val Ile Asp Asp Gly Ser Leu Gly Asp Ile Glu Pro Tyr
```

```
                       4795        4800        4805
gac agc tcg taataattag tccctatcgt gcagaacgat cgaagctccg      15279
Asp Ser Ser cggtacctgg aagtcttgga ctgatccata tgacaatagt aagaaaaact tacaagaaga   15339
caagaaaatt taaaagaata catatctctt aaactcttgt ctggt                  15384

<210> SEQ ID NO 3
<211> LENGTH: 15384
<212> TYPE: RNA
<213> ORGANISM: Sendai virus
<220> FEATURE:
<223> OTHER INFORMATION: Sendai virus nagoya genome RNA

<400> SEQUENCE: 3
accagacaag aguuaagag auauguauuc uuuuaaauuu ucuugucuuc uuguaaguuu       60
uucuuacuau ugucauaugg auaaguccaa gacuuccagg uaccgcggag cuucgaucgu     120
ucugcacgau agggacuaau uauuacgagc ugucauaugg cucgauauca cccagugauc     180
caucaucaau cacggucgug uauucauuuu gccuggcccc gaacaucuug acugccccua     240
aaaucuucau caaaaucuuu auucuuuggu gaggaaucu guacguuaua cuauguauaa      300
uauccucaaa ccugucuaau aaaguuuuug ugauaacccu cagguuccug auuucacggg    360
augauaauga aacuauuccc aauugaaguc uugcuucaaa cuucggguca gggaaugacc    420
caguuaccaa ucuuguggac auagauaaag auaccaaga uagcacaagu cuucuagaaa     480
cugucuucaa uuugccugaa ucucucacag gauacagguc auacuuacca guuaguuuaa   540
gccuuuuauc ugacucaguu auucuagccc auucgaagau uguauccuuc aaacccugu    600 ugaaagcuau caugcaguug uguguaucag cuauguucau gguggacaag aaaucucugc   660
ucaauuuaua caaguuuggu ucaaagccaa acgucugcag ugcuugaugg uaaggucuaa    720
gcaucccuga ugaagagcuu ccuucucuca auuccccagu aacccauucg ugagccuuug     780
ccuucucuau uaagauccac uuuucuaucu ugaugcuauc uucuuuugac aaagggagga    840
gacuagcuaa caccgucuug cugucccucua uaaugucaga uuuggggugc ucgauagga    900 gauacaucuc uguggaagca ggguuagaug uuuuaagcac uauuagguua accucgcccc   960
aguaucucag auauaggcug agcugccugg uccaauccgu gcccagccua ggagcaaucu   1020
ugcuuauaag cacaacgucu cgauccccca ccagauacgc gauccggauu acacuguaau   1080
gcucaugcag uacaacuuga ucauccuuau gaucucccuc cuccaugucu caguggacua   1140
ggccuaucga gcuauucugc aauucauucc aaaucaaagc cucacacuca ucauuuccaa   1200
uccaugucga gccaggauuc ccguugaaua acacuuuaac ucuugacccc agacuaguaa    1260
cauuguuuaa uuucuuuccc accagugcca ccucagcagg auauauauuu aaccucucucu   1320 gcccauugac aucacaagag uauaccccug aguuauaaua guugaugcau gggccaagag   1380
uagcgucaua acaggaaagc augggcccag uccuuccccc uaaauauagc cuaucuuuau    1440
ccuugucaac uaaggggcuc aauaggguagg uaaguucaag ugcuuucaag cagcuaguac   1500
uguugaugcc aaagagccuc agcuggugag auagauaucu uccaucgaau gguaacguca    1560
gaccaacgcc ugaucugccu aucuccacccuc uugugaucuc cuuguaccccc cggagacgca   1620 guaccuguga cuuggauacu cucaaccccc aaaaagggggc ucuagucuga uguccaaag     1680 gaauauucug uuguauuucu gccgcgauac caucuaacag ugcauuaucu gcccugggau    1740
cccaaucuuc uaagacuuca gggacuccua uaccucuugu ccuuaacacu uuuauagaug    1800
```

```
acuuccggau auaggucaaa guagaugggA auacuuugau gacuaggcca gucaacugac    1860
uguaccucag uaccgggucA ucaagaaaug ugaguccag guaacucuuu agugacucga    1920
gccucucuag agaguucauu gauucuaauc uuggcccauc ccuagauauc ucugccaagc    1980
ugcauaggua ugcaagaugu cuugccaaga aagaggaccu ccucaugucg cccacaucug    2040
ggucauuguc acagauaaag aucucaagcg guacaccccc uugccaaucg ugcaugaaua    2100
gauccacaga auauucacag acagagaggg ccaagaguau cuuguccuga uuugagaggu    2160
uaggcccaua cacagguucc acgacaccug cauuccagaa ucguuugaag auuuugggau    2220
gagauagagc auuagauaag acuuuuagaa cugcgugggA gguaucuuua agaauccgga    2280
cuacaugucc ccauauuucu ucccuuccuc ugauguuuaa gccguagagu gaguaugcaa    2340
acugauugac uagaauaccc ccgaacguug agcaaaauaa aggaacauca auccaccauaa   2400 acucaguaau caggcuguug acaucaucgu cauuuacuag cgcgaucauc ucuuuuaggu    2460
ugucucuauc uaauugagac auuguacag cuaucgucau ugcaguacag auacugguug    2520
cucugauaac uucaucaucu gaccaauaag ucaugucaac uguauguaca acaucucuga    2580
ccuugcuaaa uagcucaagg uccacauccu ugaguggauc aggaucauag aucaauuuau    2640
uguucucuug uguaaucucu aaaucuaaug uggaccuugg ggggauauuc gccuccugug    2700
gggacuccau uauacagcac ccguuauuaa gauguaagug caauaucagu ggcuucccua    2760
aggaaccuuu cuuauaucuc auauugaacu cgaacaagcu uagcccaguu agcauaaucu    2820
gcugauacac gagauuagua uccuucgacu ccccugcuuc uuugagugcc auguuaucau    2880
uugauauugu uauguaaccga cuugcacgga cuaguguugc acuagagaac uucaucuggg   2940
uugccguauc uuucaaccua ugagauagau uaguggaggu ugaaacagga gucagcagcu   3000
uuagauucuc uaagcucaga uuggcucuug uuugggcuau aagagcggcu uccauccacg    3060
auaucucauc aguccguag gcccacguau acaccauagc uauccggaug gccgccuuug    3120
cggguuugcu uagauuucuu acauacccga guugggcuuc cgaccuuuca ucagguggcug   3180 auccaaaauA ggggauucuu uagccggac uuccguuugu aagcgugucc aggucuauau    3240 ugucaggag auagaaccau guauagaugg ggcugcucc cucagaccug caaagcuugc     3300
acaccucuga accuucgaua aauguucccc ucaagagcuc uaaagggucu gguguuucua    3360
gcccauguau gggucucccg uaaguuaggu ggauccacau uuucugccuu agaccgacag    3420
cuagcucaac ugaacacaua uacucauauu cgauguuguc uuucaccggu uccugagag    3480 uucuagucag ugucucguac ugcaauagau cauaauugac aagccuccuc aauaucccau    3540
augauaaucc uccuuucuuA acgcuggcuc ucacuagaga cuuggucgua ucaagcaucc    3600
cugcaaucgc cucccuaacu ccaguuaagg aauuaccag gaucaugA gccacucucg      3660 gcaggaugac uuuccggucc auaaggaacg aggccagguu gagauccucu ucuccacuag    3720
ucucggugaa gagaccagac aguagaggau ucgggauuc cugcagcaca gaucuagcag    3780
ugauauucuu uauaaucgua guuauacucu gagaaugcgg gagguuacau gaauaagggu    3840
cugaagccca aucuagaaag cuagagucac cggguucuug auucaugauc cuguauagua    3900
ccugcuuguc uaacagaucc gcucugauga aucuuugag aucagcuagg gcugcuacug    3960
cggggucucc aauauuucua acaaagcauc uagauguaga cauguaguug aauccuccaa    4020
cauuugcugg aaucaacacu gcacaucuca gccaauucuu acccuuaaag uauugaucuc    4080
uuacggucgg gcugauaguu gggauuuaag ucaucccuag ugauaugcac acuugcugac    4140
aggucuuaua caacgcaaug caguagccua guauaggaga auacccauuu ucgauagcuu    4200
```

```
uugcuaugga uguugagaug uucgaacaag cagaucuguu ucaucuacc agugucucgg   4260
accagaauac acaccgguc aaggcuuuca ggcacugugg uaaaaucuuc ccaucauagu   4320
auauucuuuu acuauagaca acaucuugc uacuaaugau ggucucguuc aauuuuagcu   4380
cgugcccuac aucaaacaug acgugucuua gagcaccaaa auauuggug aucuccuuau   4440
agacaugauu uuucuucugc uuguaagucu gagcuacagg uacucuugau gucacggcua   4500
uagcuugauu gucacccuga accauugcag agaccugac acccacucuc acagcugcua   4560
ggugauugc acugauugag auuaaggucc acagcuucug gcaguaaccu ucuaugcccc   4620
cccuaggauu auguaugaaa augccagagu cugcaugauc cuggaguugu cgaugcaucc   4680
ggucggcgac uggacaguaa ggaucccaa cauauauugu acaccuuuca aggacuggau   4740
gcauccaguu aaagaaggcuc uugaagccaa auaucucguu gcaucucuga ccaaacaaug   4800
caguacuuuc aaaucuccag uuuaagcagu auuucuugag gucuguugug aggaagcaac   4860
uuaacguuuc auagccgucu guugaugaau cuguugccuu gaauucaugu cuggaccucu   4920
ucuuuucguc ccaguacccc ccagaguucu ucuuuucau gccucguuu ucuucucug    4980
augauuuaga guuauuguac acugaaucag uccggggac uccgagaca gaaagaguag    5040
ucaaucuuuu aaguaggucu aucucuccuu uaaccauccc auuucgcug aacagcucuc    5100
cuauuccuuu agccaguagu gucucugcca gcaccguac ggcucgcauc uuauaagcua    5160
uuuugcaaa uagcgacccc ucuugcuuga ucucuuucuc uuugagacug uacgagaugu    5220
ugaacuucuc gucuuucaac caaucuccug acuccacaua auugauaauu cuucugggu    5280
ugaaauucuc aucauuuaug aacacuucaa uaagccgccg ggucucuuca gauucugggg    5340
cuuuauagua cagauuacua uccggguaua cagagucccca ugccuccuuc cuggggaua    5400
gugcuuuguc uuucauauau auugugagau cuucaucuag uugugguucu auaaacuucc    5460
gaaacuugaa gccaugaaaa cuuguauagu ugcuacagc acauucauaa gagauugccg    5520
uauuggaccc uugagcguuc cuuaguucua gacacacgug aucagggaag ucacagggg    5580
gccacugucc gccaugccuc ucucuauacc cauuuaugau gauagugcaa aaaacugcau    5640
gacacucgua uagggucuua agcuuuauug ccuuugugc auacauaugg gcccuuaccu    5700
ugucggcggc agugacagcc ucuaagcugg gguggccaaa uguccuaaag aaggaaaaga    5760
ucucugcuuu cucaucaaua gagguuccau ggaaaauggc gaguaacgac uccacaauag    5820
ugucugcuuc agcaucugug uacacgucccc uacuuguuaa aacagccugu agcucuguca    5880
acacaugccu cauaaaugcc ccacuagag guauaacagg aucauuuagu uguaugagag    5940
caagugauag gggcuccaau agugcgauga cauuguauau uccucucca agacuugaga    6000
agagggaauc cacuaguucc cauaauuccu caccuuugcu uguuacccca auggacuucu    6060
uaucuagaug cccugcagca gacauauucc accuucccuc uacaacauca caauacauca    6120
agaccagcuc agggguuagg auauacccug ucaaugucaa cuuguucagu aucaugauaa    6180
gaucuccgua uguuacuaga guguaugauu ugcauucuag gagguuaugu gaauuagagg    6240
uaucgagggg ucccccggu cuggucuucu gcaccaccg caugcauau uugaugcuga    6300
accaaguuag gaauggccua uaccaucuau uccgcuguaa uuuaucaguu aucucgggaa    6360
uggugccgau auccugcaac ggaucguacc ccucucuucc uucuauauug ccuaguugcu    6420
ugaagauauu caaccaaaga uccuggaacc cacuagauaa cucccgguc agccgauccg    6480
agaccgcgaa gacggaucgg auuuugucac auaucucugg uauaucaagc cuaaguaauu    6540
```

```
ccugagagua gguuggguac gguucaaagg uguaucgguc uaaauccuuu auugugcguu    6600
gaagagccuu acccagagac cugaucuuaa uuugacgagg ggacaauccu ccguuccuaa    6660
uuuugugcuu uguaauauuu auuaugcugu cguccuuuag ucuguagggc ugguucacau    6720
cuaacaagac gugcaacugu gcuaucucc cccugacuau gggagaguuc aggugcauu     6780 cuggauagag uaugucagaa ggguuuuggg aggacuccug cccauccaug accauggca    6840 agcuucccau ucacccuggg uuuuucuuaa uacugugaga gacguaagag acugagagau    6900 auugugaug uuaggagaug acucuagugu cagcaaagcc gacaagccug cuagucaguu    6960
aaauuuaaga cucggccuug cauaauuuag ggaugcuagu cuuaaagagc aucggcugua    7020
agguauucag gcucuucuga uugaucucga ugaugugaaa gcaguagccc uuaccaaaau    7080
gcgugauaca cgaugucgug guauaugcag cccucuaauug aacauccuuu auccuuaaca    7140
uauuuauaau guuaguagug uuagaauaca ugauuguugg guugacacgu gauguauugg    7200
cauauagcgu gacgguagcg acguuagcug caucagggga caauggauaa gcaucagugu    7260
auacgccuga uaugcauucc uucgacacg uauuguacca auugcacucu uuauuuccgg    7320
gucuagacaa ggccucauga ggugccagu ugauagucaa agggugccug auaucaagua    7380 cucccuaucug caguugagag ugccagccug augaucuuga uagaugauau acccgaucac    7440
ccaauuuuaa uaaucuaccu uccgccccga gauaguuuug agugauugga augguuguga    7500
cucuuaucuu uggccucucu gagagauagu cauugaccug gaugaucacg cugaccaccu    7560
guuucccucc uagccaugua auuuucagag ccucaugcaa uguguucuugc gacaccuguu    7620 ggcauccuuu aguccauacau uuuguauac ccugcagagg aguggguuagu ccaccauacc    7680 caagaaauau caaugugccu ucuguugcaa ugccguugcc uacacugggg uauagugcag    7740
agaacgggug aucaagaucu accucgcugu ugcgauaccg gugagacuua guucccccuu    7800
ugagauccag gacaucaagg accagauccu cgauaccguc acuagaguag ucgguucuuu    7860
cgucuacagu cggcauggag caaagcugau aaccccuagu cccgguugcc accacagagc    7920
augauuuccg auugucguug augucauaag guggggacac uacgggguua agaucaggga    7980 acauacuga auugagugau auauacccua gcugcaggac cugauaugau ucccuauau    8040 cagcacaacc uuguguaaug agauuugaug aauaggcaua gauugccucg ccaauugaga    8100
gugaagggag ccuaacacau ccagagaucg uuguagaacc agguaacaag cucgaccag     8160 gcagcaauga gauuuagga ucugagcuaa gauacgguuc uccgacaggg caucccaga    8220 aacuaugugg cucaagugg guaauuccu cggcauggug gacugcgauc guacucucac    8280
agagcugagu gagcucuugu cugcugcacg acuuaucaau caucuggaug acaucccugc    8340
uguuuugguu caacaagacu gggauuccgg uuugcacaga gcucgaaug uugacagccc    8400 uugcuauaac cucuugccuu auuagacugg uaagugacuc uuucacccuc cugcugcuca    8460
uguucaaugc cucuacaguc auugaguacu cuuucauacu uacccuuugu cuagcagaaa    8520
uuaugauaca gaugaucacu guggcaauug acaaagccca cggguguaau gagagaauca    8580
gcaaccaugu gucaacuuua cuugaccucu cccaacuuga ugcuaauuuu guagugcuac    8640
cacuaggaga gguagaccag uacgagucac guuugcccu aucaccaucc augaucugug    8700
cuuguuugag augaaagcua caauaccgcg caaccucacu uucacccuaa guuuucuua    8760 uuauauacag aucucaaugg auaccaugcc ugcuuuacaa gacaucugau aauagucgug    8820
aucaucuuuu cucagccauu gcaucaaacc caccguuugu guacauaugu cugaucuucg    8880
gcucuaaugu guauguguucc cucgguauac ggucaucugg auuacccauu aacauugacc    8940
```

```
uucugagucu auaaagcaug augacgauca cuauaaugac caccaauauu acgaccauga    9000
cuacuaugau cguaaucaca gucucucuug aguuguacca ucuaccuacc ucagagagga    9060
uuuuccgugc uuucucaagc ucagccuuag agucuugcaa gaaauucgua gcaucagcaa    9120
gguugagaga aauaucaacg ggucugauag caauugcagg accgacuguc aaguucugga    9180 cccccccaagu ggcaucgugc ccucuccgau uagcauacaa uucuaccccca uugacaccua   9240
```

| | |
|---|---|
| ucauucccug ucucagcuua ccugaccaug guaggaguGG agcaccaauc aaauccacca | 11340 |
| uguauacgau caucucuccu gcucgaacag uccuccucac cgugauucug agaucggugc | 11400 |
| aggccuuuaa gaguuccuga ucagucccgu aguauuggc cacaccuaug gguaacgacc | 11460 |
| cggagccgca uauugaguag cuggucggcu cugucaaguc agaucgcuc ccuagauugg | 11520 |
| uuguuuguuu cggugucuca aagaaaccca agagcaauaa aucuagguau cucacuccau | 11580 |
| guuuaggagg gucuccuacc uugacaauCC ugaugggGG gauggcuuuc uuauccggac | 11640 |
| caguucucag aggcaggggc uccacaguac cguuauccuc auaugagaac uugggaauc | 11700 |
| uauagauauc ugccauugcg ccguguuagg ugaaauuucu uucacccuaa guuuucuua | 11760 |
| aucuuuacug gcugaugcug augguagauu gggucucucu gugacugagg auggugggau | 11820 |
| gccucacccg ggaucuaguu ggucagugac ucuaugccuu cuucuacgag uuccaugacu | 11880 |
| gccuuaaccu cuuggucugu cuugcacuug gauaaugauu ucacauaugc ugcuuucuca | 11940 |
| gcucugcuua ggggacugcu ucuaugacg agccugagag agugcauugu gugcuuucucu | 12000 |
| uuggagggga agagacguga ugcguuugag gcccugggGU cugugucccu ucucugguac | 12060 |
| accggguugc ggaucucauc ucuaaauuca uccucucgga uuaggaccgg uuuguacuuc | 12120 |
| auaucuucua aggucuccau agaugggguCa aaccugguag ccuuagucuu guucucuuuu | 12180 |
| gauuuugcaa aaacgagggg ggaccuugua agggagucug uguucagu cuugccaccu | 12240 |
| cuaucuguga ugauaugaag uguagauagg ugggacauca gcaaugaguu cuguucuuuc | 12300 |
| ugauacucag agaaucucuu guaaauaucc cggaaugauu ccacgcucuc uuggaucugu | 12360 |
| uugagcaguu guuuguucuc aucaccuua cgagcggaag auuucucggc agaaaggauc | 12420 |
| aggccgcaua cauugaaugu caucucugca uaguugcag acuuuagggc acgucuugca | 12480 |
| aacacauaac ucgcgucucg ggaugacucg aauucuugag cagacuggau uacaccaaga | 12540 |
| cucgucaaca auguagccau aucuuucaua gaugaugugu ucucuccuau gcccuuuuuu | 12600 |
| guugagucgg ucucuauacc cggauggauu gggcggccgu uggcuggaca aucgagaca | 12660 |
| gagcgagucc cuauugaugg uuccggucu uugacccuga cggcgggGGu gucccaGag | 12720 |
| uugaugugcu cauccugugu agauggGGgu uuuccuggug ugacccugu gcuguuguaa | 12780 |
| cgauucagcg ugggGGaccg ggugccaggc acgguugcug gaguaagagg uuuggaccca | 12840 |
| cuguugguag gucuucuuuu guuccuccgu agcacagccu cuucaaguuc ggGGcuagga | 12900 |
| aucaccagga ccccaguuac ucuugcacua ugugagcugc caggcuccau gcuucuucca | 12960 |
| uuauuacuug cuccaccuuc uccuucauca gguaggaug uaccuccucg uaccucuucu | 13020 |
| ggaguccuuu cagcuugguc uucucccuc uuaucagggu gcgcagccau cucucuguuu | 13080 |
| ucaucuucaa uaccgaucu cggauauccu cucucauuug gaggauuuuc aaggauuccg | 13140 |
| gagucccuc caucguccag auccugagau acagaguuug uaccaguucu uccccuaaag | 13200 |
| gcccagugua uauuuuguuu aucaagguuu ccagcauguG cuucugccuc uggcuugcuu | 13260 |
| guucucccag agacucuacu cucccaccu gaucgauuau cuuggGUCga cgguguugag | 13320 |
| acuucuccuu cgcccucacu uuuggcucua ugagcagagc cuggccuug gggaguguug | 13380 |
| auggugguugu ggagccagcu ucuguccccu ccgaugucag uugguucauu cgacaggaca | 13440 |
| gcaucgagga auccgauaac auccgagagc gacucucguc cuccuggcgc cuuccucuca | 13500 |
| acuucagaau cuucuuuaag aaugaaggca ucuugaucca ugcgguaagu guagccgaag | 13560 |
| ccgugggcugu cucgacugcu gggguggGuc gguggGGuug gguguggccu ugccugagcc | 13620 |
| gaucggugga ugaacuuuca cccuaaguuu uucuuacugc ggaucaagua ccuugaggcc | 13680 |

```
ucguaugauc cuagauuccu ccuaucccag cugcugcugc ggcaucguca ucuucuucgu   13740
gaucaacacc guuauugcgg ccuucaucuc caugggnugc agaauccucu ugccgucucu   13800
cugcgagucu cauggcuauu cuucucucua ugcugauac auccucauca uugguuuccu   13860
ccucuaaccg uucagcccca uguaguguga caaaguggcc accacucacc ugacgugccc   13920
aucuuucacc acuaucucca ccccaaccac uagcguccug guccgcauga gcuucuguuu   13980
ccaggucgau aucggcauug ucuagagcua ccucaauugc accaccgccu guuguuugu    14040 gguaagcacc auccccaccg gacaaguuug ccagaugaug ucugagccuc uccuuggcug   14100
uauccgucac uccuaacuca ucuuccaagg cacugcugau cuucgauuca gcauccuuug   14160
ccacggcuug uccuaguaag aacauuucca uaucaaggua uguccucccu gugacguacu   14220
gcugcauuga cuuguucugu acgacggcga ucccauggc guaacuccau agucaggau     14280 aauugccugg agcaaauuca ccaugaacag gguccuugag gauacagaua aagggagcuc   14340
uggggccuuu ugacagguag gugucuauga ggcuucuaag cuuauuaaua ucgggccuca   14400
gguuugacaa cguuagagcu gccaucuuug ucuccacccc auauuaaua guucauga     14460 aggaagccag cccugcaucu cggauguagu ucccaacgau cuggauguuc uucucuaaug   14520
uggugagauc agaucuugca guauucauag ucacaagggu cucaaccaug agagauacaa   14580
ggcuuugcug agaucucaua accgagccua uccccucaac ugucccca gugaaaacua    14640 aggcaccuuu cacggugccg ucuugucuga acgccucuaa ccuguugaag aacccuuucc   14700
uuaagccggc gcugcuugug auggccuuca ccagcacaau ccagacuugg acaauuauug   14760
cuccuaggca ugcaggauac ccauagauuu gaaggagugu gucagggucu gcagcauccc   14820
guugacccug gaagagugg cucuuguuga ccauaggucc aaacagccau ucugugguccc   14880 ucucauauuc cauaucucuc gucuucacaa ugaauccguc ugucuucguc cucuuagggu   14940
cuuucucuau guuguagauc acauauuuga caucggcguu uacuccguuu guugucaagu   15000
acaaucuugg acuacuguaa gccauggcaa gcagagagac gaggaacccu ccucucugag   15060 agucugcuu aucuguguc aaugagugag cuaggaaggu uguugcaaug aauaacuugu     15120
cugcaucauc agucacacuu gggccuagua ugaacacuga gacugugcuc cucuggccgg   15180
ggauaacagc accuccuccc gacuuauuaa uacuuucgcu ccuccuagag cuaaauguau   15240
cgaaggugcu caacaacccg gccaucguga acuuuggcag caaagaaaag gaucggaac    15300 cugcuccuca gguggauac uuugacccua aaaccugcuc uaacuucauu auauauccca    15360
uacauguuuc uucucuuguu uggu                                          15384
```

<210> SEQ ID NO 4
<211> LENGTH: 15384
<212> TYPE: DNA
<213> ORGANISM: Artificial Sequence
<220> FEATURE:
<223> OTHER INFORMATION: Description of Artificial Sequence: Synthetic
      complete length gene cDNA of Sendai virus nagoya
<220> FEATURE:
<221> NAME/KEY: CDS
<222> LOCATION: (120)..(1691)
<223> OTHER INFORMATION: NP protein
<220> FEATURE:
<221> NAME/KEY: CDS
<222> LOCATION: (1844)..(3547)
<223> OTHER INFORMATION: P protein
<220> FEATURE:
<221> NAME/KEY: CDS
<222> LOCATION: (3669)..(4712)
<223> OTHER INFORMATION: M protein

```
<220> FEATURE:
<221> NAME/KEY: CDS
<222> LOCATION: (4866)..(6560)
<223> OTHER INFORMATION: F protein
<220> FEATURE:
<221> NAME/KEY: CDS
<222> LOCATION: (6693)..(8417)
<223> OTHER INFORMATION: HN protein
<220> FEATURE:
<221> NAME/KEY: CDS
<222> LOCATION: (8556)..(15239)
<223> OTHER INFORMATION: L protein

<400> SEQUENCE: 4
```

| | | |
|---|---|---|
| accaaacaag agaagaaaca tgtatggaat atataatgaa gttagacagg attttagggt | 60 |
| caaagtatcc accctgagga gcaggttcca gatccttttc tttgctgcca aagttcacg | 119 |

| atg gcc ggg ttg ttg agc acc ttc gat aca ttt agc tct agg agg agc | 167 |
|---|---|
| Met Ala Gly Leu Leu Ser Thr Phe Asp Thr Phe Ser Ser Arg Arg Ser | |
| 1               5                   10                  15 | |

| gaa agt att aat aag tcg gga gga ggt gct gtt atc ccc ggc cag agg | 215 |
|---|---|
| Glu Ser Ile Asn Lys Ser Gly Gly Gly Ala Val Ile Pro Gly Gln Arg | |
|         20                  25                  30 | |

| agc aca gtc tca gtg ttc ata cta ggc cca agt gtg act gat gat gca | 263 |
|---|---|
| Ser Thr Val Ser Val Phe Ile Leu Gly Pro Ser Val Thr Asp Asp Ala | |
|     35                  40                  45 | |

| gac aag tta ttc att gca aca acc ttc cta gct cac tca ttg gac aca | 311 |
|---|---|
| Asp Lys Leu Phe Ile Ala Thr Thr Phe Leu Ala His Ser Leu Asp Thr | |
| 50                  55                  60 | |

| gat aag cag cac tct cag aga gga ggg ttc ctc gtc tct ctg ctt gcc | 359 |
|---|---|
| Asp Lys Gln His Ser Gln Arg Gly Gly Phe Leu Val Ser Leu Leu Ala | |
| 65              70                  75                  80 | |

| atg gct tac agt agt cca gaa ttg tac ttg aca aca aac gga gta aac | 407 |
|---|---|
| Met Ala Tyr Ser Ser Pro Glu Leu Tyr Leu Thr Thr Asn Gly Val Asn | |
|             85                  90                  95 | |

| gcc gat gtc aaa tat gtg atc tac aac ata gag aaa gac cct aag agg | 455 |
|---|---|
| Ala Asp Val Lys Tyr Val Ile Tyr Asn Ile Glu Lys Asp Pro Lys Arg | |
|         100                 105                 110 | |

| acg aag aca gac gga ttc att gtg aag acg aga gat atg gaa tat gag | 503 |
|---|---|
| Thr Lys Thr Asp Gly Phe Ile Val Lys Thr Arg Asp Met Glu Tyr Glu | |
|     115                 120                 125 | |

| agg acc aca gaa tgg ctg ttt gga cct atg gtc aac aag agc cca ctc | 551 |
|---|---|
| Arg Thr Thr Glu Trp Leu Phe Gly Pro Met Val Asn Lys Ser Pro Leu | |
| 130                 135                 140 | |

| ttc cag ggt caa cgg gat gct gca gac cct gac aca ctc ctt caa atc | 599 |
|---|---|
| Phe Gln Gly Gln Arg Asp Ala Ala Asp Pro Asp Thr Leu Leu Gln Ile | |
| 145                 150                 155                 160 | |

| tat ggg tat cct gca tgc cta gga gca ata att gtc caa gtc tgg att | 647 |
|---|---|
| Tyr Gly Tyr Pro Ala Cys Leu Gly Ala Ile Ile Val Gln Val Trp Ile | |
|             165                 170                 175 | |

| gtg ctg gtg aag gcc atc aca agc agc gcc ggc tta agg aaa ggg ttc | 695 |
|---|---|
| Val Leu Val Lys Ala Ile Thr Ser Ser Ala Gly Leu Arg Lys Gly Phe | |
|         180                 185                 190 | |

| ttc aac agg tta gag gcg ttc aga caa gac ggc acc gtg aaa ggt gcc | 743 |
|---|---|
| Phe Asn Arg Leu Glu Ala Phe Arg Gln Asp Gly Thr Val Lys Gly Ala | |
|     195                 200                 205 | |

| tta gtt ttc act ggg gag aca gtt gag ggg ata ggc tcg gtt atg aga | 791 |
|---|---|
| Leu Val Phe Thr Gly Glu Thr Val Glu Gly Ile Gly Ser Val Met Arg | |
| 210                 215                 220 | |

| tct cag caa agc ctt gta tct ctc atg gtt gag acc ctt gtg act atg | 839 |
|---|---|
| Ser Gln Gln Ser Leu Val Ser Leu Met Val Glu Thr Leu Val Thr Met | |
| 225                 230                 235                 240 | |

| | | |
|---|---|---|
| aat act gca aga tct gat ctc acc aca tta gag aag aac atc cag atc<br>Asn Thr Ala Arg Ser Asp Leu Thr Thr Leu Glu Lys Asn Ile Gln Ile<br>                      245                    250                    255 | 887 |
| gtt ggg aac tac atc cga gat gca ggg ctg gct tcc ttc atg aac act<br>Val Gly Asn Tyr Ile Arg Asp Ala Gly Leu Ala Ser Phe Met Asn Thr<br>            260                    265                    270 | 935 |
| att aaa tat ggg gtg gag aca aag atg gca gct cta acg ttg tca aac<br>Ile Lys Tyr Gly Val Glu Thr Lys Met Ala Ala Leu Thr Leu Ser Asn<br>        275                    280                    285 | 983 |
| ctg agg ccc gat att aat aag ctt aga agc ctc ata gac acc tac ctg<br>Leu Arg Pro Asp Ile Asn Lys Leu Arg Ser Leu Ile Asp Thr Tyr Leu<br>290                    295                    300 | 1031 |
| tca aaa ggc ccc aga gct ccc ttt atc tgt atc ctc aag gac cct gtt<br>Ser Lys Gly Pro Arg Ala Pro Phe Ile Cys Ile Leu Lys Asp Pro Val<br>305                    310                    315                    320 | 1079 |
| cat ggt gaa ttt gct cca ggc aat tat cct gca cta tgg agt tac gcc<br>His Gly Glu Phe Ala Pro Gly Asn Tyr Pro Ala Leu Trp Ser Tyr Ala<br>            325                    330                    335 | 1127 |
| atg gga gtc gcc gtc gta cag aac aag tca atg cag cag tac gtc aca<br>Met Gly Val Ala Val Val Gln Asn Lys Ser Met Gln Gln Tyr Val Thr<br>        340                    345                    350 | 1175 |
| ggg agg aca tac ctt gat atg gaa atg ttc tta cta gga caa gcc gtg<br>Gly Arg Thr Tyr Leu Asp Met Glu Met Phe Leu Leu Gly Gln Ala Val<br>                355                    360                    365 | 1223 |
| gca aag gat gct gaa tcg aag atc agc agt gcc ttg gaa gat gag tta<br>Ala Lys Asp Ala Glu Ser Lys Ile Ser Ser Ala Leu Glu Asp Glu Leu<br>370                    375                    380 | 1271 |
| gga gtg acg gat aca gcc aag gag agg ctc aga cat cat ctg gca aac<br>Gly Val Thr Asp Thr Ala Lys Glu Arg Leu Arg His His Leu Ala Asn<br>385                    390                    395                    400 | 1319 |
| ttg tcc ggt ggg gat ggt gct tac cac aaa cca aca ggc ggt ggt gca<br>Leu Ser Gly Gly Asp Gly Ala Tyr His Lys Pro Thr Gly Gly Gly Ala<br>                    405                    410                    415 | 1367 |
| att gag gta gct cta gac aat gcc gat atc gac ctg gaa aca gaa gct<br>Ile Glu Val Ala Leu Asp Asn Ala Asp Ile Asp Leu Glu Thr Glu Ala<br>                  420                    425                    430 | 1415 |
| cat gcg gac cag gac gct agg ggt tgg ggt gga gat agt ggt gaa aga<br>His Ala Asp Gln Asp Ala Arg Gly Trp Gly Gly Asp Ser Gly Glu Arg<br>        435                    440                    445 | 1463 |
| tgg gca cgt cag gtg agt ggt ggc cac ttt gtc aca cta cat ggg gct<br>Trp Ala Arg Gln Val Ser Gly Gly His Phe Val Thr Leu His Gly Ala<br>450                    455                    460 | 1511 |
| gaa cgg tta gag gag gaa acc aat gat gag gat gta tca gac ata gag<br>Glu Arg Leu Glu Glu Glu Thr Asn Asp Glu Asp Val Ser Asp Ile Glu<br>465                    470                    475                    480 | 1559 |
| aga aga ata gcc atg aga ctc gca gag aga cgg caa gag gat tct gca<br>Arg Arg Ile Ala Met Arg Leu Ala Glu Arg Arg Gln Glu Asp Ser Ala<br>                  485                    490                    495 | 1607 |
| acc cat gga gat gaa ggc cgc aat aac ggt gtt gat cac gaa gaa gat<br>Thr His Gly Asp Glu Gly Arg Asn Asn Gly Val Asp His Glu Glu Asp<br>            500                    505                    510 | 1655 |
| gac gat gcc gca gca gca gct ggg ata gga gga atc taggatcata<br>Asp Asp Ala Ala Ala Ala Ala Gly Ile Gly Gly Ile<br>        515                    520 | 1701 |
| cgaggcctca aggtacttga tccgcagtaa gaaaaactta gggtgaaagt tcatccaccg | 1761 |
| atcggctcag gcaaggccac acccaacccc accgaccaca cccagcagtc gagacagcca | 1821 |
| cggcttcggc tacacttacc gc atg gat caa gat gcc ttc att ctt aaa gaa<br>                                  Met Asp Gln Asp Ala Phe Ile Leu Lys Glu<br>                                    525                    530 | 1873 |

```
gat tct gaa gtt gag agg aag gcg cca gga gga cga gag tcg ctc tcg    1921
Asp Ser Glu Val Glu Arg Lys Ala Pro Gly Gly Arg Glu Ser Leu Ser
535                 540                 545                 550 gat gtt atc gga ttc ctc gat gct gtc ctg tcg aat gaa cca act gac    1969
Asp Val Ile Gly Phe Leu Asp Ala Val Leu Ser Asn Glu Pro Thr Asp
                555                 560                 565 atc gga ggg gac aga agc tgg ctc cac aac acc atc aac act ccc caa    2017
Ile Gly Gly Asp Arg Ser Trp Leu His Asn Thr Ile Asn Thr Pro Gln
        570                 575                 580 gga cca ggc tct gct cat aga gcc aaa agt gag ggc gaa gga gaa gtc    2065
Gly Pro Gly Ser Ala His Arg Ala Lys Ser Glu Gly Glu Gly Glu Val
585                 590                 595 tca aca ccg tcg acc caa gat aat cga tca ggt gag gag agt aga gtc    2113
Ser Thr Pro Ser Thr Gln Asp Asn Arg Ser Gly Glu Glu Ser Arg Val
                600                 605                 610 tct ggg aga aca agc aag cca gag gca gaa gca cat gct gga aac ctt    2161
Ser Gly Arg Thr Ser Lys Pro Glu Ala Glu Ala His Ala Gly Asn Leu
615                 620                 625                 630 gat aaa caa aat ata cac tgg gcc ttt agg gga aga act ggt aca aac    2209
Asp Lys Gln Asn Ile His Trp Ala Phe Arg Gly Arg Thr Gly Thr Asn
                635                 640                 645 tct gta tct cag gat ctg gac gat gga gga gac tcc gga atc ctt gaa    2257
Ser Val Ser Gln Asp Leu Asp Asp Gly Gly Asp Ser Gly Ile Leu Glu
        650                 655                 660 aat cct cca aat gag aga gga tat ccg aga tca ggt att gaa gat gaa    2305
Asn Pro Pro Asn Glu Arg Gly Tyr Pro Arg Ser Gly Ile Glu Asp Glu
            665                 670                 675 aac aga gag atg gct gcg cac cct gat aag agg gga gaa gac caa gct    2353
Asn Arg Glu Met Ala Ala His Pro Asp Lys Arg Gly Glu Asp Gln Ala
                680                 685                 690 gaa gga ctt cca gaa gag gta cga gga ggt aca tcc cta cct gat gaa    2401
Glu Gly Leu Pro Glu Glu Val Arg Gly Gly Thr Ser Leu Pro Asp Glu
695                 700                 705                 710 gga gaa ggt gga gca agt aat aat gga aga agc atg gag cct ggc agc    2449
Gly Glu Gly Gly Ala Ser Asn Asn Gly Arg Ser Met Glu Pro Gly Ser
                715                 720                 725 tca cat agt gca aga gta act ggg gtc ctg gtg att cct agc ccc gaa    2497
Ser His Ser Ala Arg Val Thr Gly Val Leu Val Ile Pro Ser Pro Glu
            730                 735                 740 ctt gaa gag gct gtg cta cgg agg aac aaa aga aga cct acc aac agt    2545
Leu Glu Glu Ala Val Leu Arg Arg Asn Lys Arg Arg Pro Thr Asn Ser
                745                 750                 755 ggg tcc aaa cct ctt act cca gca acc gtg cct ggc acc cgg tcc cca    2593
Gly Ser Lys Pro Leu Thr Pro Ala Thr Val Pro Gly Thr Arg Ser Pro
760                 765                 770 ccg ctg aat cgt tac aac agc aca ggg tca cca cca gga aaa ccc cca    2641
Pro Leu Asn Arg Tyr Asn Ser Thr Gly Ser Pro Pro Gly Lys Pro Pro
775                 780                 785                 790 tct aca cag gat gag cac atc aac tct ggg gac acc ccc gcc gtc agg    2689
Ser Thr Gln Asp Glu His Ile Asn Ser Gly Asp Thr Pro Ala Val Arg
                795                 800                 805 gtc aaa gac cgg aaa cca tca ata ggg act cgc tct gtc tca gat tgt    2737
Val Lys Asp Arg Lys Pro Ser Ile Gly Thr Arg Ser Val Ser Asp Cys
        810                 815                 820 cca gcc aac ggc cgc cca atc cat ccg ggt ata gag acc gac tca aca    2785
Pro Ala Asn Gly Arg Pro Ile His Pro Gly Ile Glu Thr Asp Ser Thr
            825                 830                 835 aaa aag ggc ata gga gag aac aca tca tct atg aaa gat atg gct aca    2833
Lys Lys Gly Ile Gly Glu Asn Thr Ser Ser Met Lys Asp Met Ala Thr
```

-continued

| | | |
|---|---|---|
| ttg ttg acg agt ctt ggt gta atc cag tct gct caa gaa ttc gag tca<br>Leu Leu Thr Ser Leu Gly Val Ile Gln Ser Ala Gln Glu Phe Glu Ser<br>855                           860                             865                     870 | 2881 |

840                            845                            850 ttg ttg acg agt ctt ggt gta atc cag tct gct caa gaa ttc gag tca        2881
    Leu Leu Thr Ser Leu Gly Val Ile Gln Ser Ala Gln Glu Phe Glu Ser
    855                     860                     865                     870 tcc cga gac gcg agt tat gtg ttt gca aga cgt gcc cta aag tct gca        2929
    Ser Arg Asp Ala Ser Tyr Val Phe Ala Arg Arg Ala Leu Lys Ser Ala
                            875                     880                     885 aac tat gca gag atg aca ttc aat gta tgc ggc ctg atc ctt tct gcc        2977
    Asn Tyr Ala Glu Met Thr Phe Asn Val Cys Gly Leu Ile Leu Ser Ala
                    890                     895                     900 gag aaa tct tcc gct cgt aag gta gat gag aac aaa caa ctg ctc aaa        3025
    Glu Lys Ser Ser Ala Arg Lys Val Asp Glu Asn Lys Gln Leu Leu Lys
            905                     910                     915 cag atc caa gag agc gtg gaa tca ttc cgg gat att tac aag aga ttc        3073
    Gln Ile Gln Glu Ser Val Glu Ser Phe Arg Asp Ile Tyr Lys Arg Phe
    920                     925                     930 tct gag tat cag aaa gaa cag aac tca ttg ctg atg tcc aac cta tct        3121
    Ser Glu Tyr Gln Lys Glu Gln Asn Ser Leu Leu Met Ser Asn Leu Ser
    935                     940                     945                     950 aca ctt cat atc atc aca gat aga ggt ggc aag act gac aac aca gac        3169
    Thr Leu His Ile Ile Thr Asp Arg Gly Gly Lys Thr Asp Asn Thr Asp
                    955                     960                     965 tcc ctt aca agg tcc ccc tcc gtt ttt gca aaa tca aaa gag aac aag        3217
    Ser Leu Thr Arg Ser Pro Ser Val Phe Ala Lys Ser Lys Glu Asn Lys
                            970                     975                     980 act aag gct acc agg ttt gac cca tct atg gag acc tta gaa gat atg        3265
    Thr Lys Ala Thr Arg Phe Asp Pro Ser Met Glu Thr Leu Glu Asp Met
                    985                     990                     995 aag tac aaa ccg gac cta atc cga gag gat gaa ttt aga gat gag           3310
    Lys Tyr Lys Pro Asp Leu Ile Arg Glu Asp Glu Phe Arg Asp Glu
            1000                    1005                    1010 atc cgc aac ccg gtg tac caa gag agg gac aca gaa ccc agg gcc           3355
    Ile Arg Asn Pro Val Tyr Gln Glu Arg Asp Thr Glu Pro Arg Ala
        1015                    1020                    1025 tca aac gca tca cgt ctc ttc ccc tcc aaa gag aag cac aca atg           3400
    Ser Asn Ala Ser Arg Leu Phe Pro Ser Lys Glu Lys His Thr Met
        1030                    1035                    1040 cac tct ctc agg ctc gtc ata gag agc agt ccc cta agc aga gct           3445
    His Ser Leu Arg Leu Val Ile Glu Ser Ser Pro Leu Ser Arg Ala
        1045                    1050                    1055 gag aaa gca gca tat gtg aaa tca tta tcc aag tgc aag aca gac           3490
    Glu Lys Ala Ala Tyr Val Lys Ser Leu Ser Lys Cys Lys Thr Asp
        1060                    1065                    1070 caa gag gtt aag gca gtc atg gaa ctc gta gaa gag gac ata gag           3535
    Gln Glu Val Lys Ala Val Met Glu Leu Val Glu Glu Asp Ile Glu
        1075                    1080                    1085 tca ctg acc aac tagatcccgg gtgaggcatc ccaccatcct cagtcacaga           3587
    Ser Leu Thr Asn
        1090 gagacccaat ctaccatcag catcagccag taaagattaa gaaaaactta gggtgaaaga    3647 aatttcacct aacacggcgc a atg gca gat  atc tat aga ttc cct  aag ttc     3698
                             Met Ala Asp Ile Tyr Arg Phe Pro Lys Phe
                                        1095                    1100 tca tat gag gat aac ggt act gtg gag ccc ctg cct ctg aga act           3743
    Ser Tyr Glu Asp Asn Gly Thr Val Glu Pro Leu Pro Leu Arg Thr
        1105                    1110                    1115 ggt ccg gat aag aaa gcc atc ccc cac atc agg att gtc aag gta           3788
    Gly Pro Asp Lys Lys Ala Ile Pro His Ile Arg Ile Val Lys Val
        1120                    1125                    1130

```
gga gac cct cct aaa cat gga gtg aga tac cta gat tta ttg ctc      3833
Gly Asp Pro Pro Lys His Gly Val Arg Tyr Leu Asp Leu Leu Leu
            1135                1140                1145 ttg ggt ttc ttt gag aca ccg aaa caa aca acc aat cta ggg agc      3878
Leu Gly Phe Phe Glu Thr Pro Lys Gln Thr Thr Asn Leu Gly Ser
        1150                1155                1160 gta tct gac ttg aca gag ccg acc agc tac tca ata tgc ggc tcc      3923
Val Ser Asp Leu Thr Glu Pro Thr Ser Tyr Ser Ile Cys Gly Ser
    1165                1170                1175 ggg tcg tta ccc ata ggt gtg gcc aaa tac tac ggg act gat cag      3968
Gly Ser Leu Pro Ile Gly Val Ala Lys Tyr Tyr Gly Thr Asp Gln
1180                1185                1190 gaa ctc tta aag gcc tgc acc gat ctc aga atc acg gtg agg agg      4013
Glu Leu Leu Lys Ala Cys Thr Asp Leu Arg Ile Thr Val Arg Arg
        1195                1200                1205 act gtt cga gca gga gag atg atc gta tac atg gtg gat ttg att      4058
Thr Val Arg Ala Gly Glu Met Ile Val Tyr Met Val Asp Leu Ile
    1210                1215                1220 ggt gct cca ctc cta cca tgg tca ggt aag ctg aga cag gga atg      4103
Gly Ala Pro Leu Leu Pro Trp Ser Gly Lys Leu Arg Gln Gly Met
1225                1230                1235 ata ttt aat gca aac aag gtc gca cta gct ccc caa tgc ctc cct      4148
Ile Phe Asn Ala Asn Lys Val Ala Leu Ala Pro Gln Cys Leu Pro
        1240                1245                1250 gtg gac aag gac ata aga ttc aga gtg gtg ttt gtc aat ggg aca      4193
Val Asp Lys Asp Ile Arg Phe Arg Val Val Phe Val Asn Gly Thr
    1255                1260                1265 tct cta ggg gca atc acc ata gcc aag atc cca aag acc ctt gca      4238
Ser Leu Gly Ala Ile Thr Ile Ala Lys Ile Pro Lys Thr Leu Ala
1270                1275                1280 gac ctt gca ttg ccc aac tct ata tcc gtt aat cta ctg gtg aca      4283
Asp Leu Ala Leu Pro Asn Ser Ile Ser Val Asn Leu Leu Val Thr
        1285                1290                1295 ctc aag acc ggg atc tcc aca gaa caa aag ggg gta ctc cca gta      4328
Leu Lys Thr Gly Ile Ser Thr Glu Gln Lys Gly Val Leu Pro Val
    1300                1305                1310 ctt gat gat caa ggg gag aaa aag ctc aat ttt atg gtg cac ctc      4373
Leu Asp Asp Gln Gly Glu Lys Lys Leu Asn Phe Met Val His Leu
1315                1320                1325 ggg ttg atc agg aga aag gtc ggg aag ata tac tct gtt gag tac      4418
Gly Leu Ile Arg Arg Lys Val Gly Lys Ile Tyr Ser Val Glu Tyr
        1330                1335                1340 tgc aag agc aag att gag aga atg cgg ctg att ttc tca ctt ggg      4463
Cys Lys Ser Lys Ile Glu Arg Met Arg Leu Ile Phe Ser Leu Gly
    1345                1350                1355 tta atc ggc ggt ata agc ttc cat gtt cag gtt act ggg aca cta      4508
Leu Ile Gly Gly Ile Ser Phe His Val Gln Val Thr Gly Thr Leu
1360                1365                1370 tct aag aca ttc atg agt cag ctc gca tgg aag agg gca gtc tgc      4553
Ser Lys Thr Phe Met Ser Gln Leu Ala Trp Lys Arg Ala Val Cys
        1375                1380                1385 ttc cca ttg atg gat gtg aat ccc cat atg aac atg gtg att tgg      4598
Phe Pro Leu Met Asp Val Asn Pro His Met Asn Met Val Ile Trp
    1390                1395                1400 gcg gca tct gta gaa atc aca ggc gtc gat gcg gtg ttc caa ccg      4643
Ala Ala Ser Val Glu Ile Thr Gly Val Asp Ala Val Phe Gln Pro
1405                1410                1415 gcc atc cct cgt gat ttc cgc tac tac cct aat gtt gtg gct aag      4688
Ala Ile Pro Arg Asp Phe Arg Tyr Tyr Pro Asn Val Val Ala Lys
```

```
                 1420                1425                1430
aac atc gga  agg atc aga  aag ctg  taaatgtgca cccatcagag              4732
Asn Ile Gly  Arg Ile Arg  Lys Leu
         1435               1440 acctgcaaca atgtctcaag cagacaccac ctggcagtcg gagccaccgg gtcactcctt     4792
gtcttaaata agaaaaactt agggataaag tcccttgtga gtgcttggtt gcaaaactct     4852
ccccttggga aac atg aca gca tat atc  cag agg tca cag tgc  atc tca     4901
            Met Thr Ala Tyr Ile  Gln Arg Ser Gln Cys  Ile Ser
                         1445                  1450 aca tca cta  ctg gtt gtt ctc acc  aca ttg gtc tcg tgt  cag att       4946
Thr Ser Leu  Leu Val Val Leu Thr  Thr Leu Val Ser Cys  Gln Ile
         1455               1460                   1465 ccc agg gat  atg ctc tct aac ata  ggg gtc ata gtc gat  gaa ggg       4991
Pro Arg Asp  Met Leu Ser Asn Ile  Gly Val Ile Val Asp  Glu Gly
         1470               1475                   1480 aaa tca ctg  aag ata gct ggg tcc  cac gaa tcg agg tac  ata gta       5036
Lys Ser Leu  Lys Ile Ala Gly Ser  His Glu Ser Arg Tyr  Ile Val
         1485               1490                   1495 ctg agt cta  gtt ccg ggg gta gac  ctt gag aat gga tgc  gga aca       5081
Leu Ser Leu  Val Pro Gly Val Asp  Leu Glu Asn Gly Cys  Gly Thr
         1500               1505                   1510 gct cag gtt  atc cag tac aag agc  cta ctg aac agg ctg  tta atc       5126
Ala Gln Val  Ile Gln Tyr Lys Ser  Leu Leu Asn Arg Leu  Leu Ile
         1515               1520                   1525 cca ttg agg  gat gcc tta gat ctt  cag gag gct ctg ata  act gtc       5171
Pro Leu Arg  Asp Ala Leu Asp Leu  Gln Glu Ala Leu Ile  Thr Val
         1530               1535                   1540 acc aat gat  acg aca caa aat gcc  ggt gtt cca cag tcg  aga ttc       5216
Thr Asn Asp  Thr Thr Gln Asn Ala  Gly Val Pro Gln Ser  Arg Phe
         1545               1550                   1555 ttc ggt gct  gtg att ggt act gtc  gca ctt gga gtg gcg  aca tca       5261
Phe Gly Ala  Val Ile Gly Thr Val  Ala Leu Gly Val Ala  Thr Ser
         1560               1565                   1570 gca cag atc  acc gca ggg att gca  cta gcc gaa gcg agg  gag gcc       5306
Ala Gln Ile  Thr Ala Gly Ile Ala  Leu Ala Glu Ala Arg  Glu Ala
         1575               1580                   1585 aaa aga gac  ata gcg ctc atc aag  gaa tcg atg aca aaa  aca cac       5351
Lys Arg Asp  Ile Ala Leu Ile Lys  Glu Ser Met Thr Lys  Thr His
         1590               1595                   1600 aag tct ata  gaa ctg ctg caa aac  gct gtg ggg gaa caa  att ctt       5396
Lys Ser Ile  Glu Leu Leu Gln Asn  Ala Val Gly Glu Gln  Ile Leu
         1605               1610                   1615 gct cta aag  aca ctc cag gat ttc  gtg aat gat gag atc  aaa ccc       5441
Ala Leu Lys  Thr Leu Gln Asp Phe  Val Asn Asp Glu Ile  Lys Pro
         1620               1625                   1630 gca ata agc  gaa tta ggc tgt gag  act gct gcc tta aga  ctg ggt       5486
Ala Ile Ser  Glu Leu Gly Cys Glu  Thr Ala Ala Leu Arg  Leu Gly
         1635               1640                   1645 ata aaa ttt  aca cag cat tac tcc  gag ctg tta act gcg  ttc ggc       5531
Ile Lys Phe  Thr Gln His Tyr Ser  Glu Leu Leu Thr Ala  Phe Gly
         1650               1655                   1660 tcg aat ttc  gga acc atc gga gag  aag agc ctc acg ctg  cag gcg       5576
Ser Asn Phe  Gly Thr Ile Gly Glu  Lys Ser Leu Thr Leu  Gln Ala
         1665               1670                   1675 ctg tct tca  ctt tac tct gct aac  att act gag att atg  act aca       5621
Leu Ser Ser  Leu Tyr Ser Ala Asn  Ile Thr Glu Ile Met  Thr Thr
         1680               1685                   1690 atc agg aca  ggg cag tct aac atc  tat gat gtc att tat  aca gaa       5666
```

```
Ile Arg Thr Gly Gln Ser Asn Ile Tyr Asp Val Ile Tyr Thr Glu
            1695            1700            1705 cag atc aaa gga acg gtg ata gat gtg gat ctg gag aga tac atg    5711
Gln Ile Lys Gly Thr Val Ile Asp Val Asp Leu Glu Arg Tyr Met
        1710            1715            1720 gtt acc ctg tct gtg aag atc cct att ctt tct gaa gtc cca ggt    5756
Val Thr Leu Ser Val Lys Ile Pro Ile Leu Ser Glu Val Pro Gly
            1725            1730            1735 gtg ctc ata cac aag gca tcg tct att tct tac aac ata gac ggg    5801
Val Leu Ile His Lys Ala Ser Ser Ile Ser Tyr Asn Ile Asp Gly
        1740            1745            1750 gag gaa tgg tat gtg act gtc ccc agc cat ata ctc agt cgt gct    5846
Glu Glu Trp Tyr Val Thr Val Pro Ser His Ile Leu Ser Arg Ala
            1755            1760            1765 tct ttc tta ggg ggt gca gac ata acc gat tgt gtt gag tcc aga    5891
Ser Phe Leu Gly Gly Ala Asp Ile Thr Asp Cys Val Glu Ser Arg
        1770            1775            1780 ttg acc tat ata tgc ccc agg gat ccc gca caa ctg ata cct gac    5936
Leu Thr Tyr Ile Cys Pro Arg Asp Pro Ala Gln Leu Ile Pro Asp
            1785            1790            1795 agc cag caa aag tgt atc ctg ggg gac aca aca aag tgt cct gtc    5981
Ser Gln Gln Lys Cys Ile Leu Gly Asp Thr Thr Lys Cys Pro Val
        1800            1805            1810 aca aaa gtt gtg gac agc ctt atc ccc aag ttt gct ttt gtg aat    6026
Thr Lys Val Val Asp Ser Leu Ile Pro Lys Phe Ala Phe Val Asn
            1815            1820            1825 ggg ggc gtt gtt gct aac tgc ata gca tcc aca tgt acc tgc ggg    6071
Gly Gly Val Val Ala Asn Cys Ile Ala Ser Thr Cys Thr Cys Gly
        1830            1835            1840 aca ggc cga aga cca atc agt cag gat cgc tct aaa ggt gta gta    6116
Thr Gly Arg Arg Pro Ile Ser Gln Asp Arg Ser Lys Gly Val Val
            1845            1850            1855 ttc cta acc cat gac aac tgt ggt ctt ata ggt gtc aat ggg gta    6161
Phe Leu Thr His Asp Asn Cys Gly Leu Ile Gly Val Asn Gly Val
        1860            1865            1870 gaa ttg tat gct aat cgg aga ggg cac gat gcc act tgg ggg gtc    6206
Glu Leu Tyr Ala Asn Arg Arg Gly His Asp Ala Thr Trp Gly Val
            1875            1880            1885 cag aac ttg aca gtc ggt cct gca att gct atc aga ccc gtt gat    6251
Gln Asn Leu Thr Val Gly Pro Ala Ile Ala Ile Arg Pro Val Asp
        1890            1895            1900 att tct ctc aac ctt gct gat gct acg aat ttc ttg caa gac tct    6296
Ile Ser Leu Asn Leu Ala Asp Ala Thr Asn Phe Leu Gln Asp Ser
            1905            1910            1915 aag gct gag ctt gag aaa gca cgg aaa atc ctc tct gag gta ggt    6341
Lys Ala Glu Leu Glu Lys Ala Arg Lys Ile Leu Ser Glu Val Gly
        1920            1925            1930 aga tgg tac aac tca aga gag act gtg att acg atc ata gta gtc    6386
Arg Trp Tyr Asn Ser Arg Glu Thr Val Ile Thr Ile Ile Val Val
            1935            1940            1945 atg gtc gta ata ttg gtg gtc att ata gtg atc gtc atc atg ctt    6431
Met Val Val Ile Leu Val Val Ile Ile Val Ile Val Ile Met Leu
        1950            1955            1960 tat aga ctc aga agg tca atg tta atg ggt aat cca gat gac cgt    6476
Tyr Arg Leu Arg Arg Ser Met Leu Met Gly Asn Pro Asp Asp Arg
            1965            1970            1975 ata ccg agg gac aca tac aca tta gag ccg aag atc aga cat atg    6521
Ile Pro Arg Asp Thr Tyr Thr Leu Glu Pro Lys Ile Arg His Met
        1980            1985            1990
```

```
tac aca aac ggt ggg ttt gat gca atg gct gag aaa aga tgatcacgac    6570
Tyr Thr Asn Gly Gly Phe Asp Ala Met Ala Glu Lys Arg
            1995                2000            2005 tattatcaga tgtcttgtaa agcaggcatg gtatccattg agatctgtat ataataagaa   6630
aaacttaggg tgaaagtgag gttgcgcggt attgtagctt tcatctcaaa caagcacaga   6690 tc atg gat ggt gat agg ggc aaa cgt gac tcg tac tgg tct acc tct     6737
   Met Asp Gly Asp Arg Gly Lys Arg Asp Ser Tyr Trp Ser Thr Ser
                   2010            2015                2020 cct agt ggt agc act aca aaa tta gca tca agt tgg gag agg tca        6782
Pro Ser Gly Ser Thr Thr Lys Leu Ala Ser Ser Trp Glu Arg Ser
                2025            2030            2035 agt aaa gtt gac aca tgg ttg ctg att ctc tca ttc acc cag tgg        6827
Ser Lys Val Asp Thr Trp Leu Leu Ile Leu Ser Phe Thr Gln Trp
                2040            2045            2050 gct ttg tca att gcc aca gtg atc atc tgt atc ata att tct gct        6872
Ala Leu Ser Ile Ala Thr Val Ile Ile Cys Ile Ile Ile Ser Ala
                2055            2060            2065 aga caa ggg tat agt atg aaa gag tac tca atg act gta gag gca        6917
Arg Gln Gly Tyr Ser Met Lys Glu Tyr Ser Met Thr Val Glu Ala
                2070            2075            2080 ttg aac atg agc agc agg gag gtg aaa gag tca ctt acc agt cta        6962
Leu Asn Met Ser Ser Arg Glu Val Lys Glu Ser Leu Thr Ser Leu
                2085            2090            2095 ata agg caa gag gtt ata gca agg gct gtc aac att cag agc tct        7007
Ile Arg Gln Glu Val Ile Ala Arg Ala Val Asn Ile Gln Ser Ser
                2100            2105            2110 gtg caa acc gga atc cca gtc ttg ttg aac aaa aac agc agg gat        7052
Val Gln Thr Gly Ile Pro Val Leu Leu Asn Lys Asn Ser Arg Asp
                2115            2120            2125 gtc atc cag atg att gat aag tcg tgc agc aga caa gag ctc act        7097
Val Ile Gln Met Ile Asp Lys Ser Cys Ser Arg Gln Glu Leu Thr
                2130            2135            2140 cag ctc tgt gag agt acg atc gca gtc cac cat gcc gag gga att        7142
Gln Leu Cys Glu Ser Thr Ile Ala Val His His Ala Glu Gly Ile
                2145            2150            2155 acc cca ctt gag cca cat agt ttc tgg aga tgc cct gtc gga gaa        7187
Thr Pro Leu Glu Pro His Ser Phe Trp Arg Cys Pro Val Gly Glu
                2160            2165            2170 ccg tat ctt agc tca gat cct aaa atc tca ttg ctg cct ggt ccg        7232
Pro Tyr Leu Ser Ser Asp Pro Lys Ile Ser Leu Leu Pro Gly Pro
                2175            2180            2185 agc ttg tta cct ggt tct aca acg atc tct gga tgt gtt agg ctc        7277
Ser Leu Leu Pro Gly Ser Thr Thr Ile Ser Gly Cys Val Arg Leu
                2190            2195            2200 cct tca ctc tca att ggc gag gca atc tat gcc tat tca tca aat        7322
Pro Ser Leu Ser Ile Gly Glu Ala Ile Tyr Ala Tyr Ser Ser Asn
                2205            2210            2215 ctc att aca caa ggt tgt gct gat ata ggg aaa tca tat cag gtc        7367
Leu Ile Thr Gln Gly Cys Ala Asp Ile Gly Lys Ser Tyr Gln Val
                2220            2225            2230 ctg cag cta ggg tat ata tca ctc aat tca gat atg ttc cct gat        7412
Leu Gln Leu Gly Tyr Ile Ser Leu Asn Ser Asp Met Phe Pro Asp
                2235            2240            2245 ctt aac ccc gta gtg tcc cac act tat gac atc aac gac aat cgg        7457
Leu Asn Pro Val Val Ser His Thr Tyr Asp Ile Asn Asp Asn Arg
                2250            2255            2260 aaa tca tgc tct gtg gtg gca acc ggg act agg ggt tat cag ctt        7502
Lys Ser Cys Ser Val Val Ala Thr Gly Thr Arg Gly Tyr Gln Leu
                2265            2270            2275
```

-continued

| | | | | | | | | | | | | | |
|---|---|---|---|---|---|---|---|---|---|---|---|---|---|
| tgc | tcc | atg | ccg | act | gta | gac | gaa | aga | acc | gac | tac | tct | agt | gac | 7547 |
| Cys | Ser | Met | Pro | Thr | Val | Asp | Glu | Arg | Thr | Asp | Tyr | Ser | Ser | Asp |
| | | | 2280 | | | | 2285 | | | | 2290 | | | | ggt atc gag gat ctg gtc ctt gat gtc ctg gat ctc aaa ggg aga  7592
Gly Ile Glu Asp Leu Val Leu Asp Val Leu Asp Leu Lys Gly Arg
                2295                2300                2305 act aag tct cac cgg tat cgc aac agc gag gta gat ctt gat cac  7637
Thr Lys Ser His Arg Tyr Arg Asn Ser Glu Val Asp Leu Asp His
                2310                2315                2320 ccg ttc tct gca cta tac ccc agt gta ggc aac ggc att gca aca  7682
Pro Phe Ser Ala Leu Tyr Pro Ser Val Gly Asn Gly Ile Ala Thr
                2325                2330                2335 gaa ggc aca ttg ata ttt ctt ggg tat ggt gga cta acc act cct  7727
Glu Gly Thr Leu Ile Phe Leu Gly Tyr Gly Gly Leu Thr Thr Pro
                2340                2345                2350 ctg cag ggt gat aca aaa tgt agg act aaa gga tgc caa cag gtg  7772
Leu Gln Gly Asp Thr Lys Cys Arg Thr Lys Gly Cys Gln Gln Val
                2355                2360                2365 tcg caa gac aca tgc aat gag gct ctg aaa att aca tgg cta gga  7817
Ser Gln Asp Thr Cys Asn Glu Ala Leu Lys Ile Thr Trp Leu Gly
                2370                2375                2380 ggg aaa cag gtg gtc agc gtg atc atc cag gtc aat gac tat ctc  7862
Gly Lys Gln Val Val Ser Val Ile Ile Gln Val Asn Asp Tyr Leu
                2385                2390                2395 tca gag agg cca aag ata aga gtc aca acc att cca atc act caa  7907
Ser Glu Arg Pro Lys Ile Arg Val Thr Thr Ile Pro Ile Thr Gln
                2400                2405                2410 aac tat ctc ggg gcg gaa ggt aga tta tta aaa ttg ggt gat cgg  7952
Asn Tyr Leu Gly Ala Glu Gly Arg Leu Leu Lys Leu Gly Asp Arg
                2415                2420                2425 gta tac atc tat aca aga tca tca ggc tgg cac tct caa ctg cag  7997
Val Tyr Ile Tyr Thr Arg Ser Ser Gly Trp His Ser Gln Leu Gln
                2430                2435                2440 ata gga gta ctt gat atc agc cac cct ttg act atc aac tgg aca  8042
Ile Gly Val Leu Asp Ile Ser His Pro Leu Thr Ile Asn Trp Thr
                2445                2450                2455 cct cat gag gcc ttg tct aga cca gga aat aaa gag tgc aat tgg  8087
Pro His Glu Ala Leu Ser Arg Pro Gly Asn Lys Glu Cys Asn Trp
                2460                2465                2470 tac aat acg tgt ccg aag gaa tgc ata tca ggc gta tac act gat  8132
Tyr Asn Thr Cys Pro Lys Glu Cys Ile Ser Gly Val Tyr Thr Asp
                2475                2480                2485 gct tat cca ttg tcc cct gat gca gct aac gtc gct acc gtc acg  8177
Ala Tyr Pro Leu Ser Pro Asp Ala Ala Asn Val Ala Thr Val Thr
                2490                2495                2500 cta tat gcc aat aca tca cgt gtc aac cca aca atc atg tat tct  8222
Leu Tyr Ala Asn Thr Ser Arg Val Asn Pro Thr Ile Met Tyr Ser
                2505                2510                2515 aac act act aac att ata aat atg tta agg ata aag gat gtt caa  8267
Asn Thr Thr Asn Ile Ile Asn Met Leu Arg Ile Lys Asp Val Gln
                2520                2525                2530 tta gag gct gca tat acc acg aca tcg tgt atc acg cat ttt ggt  8312
Leu Glu Ala Ala Tyr Thr Thr Thr Ser Cys Ile Thr His Phe Gly
                2535                2540                2545 aag ggc tac tgc ttt cac atc atc gag atc aat cag aag agc ctg  8357
Lys Gly Tyr Cys Phe His Ile Ile Glu Ile Asn Gln Lys Ser Leu
                2550                2555                2560 aat acc tta cag ccg atg ctc ttt aag act agc atc cct aaa tta  8402
Asn Thr Leu Gln Pro Met Leu Phe Lys Thr Ser Ile Pro Lys Leu

|  |  |  |  |  |  |
|---|---|---|---|---|---|
|  | 2565 |  | 2570 |  | 2575 |

```
tgc aag gcc gag tct  taaatttaac tgactagcag gcttgtcggc tttgctgaca        8457
Cys Lys Ala Glu Ser
                2580 ctagagtcat ctcctaacat ccacaatatc tctcagtctc ttacgtctct cacagtatta       8517 agaaaaaccc agggtgaatg ggaagcttgc cataggtc atg gat ggg cag gag           8570
                                          Met Asp Gly Gln Glu
                                                        2585 tcc tcc caa aac cct tct gac ata ctc tat cca gaa tgc cac ctg             8615
Ser Ser Gln Asn Pro Ser Asp Ile Leu Tyr Pro Glu Cys His Leu
                2590                2595                2600 aac tct ccc ata gtc agg ggg aag ata gca cag ttg cac gtc ttg             8660
Asn Ser Pro Ile Val Arg Gly Lys Ile Ala Gln Leu His Val Leu
                2605                2610                2615 tta gat gtg aac cag ccc tac aga cta aag gac gac agc ata ata             8705
Leu Asp Val Asn Gln Pro Tyr Arg Leu Lys Asp Asp Ser Ile Ile
                2620                2625                2630 aat att aca aag cac aaa att agg aac gga gga ttg tcc cct cgt             8750
Asn Ile Thr Lys His Lys Ile Arg Asn Gly Gly Leu Ser Pro Arg
                2635                2640                2645 caa att aag atc agg tct ctg ggt aag gct ctt caa cgc aca ata             8795
Gln Ile Lys Ile Arg Ser Leu Gly Lys Ala Leu Gln Arg Thr Ile
                2650                2655                2660 aag gat tta gac cga tac acc ttt gaa ccg tac cca acc tac tct             8840
Lys Asp Leu Asp Arg Tyr Thr Phe Glu Pro Tyr Pro Thr Tyr Ser
                2665                2670                2675 cag gaa tta ctt agg ctt gat ata cca gag ata tgt gac aaa atc             8885
Gln Glu Leu Leu Arg Leu Asp Ile Pro Glu Ile Cys Asp Lys Ile
                2680                2685                2690 cga tcc gtc ttc gcg gtc tcg gat cgg ctg acc agg gag tta tct             8930
Arg Ser Val Phe Ala Val Ser Asp Arg Leu Thr Arg Glu Leu Ser
                2695                2700                2705 agt ggg ttc cag gat ctt tgg ttg aat atc ttc aag caa cta ggc             8975
Ser Gly Phe Gln Asp Leu Trp Leu Asn Ile Phe Lys Gln Leu Gly
                2710                2715                2720 aat ata gaa gga aga gag ggg tac gat ccg ttg cag gat atc ggc             9020
Asn Ile Glu Gly Arg Glu Gly Tyr Asp Pro Leu Gln Asp Ile Gly
                2725                2730                2735 acc atc ccg gag ata act gat aaa tac agc agg aat aga tgg tat             9065
Thr Ile Pro Glu Ile Thr Asp Lys Tyr Ser Arg Asn Arg Trp Tyr
                2740                2745                2750 agg cca ttc cta act tgg ttc agc atc aaa tat gac atg cgg tgg             9110
Arg Pro Phe Leu Thr Trp Phe Ser Ile Lys Tyr Asp Met Arg Trp
                2755                2760                2765 atg cag aag acc aga ccg ggg gga ccc ctc gat acc tct aat tca             9155
Met Gln Lys Thr Arg Pro Gly Gly Pro Leu Asp Thr Ser Asn Ser
                2770                2775                2780 cat aac ctc cta gaa tgc aaa tca tac act cta gta aca tac gga             9200
His Asn Leu Leu Glu Cys Lys Ser Tyr Thr Leu Val Thr Tyr Gly
                2785                2790                2795 gat ctt atc atg ata ctg aac aag ttg aca ttg aca ggg tat atc             9245
Asp Leu Ile Met Ile Leu Asn Lys Leu Thr Leu Thr Gly Tyr Ile
                2800                2805                2810 cta acc cct gag ctg gtc ttg atg tat tgt gat gtt gta gag gga             9290
Leu Thr Pro Glu Leu Val Leu Met Tyr Cys Asp Val Val Glu Gly
                2815                2820                2825 agg tgg aat atg tct gct gca ggg cat cta gat aag aag tcc att             9335
Arg Trp Asn Met Ser Ala Ala Gly His Leu Asp Lys Lys Ser Ile
                2830                2835                2840
```

```
ggg ata aca agc aaa ggt gag gaa tta tgg gaa cta gtg gat tcc      9380
Gly Ile Thr Ser Lys Gly Glu Glu Leu Trp Glu Leu Val Asp Ser
            2845                2850                2855 ctc ttc tca agt ctt gga gag gaa ata tac aat gtc atc gca cta      9425
Leu Phe Ser Ser Leu Gly Glu Glu Ile Tyr Asn Val Ile Ala Leu
            2860                2865                2870 ttg gag ccc cta tca ctt gct ctc ata caa cta aat gat cct gtt      9470
Leu Glu Pro Leu Ser Leu Ala Leu Ile Gln Leu Asn Asp Pro Val
            2875                2880                2885 ata cct cta cgt ggg gca ttt atg agg cat gtg ttg aca gag cta      9515
Ile Pro Leu Arg Gly Ala Phe Met Arg His Val Leu Thr Glu Leu
            2890                2895                2900 cag gct gtt tta aca agt agg gac gtg tac aca gat gct gaa gca      9560
Gln Ala Val Leu Thr Ser Arg Asp Val Tyr Thr Asp Ala Glu Ala
            2905                2910                2915 gac act att gtg gag tcg tta ctc gcc att ttc cat gga acc tct      9605
Asp Thr Ile Val Glu Ser Leu Leu Ala Ile Phe His Gly Thr Ser
            2920                2925                2930 att gat gag aaa gca gag atc ttt tcc ttc ttt agg aca ttt ggc      9650
Ile Asp Glu Lys Ala Glu Ile Phe Ser Phe Phe Arg Thr Phe Gly
            2935                2940                2945 cac ccc agc tta gag gct gtc act gcc gcc gac aag gta agg gcc      9695
His Pro Ser Leu Glu Ala Val Thr Ala Ala Asp Lys Val Arg Ala
            2950                2955                2960 cat atg tat gca caa aag gca ata aag ctt aag acc cta tac gag      9740
His Met Tyr Ala Gln Lys Ala Ile Lys Leu Lys Thr Leu Tyr Glu
            2965                2970                2975 tgt cat gca gtt ttt tgc act atc atc ata aat ggg tat aga gag      9785
Cys His Ala Val Phe Cys Thr Ile Ile Ile Asn Gly Tyr Arg Glu
            2980                2985                2990 agg cat ggc gga cag tgg ccc ccc tgt gac ttc cct gat cac gtg      9830
Arg His Gly Gly Gln Trp Pro Pro Cys Asp Phe Pro Asp His Val
            2995                3000                3005 tgt cta gaa cta agg aac gct caa ggg tcc aat acg gca atc tct      9875
Cys Leu Glu Leu Arg Asn Ala Gln Gly Ser Asn Thr Ala Ile Ser
            3010                3015                3020 tat gaa tgt gct gta gac aac tat aca agt ttc ata ggc ttc aag      9920
Tyr Glu Cys Ala Val Asp Asn Tyr Thr Ser Phe Ile Gly Phe Lys
            3025                3030                3035 ttt cgg aag ttt ata gaa cca caa cta gat gaa gat ctc aca ata      9965
Phe Arg Lys Phe Ile Glu Pro Gln Leu Asp Glu Asp Leu Thr Ile
            3040                3045                3050 tat atg aaa gac aaa gca cta tcc ccc agg aag gag gca tgg gac     10010
Tyr Met Lys Asp Lys Ala Leu Ser Pro Arg Lys Glu Ala Trp Asp
            3055                3060                3065 tct gta tac ccg gat agt aat ctg tac tat aaa gcc cca gaa tct     10055
Ser Val Tyr Pro Asp Ser Asn Leu Tyr Tyr Lys Ala Pro Glu Ser
            3070                3075                3080 gaa gag acc cgg cgg ctt att gaa gtg ttc ata aat gat gag aat     10100
Glu Glu Thr Arg Arg Leu Ile Glu Val Phe Ile Asn Asp Glu Asn
            3085                3090                3095 ttc aac cca gaa gaa att atc aat tat gtg gag tca gga gat tgg     10145
Phe Asn Pro Glu Glu Ile Ile Asn Tyr Val Glu Ser Gly Asp Trp
            3100                3105                3110 ttg aaa gac gag aag ttc aac atc tcg tac agt ctc aaa gag aaa     10190
Leu Lys Asp Glu Lys Phe Asn Ile Ser Tyr Ser Leu Lys Glu Lys
            3115                3120                3125 gag atc aag caa gag ggt cgt cta ttc gca aaa atg act tat aag     10235
Glu Ile Lys Gln Glu Gly Arg Leu Phe Ala Lys Met Thr Tyr Lys
```

```
              3130              3135              3140
atg cga gcc gta cag gtg ctg gca gag aca cta ctg gct aaa gga          10280
Met Arg Ala Val Gln Val Leu Ala Glu Thr Leu Leu Ala Lys Gly
                3145              3150              3155 ata gga gag ctg ttc agc gaa aat ggg atg gtt aaa gga gag ata          10325
Ile Gly Glu Leu Phe Ser Glu Asn Gly Met Val Lys Gly Glu Ile
                3160              3165              3170 gac cta ctt aaa aga ttg act act ctt tct gtc tca gga gtc ccc          10370
Asp Leu Leu Lys Arg Leu Thr Thr Leu Ser Val Ser Gly Val Pro
                3175              3180              3185 agg act gat tca gtg tac aat aac tct aaa tca tca gag aag aga          10415
Arg Thr Asp Ser Val Tyr Asn Asn Ser Lys Ser Ser Glu Lys Arg
                3190              3195              3200 aac gaa ggc atg aaa aag aag aac tct ggg ggg tac tgg gac gaa          10460
Asn Glu Gly Met Lys Lys Lys Asn Ser Gly Gly Tyr Trp Asp Glu
                3205              3210              3215 aag aag agg tcc aga cat gaa ttc aag gca aca gat tca tca aca          10505
Lys Lys Arg Ser Arg His Glu Phe Lys Ala Thr Asp Ser Ser Thr
                3220              3225              3230 gac ggc tat gaa acg tta agt tgc ttc ctc aca aca gac ctc aag          10550
Asp Gly Tyr Glu Thr Leu Ser Cys Phe Leu Thr Thr Asp Leu Lys
                3235              3240              3245 aaa tac tgc tta aac tgg aga ttt gaa agt act gca ttg ttt ggt          10595
Lys Tyr Cys Leu Asn Trp Arg Phe Glu Ser Thr Ala Leu Phe Gly
                3250              3255              3260 cag aga tgc aac gag ata ttt ggc ttc aag acc ttc ttt aac tgg          10640
Gln Arg Cys Asn Glu Ile Phe Gly Phe Lys Thr Phe Phe Asn Trp
                3265              3270              3275 atg cat cca gtc ctt gaa agg tgt aca ata tat gtt ggg gat cct          10685
Met His Pro Val Leu Glu Arg Cys Thr Ile Tyr Val Gly Asp Pro
                3280              3285              3290 tac tgt cca gtc gcc gac cgg atg cat cga caa ctc cag gat cat          10730
Tyr Cys Pro Val Ala Asp Arg Met His Arg Gln Leu Gln Asp His
                3295              3300              3305 gca gac tct ggc att ttc ata cat aat cct agg ggg ggc ata gaa          10775
Ala Asp Ser Gly Ile Phe Ile His Asn Pro Arg Gly Gly Ile Glu
                3310              3315              3320 ggt tac tgc cag aag ctg tgg acc tta atc tca atc agt gca atc          10820
Gly Tyr Cys Gln Lys Leu Trp Thr Leu Ile Ser Ile Ser Ala Ile
                3325              3330              3335 cac cta gca gct gtg aga gtg ggt gtc agg gtc tct gca atg gtt          10865
His Leu Ala Ala Val Arg Val Gly Val Arg Val Ser Ala Met Val
                3340              3345              3350 cag ggt gac aat caa gct ata gcc gtg aca tca aga gta cct gta          10910
Gln Gly Asp Asn Gln Ala Ile Ala Val Thr Ser Arg Val Pro Val
                3355              3360              3365 gct cag act tac aag cag aag aaa aat cat gtc tat aag gag atc          10955
Ala Gln Thr Tyr Lys Gln Lys Lys Asn His Val Tyr Lys Glu Ile
                3370              3375              3380 acc aaa tat ttt ggt gct cta aga cac gtc atg ttt gat gta ggg          11000
Thr Lys Tyr Phe Gly Ala Leu Arg His Val Met Phe Asp Val Gly
                3385              3390              3395 cac gag cta aaa ttg aac gag acc atc att agt agc aag atg ttt          11045
His Glu Leu Lys Leu Asn Glu Thr Ile Ile Ser Ser Lys Met Phe
                3400              3405              3410 gtc tat agt aaa aga ata tac tat gat ggg aag att tta cca cag          11090
Val Tyr Ser Lys Arg Ile Tyr Tyr Asp Gly Lys Ile Leu Pro Gln
                3415              3420              3425 tgc ctg aaa gcc ttg acc agg tgt gta ttc tgg tcc gag aca ctg          11135
```

-continued

| | | | | | | | | | | | | |
|---|---|---|---|---|---|---|---|---|---|---|---|---|
| Cys | Leu | Lys | Ala | Leu | Thr | Arg | Cys | Val | Phe | Trp | Ser | Glu | Thr | Leu |
| | | | 3430 | | | | | 3435 | | | | | 3440 | |

```
gta gat gaa aac aga tct gct tgt tcg aac atc tca aca tcc ata        11180
Val Asp Glu Asn Arg Ser Ala Cys Ser Asn Ile Ser Thr Ser Ile
            3445                3450                3455 gca aaa gct atc gaa aat ggg tat tct cct ata cta ggc tac tgc        11225
Ala Lys Ala Ile Glu Asn Gly Tyr Ser Pro Ile Leu Gly Tyr Cys
            3460                3465                3470 att gcg ttg tat aag acc tgt cag caa gtg tgc ata tca cta ggg        11270
Ile Ala Leu Tyr Lys Thr Cys Gln Gln Val Cys Ile Ser Leu Gly
            3475                3480                3485 atg act ata aat cca act atc agc ccg acc gta aga gat caa tac        11315
Met Thr Ile Asn Pro Thr Ile Ser Pro Thr Val Arg Asp Gln Tyr
            3490                3495                3500 ttt aag ggt aag aat tgg ctg aga tgt gca gtg ttg att cca gca        11360
Phe Lys Gly Lys Asn Trp Leu Arg Cys Ala Val Leu Ile Pro Ala
            3505                3510                3515 aat gtt gga gga ttc aac tac atg tct aca tct aga tgc ttt gtt        11405
Asn Val Gly Gly Phe Asn Tyr Met Ser Thr Ser Arg Cys Phe Val
            3520                3525                3530 aga aat att gga gac ccc gca gta gca gcc cta gct gat ctc aaa        11450
Arg Asn Ile Gly Asp Pro Ala Val Ala Ala Leu Ala Asp Leu Lys
            3535                3540                3545 aga ttc atc aga gcg gat ctg tta gac aag cag gta cta tac agg        11495
Arg Phe Ile Arg Ala Asp Leu Leu Asp Lys Gln Val Leu Tyr Arg
            3550                3555                3560 atc atg aat caa gaa ccc ggt gac tct agc ttt cta gat tgg gct        11540
Ile Met Asn Gln Glu Pro Gly Asp Ser Ser Phe Leu Asp Trp Ala
            3565                3570                3575 tca gac cct tat tca tgt aac ctc ccg cat tct cag agt ata act        11585
Ser Asp Pro Tyr Ser Cys Asn Leu Pro His Ser Gln Ser Ile Thr
            3580                3585                3590 acg att ata aag aat atc act gct aga tct gtg ctg cag gaa tcc        11630
Thr Ile Ile Lys Asn Ile Thr Ala Arg Ser Val Leu Gln Glu Ser
            3595                3600                3605 ccg aat cct cta ctg tct ggt ctc ttc acc gag act agt gga gaa        11675
Pro Asn Pro Leu Leu Ser Gly Leu Phe Thr Glu Thr Ser Gly Glu
            3610                3615                3620 gag gat ctc aac ctg gcc tcg ttc ctt atg gac cgg aaa gtc atc        11720
Glu Asp Leu Asn Leu Ala Ser Phe Leu Met Asp Arg Lys Val Ile
            3625                3630                3635 ctg ccg aga gtg gct cat gag atc ctg ggt aat tcc tta act gga        11765
Leu Pro Arg Val Ala His Glu Ile Leu Gly Asn Ser Leu Thr Gly
            3640                3645                3650 gtt agg gag gcg att gca ggg atg ctt gat acg acc aag tct cta        11810
Val Arg Glu Ala Ile Ala Gly Met Leu Asp Thr Thr Lys Ser Leu
            3655                3660                3665 gtg aga gcc agc gtt aag aaa gga gga tta tca tat ggg ata ttg        11855
Val Arg Ala Ser Val Lys Lys Gly Gly Leu Ser Tyr Gly Ile Leu
            3670                3675                3680 agg agg ctt gtc aat tat gat cta ttg cag tac gag aca ctg act        11900
Arg Arg Leu Val Asn Tyr Asp Leu Leu Gln Tyr Glu Thr Leu Thr
            3685                3690                3695 aga act ctc agg aaa ccg gtg aaa gac aac atc gaa tat gag tat        11945
Arg Thr Leu Arg Lys Pro Val Lys Asp Asn Ile Glu Tyr Glu Tyr
            3700                3705                3710 atg tgt tca gtt gag cta gct gtc ggt cta agg cag aaa atg tgg        11990
Met Cys Ser Val Glu Leu Ala Val Gly Leu Arg Gln Lys Met Trp
            3715                3720                3725
```

```
                                                   -continued atc cac cta act tac ggg aga ccc ata cat ggg cta gaa aca cca            12035
Ile His Leu Thr Tyr Gly Arg Pro Ile His Gly Leu Glu Thr Pro
                3730                3735                3740 gac cct tta gag ctc ttg agg gga aca ttt atc gaa ggt tca gag            12080
Asp Pro Leu Glu Leu Leu Arg Gly Thr Phe Ile Glu Gly Ser Glu
                3745                3750                3755 gtg tgc aag ctt tgc agg tct gag gga gca gac ccc atc tat aca            12125
Val Cys Lys Leu Cys Arg Ser Glu Gly Ala Asp Pro Ile Tyr Thr
                3760                3765                3770 tgg ttc tat ctc cct gac aat ata gac ctg gac acg ctt aca aac            12170
Trp Phe Tyr Leu Pro Asp Asn Ile Asp Leu Asp Thr Leu Thr Asn
                3775                3780                3785 gga agt ccg gct ata aga atc ccc tat ttt gga tca gcc act gat            12215
Gly Ser Pro Ala Ile Arg Ile Pro Tyr Phe Gly Ser Ala Thr Asp
                3790                3795                3800 gaa agg tcg gaa gcc caa ctc ggg tat gta aga aat cta agc aaa            12260
Glu Arg Ser Glu Ala Gln Leu Gly Tyr Val Arg Asn Leu Ser Lys
                3805                3810                3815 ccc gca aag gcg gcc atc cgg ata gct atg gtg tat acg tgg gcc            12305
Pro Ala Lys Ala Ala Ile Arg Ile Ala Met Val Tyr Thr Trp Ala
                3820                3825                3830 tac ggg act gat gag ata tcg tgg atg gaa gcc gct ctt ata gcc            12350
Tyr Gly Thr Asp Glu Ile Ser Trp Met Glu Ala Ala Leu Ile Ala
                3835                3840                3845 caa aca aga gcc aat ctg agc tta gag aat cta aag ctg ctg act            12395
Gln Thr Arg Ala Asn Leu Ser Leu Glu Asn Leu Lys Leu Leu Thr
                3850                3855                3860 cct gtt tca acc tcc act aat cta tct cat agg ttg aaa gat acg            12440
Pro Val Ser Thr Ser Thr Asn Leu Ser His Arg Leu Lys Asp Thr
                3865                3870                3875 gca acc cag atg aag ttc tct agt gca aca cta gtc cgt gca agt            12485
Ala Thr Gln Met Lys Phe Ser Ser Ala Thr Leu Val Arg Ala Ser
                3880                3885                3890 cgg ttc ata aca ata tca aat gat aac atg gca ctc aaa gaa gca            12530
Arg Phe Ile Thr Ile Ser Asn Asp Asn Met Ala Leu Lys Glu Ala
                3895                3900                3905 ggg gag tcg aag gat act aat ctc gtg tat cag cag att atg cta            12575
Gly Glu Ser Lys Asp Thr Asn Leu Val Tyr Gln Gln Ile Met Leu
                3910                3915                3920 act ggg cta agc ttg ttc gag ttc aat atg aga tat aag aaa ggt            12620
Thr Gly Leu Ser Leu Phe Glu Phe Asn Met Arg Tyr Lys Lys Gly
                3925                3930                3935 tcc tta ggg aag cca ctg ata ttg cac tta cat ctt aat aac ggg            12665
Ser Leu Gly Lys Pro Leu Ile Leu His Leu His Leu Asn Asn Gly
                3940                3945                3950 tgc tgt ata atg gag tcc cca cag gag gcg aat atc ccc cca agg            12710
Cys Cys Ile Met Glu Ser Pro Gln Glu Ala Asn Ile Pro Pro Arg
                3955                3960                3965 tcc aca tta gat tta gag att aca caa gag aac aat aaa ttg atc            12755
Ser Thr Leu Asp Leu Glu Ile Thr Gln Glu Asn Asn Lys Leu Ile
                3970                3975                3980 tat gat cct gat cca ctc aag gat gtg gac ctt gag cta ttt agc            12800
Tyr Asp Pro Asp Pro Leu Lys Asp Val Asp Leu Glu Leu Phe Ser
                3985                3990                3995 aag gtc aga gat gtt gta cat aca gtt gac atg act tat tgg tca            12845
Lys Val Arg Asp Val Val His Thr Val Asp Met Thr Tyr Trp Ser
                4000                4005                4010 gat gat gaa gtt atc aga gca acc agt atc tgt act gca atg acg            12890
Asp Asp Glu Val Ile Arg Ala Thr Ser Ile Cys Thr Ala Met Thr
                4015                4020                4025
```

| | | | | | | | | | | | | |
|---|---|---|---|---|---|---|---|---|---|---|---|---|
| ata | gct | gat | aca | atg | tct | caa | tta | gat | aga | gac | aac | cta | aaa | gag | 12935 |
| Ile | Ala | Asp | Thr | Met | Ser | Gln | Leu | Asp | Arg | Asp | Asn | Leu | Lys | Glu | |
| | | | 4030 | | | | 4035 | | | | 4040 | | | | |

```
ata gct gat aca atg tct caa tta gat aga gac aac cta aaa gag    12935
Ile Ala Asp Thr Met Ser Gln Leu Asp Arg Asp Asn Leu Lys Glu
            4030            4035            4040 atg atc gcg cta gta aat gac gat gat gtc aac agc ctg att act    12980
Met Ile Ala Leu Val Asn Asp Asp Asp Val Asn Ser Leu Ile Thr
            4045            4050            4055 gag ttt atg gtg att gat gtt cct tta ttt tgc tca acg ttc ggg    13025
Glu Phe Met Val Ile Asp Val Pro Leu Phe Cys Ser Thr Phe Gly
            4060            4065            4070 ggt att cta gtc aat cag ttt gca tac tca ctc tac ggc tta aac    13070
Gly Ile Leu Val Asn Gln Phe Ala Tyr Ser Leu Tyr Gly Leu Asn
            4075            4080            4085 atc aga gga agg gaa gaa ata tgg gga cat gta gtc cgg att ctt    13115
Ile Arg Gly Arg Glu Glu Ile Trp Gly His Val Val Arg Ile Leu
            4090            4095            4100 aaa gat acc tcc cac gca gtt cta aaa gtc tta tct aat gct cta    13160
Lys Asp Thr Ser His Ala Val Leu Lys Val Leu Ser Asn Ala Leu
            4105            4110            4115 tct cat ccc aaa atc ttc aaa cga ttc tgg aat gca ggt gtc gtg    13205
Ser His Pro Lys Ile Phe Lys Arg Phe Trp Asn Ala Gly Val Val
            4120            4125            4130 gaa cct gtg tat ggg cct aac ctc tca aat cag gac aag ata ctc    13250
Glu Pro Val Tyr Gly Pro Asn Leu Ser Asn Gln Asp Lys Ile Leu
            4135            4140            4145 ttg gcc ctc tct gtc tgt gaa tat tct gtg gat cta ttc atg cac    13295
Leu Ala Leu Ser Val Cys Glu Tyr Ser Val Asp Leu Phe Met His
            4150            4155            4160 gat tgg caa ggg ggt gta ccg ctt gag atc ttt atc tgt gac aat    13340
Asp Trp Gln Gly Gly Val Pro Leu Glu Ile Phe Ile Cys Asp Asn
            4165            4170            4175 gac cca gat gtg gcc gac atg agg agg tcc tct ttc ttg gca aga    13385
Asp Pro Asp Val Ala Asp Met Arg Arg Ser Ser Phe Leu Ala Arg
            4180            4185            4190 cat ctt gca tac cta tgc agc ttg gca gag ata tct agg gat ggg    13430
His Leu Ala Tyr Leu Cys Ser Leu Ala Glu Ile Ser Arg Asp Gly
            4195            4200            4205 cca aga tta gaa tca atg aac tct cta gag agg ctc gag tca cta    13475
Pro Arg Leu Glu Ser Met Asn Ser Leu Glu Arg Leu Glu Ser Leu
            4210            4215            4220 aag agt tac ctg gaa ctc aca ttt ctt gat gac ccg gta ctg agg    13520
Lys Ser Tyr Leu Glu Leu Thr Phe Leu Asp Asp Pro Val Leu Arg
            4225            4230            4235 tac agt cag ttg act ggc cta gtc atc aaa gta ttc cca tct act    13565
Tyr Ser Gln Leu Thr Gly Leu Val Ile Lys Val Phe Pro Ser Thr
            4240            4245            4250 ttg acc tat atc cgg aag tca tct ata aaa gtg tta agg aca aga    13610
Leu Thr Tyr Ile Arg Lys Ser Ser Ile Lys Val Leu Arg Thr Arg
            4255            4260            4265 ggt ata gga gtc cct gaa gtc tta gaa gat tgg gat ccc gag gca    13655
Gly Ile Gly Val Pro Glu Val Leu Glu Asp Trp Asp Pro Glu Ala
            4270            4275            4280 gat aat gca ctg tta gat ggt atc gcg gca gaa ata caa cag aat    13700
Asp Asn Ala Leu Leu Asp Gly Ile Ala Ala Glu Ile Gln Gln Asn
            4285            4290            4295 att cct ttg gga cat cag act aga gcc cct ttt tgg ggg ttg aga    13745
Ile Pro Leu Gly His Gln Thr Arg Ala Pro Phe Trp Gly Leu Arg
            4300            4305            4310 gta tcc aag tca cag gta ctg cgt ctc cgg ggg tac aag gag atc    13790
Val Ser Lys Ser Gln Val Leu Arg Leu Arg Gly Tyr Lys Glu Ile
```

```
                      4315                 4320                 4325
aca aga ggt gag ata  ggc aga tca ggc gtt  ggt ctg acg tta cca              13835
Thr Arg Gly Glu Ile  Gly Arg Ser Gly Val  Gly Leu Thr Leu Pro
                4330                 4335                 4340 ttc gat gga aga tat  cta tct cac cag ctg  agg ctc ttt ggc atc              13880
Phe Asp Gly Arg Tyr  Leu Ser His Gln Leu  Arg Leu Phe Gly Ile
                4345                 4350                 4355 aac agt act agc tgc  ttg aaa gca ctt gaa  ctt acc tac cta ttg              13925
Asn Ser Thr Ser Cys  Leu Lys Ala Leu Glu  Leu Thr Tyr Leu Leu
                4360                 4365                 4370 agc ccc tta gtt gac  aag gat aaa gat agg  cta tat tta ggg gaa              13970
Ser Pro Leu Val Asp  Lys Asp Lys Asp Arg  Leu Tyr Leu Gly Glu
                4375                 4380                 4385 gga gct ggg gcc atg  ctt tcc tgt tat gac  gct act ctt ggc cca              14015
Gly Ala Gly Ala Met  Leu Ser Cys Tyr Asp  Ala Thr Leu Gly Pro
                4390                 4395                 4400 tgc atc aac tat tat  aac tca ggg gta tac  tct tgt gat gtc aat              14060
Cys Ile Asn Tyr Tyr  Asn Ser Gly Val Tyr  Ser Cys Asp Val Asn
                4405                 4410                 4415 ggg cag aga gag tta  aat ata tat cct gct  gag gtg gca ctg gtg              14105
Gly Gln Arg Glu Leu  Asn Ile Tyr Pro Ala  Glu Val Ala Leu Val
                4420                 4425                 4430 gga aag aaa tta aac  aat gtt act agt ctg  ggt caa aga gtt aaa              14150
Gly Lys Lys Leu Asn  Asn Val Thr Ser Leu  Gly Gln Arg Val Lys
                4435                 4440                 4445 gtg tta ttc aac ggg  aat cct ggc tcg aca  tgg att gga aat gat              14195
Val Leu Phe Asn Gly  Asn Pro Gly Ser Thr  Trp Ile Gly Asn Asp
                4450                 4455                 4460 gag tgt gag gct ttg  att tgg aat gaa ttg  cag aat agc tcg ata              14240
Glu Cys Glu Ala Leu  Ile Trp Asn Glu Leu  Gln Asn Ser Ser Ile
                4465                 4470                 4475 ggc cta gtc cac tgt  gac atg gag gga gga  gat cat aag gat gat              14285
Gly Leu Val His Cys  Asp Met Glu Gly Gly  Asp His Lys Asp Asp
                4480                 4485                 4490 caa gtt gta ctg cat  gag cat tac agt gta  atc cgg atc gcg tat              14330
Gln Val Val Leu His  Glu His Tyr Ser Val  Ile Arg Ile Ala Tyr
                4495                 4500                 4505 ctg gtg ggg gat cga  gac gtt gtg ctt ata  agc aag att gct cct              14375
Leu Val Gly Asp Arg  Asp Val Val Leu Ile  Ser Lys Ile Ala Pro
                4510                 4515                 4520 agg ctg ggc acg gat  tgg acc agg cag ctc  agc cta tat ctg aga              14420
Arg Leu Gly Thr Asp  Trp Thr Arg Gln Leu  Ser Leu Tyr Leu Arg
                4525                 4530                 4535 tac tgg gac gag gtt  aac cta ata gtg ctt  aaa aca tct aac cct              14465
Tyr Trp Asp Glu Val  Asn Leu Ile Val Leu  Lys Thr Ser Asn Pro
                4540                 4545                 4550 gct tcc aca gag atg  tat ctc cta tcg agg  cac ccc aaa tct gac              14510
Ala Ser Thr Glu Met  Tyr Leu Leu Ser Arg  His Pro Lys Ser Asp
                4555                 4560                 4565 att ata gag gac agc  aag acg gtg tta gct  agt ctc ctc cct ttg              14555
Ile Ile Glu Asp Ser  Lys Thr Val Leu Ala  Ser Leu Leu Pro Leu
                4570                 4575                 4580 tca aaa gaa gat agc  atc aag ata gaa aag  tgg atc tta ata gag              14600
Ser Lys Glu Asp Ser  Ile Lys Ile Glu Lys  Trp Ile Leu Ile Glu
                4585                 4590                 4595 aag gca aag gct cac  gaa tgg gtt act cgg  gaa ttg aga gaa gga              14645
Lys Ala Lys Ala His  Glu Trp Val Thr Arg  Glu Leu Arg Glu Gly
                4600                 4605                 4610 agc tct tca tca ggg  atg ctt aga cct tac  cat caa gca ctg cag              14690
Ser Ser Ser Ser Gly  Met Leu Arg Pro Tyr  His Gln Ala Leu Gln
```

```
Ser Ser Ser Ser Gly Met Leu Arg Pro Tyr His Gln Ala Leu Gln
            4615                4620                4625 acg ttt ggc ttt gaa cca aac ttg tat aaa ttg agc aga gat ttc     14735
Thr Phe Gly Phe Glu Pro Asn Leu Tyr Lys Leu Ser Arg Asp Phe
            4630                4635                4640 ttg tcc acc atg aac ata gct gat aca cac aac tgc atg ata gct     14780
Leu Ser Thr Met Asn Ile Ala Asp Thr His Asn Cys Met Ile Ala
            4645                4650                4655 ttc aac agg gtt ttg aag gat aca atc ttc gaa tgg gct aga ata     14825
Phe Asn Arg Val Leu Lys Asp Thr Ile Phe Glu Trp Ala Arg Ile
            4660                4665                4670 act gag tca gat aaa agg ctt aaa cta act ggt aag tat gac ctg     14870
Thr Glu Ser Asp Lys Arg Leu Lys Leu Thr Gly Lys Tyr Asp Leu
            4675                4680                4685 tat cct gtg aga gat tca ggc aaa ttg aag aca gtt tct aga aga     14915
Tyr Pro Val Arg Asp Ser Gly Lys Leu Lys Thr Val Ser Arg Arg
            4690                4695                4700 ctt gtg cta tct tgg ata tct tta tct atg tcc aca aga ttg gta     14960
Leu Val Leu Ser Trp Ile Ser Leu Ser Met Ser Thr Arg Leu Val
            4705                4710                4715 act ggg tca ttc cct gac cag aag ttt gaa gca aga ctt caa ttg     15005
Thr Gly Ser Phe Pro Asp Gln Lys Phe Glu Ala Arg Leu Gln Leu
            4720                4725                4730 gga ata gtt tca tta tca tcc cgt gaa atc agg aac ctg agg gtt     15050
Gly Ile Val Ser Leu Ser Ser Arg Glu Ile Arg Asn Leu Arg Val
            4735                4740                4745 atc aca aaa act tta tta gac agg ttt gag gat att ata cat agt     15095
Ile Thr Lys Thr Leu Leu Asp Arg Phe Glu Asp Ile Ile His Ser
            4750                4755                4760 ata acg tac aga ttc ctc acc aaa gaa ata aag att ttg atg aag     15140
Ile Thr Tyr Arg Phe Leu Thr Lys Glu Ile Lys Ile Leu Met Lys
            4765                4770                4775 att tta ggg gca gtc aag atg ttc ggg gcc agg caa aat gaa tac     15185
Ile Leu Gly Ala Val Lys Met Phe Gly Ala Arg Gln Asn Glu Tyr
            4780                4785                4790 acg acc gtg att gat gat gga tca ctg ggt gat atc gag cca tat     15230
Thr Thr Val Ile Asp Asp Gly Ser Leu Gly Asp Ile Glu Pro Tyr
            4795                4800                4805 gac agc tcg taataattag tccctatcgt gcagaacgat cgaagctccg         15279
Asp Ser Ser cggtacctgg aagtcttgga cttatccata tgacaatagt aagaaaaact tacaagaaga  15339
caagaaaatt taaagaata catatctctt aaactcttgt ctggt                   15384

<210> SEQ ID NO 5
<211> LENGTH: 524
<212> TYPE: PRT
<213> ORGANISM: Artificial Sequence
<220> FEATURE:
<223> OTHER INFORMATION: Description of Artificial Sequence: Synthetic
      NP protein of Sendai virus nagoya

<400> SEQUENCE: 5

Met Ala Gly Leu Leu Ser Thr Phe Asp Thr Phe Ser Ser Arg Arg Ser
1               5                   10                  15

Glu Ser Ile Asn Lys Ser Gly Gly Gly Ala Val Ile Pro Gly Gln Arg
            20                  25                  30

Ser Thr Val Ser Val Phe Ile Leu Gly Pro Ser Val Thr Asp Asp Ala
        35                  40                  45

Asp Lys Leu Phe Ile Ala Thr Thr Phe Leu Ala His Ser Leu Asp Thr
```

```
              50                  55                  60
Asp Lys Gln His Ser Gln Arg Gly Gly Phe Leu Val Ser Leu Leu Ala
 65                  70                  75                  80

Met Ala Tyr Ser Ser Pro Glu Leu Tyr Leu Thr Thr Asn Gly Val Asn
                 85                  90                  95

Ala Asp Val Lys Tyr Val Ile Tyr Asn Ile Glu Lys Asp Pro Lys Arg
                100                 105                 110

Thr Lys Thr Asp Gly Phe Ile Val Lys Thr Arg Asp Met Glu Tyr Glu
                115                 120                 125

Arg Thr Thr Glu Trp Leu Phe Gly Pro Met Val Asn Lys Ser Pro Leu
                130                 135                 140

Phe Gln Gly Gln Arg Asp Ala Ala Asp Pro Asp Thr Leu Leu Gln Ile
145                 150                 155                 160

Tyr Gly Tyr Pro Ala Cys Leu Gly Ala Ile Val Gln Val Trp Ile
                165                 170                 175

Val Leu Val Lys Ala Ile Thr Ser Ser Ala Gly Leu Arg Lys Gly Phe
                180                 185                 190

Phe Asn Arg Leu Glu Ala Phe Arg Gln Asp Gly Thr Val Lys Gly Ala
                195                 200                 205

Leu Val Phe Thr Gly Glu Thr Val Glu Gly Ile Gly Ser Val Met Arg
                210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
                245                 250                 255

Val Gly Asn Tyr Ile Arg Asp Ala Gly Leu Ala Ser Phe Met Asn Thr
                260                 265                 270

Ile Lys Tyr Gly Val Glu Thr Lys Met Ala Ala Leu Thr Leu Ser Asn
                275                 280                 285

Leu Arg Pro Asp Ile Asn Lys Leu Arg Ser Leu Ile Asp Thr Tyr Leu
                290                 295                 300

Ser Lys Gly Pro Arg Ala Pro Phe Ile Cys Ile Leu Lys Asp Pro Val
305                 310                 315                 320

His Gly Glu Phe Ala Pro Gly Asn Tyr Pro Ala Leu Trp Ser Tyr Ala
                325                 330                 335

Met Gly Val Ala Val Gln Asn Lys Ser Met Gln Gln Tyr Val Thr
                340                 345                 350

Gly Arg Thr Tyr Leu Asp Met Glu Met Phe Leu Leu Gly Gln Ala Val
                355                 360                 365

Ala Lys Asp Ala Glu Ser Lys Ile Ser Ser Ala Leu Glu Asp Glu Leu
                370                 375                 380

Gly Val Thr Asp Thr Ala Lys Glu Arg Leu Arg His Leu Ala Asn
385                 390                 395                 400

Leu Ser Gly Gly Asp Gly Ala Tyr His Lys Pro Thr Gly Gly Ala
                405                 410                 415

Ile Glu Val Ala Leu Asp Asn Ala Asp Ile Asp Leu Glu Thr Glu Ala
                420                 425                 430

His Ala Asp Gln Asp Ala Arg Gly Trp Gly Gly Asp Ser Gly Glu Arg
                435                 440                 445

Trp Ala Arg Gln Val Ser Gly Gly His Phe Val Thr Leu His Gly Ala
                450                 455                 460

Glu Arg Leu Glu Glu Glu Thr Asn Asp Glu Asp Val Ser Asp Ile Glu
465                 470                 475                 480
```

```
Arg Arg Ile Ala Met Arg Leu Ala Glu Arg Arg Gln Glu Asp Ser Ala
                485                 490                 495

Thr His Gly Asp Glu Gly Arg Asn Asn Gly Val Asp His Glu Glu Asp
            500                 505                 510

Asp Asp Ala Ala Ala Ala Gly Ile Gly Gly Ile
        515                 520

<210> SEQ ID NO 6
<211> LENGTH: 568
<212> TYPE: PRT
<213> ORGANISM: Artificial Sequence
<220> FEATURE:
<223> OTHER INFORMATION: Description of Artificial Sequence: Synthetic
      P protein of Sendai virus nagoya

<400> SEQUENCE: 6

Met Asp Gln Asp Ala Phe Ile Leu Lys Glu Asp Ser Glu Val Glu Arg
1               5                   10                  15

Lys Ala Pro Gly Gly Arg Glu Ser Leu Ser Asp Val Ile Gly Phe Leu
            20                  25                  30

Asp Ala Val Leu Ser Asn Glu Pro Thr Asp Ile Gly Gly Asp Arg Ser
        35                  40                  45

Trp Leu His Asn Thr Ile Asn Thr Pro Gln Gly Pro Gly Ser Ala His
    50                  55                  60

Arg Ala Lys Ser Glu Gly Glu Gly Glu Val Ser Thr Pro Ser Thr Gln
65                  70                  75                  80

Asp Asn Arg Ser Gly Glu Glu Ser Arg Val Ser Gly Arg Thr Ser Lys
                85                  90                  95

Pro Glu Ala Glu Ala His Ala Gly Asn Leu Asp Lys Gln Asn Ile His
            100                 105                 110

Trp Ala Phe Arg Gly Arg Thr Gly Thr Asn Ser Val Ser Gln Asp Leu
        115                 120                 125

Asp Asp Gly Gly Asp Ser Gly Ile Leu Glu Asn Pro Pro Asn Glu Arg
    130                 135                 140

Gly Tyr Pro Arg Ser Gly Ile Glu Asp Glu Asn Arg Glu Met Ala Ala
145                 150                 155                 160

His Pro Asp Lys Arg Gly Glu Asp Gln Ala Glu Gly Leu Pro Glu Glu
                165                 170                 175

Val Arg Gly Gly Thr Ser Leu Pro Asp Glu Gly Glu Gly Gly Ala Ser
            180                 185                 190

Asn Asn Gly Arg Ser Met Glu Pro Gly Ser Ser His Ser Ala Arg Val
        195                 200                 205

Thr Gly Val Leu Val Ile Pro Ser Pro Glu Leu Glu Glu Ala Val Leu
    210                 215                 220

Arg Arg Asn Lys Arg Arg Pro Thr Asn Ser Gly Ser Lys Pro Leu Thr
225                 230                 235                 240

Pro Ala Thr Val Pro Gly Thr Arg Ser Pro Pro Leu Asn Arg Tyr Asn
                245                 250                 255

Ser Thr Gly Ser Pro Pro Gly Lys Pro Pro Ser Thr Gln Asp Glu His
            260                 265                 270

Ile Asn Ser Gly Asp Thr Pro Ala Val Arg Val Lys Asp Arg Lys Pro
        275                 280                 285

Ser Ile Gly Thr Arg Ser Val Ser Asp Cys Pro Ala Asn Gly Arg Pro
    290                 295                 300

Ile His Pro Gly Ile Glu Thr Asp Ser Thr Lys Lys Gly Ile Gly Glu
```

```
305                 310                 315                 320
Asn Thr Ser Ser Met Lys Asp Met Ala Thr Leu Leu Thr Ser Leu Gly
                325                 330                 335
Val Ile Gln Ser Ala Gln Glu Phe Glu Ser Ser Arg Asp Ala Ser Tyr
                340                 345                 350
Val Phe Ala Arg Arg Ala Leu Lys Ser Ala Asn Tyr Ala Glu Met Thr
                355                 360                 365
Phe Asn Val Cys Gly Leu Ile Leu Ser Ala Glu Lys Ser Ser Ala Arg
    370                 375                 380
Lys Val Asp Glu Asn Lys Gln Leu Leu Lys Gln Ile Gln Glu Ser Val
385                 390                 395                 400
Glu Ser Phe Arg Asp Ile Tyr Lys Arg Phe Ser Glu Tyr Gln Lys Glu
                405                 410                 415
Gln Asn Ser Leu Leu Met Ser Asn Leu Ser Thr Leu His Ile Ile Thr
            420                 425                 430
Asp Arg Gly Gly Lys Thr Asp Asn Thr Asp Ser Leu Thr Arg Ser Pro
                435                 440                 445
Ser Val Phe Ala Lys Ser Lys Glu Asn Lys Thr Lys Ala Thr Arg Phe
    450                 455                 460
Asp Pro Ser Met Glu Thr Leu Glu Asp Met Lys Tyr Lys Pro Asp Leu
465                 470                 475                 480
Ile Arg Glu Asp Glu Phe Arg Asp Glu Ile Arg Asn Pro Val Tyr Gln
                485                 490                 495
Glu Arg Asp Thr Glu Pro Arg Ala Ser Asn Ala Ser Arg Leu Phe Pro
                500                 505                 510
Ser Lys Glu Lys His Thr Met His Ser Leu Arg Leu Val Ile Glu Ser
            515                 520                 525
Ser Pro Leu Ser Arg Ala Glu Lys Ala Ala Tyr Val Lys Ser Leu Ser
        530                 535                 540
Lys Cys Lys Thr Asp Gln Glu Val Lys Ala Val Met Glu Leu Val Glu
545                 550                 555                 560

Glu Asp Ile Glu Ser Leu Thr Asn
                565

<210> SEQ ID NO 7
<211> LENGTH: 348
<212> TYPE: PRT
<213> ORGANISM: Artificial Sequence
<220> FEATURE:
<223> OTHER INFORMATION: Description of Artificial Sequence: Synthetic
      M protein of Sendai virus nagoya

<400> SEQUENCE: 7

Met Ala Asp Ile Tyr Arg Phe Pro Lys Phe Ser Tyr Glu Asp Asn Gly
1               5                   10                  15
Thr Val Glu Pro Leu Pro Leu Arg Thr Gly Pro Asp Lys Lys Ala Ile
                20                  25                  30
Pro His Ile Arg Ile Val Lys Val Gly Asp Pro Lys His Gly Val
            35                  40                  45
Arg Tyr Leu Asp Leu Leu Leu Leu Gly Phe Phe Glu Thr Pro Lys Gln
        50                  55                  60
Thr Thr Asn Leu Gly Ser Val Ser Asp Leu Thr Glu Pro Thr Ser Tyr
65                  70                  75                  80
Ser Ile Cys Gly Ser Gly Ser Leu Pro Ile Gly Val Ala Lys Tyr Tyr
                85                  90                  95
```

```
Gly Thr Asp Gln Glu Leu Leu Lys Ala Cys Thr Asp Leu Arg Ile Thr
                100                 105                 110

Val Arg Arg Thr Val Arg Ala Gly Glu Met Ile Val Tyr Met Val Asp
            115                 120                 125

Leu Ile Gly Ala Pro Leu Leu Pro Trp Ser Gly Lys Leu Arg Gln Gly
        130                 135                 140

Met Ile Phe Asn Ala Asn Lys Val Ala Leu Ala Pro Gln Cys Leu Pro
145                 150                 155                 160

Val Asp Lys Asp Ile Arg Phe Arg Val Val Phe Val Asn Gly Thr Ser
                165                 170                 175

Leu Gly Ala Ile Thr Ile Ala Lys Ile Pro Lys Thr Leu Ala Asp Leu
            180                 185                 190

Ala Leu Pro Asn Ser Ile Ser Val Asn Leu Leu Val Thr Leu Lys Thr
        195                 200                 205

Gly Ile Ser Thr Glu Gln Lys Gly Val Leu Pro Val Leu Asp Asp Gln
210                 215                 220

Gly Glu Lys Lys Leu Asn Phe Met Val His Leu Gly Leu Ile Arg Arg
225                 230                 235                 240

Lys Val Gly Lys Ile Tyr Ser Val Glu Tyr Cys Lys Ser Lys Ile Glu
                245                 250                 255

Arg Met Arg Leu Ile Phe Ser Leu Gly Leu Ile Gly Ile Ser Phe
            260                 265                 270

His Val Gln Val Thr Gly Thr Leu Ser Lys Thr Phe Met Ser Gln Leu
        275                 280                 285

Ala Trp Lys Arg Ala Val Cys Phe Pro Leu Met Asp Val Asn Pro His
290                 295                 300

Met Asn Met Val Ile Trp Ala Ala Ser Val Glu Ile Thr Gly Val Asp
305                 310                 315                 320

Ala Val Phe Gln Pro Ala Ile Pro Arg Asp Phe Arg Tyr Tyr Pro Asn
                325                 330                 335

Val Val Ala Lys Asn Ile Gly Arg Ile Arg Lys Leu
            340                 345

<210> SEQ ID NO 8
<211> LENGTH: 565
<212> TYPE: PRT
<213> ORGANISM: Artificial Sequence
<220> FEATURE:
<223> OTHER INFORMATION: Description of Artificial Sequence: Synthetic
      F protein of Sendai virus nagoya

<400> SEQUENCE: 8

Met Thr Ala Tyr Ile Gln Arg Ser Gln Cys Ile Ser Thr Ser Leu Leu
1               5                   10                  15

Val Val Leu Thr Thr Leu Val Ser Cys Gln Ile Pro Arg Asp Met Leu
            20                  25                  30

Ser Asn Ile Gly Val Ile Val Asp Glu Gly Lys Ser Leu Lys Ile Ala
        35                  40                  45

Gly Ser His Glu Ser Arg Tyr Ile Val Leu Ser Leu Val Pro Gly Val
    50                  55                  60

Asp Leu Glu Asn Gly Cys Gly Thr Ala Gln Val Ile Gln Tyr Lys Ser
65                  70                  75                  80

Leu Leu Asn Arg Leu Leu Ile Pro Leu Arg Asp Ala Leu Asp Leu Gln
                85                  90                  95

Glu Ala Leu Ile Thr Val Thr Asn Asp Thr Thr Gln Asn Ala Gly Val
            100                 105                 110
```

```
Pro Gln Ser Arg Phe Phe Gly Ala Val Ile Gly Thr Val Ala Leu Gly
            115                 120                 125

Val Ala Thr Ser Ala Gln Ile Thr Ala Gly Ile Ala Leu Ala Glu Ala
        130                 135                 140

Arg Glu Ala Lys Arg Asp Ile Ala Leu Ile Lys Glu Ser Met Thr Lys
145                 150                 155                 160

Thr His Lys Ser Ile Glu Leu Leu Gln Asn Ala Val Gly Glu Gln Ile
                165                 170                 175

Leu Ala Leu Lys Thr Leu Gln Asp Phe Val Asn Asp Glu Ile Lys Pro
            180                 185                 190

Ala Ile Ser Glu Leu Gly Cys Glu Thr Ala Ala Leu Arg Leu Gly Ile
            195                 200                 205

Lys Phe Thr Gln His Tyr Ser Glu Leu Leu Thr Ala Phe Gly Ser Asn
        210                 215                 220

Phe Gly Thr Ile Gly Glu Lys Ser Leu Thr Leu Gln Ala Leu Ser Ser
225                 230                 235                 240

Leu Tyr Ser Ala Asn Ile Thr Glu Ile Met Thr Thr Ile Arg Thr Gly
                245                 250                 255

Gln Ser Asn Ile Tyr Asp Val Ile Tyr Thr Glu Gln Ile Lys Gly Thr
            260                 265                 270

Val Ile Asp Val Asp Leu Glu Arg Tyr Met Val Thr Leu Ser Val Lys
        275                 280                 285

Ile Pro Ile Leu Ser Glu Val Pro Gly Val Leu Ile His Lys Ala Ser
            290                 295                 300

Ser Ile Ser Tyr Asn Ile Asp Gly Glu Glu Trp Tyr Val Thr Val Pro
305                 310                 315                 320

Ser His Ile Leu Ser Arg Ala Ser Phe Leu Gly Gly Ala Asp Ile Thr
                325                 330                 335

Asp Cys Val Glu Ser Arg Leu Thr Tyr Ile Cys Pro Arg Asp Pro Ala
            340                 345                 350

Gln Leu Ile Pro Asp Ser Gln Gln Lys Cys Ile Leu Gly Asp Thr Thr
        355                 360                 365

Lys Cys Pro Val Thr Lys Val Val Asp Ser Leu Ile Pro Lys Phe Ala
370                 375                 380

Phe Val Asn Gly Gly Val Val Ala Asn Cys Ile Ala Ser Thr Cys Thr
385                 390                 395                 400

Cys Gly Thr Gly Arg Arg Pro Ile Ser Gln Asp Arg Ser Lys Gly Val
                405                 410                 415

Val Phe Leu Thr His Asp Asn Cys Gly Leu Ile Gly Val Asn Gly Val
            420                 425                 430

Glu Leu Tyr Ala Asn Arg Arg Gly His Asp Ala Thr Trp Gly Val Gln
        435                 440                 445

Asn Leu Thr Val Gly Pro Ala Ile Ala Ile Arg Pro Val Asp Ile Ser
450                 455                 460

Leu Asn Leu Ala Asp Ala Thr Asn Phe Leu Gln Asp Ser Lys Ala Glu
465                 470                 475                 480

Leu Glu Lys Ala Arg Lys Ile Leu Ser Glu Val Gly Arg Trp Tyr Asn
                485                 490                 495

Ser Arg Glu Thr Val Ile Thr Ile Ile Val Val Met Val Val Ile Leu
            500                 505                 510

Val Val Ile Ile Val Ile Val Ile Met Leu Tyr Arg Leu Arg Arg Ser
        515                 520                 525
```

```
Met Leu Met Gly Asn Pro Asp Asp Arg Ile Pro Arg Asp Thr Tyr Thr
    530                 535                 540

Leu Glu Pro Lys Ile Arg His Met Tyr Thr Asn Gly Gly Phe Asp Ala
545                 550                 555                 560

Met Ala Glu Lys Arg
                565

<210> SEQ ID NO 9
<211> LENGTH: 575
<212> TYPE: PRT
<213> ORGANISM: Artificial Sequence
<220> FEATURE:
<223> OTHER INFORMATION: Description of Artificial Sequence: Synthetic
      HN protein of Sendai virus nagoya

<400> SEQUENCE: 9

Met Asp Gly Asp Arg Gly Lys Arg Asp Ser Tyr Trp Ser Thr Ser Pro
1               5                   10                  15

Ser Gly Ser Thr Thr Lys Leu Ala Ser Ser Trp Glu Arg Ser Ser Lys
            20                  25                  30

Val Asp Thr Trp Leu Leu Ile Leu Ser Phe Thr Gln Trp Ala Leu Ser
        35                  40                  45

Ile Ala Thr Val Ile Ile Cys Ile Ile Ser Ala Arg Gln Gly Tyr
    50                  55                  60

Ser Met Lys Glu Tyr Ser Met Thr Val Glu Ala Leu Asn Met Ser Ser
65                  70                  75                  80

Arg Glu Val Lys Glu Ser Leu Thr Ser Leu Ile Arg Gln Glu Val Ile
                85                  90                  95

Ala Arg Ala Val Asn Ile Gln Ser Ser Val Gln Thr Gly Ile Pro Val
            100                 105                 110

Leu Leu Asn Lys Asn Ser Arg Asp Val Ile Gln Met Ile Asp Lys Ser
        115                 120                 125

Cys Ser Arg Gln Glu Leu Thr Gln Leu Cys Glu Ser Thr Ile Ala Val
    130                 135                 140

His His Ala Glu Gly Ile Thr Pro Leu Glu Pro His Ser Phe Trp Arg
145                 150                 155                 160

Cys Pro Val Gly Glu Pro Tyr Leu Ser Ser Asp Pro Lys Ile Ser Leu
                165                 170                 175

Leu Pro Gly Pro Ser Leu Leu Pro Gly Ser Thr Thr Ile Ser Gly Cys
            180                 185                 190

Val Arg Leu Pro Ser Leu Ser Ile Gly Glu Ala Ile Tyr Ala Tyr Ser
        195                 200                 205

Ser Asn Leu Ile Thr Gln Gly Cys Ala Asp Ile Gly Lys Ser Tyr Gln
    210                 215                 220

Val Leu Gln Leu Gly Tyr Ile Ser Leu Asn Ser Asp Met Phe Pro Asp
225                 230                 235                 240

Leu Asn Pro Val Val Ser His Thr Tyr Asp Ile Asn Asp Asn Arg Lys
                245                 250                 255

Ser Cys Ser Val Val Ala Thr Gly Thr Arg Gly Tyr Gln Leu Cys Ser
            260                 265                 270

Met Pro Thr Val Asp Glu Arg Thr Asp Tyr Ser Ser Asp Gly Ile Glu
        275                 280                 285

Asp Leu Val Leu Asp Val Leu Asp Leu Lys Gly Arg Thr Lys Ser His
    290                 295                 300

Arg Tyr Arg Asn Ser Glu Val Asp Leu Asp His Pro Phe Ser Ala Leu
305                 310                 315                 320
```

```
Tyr Pro Ser Val Gly Asn Gly Ile Ala Thr Glu Gly Thr Leu Ile Phe
                325                 330                 335

Leu Gly Tyr Gly Gly Leu Thr Thr Pro Leu Gln Gly Asp Thr Lys Cys
            340                 345                 350

Arg Thr Lys Gly Cys Gln Gln Val Ser Gln Asp Thr Cys Asn Glu Ala
        355                 360                 365

Leu Lys Ile Thr Trp Leu Gly Gly Lys Gln Val Val Ser Val Ile Ile
370                 375                 380

Gln Val Asn Asp Tyr Leu Ser Glu Arg Pro Lys Ile Arg Val Thr Thr
385                 390                 395                 400

Ile Pro Ile Thr Gln Asn Tyr Leu Gly Ala Glu Gly Arg Leu Leu Lys
                405                 410                 415

Leu Gly Asp Arg Val Tyr Ile Tyr Thr Arg Ser Ser Gly Trp His Ser
            420                 425                 430

Gln Leu Gln Ile Gly Val Leu Asp Ile Ser His Pro Leu Thr Ile Asn
        435                 440                 445

Trp Thr Pro His Glu Ala Leu Ser Arg Pro Gly Asn Lys Glu Cys Asn
            450                 455                 460

Trp Tyr Asn Thr Cys Pro Lys Glu Cys Ile Ser Gly Val Tyr Thr Asp
465                 470                 475                 480

Ala Tyr Pro Leu Ser Pro Asp Ala Ala Asn Val Ala Thr Val Thr Leu
                485                 490                 495

Tyr Ala Asn Thr Ser Arg Val Asn Pro Thr Ile Met Tyr Ser Asn Thr
            500                 505                 510

Thr Asn Ile Ile Asn Met Leu Arg Ile Lys Asp Val Gln Leu Glu Ala
        515                 520                 525

Ala Tyr Thr Thr Thr Ser Cys Ile Thr His Phe Gly Lys Gly Tyr Cys
        530                 535                 540

Phe His Ile Ile Glu Ile Asn Gln Lys Ser Leu Asn Thr Leu Gln Pro
545                 550                 555                 560

Met Leu Phe Lys Thr Ser Ile Pro Lys Leu Cys Lys Ala Glu Ser
                565                 570                 575

<210> SEQ ID NO 10
<211> LENGTH: 2228
<212> TYPE: PRT
<213> ORGANISM: Artificial Sequence
<220> FEATURE:
<223> OTHER INFORMATION: Description of Artificial Sequence: Synthetic
      L protein of Sendai virus nagoya

<400> SEQUENCE: 10

Met Asp Gly Gln Glu Ser Ser Gln Asn Pro Ser Asp Ile Leu Tyr Pro
1               5                   10                  15

Glu Cys His Leu Asn Ser Pro Ile Val Arg Gly Lys Ile Ala Gln Leu
            20                  25                  30

His Val Leu Leu Asp Val Asn Gln Pro Tyr Arg Leu Lys Asp Asp Ser
        35                  40                  45

Ile Ile Asn Ile Thr Lys His Lys Ile Arg Asn Gly Gly Leu Ser Pro
    50                  55                  60

Arg Gln Ile Lys Ile Arg Ser Leu Gly Lys Ala Leu Gln Arg Thr Ile
65                  70                  75                  80

Lys Asp Leu Asp Arg Tyr Thr Phe Glu Pro Tyr Pro Thr Tyr Ser Gln
                85                  90                  95

Glu Leu Leu Arg Leu Asp Ile Pro Glu Ile Cys Asp Lys Ile Arg Ser
```

```
            100                 105                 110
Val Phe Ala Val Ser Asp Arg Leu Thr Arg Glu Leu Ser Ser Gly Phe
            115                 120                 125

Gln Asp Leu Trp Leu Asn Ile Phe Lys Gln Leu Gly Asn Ile Glu Gly
            130                 135                 140

Arg Glu Gly Tyr Asp Pro Leu Gln Asp Ile Gly Thr Ile Pro Glu Ile
145                 150                 155                 160

Thr Asp Lys Tyr Ser Arg Asn Arg Trp Tyr Arg Pro Phe Leu Thr Trp
                165                 170                 175

Phe Ser Ile Lys Tyr Asp Met Arg Trp Met Gln Lys Thr Arg Pro Gly
                180                 185                 190

Gly Pro Leu Asp Thr Ser Asn Ser His Asn Leu Leu Glu Cys Lys Ser
            195                 200                 205

Tyr Thr Leu Val Thr Tyr Gly Asp Leu Ile Met Ile Leu Asn Lys Leu
            210                 215                 220

Thr Leu Thr Gly Tyr Ile Leu Thr Pro Glu Leu Val Leu Met Tyr Cys
225                 230                 235                 240

Asp Val Val Glu Gly Arg Trp Asn Met Ser Ala Ala Gly His Leu Asp
                245                 250                 255

Lys Lys Ser Ile Gly Ile Thr Ser Lys Gly Glu Leu Trp Glu Leu
                260                 265                 270

Val Asp Ser Leu Phe Ser Ser Leu Gly Glu Glu Ile Tyr Asn Val Ile
            275                 280                 285

Ala Leu Leu Glu Pro Leu Ser Leu Ala Leu Ile Gln Leu Asn Asp Pro
            290                 295                 300

Val Ile Pro Leu Arg Gly Ala Phe Met Arg His Val Leu Thr Glu Leu
305                 310                 315                 320

Gln Ala Val Leu Thr Ser Arg Asp Val Tyr Thr Asp Ala Glu Ala Asp
                325                 330                 335

Thr Ile Val Glu Ser Leu Leu Ala Ile Phe His Gly Thr Ser Ile Asp
                340                 345                 350

Glu Lys Ala Glu Ile Phe Ser Phe Arg Thr Phe Gly His Pro Ser
                355                 360                 365

Leu Glu Ala Val Thr Ala Ala Asp Lys Val Arg Ala His Met Tyr Ala
            370                 375                 380

Gln Lys Ala Ile Lys Leu Lys Thr Leu Tyr Glu Cys His Ala Val Phe
385                 390                 395                 400

Cys Thr Ile Ile Ile Asn Gly Tyr Arg Glu Arg His Gly Gly Gln Trp
                405                 410                 415

Pro Pro Cys Asp Phe Pro Asp His Val Cys Leu Glu Leu Arg Asn Ala
                420                 425                 430

Gln Gly Ser Asn Thr Ala Ile Ser Tyr Glu Cys Ala Val Asp Asn Tyr
            435                 440                 445

Thr Ser Phe Ile Gly Phe Lys Phe Arg Lys Phe Ile Glu Pro Gln Leu
            450                 455                 460

Asp Glu Asp Leu Thr Ile Tyr Met Lys Asp Lys Ala Leu Ser Pro Arg
465                 470                 475                 480

Lys Glu Ala Trp Asp Ser Val Tyr Pro Asp Ser Asn Leu Tyr Tyr Lys
                485                 490                 495

Ala Pro Glu Ser Glu Glu Thr Arg Arg Leu Ile Glu Val Phe Ile Asn
            500                 505                 510

Asp Glu Asn Phe Asn Pro Glu Glu Ile Ile Asn Tyr Val Glu Ser Gly
            515                 520                 525
```

```
Asp Trp Leu Lys Asp Glu Lys Phe Asn Ile Ser Tyr Ser Leu Lys Glu
        530                 535                 540

Lys Glu Ile Lys Gln Glu Gly Arg Leu Phe Ala Lys Met Thr Tyr Lys
545                 550                 555                 560

Met Arg Ala Val Gln Val Leu Ala Glu Thr Leu Leu Ala Lys Gly Ile
                565                 570                 575

Gly Glu Leu Phe Ser Glu Asn Gly Met Val Lys Gly Glu Ile Asp Leu
                580                 585                 590

Leu Lys Arg Leu Thr Thr Leu Ser Val Ser Gly Val Pro Arg Thr Asp
        595                 600                 605

Ser Val Tyr Asn Asn Ser Lys Ser Glu Lys Arg Asn Glu Gly Met
        610                 615                 620

Lys Lys Lys Asn Ser Gly Gly Tyr Trp Asp Glu Lys Lys Arg Ser Arg
625                 630                 635                 640

His Glu Phe Lys Ala Thr Asp Ser Ser Thr Asp Gly Tyr Glu Thr Leu
                645                 650                 655

Ser Cys Phe Leu Thr Thr Asp Leu Lys Lys Tyr Cys Leu Asn Trp Arg
                660                 665                 670

Phe Glu Ser Thr Ala Leu Phe Gly Gln Arg Cys Asn Glu Ile Phe Gly
        675                 680                 685

Phe Lys Thr Phe Phe Asn Trp Met His Pro Val Leu Glu Arg Cys Thr
        690                 695                 700

Ile Tyr Val Gly Asp Pro Tyr Cys Pro Val Ala Asp Arg Met His Arg
705                 710                 715                 720

Gln Leu Gln Asp His Ala Asp Ser Gly Ile Phe Ile His Asn Pro Arg
                725                 730                 735

Gly Gly Ile Glu Gly Tyr Cys Gln Lys Leu Trp Thr Leu Ile Ser Ile
                740                 745                 750

Ser Ala Ile His Leu Ala Ala Val Arg Val Gly Val Arg Val Ser Ala
        755                 760                 765

Met Val Gln Gly Asp Asn Gln Ala Ile Ala Val Thr Ser Arg Val Pro
770                 775                 780

Val Ala Gln Thr Tyr Lys Gln Lys Asn His Val Tyr Lys Glu Ile
785                 790                 795                 800

Thr Lys Tyr Phe Gly Ala Leu Arg His Val Met Phe Asp Val Gly His
                805                 810                 815

Glu Leu Lys Leu Asn Glu Thr Ile Ile Ser Ser Lys Met Phe Val Tyr
        820                 825                 830

Ser Lys Arg Ile Tyr Tyr Asp Gly Lys Ile Leu Pro Gln Cys Leu Lys
        835                 840                 845

Ala Leu Thr Arg Cys Val Phe Trp Ser Glu Thr Leu Val Asp Glu Asn
850                 855                 860

Arg Ser Ala Cys Ser Asn Ile Ser Thr Ser Ile Ala Lys Ala Ile Glu
865                 870                 875                 880

Asn Gly Tyr Ser Pro Ile Leu Gly Tyr Cys Ile Ala Leu Tyr Lys Thr
                885                 890                 895

Cys Gln Gln Val Cys Ile Ser Leu Gly Met Thr Ile Asn Pro Thr Ile
                900                 905                 910

Ser Pro Thr Val Arg Asp Gln Tyr Phe Lys Gly Lys Asn Trp Leu Arg
        915                 920                 925

Cys Ala Val Leu Ile Pro Ala Asn Val Gly Gly Phe Asn Tyr Met Ser
930                 935                 940
```

```
Thr Ser Arg Cys Phe Val Arg Asn Ile Gly Asp Pro Ala Val Ala Ala
945                 950                 955                 960

Leu Ala Asp Leu Lys Arg Phe Ile Arg Ala Asp Leu Leu Asp Lys Gln
            965                 970                 975

Val Leu Tyr Arg Ile Met Asn Gln Glu Pro Gly Asp Ser Ser Phe Leu
            980                 985                 990

Asp Trp Ala Ser Asp Pro Tyr Ser Cys Asn Leu Pro His Ser Gln Ser
            995                 1000                1005

Ile Thr Thr Ile Ile Lys Asn Ile Thr Ala Arg Ser Val Leu Gln
    1010                1015                1020

Glu Ser Pro Asn Pro Leu Leu Ser Gly Leu Phe Thr Glu Thr Ser
    1025                1030                1035

Gly Glu Glu Asp Leu Asn Leu Ala Ser Phe Leu Met Asp Arg Lys
    1040                1045                1050

Val Ile Leu Pro Arg Val Ala His Glu Ile Leu Gly Asn Ser Leu
    1055                1060                1065

Thr Gly Val Arg Glu Ala Ile Ala Gly Met Leu Asp Thr Thr Lys
    1070                1075                1080

Ser Leu Val Arg Ala Ser Val Lys Lys Gly Gly Leu Ser Tyr Gly
    1085                1090                1095

Ile Leu Arg Arg Leu Val Asn Tyr Asp Leu Leu Gln Tyr Glu Thr
    1100                1105                1110

Leu Thr Arg Thr Leu Arg Lys Pro Val Lys Asp Asn Ile Glu Tyr
    1115                1120                1125

Glu Tyr Met Cys Ser Val Glu Leu Ala Val Gly Leu Arg Gln Lys
    1130                1135                1140

Met Trp Ile His Leu Thr Tyr Gly Arg Pro Ile His Gly Leu Glu
    1145                1150                1155

Thr Pro Asp Pro Leu Glu Leu Leu Arg Gly Thr Phe Ile Glu Gly
    1160                1165                1170

Ser Glu Val Cys Lys Leu Cys Arg Ser Glu Gly Ala Asp Pro Ile
    1175                1180                1185

Tyr Thr Trp Phe Tyr Leu Pro Asp Asn Ile Asp Leu Asp Thr Leu
    1190                1195                1200

Thr Asn Gly Ser Pro Ala Ile Arg Ile Pro Tyr Phe Gly Ser Ala
    1205                1210                1215

Thr Asp Glu Arg Ser Glu Ala Gln Leu Gly Tyr Val Arg Asn Leu
    1220                1225                1230

Ser Lys Pro Ala Lys Ala Ala Ile Arg Ile Ala Met Val Tyr Thr
    1235                1240                1245

Trp Ala Tyr Gly Thr Asp Glu Ile Ser Trp Met Glu Ala Ala Leu
    1250                1255                1260

Ile Ala Gln Thr Arg Ala Asn Leu Ser Leu Glu Asn Leu Lys Leu
    1265                1270                1275

Leu Thr Pro Val Ser Thr Ser Thr Asn Leu Ser His Arg Leu Lys
    1280                1285                1290

Asp Thr Ala Thr Gln Met Lys Phe Ser Ser Ala Thr Leu Val Arg
    1295                1300                1305

Ala Ser Arg Phe Ile Thr Ile Ser Asn Asp Asn Met Ala Leu Lys
    1310                1315                1320

Glu Ala Gly Glu Ser Lys Asp Thr Asn Leu Val Tyr Gln Gln Ile
    1325                1330                1335

Met Leu Thr Gly Leu Ser Leu Phe Glu Phe Asn Met Arg Tyr Lys
```

-continued

|      |      |      | 1340 |      |      |      | 1345 |      |      |      | 1350 |      |      |
|------|------|------|------|------|------|------|------|------|------|------|------|------|------|

Lys Gly Ser Leu Gly Lys Pro Leu Ile Leu His Leu His Leu Asn
    1355                1360                1365

Asn Gly Cys Cys Ile Met Glu Ser Pro Gln Glu Ala Asn Ile Pro
    1370                1375                1380

Pro Arg Ser Thr Leu Asp Leu Glu Ile Thr Gln Glu Asn Asn Lys
    1385                1390                1395

Leu Ile Tyr Asp Pro Asp Pro Leu Lys Asp Val Asp Leu Glu Leu
    1400                1405                1410

Phe Ser Lys Val Arg Asp Val His Thr Val Asp Met Thr Tyr
    1415                1420                1425

Trp Ser Asp Asp Glu Val Ile Arg Ala Thr Ser Ile Cys Thr Ala
    1430                1435                1440

Met Thr Ile Ala Asp Thr Met Ser Gln Leu Asp Arg Asp Asn Leu
    1445                1450                1455

Lys Glu Met Ile Ala Leu Val Asn Asp Asp Val Asn Ser Leu
    1460                1465                1470

Ile Thr Glu Phe Met Val Ile Asp Val Pro Leu Phe Cys Ser Thr
    1475                1480                1485

Phe Gly Gly Ile Leu Val Asn Gln Phe Ala Tyr Ser Leu Tyr Gly
    1490                1495                1500

Leu Asn Ile Arg Gly Arg Glu Glu Ile Trp Gly His Val Val Arg
    1505                1510                1515

Ile Leu Lys Asp Thr Ser His Ala Val Leu Lys Val Leu Ser Asn
    1520                1525                1530

Ala Leu Ser His Pro Lys Ile Phe Lys Arg Phe Trp Asn Ala Gly
    1535                1540                1545

Val Val Glu Pro Val Tyr Gly Pro Asn Leu Ser Asn Gln Asp Lys
    1550                1555                1560

Ile Leu Leu Ala Leu Ser Val Cys Glu Tyr Ser Val Asp Leu Phe
    1565                1570                1575

Met His Asp Trp Gln Gly Gly Val Pro Leu Glu Ile Phe Ile Cys
    1580                1585                1590

Asp Asn Asp Pro Asp Val Ala Asp Met Arg Arg Ser Ser Phe Leu
    1595                1600                1605

Ala Arg His Leu Ala Tyr Leu Cys Ser Leu Ala Glu Ile Ser Arg
    1610                1615                1620

Asp Gly Pro Arg Leu Glu Ser Met Asn Ser Leu Glu Arg Leu Glu
    1625                1630                1635

Ser Leu Lys Ser Tyr Leu Glu Leu Thr Phe Leu Asp Asp Pro Val
    1640                1645                1650

Leu Arg Tyr Ser Gln Leu Thr Gly Leu Val Ile Lys Val Phe Pro
    1655                1660                1665

Ser Thr Leu Thr Tyr Ile Arg Lys Ser Ser Ile Lys Val Leu Arg
    1670                1675                1680

Thr Arg Gly Ile Gly Val Pro Glu Val Leu Glu Asp Trp Asp Pro
    1685                1690                1695

Glu Ala Asp Asn Ala Leu Leu Asp Gly Ile Ala Ala Glu Ile Gln
    1700                1705                1710

Gln Asn Ile Pro Leu Gly His Gln Thr Arg Ala Pro Phe Trp Gly
    1715                1720                1725

Leu Arg Val Ser Lys Ser Gln Val Leu Arg Leu Arg Gly Tyr Lys
    1730                1735                1740

```
Glu Ile Thr Arg Gly Glu Ile Gly Arg Ser Gly Val Gly Leu Thr
    1745            1750                1755

Leu Pro Phe Asp Gly Arg Tyr Leu Ser His Gln Leu Arg Leu Phe
    1760            1765                1770

Gly Ile Asn Ser Thr Ser Cys Leu Lys Ala Leu Glu Leu Thr Tyr
    1775            1780                1785

Leu Leu Ser Pro Leu Val Asp Lys Asp Lys Asp Arg Leu Tyr Leu
    1790            1795                1800

Gly Glu Gly Ala Gly Ala Met Leu Ser Cys Tyr Asp Ala Thr Leu
    1805            1810                1815

Gly Pro Cys Ile Asn Tyr Tyr Asn Ser Gly Val Tyr Ser Cys Asp
    1820            1825                1830

Val Asn Gly Gln Arg Glu Leu Asn Ile Tyr Pro Ala Glu Val Ala
    1835            1840                1845

Leu Val Gly Lys Lys Leu Asn Asn Val Thr Ser Leu Gly Gln Arg
    1850            1855                1860

Val Lys Val Leu Phe Asn Gly Asn Pro Gly Ser Thr Trp Ile Gly
    1865            1870                1875

Asn Asp Glu Cys Glu Ala Leu Ile Trp Asn Glu Leu Gln Asn Ser
    1880            1885                1890

Ser Ile Gly Leu Val His Cys Asp Met Glu Gly Gly Asp His Lys
    1895            1900                1905

Asp Asp Gln Val Val Leu His Glu His Tyr Ser Val Ile Arg Ile
    1910            1915                1920

Ala Tyr Leu Val Gly Asp Arg Asp Val Val Leu Ile Ser Lys Ile
    1925            1930                1935

Ala Pro Arg Leu Gly Thr Asp Trp Thr Arg Gln Leu Ser Leu Tyr
    1940            1945                1950

Leu Arg Tyr Trp Asp Glu Val Asn Leu Ile Val Leu Lys Thr Ser
    1955            1960                1965

Asn Pro Ala Ser Thr Glu Met Tyr Leu Leu Ser Arg His Pro Lys
    1970            1975                1980

Ser Asp Ile Ile Glu Asp Ser Lys Thr Val Leu Ala Ser Leu Leu
    1985            1990                1995

Pro Leu Ser Lys Glu Asp Ser Ile Lys Ile Glu Lys Trp Ile Leu
    2000            2005                2010

Ile Glu Lys Ala Lys Ala His Glu Trp Val Thr Arg Glu Leu Arg
    2015            2020                2025

Glu Gly Ser Ser Ser Ser Gly Met Leu Arg Pro Tyr His Gln Ala
    2030            2035                2040

Leu Gln Thr Phe Gly Phe Glu Pro Asn Leu Tyr Lys Leu Ser Arg
    2045            2050                2055

Asp Phe Leu Ser Thr Met Asn Ile Ala Asp Thr His Asn Cys Met
    2060            2065                2070

Ile Ala Phe Asn Arg Val Leu Lys Asp Thr Ile Phe Glu Trp Ala
    2075            2080                2085

Arg Ile Thr Glu Ser Asp Lys Arg Leu Lys Leu Thr Gly Lys Tyr
    2090            2095                2100

Asp Leu Tyr Pro Val Arg Asp Ser Gly Lys Leu Lys Thr Val Ser
    2105            2110                2115

Arg Arg Leu Val Leu Ser Trp Ile Ser Leu Ser Met Ser Thr Arg
    2120            2125                2130
```

-continued

```
Leu Val Thr Gly Ser Phe Pro Asp Gln Lys Phe Glu Ala Arg Leu
    2135                2140                2145

Gln Leu Gly Ile Val Ser Leu Ser Ser Arg Glu Ile Arg Asn Leu
    2150                2155                2160

Arg Val Ile Thr Lys Thr Leu Leu Asp Arg Phe Glu Asp Ile Ile
    2165                2170                2175

His Ser Ile Thr Tyr Arg Phe Leu Thr Lys Glu Ile Lys Ile Leu
    2180                2185                2190

Met Lys Ile Leu Gly Ala Val Lys Met Phe Gly Ala Arg Gln Asn
    2195                2200                2205

Glu Tyr Thr Thr Val Ile Asp Asp Gly Ser Leu Gly Asp Ile Glu
    2210                2215                2220

Pro Tyr Asp Ser Ser
    2225

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gccaaagttc acgcggccgc agatcttcac gatggccggg ttgt                44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acaacccggc catcgtgaag atctgcggcc gcgtgaactt tggc                44

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acttgcggcc gctcgccacc atggtgagca agggcgagga                    40

<210> SEQ ID NO 14
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acttgcggcc gcgatgaact ttcaccctaa gttttcttta cggccgct ttacttgtac    60 agctcgtcca                                                         70

<210> SEQ ID NO 15
<211> LENGTH: 30
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 15
gcatacctat gcagcgtggc agagatatct                                      30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agatatctct gccacgctgc ataggtatgc                                      30

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgcggatcct aatacgactc actataggg                                       29

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccaaacagcc attctgtggt                                                 20

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgctctagaa gctgctgact cctgtttca                                       29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgcggatcca tagctcaagg tccacatcc                                       29

<210> SEQ ID NO 21
<211> LENGTH: 41
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 21
cgcggatcca tcgtggggcg ccccaggcac cagggcgtga t                           41

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgctctagaa ggagccacac gcagctcatt gtagaaggtg t                           41

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggaaacagct atgaccatg                                                    19

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctgcggccgc gctagctttg gcagcaaaga a                                      31

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aagctagcgc ggccgcagat cttc                                              24

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccggaattcg tatgatccta gattcctcct                                        30

<210> SEQ ID NO 27
<211> LENGTH: 48
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 27
gaaagaaatt tcaccgctag cgcggccgca tgctaacacg gcgcaatg           48

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cattgcgccg tgttagcatg cggccgcgct agcggtgaaa tttctttc           48

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
actagctagc agaatatatg aaaacattta acatttctca                    40

<210> SEQ ID NO 30
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acttgcggcc gcgatgaact ttcaccctaa gttttcttta ggtaaaactt ttaatttcgg   60
gtatatttga                                                         70

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaagaaattt cagctagcac ggcgcaatgg                               30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccattgcgcc gtgctagctg aaatttcttt                               30

<210> SEQ ID NO 33
<211> LENGTH: 30
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 33
ctgtaaatgt gcacgcgtca gagacctgca                                      30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgcaggtctc tgacgcgtgc acatttacag                                      30

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggtccacgcg ttttaatttc gggtatattt ga                                   32

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcggtatttt agctagcatc tcaaacaagc                                      30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcttgtttga gatgctagct aaaataccgc                                      30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
taactgacta gcacgcgtgt cggctttgct                                      30

<210> SEQ ID NO 39
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 39
agcaaagccg acacgcgtgc tagtcagtta                                           30

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gggataaagt cccttagatc tgcttggttg caaaa                                     35

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttttgcaacc aagcagatct aagggacttt atccc                                     35

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgcggatccg aagaatatat gaaaacatt                                            29

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgcggatcct taatttcggg tatatttga                                            29

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccggaattcg gcgcaatggc agatatcta                                            29

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 45
acttgcggcc gcggtgcaca tttacagctt tc                                  32

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccggaattcg aaacatgaca gcatatatc                                      29

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acttgcggcc gcgtcgtgat catcttttct                                     30

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccggaattct catggatggt gataggggc                                      29

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acttgcggcc gcttaagact cggccttgca                                     30

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gggcttggga aacatgacag c                                              21

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gaagaatctc ttctggcgac gaccggc        27

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gacatcctga taatggtcgt gatc        24

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agggtgaaag aaatgcggcc gcttgctagc agaatata        38

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tatattctgc tagcaagcgg ccgcatttct ttcaccct        38

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
actagctagc caccatggtg agcaagggcg        30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acgaagatct ccggtcgcca ccatggtgag        30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acgaagatct ttacttgtac agctcgtcca                                    30

<210> SEQ ID NO 58
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggtccacgcg ttttacttgt acagctcgtc ca                                 32

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aaatgcggcc gcttggcgcc agaatatatg aaaa                               34

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttttcatata ttctggcgcc aagcggccgc attt                               34

<210> SEQ ID NO 61
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tacccgaaat taaagcatgc gtcggctttg ctga                               34

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcagcaaagc cgacgcatgc tttaatttcg ggta                               34

<210> SEQ ID NO 63
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63

-continued

```
actagctagc ccttatgaag accttaattc ttgc                          34
```

<210> SEQ ID NO 64
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64

```
ggtccgcatg ctctatttgc attcatctgg tact                          34
```

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65

```
actagctagc tgccaccatg gggaactggg ctgtgaatga                    40
```

<210> SEQ ID NO 66
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66

```
acttgcggcc gcgatgaact ttcaccctaa gttttcctta aagagacaag ttagaagttt    60
```

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      amino acid
      sequence for F protein cleaving
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys or Arg

<400> SEQUENCE: 67

Arg Arg Xaa Xaa Arg
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      amino acid sequence for F protein cleaving

<400> SEQUENCE: 68

Arg Arg Gln Lys Arg
1               5

<210> SEQ ID NO 69
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cacgctcgag taatacgact cactataggg accaaacaag agaagaaaca tgtatggaat    60
atataatgaa gtttaagaaa aacttagggt caaagtatcc                         100

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
actcccatgg cgtaactcca tagtg                                          25

<210> SEQ ID NO 71
<211> LENGTH: 61
<212> TYPE: DNA
<213> ORGANISM: Artificial Sequence
<220> FEATURE:
<223> OTHER INFORMATION: Description of Artificial Sequence: Synthetic
      oligo DNA for inserting transcription signal

<400> SEQUENCE: 71
ctagcgaatt cgcggccgcc gtacggtaaa gatttaagaa aaacttaggg tgaaagttca    60
t                                                                    61

<210> SEQ ID NO 72
<211> LENGTH: 61
<212> TYPE: DNA
<213> ORGANISM: Artificial Sequence
<220> FEATURE:
<223> OTHER INFORMATION: Description of Artificial Sequence: Synthetic
      oligo DNA for inserting transcription signal

<400> SEQUENCE: 72
ggccatgaac tttcaccta agttttttctt aaatctttac cgtacggcgg ccgcgaattc    60
g                                                                    61

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cggaattcgt gacaatgcag ctgaggaacc cag                                 33

<210> SEQ ID NO 74
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gtgcggccgc ttaaagtaag tcttttaatg acatctgc                                       38

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgaatgcaaa tagaaccggt gtcggctttg ctga                                           34

<210> SEQ ID NO 76
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tcagcaaagc cgacaccggt tctatttgca ttca                                           34

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggtccaccgg tgttagaagt tttccttgtt ga                                             32

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aattggcgcc agccaccatg gccaagttga ccagtgccgt                                     40

<210> SEQ ID NO 79
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggtccacgcg tttcagtcct gctcctcggc cacgaagtg                                      39

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 80
acgaagatct agcctagggg gaccatggtg agcgtgatca                                   40

<210> SEQ ID NO 81
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acgaagatct gacgtcttca gcagtgggcc acggcgt                                     37

<210> SEQ ID NO 82
<211> LENGTH: 524
<212> TYPE: PRT
<213> ORGANISM: Artificial Sequence
<220> FEATURE:
<223> OTHER INFORMATION: Description of Artificial Sequence: Synthetic
      NP protein of Sendai virus Cl.151

<400> SEQUENCE: 82

Met Ala Gly Leu Leu Ser Thr Phe Asp Thr Phe Ser Ser Arg Arg Ser
1               5                   10                  15

Glu Ser Ile Asn Lys Ser Gly Gly Ala Val Ile Pro Gly Gln Arg
            20                  25                  30

Ser Thr Val Ser Val Phe Ile Leu Gly Pro Ser Val Thr Asp Asp Ala
        35                  40                  45

Asp Lys Leu Phe Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
            100                 105                 110

Thr Lys Thr Asp Gly Phe Ile Val Lys Thr Arg Asp Met Glu Tyr Glu
        115                 120                 125

Arg Thr Thr Glu Trp Leu Phe Gly Pro Arg Val Asn Lys Ser Pro Leu
    130                 135                 140

Phe Gln Gly Gln Arg Asp Ala Ala Asp Pro Asp Thr Leu Leu Gln Ile
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Gly Val
        195                 200                 205

Leu Val Phe Thr Gly Glu Thr Val Glu Gly Ile Gly Ser Val Met Arg
    210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
                245                 250                 255

Val Gly Asn Tyr Ile Arg Asp Ala Gly Leu Ala Ser Phe Met Asn Thr
            260                 265                 270

Ile Lys Tyr Gly Val Glu Thr Lys Met Ala Ala Leu Thr Leu Ser Asn
275 280 285

Leu Arg Pro Asp Ile Asn Lys Leu Arg Ser Leu Ile Asp Thr Tyr Leu
290 295 300

Ser Lys Gly Pro Arg Ala Pro Phe Ile Cys Ile Leu Lys Asp Pro Val
305 310 315 320

His Gly Glu Phe Ala Pro Gly Asn Tyr Pro Ala Leu Trp Ser Tyr Ala
325 330 335

Met Gly Val Ala Val Val Gln Asn Lys Ala Met Gln Gln Tyr Val Thr
340 345 350

Gly Arg Thr Tyr Leu Asp Met Glu Met Phe Leu Leu Gly Gln Ala Val
355 360 365

Ala Lys Asp Ala Glu Ser Lys Ile Ser Ser Ala Leu Glu Asp Glu Leu
370 375 380

Gly Val Thr Asp Thr Ala Lys Glu Arg Leu Arg His His Leu Ala Asn
385 390 395 400

Leu Ser Gly Gly Asp Gly Ala Tyr His Lys Pro Thr Gly Gly Gly Ala
405 410 415

Ile Glu Val Ala Leu Asp Asn Ala Asp Ile Asp Leu Glu Thr Glu Ala
420 425 430

His Ala Asp Gln Asp Ala Arg Gly Trp Gly Gly Asp Ser Gly Glu Arg
435 440 445

Trp Ala Arg Gln Val Ser Gly Gly His Phe Val Thr Leu His Gly Ala
450 455 460

Glu Arg Leu Glu Glu Thr Asn Asp Glu Asp Val Ser Asp Ile Glu
465 470 475 480

Arg Arg Ile Ala Met Arg Leu Ala Glu Arg Gln Glu Asp Ser Ala
485 490 495

Thr His Gly Asp Glu Gly Arg Asn Asn Gly Val Asp His Glu Glu Asp
500 505 510

Asp Asp Ala Ala Ala Ala Gly Ile Gly Gly Ile
515 520

<210> SEQ ID NO 83
<211> LENGTH: 568
<212> TYPE: PRT
<213> ORGANISM: Artificial Sequence
<220> FEATURE:
<223> OTHER INFORMATION: Description of Artificial Sequence: Synthetic
      P protein of Sendai virus Cl.151

<400> SEQUENCE: 83

Met Asp Gln Asp Ala Phe Ile Leu Lys Glu Asp Ser Glu Val Glu Arg
1 5 10 15

Lys Ala Pro Gly Gly Arg Glu Ser Leu Ser Asp Val Ile Gly Phe Leu
20 25 30

Asp Ala Val Leu Ser Ser Glu Pro Thr Asp Ile Gly Gly Asp Arg Ser
35 40 45

Trp Leu His Asn Thr Ile Asn Thr Ser Gln Gly Pro Gly Ser Ala His
50 55 60

Arg Ala Lys Ser Glu Gly Glu Gly Glu Val Ser Thr Pro Ser Thr Gln
65 70 75 80

Asp Asn Arg Ser Gly Glu Glu Ser Arg Val Ser Gly Arg Thr Ser Lys
85 90 95

Pro Glu Ala Glu Ala His Ala Arg Asn Leu Asp Lys Gln Asn Ile His
100 105 110

-continued

```
Trp Ala Phe Arg Gly Arg Thr Gly Thr Lys Ser Val Ser Gln Asp Leu
            115                 120                 125

Gly Asp Gly Gly Asp Ser Gly Ile Leu Glu Asn Pro Pro Asn Glu Arg
        130                 135                 140

Gly Tyr Pro Arg Ser Gly Ile Glu Asp Glu Asn Arg Glu Met Ala Ala
145                 150                 155                 160

His Pro Asp Lys Arg Gly Glu Asp Gln Ala Glu Gly Leu Pro Glu Glu
                165                 170                 175

Val Arg Gly Gly Thr Ser Leu Pro Asp Glu Gly Glu Gly Gly Ala Ser
                180                 185                 190

Asn Asn Gly Arg Ser Met Glu Pro Gly Ser Ser His Ser Ala Arg Val
            195                 200                 205

Thr Gly Val Leu Val Ile Pro Ser Pro Glu Leu Glu Glu Ala Val Leu
        210                 215                 220

Arg Arg Asn Lys Arg Arg Pro Thr Asn Ser Gly Ser Lys Pro Leu Thr
225                 230                 235                 240

Pro Ala Thr Val Pro Gly Thr Arg Ser Pro Pro Leu Asn Arg Tyr Asn
                245                 250                 255

Ser Thr Gly Ser Pro Pro Gly Lys Pro Pro Ser Thr Gln Asp Glu His
            260                 265                 270

Ile Asn Ser Gly Asp Thr Pro Ala Val Arg Val Lys Asp Arg Lys Pro
        275                 280                 285

Pro Ile Gly Thr Arg Ser Val Ser Asp Cys Pro Ala Asn Gly Arg Pro
    290                 295                 300

Ile His Pro Gly Ile Glu Thr Asp Ser Thr Lys Lys Gly Ile Gly Glu
305                 310                 315                 320

Asn Thr Ser Ser Met Lys Glu Met Ala Thr Leu Leu Thr Ser Leu Gly
                325                 330                 335

Val Ile Gln Ser Ala Gln Glu Phe Glu Ser Ser Arg Asp Ala Ser Tyr
            340                 345                 350

Val Phe Ala Arg Arg Ala Leu Lys Ser Ala Asn Tyr Ala Glu Met Thr
        355                 360                 365

Phe Asn Val Cys Gly Leu Ile Leu Ser Ala Glu Lys Ser Ser Ala Arg
    370                 375                 380

Lys Val Asp Glu Asn Lys Gln Leu Leu Lys Gln Ile Gln Glu Ser Val
385                 390                 395                 400

Glu Ser Phe Arg Asp Ile Tyr Lys Arg Phe Ser Glu Tyr Gln Lys Glu
                405                 410                 415

Gln Asn Ser Leu Leu Met Ser Asn Leu Ser Thr Leu His Ile Ile Thr
            420                 425                 430

Asp Arg Gly Gly Lys Thr Asp Asn Thr Asp Ser Leu Thr Arg Ser Pro
        435                 440                 445

Ser Val Phe Ala Lys Ser Lys Glu Asn Lys Thr Lys Ala Thr Arg Phe
    450                 455                 460

Asp Pro Ser Met Glu Thr Leu Glu Asp Met Lys Tyr Lys Pro Asp Leu
465                 470                 475                 480

Ile Arg Glu Asp Glu Phe Arg Asp Glu Ile Arg Asn Pro Val Tyr Gln
                485                 490                 495

Glu Arg Asp Thr Glu Pro Arg Ala Ser Asn Ala Ser Arg Leu Phe Pro
            500                 505                 510

Ser Lys Glu Lys Pro Thr Met His Ser Leu Arg Leu Val Ile Glu Ser
        515                 520                 525
```

Ser Pro Leu Ser Arg Ala Glu Lys Ala Ala Tyr Val Lys Ser Leu Ser
    530                 535                 540

Lys Cys Lys Thr Asp Gln Glu Val Lys Ala Val Met Glu Leu Val Glu
545                 550                 555                 560

Glu Asp Ile Glu Ser Leu Thr Asn
                565

<210> SEQ ID NO 84
<211> LENGTH: 348
<212> TYPE: PRT
<213> ORGANISM: Artificial Sequence
<220> FEATURE:
<223> OTHER INFORMATION: Description of Artificial Sequence: Synthetic
      M protein of Sendai virus Cl.151

<400> SEQUENCE: 84

Met Ala Asp Ile Tyr Arg Phe Pro Lys Phe Ser Tyr Glu Asp Asn Gly
1               5                   10                  15

Thr Val Glu Pro Leu Pro Leu Arg Thr Gly Pro Asp Lys Lys Ala Ile
            20                  25                  30

Pro His Ile Arg Ile Val Lys Val Gly Asp Pro Pro Lys His Gly Val
        35                  40                  45

Arg Tyr Leu Asp Leu Leu Leu Gly Phe Phe Glu Thr Pro Lys Gln
    50                  55                  60

Thr Thr Asn Leu Glu Ser Val Ser Asp Leu Thr Glu Pro Thr Ser Tyr
65                  70                  75                  80

Ser Ile Cys Gly Ser Gly Ser Leu Pro Ile Gly Val Ala Lys Tyr Tyr
                85                  90                  95

Gly Thr Asp Gln Glu Leu Leu Lys Ala Cys Thr Asp Leu Arg Ile Thr
            100                 105                 110

Val Arg Arg Ala Val Arg Ala Gly Glu Met Ile Val Tyr Met Val Asp
        115                 120                 125

Ser Ile Gly Ala Pro Leu Leu Pro Trp Ser Gly Arg Leu Arg Gln Gly
    130                 135                 140

Met Ile Phe Asn Ala Asn Lys Val Ala Leu Ala Pro Gln Cys Leu Pro
145                 150                 155                 160

Val Asp Lys Asp Ile Arg Phe Arg Val Val Phe Val Asn Gly Thr Ser
                165                 170                 175

Leu Gly Ala Ile Thr Ile Ser Lys Ile Pro Lys Thr Leu Ala Asp Leu
            180                 185                 190

Ala Leu Pro Asn Ser Ile Ser Val Asn Leu Leu Val Thr Leu Lys Thr
        195                 200                 205

Gly Ile Ser Thr Glu Gln Lys Gly Val Leu Pro Val Leu Asp Asp Gln
    210                 215                 220

Gly Glu Lys Lys Leu Asn Phe Met Val His Leu Gly Leu Ile Arg Arg
225                 230                 235                 240

Lys Val Gly Lys Ile Tyr Ser Val Glu Tyr Cys Lys Ser Lys Ile Glu
                245                 250                 255

Arg Met Arg Leu Ile Phe Ser Leu Gly Leu Ile Gly Gly Ile Ser Phe
            260                 265                 270

His Val Gln Val Thr Gly Thr Leu Ser Lys Thr Phe Met Ser Gln Leu
        275                 280                 285

Ala Trp Lys Arg Ala Val Cys Phe Pro Leu Met Asp Val Asn Pro His
    290                 295                 300

Met Asn Met Val Ile Trp Ala Ala Ser Val Glu Ile Thr Gly Val Asp
305                 310                 315                 320

Ala Val Phe Gln Pro Ala Ile Pro Arg Asp Phe Arg Tyr Tyr Pro Asn
                    325                 330                 335

Val Val Ala Lys Asn Ile Gly Arg Ile Arg Lys Leu
                340                 345

<210> SEQ ID NO 85
<211> LENGTH: 565
<212> TYPE: PRT
<213> ORGANISM: Artificial Sequence
<220> FEATURE:
<223> OTHER INFORMATION: Description of Artificial Sequence: Synthetic
      F protein of Sendai virus Cl.151

<400> SEQUENCE: 85

Met Thr Ala Tyr Ile Arg Arg Ser Gln Cys Ile Ser Thr Ser Leu Leu
1               5                   10                  15

Val Val Leu Thr Thr Leu Val Ser Cys Gln Ile Pro Arg Asp Met Leu
                20                  25                  30

Ser Asn Ile Gly Val Ile Val Asp Glu Gly Lys Ser Leu Lys Ile Ala
            35                  40                  45

Gly Ser His Glu Ser Arg Tyr Ile Val Leu Ser Leu Val Pro Gly Val
        50                  55                  60

Asp Leu Glu Asn Gly Cys Gly Thr Ala Gln Val Ile Gln Tyr Lys Ser
65                  70                  75                  80

Leu Leu Asn Arg Leu Leu Ile Pro Leu Arg Asp Ala Leu Asp Leu Gln
                85                  90                  95

Glu Ala Leu Ile Thr Val Thr Asn Asp Thr Thr Gln Asn Ala Gly Val
            100                 105                 110

Pro Gln Leu Arg Phe Phe Gly Ala Val Ile Gly Thr Ile Ala Leu Gly
        115                 120                 125

Val Ala Thr Ser Ala Gln Ile Thr Thr Gly Ile Ala Leu Ala Glu Ala
130                 135                 140

Arg Glu Ala Lys Arg Asp Ile Ala Leu Ile Lys Glu Ser Met Thr Lys
145                 150                 155                 160

Thr His Lys Ser Ile Glu Leu Leu Gln Asn Ala Val Gly Glu Gln Ile
                165                 170                 175

Leu Ala Leu Lys Thr Leu Gln Asp Phe Val Asn Asp Glu Ile Lys Pro
            180                 185                 190

Ala Ile Ser Glu Leu Gly Cys Glu Thr Ala Ala Leu Arg Leu Gly Ile
        195                 200                 205

Lys Leu Thr Gln His Tyr Ser Glu Leu Leu Thr Ala Phe Gly Ser Asn
210                 215                 220

Phe Gly Thr Ile Gly Glu Lys Ser Leu Thr Leu Gln Ala Leu Ser Ser
225                 230                 235                 240

Leu Tyr Ser Ala Asn Ile Thr Glu Ile Met Thr Thr Ile Arg Thr Gly
                245                 250                 255

Gln Ser Asn Ile Tyr Asp Val Ile Tyr Thr Glu Gln Ile Lys Gly Thr
            260                 265                 270

Val Ile Asp Val Asp Leu Glu Arg Tyr Met Val Thr Leu Ser Val Lys
        275                 280                 285

Ile Pro Ile Leu Ser Glu Val Pro Gly Val Leu Ile His Lys Ala Ser
        290                 295                 300

Ser Ile Ser Tyr Asn Ile Asp Gly Glu Glu Trp Tyr Val Thr Val Pro
305                 310                 315                 320

Ser His Ile Leu Ser Arg Ala Ser Phe Leu Gly Gly Ala Asp Ile Thr

```
                    325                 330                 335
Asp Cys Val Glu Ser Arg Leu Thr Tyr Ile Cys Pro Arg Asp Pro Ala
                340                 345                 350
Gln Leu Ile Pro Asp Ser Gln Gln Lys Cys Ile Leu Gly Asp Thr Thr
                355                 360                 365
Lys Cys Pro Val Thr Lys Val Val Asp Ser Leu Ile Pro Lys Phe Ala
                370                 375                 380
Phe Val Asn Gly Gly Val Val Ala Asn Cys Ile Ala Ser Thr Cys Thr
385                 390                 395                 400
Cys Gly Thr Gly Arg Arg Pro Ile Ser Gln Asp Arg Ser Lys Gly Val
                405                 410                 415
Val Phe Leu Thr His Asp Asn Cys Gly Leu Ile Gly Val Asn Gly Val
                420                 425                 430
Glu Leu Tyr Ala Asn Arg Arg Gly His Asp Ala Thr Trp Arg Val Gln
                435                 440                 445
Asn Leu Thr Val Gly Pro Ala Ile Ala Ile Arg Pro Val Asp Ile Ser
                450                 455                 460
Leu Asn Leu Ala Asp Ala Thr Asn Phe Leu Gln Asp Ser Lys Ala Glu
465                 470                 475                 480
Leu Glu Lys Ala Arg Lys Ile Leu Ser Glu Val Gly Arg Trp Tyr Asn
                485                 490                 495
Ser Arg Glu Thr Val Ile Thr Ile Ile Val Val Met Val Val Ile Leu
                500                 505                 510
Val Val Ile Ile Val Ile Val Ile Met Leu Tyr Arg Leu Arg Arg Ser
                515                 520                 525
Met Leu Met Gly Asn Pro Asp Asp Arg Ile Pro Arg Asp Thr Tyr Thr
                530                 535                 540
Leu Glu Pro Lys Ile Arg His Met Tyr Thr Asn Gly Gly Phe Asp Ala
545                 550                 555                 560
Met Ala Glu Lys Arg
                565

<210> SEQ ID NO 86
<211> LENGTH: 575
<212> TYPE: PRT
<213> ORGANISM: Artificial Sequence
<220> FEATURE:
<223> OTHER INFORMATION: Description of Artificial Sequence: Synthetic
      HN protein of Sendai virus Cl.151

<400> SEQUENCE: 86

Met Asp Gly Asp Arg Gly Lys Arg Asp Ser Tyr Trp Ser Thr Ser Pro
1               5                   10                  15
Ser Gly Ser Thr Thr Lys Leu Ala Ser Ser Trp Glu Arg Ser Ser Lys
                20                  25                  30
Val Asp Thr Trp Leu Leu Ile Leu Ser Phe Thr Gln Trp Ala Leu Ser
                35                  40                  45
Ile Ala Thr Val Ile Ile Cys Ile Ile Ile Ser Ala Arg Gln Gly Tyr
            50                  55                  60
Ser Met Lys Glu Tyr Ser Met Thr Val Glu Ala Leu Asn Met Ser Asn
65              70                  75                  80
Arg Glu Val Lys Glu Ser Leu Thr Ser Leu Ile Arg Gln Glu Val Ile
                85                  90                  95
Ala Arg Ala Val Asn Ile Gln Ser Ser Val Gln Thr Gly Ile Pro Val
                100                 105                 110
```

```
Leu Leu Asn Lys Asn Ser Arg Asp Val Ile Gln Met Ile Asp Lys Ser
        115                 120                 125

Cys Ser Arg Gln Glu Leu Thr Gln Leu Cys Glu Ser Thr Ile Ala Val
    130                 135                 140

His His Ala Glu Gly Ile Thr Pro Leu Glu Pro His Ser Phe Trp Arg
145                 150                 155                 160

Cys Pro Val Gly Glu Pro Tyr Leu Ser Ser Asp Pro Glu Ile Ser Leu
                165                 170                 175

Leu Pro Gly Pro Ser Leu Leu Ser Gly Ser Thr Thr Ile Ser Gly Cys
            180                 185                 190

Val Arg Leu Pro Ser Leu Ser Ile Gly Glu Ala Ile Tyr Ala Tyr Ser
        195                 200                 205

Ser Asn Leu Ile Thr Gln Gly Cys Ala Asp Ile Gly Lys Ser Tyr Gln
    210                 215                 220

Val Leu Gln Leu Gly Tyr Ile Ser Leu Asn Ser Asp Met Phe Pro Asp
225                 230                 235                 240

Leu Asn Pro Val Val Ser His Thr Tyr Asp Ile Asn Asp Asn Arg Lys
                245                 250                 255

Ser Cys Ser Val Val Ala Thr Gly Thr Arg Gly Tyr Gln Leu Cys Ser
            260                 265                 270

Met Pro Thr Val Asp Glu Arg Thr Asp Tyr Ser Ser Asp Gly Ile Glu
        275                 280                 285

Asp Leu Val Leu Asp Val Leu Asp Leu Lys Gly Arg Thr Lys Ser His
    290                 295                 300

Arg Tyr Arg Asn Ser Glu Val Asp Leu Asp His Pro Phe Ser Ala Leu
305                 310                 315                 320

Tyr Pro Ser Val Gly Asn Gly Ile Ala Thr Glu Gly Thr Leu Ile Phe
                325                 330                 335

Leu Gly Tyr Gly Gly Leu Thr Thr Pro Leu Gln Gly Asp Thr Lys Cys
            340                 345                 350

Arg Thr Lys Gly Cys Gln Gln Val Ser Gln Asp Thr Cys Asn Glu Ala
        355                 360                 365

Leu Lys Ile Thr Trp Leu Gly Gly Lys Gln Val Val Asn Val Ile Ile
    370                 375                 380

Gln Val Asn Asp Tyr Leu Ser Glu Arg Pro Lys Ile Arg Val Thr Thr
385                 390                 395                 400

Ile Pro Ile Thr Gln Asn Tyr Leu Gly Ala Glu Gly Arg Leu Leu Lys
                405                 410                 415

Leu Gly Asp Arg Val Tyr Ile Tyr Thr Arg Ser Ser Gly Trp His Ser
            420                 425                 430

Gln Leu Gln Ile Gly Val Leu Asp Ile Ser His Pro Leu Thr Ile Asn
        435                 440                 445

Trp Thr Pro His Glu Ala Leu Ser Arg Pro Gly Asn Lys Glu Cys Asn
    450                 455                 460

Trp Tyr Asn Thr Cys Pro Lys Glu Cys Ile Ser Gly Val Tyr Thr Asp
465                 470                 475                 480

Ala Tyr Pro Leu Ser Pro Asp Ala Ala Asn Val Ala Thr Val Thr Leu
                485                 490                 495

Tyr Ala Asn Thr Ser Arg Val Asn Pro Thr Ile Met Tyr Ser Asn Thr
            500                 505                 510

Thr Asn Ile Ile Asn Met Leu Arg Ile Lys Asp Val Arg Leu Glu Ala
        515                 520                 525

Ala Tyr Thr Thr Thr Ser Cys Ile Thr His Phe Gly Arg Gly Tyr Cys
```

```
                530             535             540
Phe His Ile Ile Glu Ile Asn Gln Lys Ser Leu Asn Thr Leu Gln Pro
545                 550             555             560

Met Leu Phe Lys Thr Ser Ile Pro Lys Leu Cys Lys Ala Glu Ser
                565             570             575

<210> SEQ ID NO 87
<211> LENGTH: 2228
<212> TYPE: PRT
<213> ORGANISM: Artificial Sequence
<220> FEATURE:
<223> OTHER INFORMATION: Description of Artificial Sequence: Synthetic L
      protein of Sendai virus Cl.151

<400> SEQUENCE: 87

Met Asp Gly Gln Glu Ser Ser Gln Asn Pro Ser Asp Ile Leu Tyr Pro
1               5                   10                  15

Glu Cys His Leu Asn Ser Pro Ile Val Arg Gly Lys Ile Ala Gln Leu
                20                  25                  30

His Val Leu Leu Asp Val Asn Gln Pro Tyr Arg Leu Lys Asp Asp Ser
            35                  40                  45

Ile Ile Asn Ile Thr Lys His Lys Ile Arg Asn Gly Gly Leu Ser Pro
    50                  55                  60

Arg Gln Ile Lys Ile Arg Ser Leu Gly Lys Ala Leu Gln Arg Thr Ile
65                  70                  75                  80

Lys Asp Leu Asp Arg Tyr Thr Phe Glu Pro Tyr Pro Thr Tyr Ser Gln
                85                  90                  95

Glu Leu Leu Arg Leu Asp Ile Pro Glu Ile Cys Asp Lys Ile Arg Ser
                100                 105                 110

Val Phe Ala Val Ser Asp Arg Leu Thr Arg Glu Leu Ser Ser Gly Phe
            115                 120                 125

Gln Asp Leu Trp Leu Asn Ile Phe Lys Gln Leu Gly Asn Ile Glu Gly
    130                 135                 140

Arg Glu Gly Tyr Asp Pro Leu Gln Asp Ile Gly Thr Ile Pro Glu Ile
145                 150                 155                 160

Thr Asp Lys Tyr Ser Arg Asn Arg Trp Tyr Arg Pro Phe Leu Thr Trp
                165                 170                 175

Phe Ser Ile Lys Tyr Asp Met Arg Trp Met Gln Lys Thr Arg Pro Gly
                180                 185                 190

Gly Pro Leu Asp Thr Ser Asn Ser His Asn Leu Leu Glu Cys Lys Ser
            195                 200                 205

Tyr Thr Leu Val Thr Tyr Gly Asp Leu Ile Met Ile Leu Asn Lys Leu
    210                 215                 220

Thr Leu Thr Gly Tyr Ile Leu Thr Pro Glu Leu Val Leu Met Tyr Cys
225                 230                 235                 240

Asp Val Val Glu Gly Arg Trp Asn Met Ser Ala Ala Gly His Leu Asp
                245                 250                 255

Lys Lys Ser Ile Gly Ile Thr Ser Lys Gly Glu Glu Leu Trp Glu Leu
                260                 265                 270

Val Asp Ser Leu Phe Ser Ser Leu Gly Glu Glu Ile Tyr Asn Val Ile
            275                 280                 285

Ala Leu Leu Glu Pro Leu Ser Leu Ala Leu Ile Gln Leu Asn Asp Pro
    290                 295                 300

Val Ile Pro Leu Arg Gly Ala Phe Met Arg His Val Leu Thr Glu Leu
305                 310                 315                 320
```

```
Gln Ala Val Leu Thr Ser Arg Asp Val Tyr Thr Asp Ala Glu Ala Asp
                325                 330                 335

Thr Ile Val Glu Ser Leu Leu Ala Ile Phe His Gly Thr Ser Ile Asp
        340                 345                 350

Glu Lys Ala Glu Ile Phe Ser Phe Phe Arg Thr Phe Gly His Pro Ser
            355                 360                 365

Leu Glu Ala Val Thr Ala Ala Asp Lys Val Arg Ala His Met Tyr Ala
    370                 375                 380

Gln Lys Ala Ile Lys Leu Lys Thr Leu Tyr Glu Cys His Ala Val Phe
385                 390                 395                 400

Cys Thr Ile Ile Ile Asn Gly Tyr Arg Glu Arg His Gly Gly Gln Trp
                405                 410                 415

Pro Pro Cys Asp Phe Pro Asp His Val Cys Leu Glu Leu Arg Asn Ala
            420                 425                 430

Gln Gly Ser Asn Thr Ala Ile Ser Tyr Glu Cys Ala Val Asp Asn Tyr
    435                 440                 445

Thr Ser Phe Ile Gly Phe Lys Phe Arg Lys Phe Ile Glu Pro Gln Leu
    450                 455                 460

Asp Glu Asp Leu Thr Ile Tyr Met Lys Asp Lys Ala Leu Ser Pro Arg
465                 470                 475                 480

Lys Glu Ala Trp Asp Ser Val Tyr Pro Asp Ser Asn Leu Tyr Tyr Lys
                485                 490                 495

Ala Pro Glu Ser Glu Glu Thr Arg Arg Leu Ile Glu Val Phe Ile Asn
            500                 505                 510

Asp Glu Asn Phe Asn Pro Glu Glu Ile Ile Asn Tyr Val Glu Ser Gly
    515                 520                 525

Asp Trp Leu Lys Asp Glu Lys Phe Asn Ile Ser Tyr Ser Leu Lys Glu
    530                 535                 540

Lys Glu Ile Lys Gln Glu Gly Arg Leu Phe Ala Lys Met Thr Tyr Lys
545                 550                 555                 560

Met Arg Ala Val Gln Val Leu Ala Glu Thr Leu Leu Ala Lys Gly Ile
                565                 570                 575

Gly Glu Leu Phe Ser Glu Asn Gly Met Val Lys Gly Glu Ile Asp Leu
            580                 585                 590

Leu Lys Arg Leu Thr Thr Leu Ser Val Ser Gly Val Pro Arg Thr Asp
    595                 600                 605

Ser Val Tyr Asn Asn Ser Lys Ser Ser Glu Lys Arg Asn Glu Gly Met
    610                 615                 620

Lys Lys Lys Asn Ser Gly Gly Tyr Trp Asp Glu Lys Lys Arg Ser Arg
625                 630                 635                 640

His Glu Phe Lys Ala Thr Asp Ser Ser Thr Asp Gly Tyr Glu Thr Leu
                645                 650                 655

Ser Cys Phe Leu Thr Thr Asp Leu Lys Lys Tyr Cys Leu Asn Trp Arg
            660                 665                 670

Phe Glu Ser Thr Ala Leu Phe Gly Gln Arg Cys Asn Glu Ile Phe Gly
    675                 680                 685

Phe Lys Thr Phe Phe Asn Trp Met His Pro Val Leu Glu Arg Cys Thr
    690                 695                 700

Ile Tyr Val Gly Asp Pro Tyr Cys Pro Val Ala Asp Arg Met His Arg
705                 710                 715                 720

Gln Leu Gln Asp His Ala Asp Ser Gly Ile Phe Ile His Asn Pro Arg
                725                 730                 735

Gly Gly Ile Glu Gly Tyr Cys Gln Lys Leu Trp Thr Leu Ile Ser Ile
```

740                 745                 750
Ser Ala Ile His Leu Ala Ala Val Arg Val Gly Val Arg Val Ser Ala
            755                 760                 765

Met Val Gln Gly Asp Asn Gln Ala Ile Ala Val Thr Ser Arg Val Pro
        770                 775                 780

Val Ala Gln Thr Tyr Lys Gln Lys Asn His Val Tyr Lys Glu Ile
785                 790                 795                 800

Thr Lys Tyr Phe Gly Ala Leu Arg His Val Met Phe Asp Val Gly His
                    805                 810                 815

Glu Leu Lys Leu Asn Glu Thr Ile Ile Ser Ser Lys Met Phe Val Tyr
            820                 825                 830

Ser Lys Arg Ile Tyr Tyr Asp Gly Lys Ile Leu Pro Gln Cys Leu Lys
            835                 840                 845

Ala Leu Thr Arg Cys Val Phe Trp Ser Glu Thr Leu Val Asp Glu Asn
        850                 855                 860

Arg Ser Ala Cys Ser Asn Ile Ser Thr Ser Ile Ala Lys Ala Ile Glu
865                 870                 875                 880

Asn Gly Tyr Ser Pro Ile Leu Gly Tyr Cys Ile Ala Leu Tyr Lys Thr
                    885                 890                 895

Cys Gln Gln Val Cys Ile Ser Leu Gly Met Thr Ile Asn Pro Thr Ile
                900                 905                 910

Ser Pro Thr Val Arg Asp Gln Tyr Phe Lys Gly Lys Asn Trp Leu Arg
            915                 920                 925

Cys Ala Val Leu Ile Pro Ala Asn Val Gly Gly Phe Asn Tyr Met Ser
        930                 935                 940

Thr Ser Arg Cys Phe Val Arg Asn Ile Gly Asp Pro Ala Val Ala Ala
945                 950                 955                 960

Leu Ala Asp Leu Lys Arg Phe Ile Arg Ala Asp Leu Leu Asp Lys Gln
                    965                 970                 975

Val Leu Tyr Arg Val Met Asn Gln Glu Pro Gly Asp Ser Ser Phe Leu
                980                 985                 990

Asp Trp Ala Ser Asp Pro Tyr Ser  Cys Asn Leu Pro His  Ser Gln Ser
            995                 1000                1005

Ile Thr  Thr Ile Ile Lys Asn  Ile Thr Ala Arg Ser  Val Leu Gln
    1010                1015                1020

Glu Ser  Pro Asn Pro Leu Leu  Ser Gly Leu Phe Thr  Glu Thr Ser
    1025                1030                1035

Gly Glu  Glu Asp Leu Asn Leu  Ala Ser Phe Leu Met  Asp Arg Lys
    1040                1045                1050

Val Ile  Leu Pro Arg Val Ala  His Glu Ile Leu Gly  Asn Ser Leu
    1055                1060                1065

Thr Gly  Val Arg Glu Ala Ile  Ala Gly Met Leu Asp  Thr Thr Lys
    1070                1075                1080

Ser Leu  Val Arg Ser Ser Val  Lys Lys Gly Gly Leu  Ser Tyr Gly
    1085                1090                1095

Ile Leu  Arg Arg Leu Val Asn  Tyr Asp Leu Leu Gln  Tyr Glu Thr
    1100                1105                1110

Leu Thr  Arg Thr Leu Arg Lys  Pro Val Lys Asp Asn  Ile Glu Tyr
    1115                1120                1125

Glu Tyr  Met Cys Ser Val Glu  Leu Ala Val Gly Leu  Arg Gln Lys
    1130                1135                1140

Met Trp  Ile His Leu Thr Tyr  Gly Arg Pro Ile His  Gly Leu Glu
    1145                1150                1155

```
Thr Pro Asp Pro Leu Glu Leu Leu Arg Gly Thr Phe Ile Glu Gly
    1160             1165                 1170

Ser Glu Val Cys Lys Leu Cys Arg Ser Glu Gly Ala Asp Pro Ile
    1175             1180                 1185

Tyr Thr Trp Phe Tyr Leu Pro Asp Asn Ile Asp Leu Asp Thr Leu
    1190             1195                 1200

Thr Asn Gly Cys Pro Ala Ile Arg Ile Pro Tyr Phe Gly Ser Ala
    1205             1210                 1215

Thr Asp Glu Arg Ser Glu Ala Gln Leu Gly Tyr Val Arg Asn Leu
    1220             1225                 1230

Ser Lys Pro Ala Lys Ala Ala Ile Arg Ile Ala Met Val Tyr Thr
    1235             1240                 1245

Trp Ala Tyr Gly Thr Asp Glu Ile Ser Trp Met Glu Ala Ala Leu
    1250             1255                 1260

Ile Ala Gln Thr Arg Ala Asn Leu Ser Leu Glu Asn Leu Lys Leu
    1265             1270                 1275

Leu Thr Pro Val Ser Thr Ser Thr Asn Leu Ser His Arg Leu Lys
    1280             1285                 1290

Asp Thr Ala Thr Gln Met Lys Phe Ser Ser Ala Thr Leu Val Arg
    1295             1300                 1305

Ala Ser Arg Phe Ile Thr Ile Ser Asn Asp Asn Met Ala Leu Lys
    1310             1315                 1320

Glu Ala Gly Glu Ser Lys Asp Thr Asn Leu Val Tyr Gln Gln Ile
    1325             1330                 1335

Met Leu Thr Gly Leu Ser Leu Phe Glu Phe Asn Met Arg Tyr Lys
    1340             1345                 1350

Lys Gly Ser Leu Gly Lys Pro Leu Ile Leu His Leu His Leu Asn
    1355             1360                 1365

Asn Gly Cys Cys Ile Met Glu Ser Pro Gln Glu Ala Asn Ile Pro
    1370             1375                 1380

Pro Arg Ser Thr Leu Asp Leu Glu Ile Thr Gln Glu Asn Asn Lys
    1385             1390                 1395

Leu Ile Tyr Asp Pro Asp Pro Leu Lys Asp Val Asp Leu Glu Leu
    1400             1405                 1410

Phe Ser Lys Val Arg Asp Val Val His Thr Val Asp Met Thr Tyr
    1415             1420                 1425

Trp Ser Asp Asp Glu Val Ile Arg Ala Thr Ser Ile Cys Thr Ala
    1430             1435                 1440

Met Thr Ile Ala Asp Thr Met Ser Gln Leu Asp Arg Asp Asn Leu
    1445             1450                 1455

Lys Glu Met Ile Ala Leu Val Asn Asp Asp Val Asn Ser Leu
    1460             1465                 1470

Ile Thr Glu Phe Met Val Ile Asp Val Pro Leu Phe Cys Ser Thr
    1475             1480                 1485

Phe Gly Gly Ile Leu Val Asn Gln Phe Ala Tyr Ser Leu Tyr Gly
    1490             1495                 1500

Leu Asn Ile Arg Gly Arg Glu Glu Ile Trp Gly His Val Val Arg
    1505             1510                 1515

Ile Leu Lys Asp Thr Ser His Ala Val Leu Lys Val Leu Ser Asn
    1520             1525                 1530

Ala Leu Ser His Pro Lys Ile Phe Lys Arg Phe Trp Asn Ala Gly
    1535             1540                 1545
```

-continued

Val Val Glu Pro Val Tyr Gly Pro Asn Leu Ser Asn Gln Asp Lys
1550            1555            1560

Ile Leu Leu Ala Leu Ser Val Cys Glu Tyr Ser Val Asp Leu Phe
1565            1570            1575

Met His Asp Trp Gln Gly Gly Val Pro Leu Glu Ile Phe Ile Cys
1580            1585            1590

Asp Asn Asp Pro Asp Val Ala Asp Met Arg Arg Ser Ser Phe Leu
1595            1600            1605

Ala Arg His Leu Ala Tyr Leu Cys Ser Val Ala Glu Ile Ser Arg
1610            1615            1620

Asp Gly Pro Arg Leu Glu Ser Met Asn Ser Leu Glu Arg Leu Glu
1625            1630            1635

Ser Leu Lys Ser Tyr Leu Glu Leu Thr Phe Leu Asp Asp Pro Val
1640            1645            1650

Leu Arg Tyr Ser Gln Leu Thr Gly Leu Val Ile Lys Val Phe Pro
1655            1660            1665

Ser Thr Leu Thr Tyr Ile Arg Lys Ser Ser Ile Lys Val Leu Arg
1670            1675            1680

Thr Arg Gly Ile Gly Val Pro Glu Val Leu Glu Asp Trp Asp Pro
1685            1690            1695

Glu Ala Asp Asn Ala Leu Leu Asp Gly Ile Ala Ala Glu Ile Gln
1700            1705            1710

Gln Asn Ile Pro Leu Gly His Gln Thr Arg Ala Pro Phe Trp Gly
1715            1720            1725

Leu Arg Val Ser Lys Ser Gln Val Leu Arg Leu Arg Gly Tyr Lys
1730            1735            1740

Glu Ile Thr Arg Gly Glu Ile Gly Arg Ser Gly Val Gly Leu Thr
1745            1750            1755

Leu Pro Phe Asp Gly Arg Tyr Leu Ser His Gln Leu Arg Leu Phe
1760            1765            1770

Gly Ile Asn Ser Thr Ser Cys Leu Lys Ala Leu Glu Leu Thr Tyr
1775            1780            1785

Leu Leu Ser Pro Leu Val Asp Lys Asp Lys Asp Arg Leu Tyr Leu
1790            1795            1800

Gly Glu Gly Ala Gly Ala Met Leu Ser Cys Tyr Asp Ala Thr Leu
1805            1810            1815

Gly Pro Cys Ile Asn Tyr Tyr Asn Ser Gly Val Tyr Ser Cys Asp
1820            1825            1830

Val Asn Gly Gln Arg Glu Leu Asn Ile Tyr Pro Ala Glu Val Ala
1835            1840            1845

Leu Val Gly Lys Lys Leu Asn Asn Val Thr Ser Leu Gly Gln Arg
1850            1855            1860

Val Lys Val Leu Phe Asn Gly Asn Pro Gly Ser Thr Trp Ile Gly
1865            1870            1875

Asn Asp Glu Cys Glu Ala Leu Ile Trp Asn Glu Leu Gln Asn Ser
1880            1885            1890

Ser Ile Gly Leu Val His Cys Asp Met Glu Gly Gly Asp His Lys
1895            1900            1905

Asp Asp Gln Val Val Leu His Glu His Tyr Ser Val Ile Arg Ile
1910            1915            1920

Ala Tyr Leu Val Gly Asp Arg Asp Val Val Leu Ile Ser Lys Ile
1925            1930            1935

Ala Pro Arg Leu Gly Thr Asp Trp Thr Arg Gln Leu Ser Leu Tyr

-continued

```
                1940                    1945                    1950
Leu Arg Tyr Trp Asp Glu Val Asn Leu Ile Val Leu Lys Thr Ser
    1955                    1960                    1965
Asn Pro Ala Ser Thr Glu Met Tyr Leu Leu Ser Arg His Pro Lys
    1970                    1975                    1980
Ser Asp Ile Ile Glu Asp Ser Lys Thr Val Leu Ala Ser Leu Leu
    1985                    1990                    1995
Pro Leu Ser Lys Glu Asp Ser Ile Lys Ile Glu Lys Trp Ile Leu
    2000                    2005                    2010
Ile Glu Lys Ala Lys Ala His Glu Trp Val Thr Arg Glu Leu Arg
    2015                    2020                    2025
Glu Gly Ser Ser Ser Ser Gly Met Leu Arg Pro Tyr His Gln Ala
    2030                    2035                    2040
Leu Gln Thr Phe Gly Phe Glu Pro Asn Leu Tyr Lys Leu Ser Arg
    2045                    2050                    2055
Asp Phe Leu Ser Thr Met Asn Ile Ala Asp Thr His Asn Cys Met
    2060                    2065                    2070
Ile Ala Phe Asn Arg Val Leu Lys Asp Thr Ile Phe Glu Trp Ala
    2075                    2080                    2085
Arg Ile Thr Glu Ser Asp Lys Arg Leu Lys Leu Thr Gly Lys Tyr
    2090                    2095                    2100
Asp Leu Tyr Pro Val Arg Asp Ser Gly Lys Leu Lys Thr Val Ser
    2105                    2110                    2115
Arg Arg Leu Val Leu Ser Trp Ile Ser Leu Ser Met Ser Thr Arg
    2120                    2125                    2130
Leu Val Thr Gly Ser Phe Pro Asp Gln Lys Phe Glu Ala Arg Leu
    2135                    2140                    2145
Gln Leu Gly Ile Val Ser Leu Ser Ser Arg Glu Ile Arg Asn Leu
    2150                    2155                    2160
Arg Val Ile Thr Lys Thr Leu Leu Asp Arg Phe Glu Asp Ile Ile
    2165                    2170                    2175
His Ser Ile Thr Tyr Arg Phe Leu Thr Lys Glu Ile Lys Ile Leu
    2180                    2185                    2190
Met Lys Ile Leu Gly Ala Val Lys Met Phe Gly Ala Arg Gln Asn
    2195                    2200                    2205
Glu Tyr Thr Thr Val Ile Asp Asp Gly Ser Leu Gly Asp Ile Glu
    2210                    2215                    2220
Pro Tyr Asp Ser Ser
    2225
```